US010570103B2

(12) United States Patent
Beaton et al.

(10) Patent No.: US 10,570,103 B2
(45) Date of Patent: *Feb. 25, 2020

(54) HETEROCYCLIC COMPOUNDS USEFUL IN THE TREATMENT OF DISEASE

(71) Applicant: EPIGEN BIOSCIENCES, INC., San Diego, CA (US)

(72) Inventors: Graham Beaton, San Diego, CA (US); Fabio C. Tucci, San Diego, CA (US); Satheesh B. Ravula, San Diego, CA (US); Chandravadan R. Shah, San Diego, CA (US); Hiep Luu, San Marcos, CA (US)

(73) Assignee: EPIGEN BIOSCIENCES, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/000,283

(22) Filed: Jun. 5, 2018

(65) Prior Publication Data

US 2019/0135767 A1    May 9, 2019

Related U.S. Application Data

(63) Continuation of application No. 14/776,954, filed as application No. PCT/US2014/030712 on Mar. 17, 2014, now Pat. No. 10,000,459.

(60) Provisional application No. 61/827,409, filed on May 24, 2013, provisional application No. 61/801,231, filed on Mar. 15, 2013, provisional application No. 61/801,426, filed on Mar. 15, 2013.

(51) Int. Cl.
| A61K 31/415 | (2006.01) |
| C07D 261/14 | (2006.01) |
| C07D 231/38 | (2006.01) |
| C07D 231/52 | (2006.01) |
| C07D 233/88 | (2006.01) |
| C07D 401/04 | (2006.01) |
| C07D 239/42 | (2006.01) |
| C07D 413/04 | (2006.01) |
| C07D 263/48 | (2006.01) |

(52) U.S. Cl.
CPC .......... *C07D 261/14* (2013.01); *A61K 31/415* (2013.01); *C07D 231/38* (2013.01); *C07D 231/52* (2013.01); *C07D 233/88* (2013.01); *C07D 239/42* (2013.01); *C07D 263/48* (2013.01); *C07D 401/04* (2013.01); *C07D 413/04* (2013.01)

(58) Field of Classification Search
CPC .................................................. A61K 31/415
See application file for complete search history.

(56) References Cited

U.S. PATENT DOCUMENTS

| 6,756,380 | B1 | 6/2004 | Bos et al. |
| 6,964,975 | B2 | 11/2005 | Ueno et al. |
| 7,288,558 | B2 | 10/2007 | Nakade et al. |
| 7,517,996 | B2 | 4/2009 | Yamamoto et al. |
| 8,048,902 | B2 | 11/2011 | Hutchinson et al. |
| 8,058,300 | B2 | 11/2011 | Hutchinson et al. |
| 8,217,066 | B2 | 7/2012 | Seiders et al. |
| 8,273,780 | B2 | 9/2012 | Hutchinson et al. |
| 8,440,707 | B2 | 5/2013 | Hutchinson et al. |
| 8,592,402 | B2 | 11/2013 | Hutchinson et al. |
| 8,664,220 | B2 | 3/2014 | Clark et al. |
| 8,778,983 | B2 | 7/2014 | Clark et al. |
| 8,785,442 | B2 | 7/2014 | An et al. |
| 8,975,235 | B2 | 3/2015 | Buckman et al. |
| 9,090,573 | B2 | 7/2015 | Seiders et al. |
| 9,272,990 | B2 | 3/2016 | Seiders et al. |
| 9,321,738 | B2 | 4/2016 | Gabriel et al. |
| 2003/0114505 | A1 | 6/2003 | Ueno et al. |
| 2004/0067908 | A1 | 4/2004 | Nakade et al. |
| 2006/0148858 | A1 | 7/2006 | Maekawa et al. |
| 2006/0194850 | A1 | 8/2006 | Yamamoto et al. |
| 2009/0036450 | A1 | 2/2009 | Takagi et al. |
| 2009/0170911 | A1 | 7/2009 | Yamamoto et al. |
| 2010/0152257 | A1 | 6/2010 | Hutchinson et al. |
| 2010/0311799 | A1 | 12/2010 | Hutchinson et al. |
| 2011/0082164 | A1 | 4/2011 | Clark et al. |
| 2011/0082181 | A1 | 4/2011 | Seiders et al. |

(Continued)

FOREIGN PATENT DOCUMENTS

| EP | 1632488 A1 | 3/2006 |
| EP | 1258484 B1 | 1/2009 |

(Continued)

OTHER PUBLICATIONS

Abarbri, et al., "Preparation of New Polyfunctional Magnesiated Heterocycles Using a Chlorine-, Bromine-, or Iodine-Magnesium Exchange", J. Org. Chem. 2000, 65, pp. 4618-4634.

(Continued)

*Primary Examiner* — Karen Cheng
(74) *Attorney, Agent, or Firm* — Harness, Dickey & Pierce, P.L.C.

(57) ABSTRACT

A method for treating a lysophosphatidic acid-dependent disease or condition in a subject in need thereof is provided. The method includes administering to the subject a therapeutically effective amount of a heterocyclic compound. The heterocyclic compound is a lysophosphatidic acid receptor ligand. Lysophosphatidic acid-dependent diseases and conditions include diseases involving fibrosis, such as fibrosis of the heart, kidney, liver and lung, and scleroderma; inflammatory diseases such as diabetic nephropathy and inflammatory bowel disease; ocular diseases such as diseases involving retinal degeneration; nerve diseases such as pruritus and pain.

24 Claims, No Drawings

(56) References Cited

U.S. PATENT DOCUMENTS

| | | |
|---|---|---|
| 2011/0105491 A1 | 5/2011 | Aissaoui et al. |
| 2011/0152081 A1 | 6/2011 | Lahm et al. |
| 2011/0196005 A1 | 8/2011 | Hutchinson et al. |
| 2011/0301142 A1 | 12/2011 | Hutchinson et al. |
| 2011/0301211 A1 | 12/2011 | Hutchinson et al. |
| 2012/0015991 A1 | 1/2012 | Hutchinson et al. |
| 2012/0031985 A1 | 2/2012 | Do et al. |
| 2012/0196839 A1 | 8/2012 | Hutchinson et al. |
| 2012/0289522 A1 | 11/2012 | Seiders et al. |
| 2013/0025733 A1 | 1/2013 | Yamakawa et al. |
| 2013/0041000 A1 | 2/2013 | Yamamoto et al. |
| 2013/0072449 A1 | 3/2013 | Buckman et al. |
| 2013/0072490 A1 | 3/2013 | Clark et al. |
| 2013/0253004 A1 | 9/2013 | Seiders et al. |
| 2013/0253019 A1 | 9/2013 | Hutchinson et al. |
| 2013/0253023 A1 | 9/2013 | Brittain et al. |
| 2014/0031353 A1 | 1/2014 | An et al. |
| 2014/0213538 A1 | 7/2014 | Buckman et al. |
| 2014/0256744 A1 | 9/2014 | Clark et al. |
| 2014/0329871 A1 | 11/2014 | Mishira et al. |
| 2015/0133512 A1 | 5/2015 | Grabriel et al. |
| 2015/0259295 A1 | 9/2015 | Gabriel et al. |
| 2015/0329502 A1 | 11/2015 | Seiders et al. |
| 2015/0376160 A1 | 12/2015 | Iwase et al. |
| 2016/0256577 A1 | 9/2016 | Seiders et al. |

FOREIGN PATENT DOCUMENTS

| | | |
|---|---|---|
| EP | 2202226 A1 | 6/2010 |
| WO | 2001060819 A1 | 8/2001 |
| WO | 2002062389 A1 | 8/2002 |
| WO | 2003099793 A1 | 12/2003 |
| WO | 2005012269 A1 | 2/2005 |
| WO | 2005044785 A1 | 5/2005 |
| WO | 2005099688 A2 | 10/2005 |
| WO | 2007002559 A1 | 1/2007 |
| WO | 2010077883 A2 | 7/2010 |
| WO | 2010077882 A3 | 10/2010 |
| WO | 2010141761 A2 | 12/2010 |
| WO | 2010141768 A2 | 12/2010 |
| WO | 2011017350 A2 | 2/2011 |
| WO | 2011041694 A2 | 4/2011 |
| WO | 2011041729 A2 | 4/2011 |
| WO | 2011159632 A1 | 12/2011 |
| WO | 2011159633 A1 | 12/2011 |
| WO | 2011159635 A1 | 12/2011 |
| WO | 2012078593 A2 | 6/2012 |
| WO | 2012078805 A1 | 6/2012 |
| WO | 2012100436 A1 | 8/2012 |
| WO | 2012138648 A1 | 10/2012 |
| WO | 2013025733 A1 | 2/2013 |
| WO | 2013070879 A1 | 5/2013 |
| WO | 2013085824 A1 | 6/2013 |
| WO | 2013142266 A1 | 9/2013 |
| WO | 2013189862 A1 | 12/2013 |
| WO | 2013189864 A1 | 12/2013 |
| WO | 2013189865 A1 | 12/2013 |
| WO | 2014104372 A1 | 7/2014 |
| WO | 2014113485 A1 | 7/2014 |
| WO | 2015066456 A1 | 5/2015 |
| WO | 2015199234 A1 | 12/2015 |

OTHER PUBLICATIONS

An, et al., "Molecular Cloning of the Human Edg2 Protein and Its Identification as a Functional Cellular Receptor for Lysophosphatidic Acid", Biochemical and Biophysical Research Communications, 231, (1997), pp. 619-622.

Choi, et al., "Oxidation of Biginelli Reaction Products: Synthesis of 2-Unsubstituted 1,4-Dihydropyrimidines, Pyrimidines, adn 2-Hydroxypyrimidines", Synlett 2009, No. 4, pp. 599-602.

Cottyn, et al., "Efficient Synthesis of 7-Substituted or 3,7-Disubstituted 1H-Indazoles", Synlett 2007, 8, p. 2007.

Dehmel, et al., "Preparation of New Magnesiated Functionalized Imidazoles and Antipyrines via an Iodine-Magnesium Exhange", Synlett 2000, No. 3, pp. 345-346.

Yamamoto et al. Synthesis and evaluation of isoxazole derivatives as lysophosphatidic acid (LPA) antagonists. Bioorganic and Medicinal Chemistry Letters, 2007, vol. 17, # 13 p. 3736-3740.

Gagnon, et al., "Contribution to the Study of Pyrazolones", Can. J. Chem., vol. 31, pp. 673-684.

Huang, et al., "Efficient Trapping of Oxonium Ylides with Imines: A Highly Diastereoselective Three-Component Reaction for the Synthesis of b-Amino-a-hydroxyesters with Quaternary Stereocenters", Angew. Chem. Int. Ed., 2007, 46, pp. 1337-1339.

Zhu, et al., "Trimethylsilyl Chloride: A Facile and Efficient Reagent for One-Pot Synthesis of 3,4-Dihydropyrimidin-2(1H)-ones", Synthetic Communications, vol. 34, No. 17, 2004, pp. 3167-3174.

Lee et al., "Syntheses and Reactions of 2-Halo-5-thiazolecarboxylates", J. Heterocyclic Chem., 22, pp. 1621-1630; Nov.-Dec. 1985.

Maiti, et al, "Synthesis of a Library of 5,6-Unsubstituted 1,4-Dihydropyridines Based on a One-Pot 4CR/Elimination Process and Their Application to the Generation of Structurally Diverse Fused Nitrogen Heterocycles", 2010 American Chemical Society; J. Comb. Chem. 2010, 12, pp. 713-722.

Malki, et al., "Total Synthesis of Monocyclic Pyrimidinium Betaines With Fatthy Alkyl Chains", Asian Journal of Chemistry, vol. 23, No. 3 (2011), pp. 961-967.

Ohta et al. Ki16425, a subtype-selective antagonist for EDG-family lysophosphatidic acid receptors. Molecular Pharmacology, 2003, vol. 64, # 4 p. 994-1005.

Pathak, et al., "An Efficient, Inexpensive 'Green Chemistry' Route to Multicomponent Biginelli Condensation Catalyzed by CuC12.2H2O—HC1", Indian Journal of Chemistry, vol. 47B, Mar. 2008, pp. 434-438.

Pierre, et al., "Novel Potent Pyrimido[4,5-c]quinoline Inhibitors of Protein Kinase CK2: SAR and Preliminary Assessment of Their Analgesic and Anti-Viral Properties", Bioorganic & Medicinal Chemistry Letters; 21 (2011), pp. 1687-1691.

Qian et al. Discovery of highly selective and orally active lysophosphatidic acid receptor-1 antagonists with potent activity on human lung fibroblasts. J Med Chem. 2012 55(17):7920-39.

Sato et al. Synthesis and biological evaluation of optically active Ki16425. Bioorganic and Medicinal Chemistry Letters, 2012, vol. 22, # 13 p. 4323-4326.

Schenone, et al., "Reaction of 2-Dimethylaminomethylene-1,3-diones with Dinucleophiles. X. Synthesis of 5-Substituted Ethyl or Methyl 4-Isoxazolecarboxylates and Methyl 4-(2,2-Dimethyl-1-oxopropyl)-5-isoxazolecarboxylate [1]", J. Heterocyclic Chem., 28, (1991), pp. 453-457.

Senecal, et al., "A General, Practival Palladium-Catalyzed Cyanation of (Hetero) Aryl Chlrorides and Bromides", Angew. Chem. Int. Ed., 2013, 52, pp. 10035-10039.

Swaney et al. A novel, orally active LPA1 receptor antagonist inhibits lung fibrosis in the mouse bleomycin model. British Journal of Pharmacology, 2010, vol. 160, # 7 p. 1699-1713.

Swaney et al. Pharmacokinetic and pharmacodynamic characterization of an oral lysophosphatidic acid type 1 receptor-selective antagonist. Journal of Pharmacology and Experimental Therapeutics, 2011, vol. 336, # 3 p. 693-700.

Patani and LaVoie, "Bioisosterism: A Rational Approach in Drug Design." Chemical Reviews, vol. 96, No. 8, pp. 3147-3176 (1996).

HETEROCYCLIC COMPOUNDS USEFUL IN THE TREATMENT OF DISEASE

CROSS REFERENCE TO RELATED APPLICATIONS

This application is a continuation of U.S. patent application Ser. No. 14/776,954, filed on Sep. 15, 2015, which is a a 371 National Phase of PCT/US2014/030712, filed on Mar. 17, 2014, which claims the benefit of U.S. Provisional Patent Application Ser. No. 61/801,426, filed Mar. 15, 2013, U.S. Provisional Patent Application Ser. No. 61/801,231, filed Mar. 15, 2013, and U.S. Provisional Patent Application Ser. No. 61/827,409, filed May 24, 2013, the entire contents of all of which are hereby incorporated by reference herein.

STATEMENT OF GOVERNMENT INTEREST

This invention was made with government support under Grants DK092005 and CA174019 awarded by the National Institutes of Health. The US government has certain rights in the invention.

FIELD OF THE INVENTION

The present invention relates to compounds having pharmacological activity, to processes for preparation of such compounds, to pharmaceutical compositions comprising them, and to their use in therapy and prophylaxis of disease in a subject in need thereof, in particular for human and veterinarian treatments of pain, pruritus, cancer, inflammation and fibrotic diseases.

BACKGROUND OF THE INVENTION

Lysophospholipids affect fundamental cellular functions that include proliferation, differentiation, survival, migration, adhesion, invasion, and morphogensis. Abnormal functions influence many biological processes leading to disease that include, but are not limited to fibrotic disease, inflammation, cancer and peripheral nerve injury. Lysophosphatidic acid (LPA) is a lysophospholipid that has been shown to act through specific G protein-coupled receptors (GPCRs) in an autocrine and paracrine fashion. Antagonists of the LPA receptors find use in the treatment of diseases, disorders or conditions in which LPA plays a role.

Agents that interact with the lysophosphatidic acid receptors [LPARs] to reduce signal transduction through those receptors (i.e., by competitive or noncompetitive inhibition or acting as inverse agonists) reduce manifestations of the diseases described herein. Diseases and conditions whose etiology, progression or persistence is effected by in whole or in part by signaling through the lysophosphatidic acid receptor subtype 1 (LPA1R) are considered LPA-dependent. New agents having therapeutic utility for treating those LPA-dependent and other conditions and diseases described herein are needed.

SUMMARY OF THE INVENTION

Disclosed herein are compounds that inhibit the physiological activity of lysophosphatidic acid (LPA), and therefore, are useful as agents for the treatment or prevention of diseases in which inhibition of the physiological activity of LPA is useful.

In one aspect, those compounds are useful for the treatment of fibrosis of organs (e.g., liver, kidney, lung, heart and the like), liver diseases (e.g., acute hepatitis, chronic hepatitis, liver fibrosis, liver cirrhosis, portal hypertension, regenerative failure, nonalcoholic steatohepatitis (NASH), liver hypofunction, hepatic blood flow disorder, and the like), cell proliferative disease such as cancers (including but not limited to solid tumor, solid tumor metastasis, vascular fibroma, myeloma, multiple myeloma, Kaposi's sarcoma, leukemia, chronic lymphocytic leukemia (CLL), invasive metastasis of cancer cell, and the like), inflammatory diseases (including but not limited to psoriasis, nephropathy, pneumonia and the like), gastrointestinal tract disease (including but not limited to (irritable bowel syndrome (IBS), inflammatory bowel disease (IBD), abnormal pancreatic secretion, and the like), renal disease, urinary tract-associated disease (including but not limited to benign prostatic hyperplasia or symptoms associated with neuropathic bladder disease, spinal cord tumor, hernia of intervertebral disk, spinal canal stenosis, symptoms derived from diabetes, lower urinary tract disease (including but not limited to obstruction of lower urinary tract, and the like), inflammatory disease of lower urinary tract, (including but not limited to dysuria, frequent urination, and the like), pancreas disease, abnormal angiogenesis-associated disease (including but not limited to arterial obstruction and the like), scleroderma, brain-associated disease (including but not limited to cerebral infarction, cerebral hemorrhage, and the like), nervous system diseases (including but not limited to neuropathic pain, peripheral neuropathy, pruritus and the like), ocular disease (including but not limited to age-related macular degeneration (AMD), diabetic retinopathy, proliferative vitreo-retinopathy (PVR), cicatricial pemphigoid, glaucoma filtration surgery scarring, and the like).

The compounds of the invention include compounds of Formula I that have the structure:

Formula I

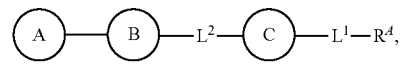

wherein $R^A$ is —$CO_2H$, —$CO_2R^B$, —CN, tetrazolyl, —C(=O)$NH_2$, —C(=O)$NHR^B$, —C(=O)$NHSO_2R^B$ or —C(=O)$NHCH_2CH_2SO_3H$ or a carboxylic acid isostere;

$L^1$ is absent or optionally substituted $C_1$-$C_6$ alkylene, optionally substituted $C_3$-$C_6$ cycloalkylene, optionally substituted $C_1$-$C_6$ fluoroalkylene, optionally substituted $C_1$-$C_6$ heteroalkylene, or —UV—Z—, wherein —UV— is defined by —OW—, —WO—, —N($R^J$)W—, —WN($R^J$)—, —N($R^J$)C(=O)—, —SW—, —S(=O)$_n$W—, or —C(=O)N($R^J$)—, wherein W is optionally substituted $C_1$-$C_3$ alkylene or optionally substituted $C_3$-$C_6$ cycloalkylene or W is —C($R^L$)$_2$—, Z is optionally substituted $C_1$-$C_6$ alkylene, optionally substituted $C_3$-$C_6$ cycloalkylene or $C_1$-$C_6$ fluoroalkylene or Z is —C($R^L$)$_2$—; and n is 0, 1, or 2;

$L^2$ is absent, or optionally substituted $C_1$-$C_6$ alkylene, optionally substituted $C_3$-$C_6$ cycloalkylene, $C_1$-$C_6$ fluoroalkylene, optionally substituted $C_1$-$C_6$ heteroalkylene, —O—, —S—, —S(=O)—, —S(=O)$_2$—, —N($R^B$)—, —C(=O)—, or —C(=O)N($R^B$)—;

wherein $R^B$ is —H or -optionally substituted $C_1$-$C_4$ alkyl, or has the structure of one of:

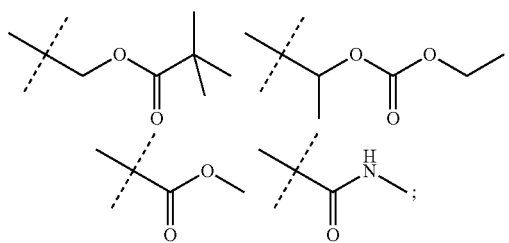

Ring A is a 5 or 6 membered heteroarene having the structure of one of:

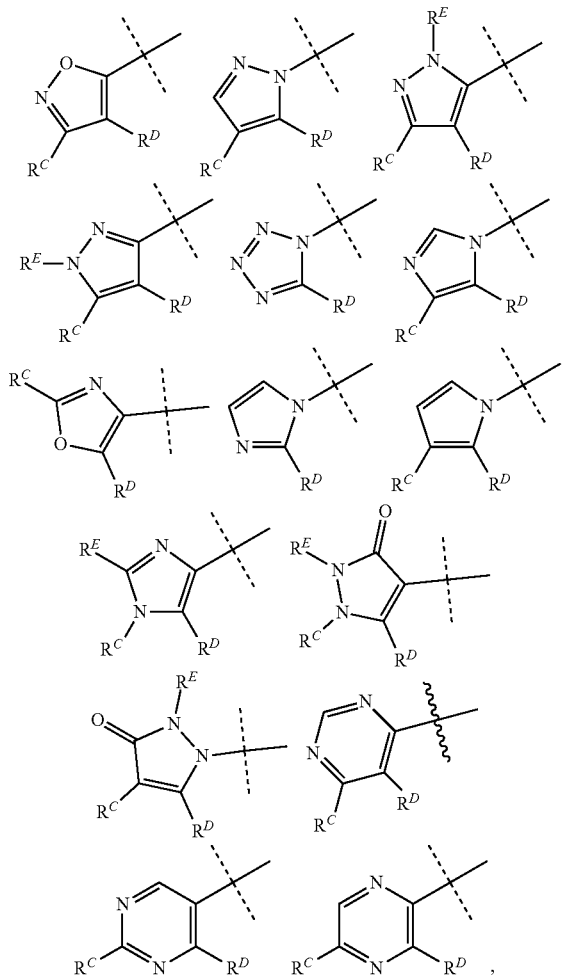

wherein the dashed line indicates the point of attachment of Ring A to Ring B;
wherein one of $R^C$ and $R^D$ is —H, —CN, —F, —Cl, —Br, —I, —$OC_1$-$C_4$ alkyl, $C_1$-$C_4$ alkyl, $C_3$-$C_6$ cycloalkyl, or $C_1$-$C_4$ fluoroalkyl,
and the other $R^C$ or $R^D$ is —N($R^F$)C(=O)XCH($R^G$)—CY, —N($R^F$)C(=O)XC($R^G$)$_2$—CY, —N($R^F$)C(=O)X—CY, —C(=O)—N($R^F$)—CH($R^G$)X—CY, or —C(=O)—N($R^F$)—C($R^G$)$_2$X—CY, wherein X is absent, —O—, —NH— or —$CH_2$—;
$R^E$ is —H, $C_1$-$C_4$ alkyl or $C_1$-$C_4$ fluoroalkyl;
$R^F$ is —H or $C_1$-$C_4$ alkyl;
$R^G$ is independently selected $R^E$, or one $R^G$ is $C_1$-$C_4$ alkaline and is taken together with CY and the carbon atom to which $R^G$ and CY is attached to define a substituted or unsubstituted carbocycle or a substituted or unsubstituted heterocycle, and the other $R^G$, if present, is as defined for $R^E$;
CY is optionally substituted $C_1$-$C_6$ alkyl, optionally substituted $C_3$-$C_{10}$ cycloalkyl, optionally substituted $C_2$-$C_{10}$ heterocycloalkyl, optionally substituted aryl, or optionally substituted heteroaryl, wherein if CY is substituted then CY is substituted with 1, 2, or 3 independently selected $R^H$,
wherein each $R^H$ is independently —H, halogen, —CN, —$NO_2$, —OH, —$OR^J$, —$SR^J$, —S(=O)$R^J$, —S(=O)$_2R^J$, —N($R^J$)S(=O)$_2R^J$, —S(=O)$_2$N($R^L$)$_2$, —C(=O)$R^J$, OC(=O)$R^J$, —C(=O)$OR^J$, —OC=O)$OR^J$, —N($R^L$)$_2$, —C(=O)N($R^L$)$_2$, —OC(=O)N($R^L$)$_2$, —N($R^J$)C(=O)N($R^L$)$_2$, —N($R^J$)C(=O)$R^J$, —N($R^J$)C(=O)$OR^J$, $C_1$-$C_4$ alkyl, $C_1$-$C_4$ fluoroalkyl, $C_1$-$C_4$ fluoroalkoxy, $C_1$-$C_4$ alkoxy, or $C_1$-$C_4$ heteroalkyl;
wherein each $R^J$ is independently optionally substituted $C_1$-$C_6$ alkyl, optionally substituted $C_1$-$C_6$ heteroalkyl, optionally substituted $C_1$-$C_6$ fluoroalkyl, optionally substituted $C_3$-$C_6$ cycloalkyl, optionally substituted heterocycloalkyl, optionally substituted aryl, optionally substituted heteroaryl, —$C_1$-$C_4$ alkylene-(optionally substituted $C_3$-$C_6$ cycloalkyl), —$C_1$-$C_4$ alkylene-(optionally substituted heterocycloalkyl), —$C_1$-$C_4$ alkylene-(optionally substituted aryl), or —$C_1$-$C_4$ alkylene-(optionally substituted heteroaryl), and
wherein $R^L$ is independently —H, optionally substituted $C_1$-$C_6$ alkyl, optionally substituted $C_1$-$C_6$ heteroalkyl, optionally substituted $C_1$-$C_6$ fluoroalkyl, optionally substituted $C_3$-$C_6$ cycloalkyl, optionally substituted heterocycloalkyl, optionally substituted aryl, optionally substituted heteroaryl, —$C_1$-$C_4$ alkylene-(optionally substituted $C_3$-$C_6$ cycloalkyl), —$C_1$-$C_4$ alkylene-(optionally substituted heterocycloalkyl), —$C_1$-$C_4$ alkylene-(optionally substituted aryl), or —$C_1$-$C_4$ alkylene-(optionally substituted heteroaryl),
or when $R^H$ is —S(=O)$_2$N($R^L$)$_2$, —N($R^L$)$_2$, —C(=O)N($R^L$)$_2$, —OC(=O)N($R^L$)$_2$ or —N($R^J$)C(=O)N($R^L$)$_2$, each $R^L$ is independently —H or $C_1$-$C_6$ alkyl, or the $R^L$ groups independently are $C_1$-$C_6$ alkyl which are taken together with the N atom to which they are attached to define a substituted or unsubstituted heterocycle,
or when W is —C($R^L$)$_2$—, or Z is —C($R^L$)$_2$— each $R^L$ is independently —H or $C_1$-$C_6$ alkyl, or the $R^L$ groups independently are $C_1$-$C_6$ alkyl which are taken together with the carbon atom to which they are attached to define a carbocycle;
Ring B is a optionally substituted $C_3$-$C_{10}$ cycloalkylene, optionally substituted $C_2$-$C_{10}$ heterocycloalkylene, optionally substituted arylene, or optionally substituted heteroarylene, wherein if ring B is substituted then ring B is substituted with 1, 2, or 3 independently selected $R^H$, wherein $R^H$ is as previously defined; and
Ring C is absent or optionally substituted $C_3$-$C_{10}$ cycloalkylene, optionally substituted $C_2$-$C_{10}$ heterocycloalkylene, optionally substituted arylene, or optionally substituted heteroarylene, where if ring C is substituted then ring C is substituted with 1, 2, or 3 independently selected $R^H$, wherein $R^H$ is as previously defined;
wherein when Ring B is substituted or unsubstituted arylene, Ring C is absent, $L^2$ is absent, $L^1$ is —UV—Z—, wherein —UV— is —N($R^J$)—C(=O)—, wherein $R^F$ is —H, $R^D$ is —N($R^F$)—C(=O)XCH($R^G$)—CY, wherein X is —O—, $R^G$ is —$CH_3$ and $R^F$ is —H, and $R^C$ is —H, —$CH_3$ or —$CF_3$, or when Ring B is optionally substituted arylene and Ring C is substituted or unsubstituted arylene or is substituted or unsubstituted $C_3$-$C_{10}$ cycloalkylene, or Ring B is substituted or unsubstituted $C_3$-$C_{10}$ cycloalkylene and Ring C is substituted or unsubstituted arylene, $L^2$ is absent, $L^1$ is $C_1$-$C_6$ alkylene, and $R^C$ is —H or —$CH_3$ and $R^A$ is —$CO_2H$ or —$CO_2R^B$, then Ring A has the structure of one of:

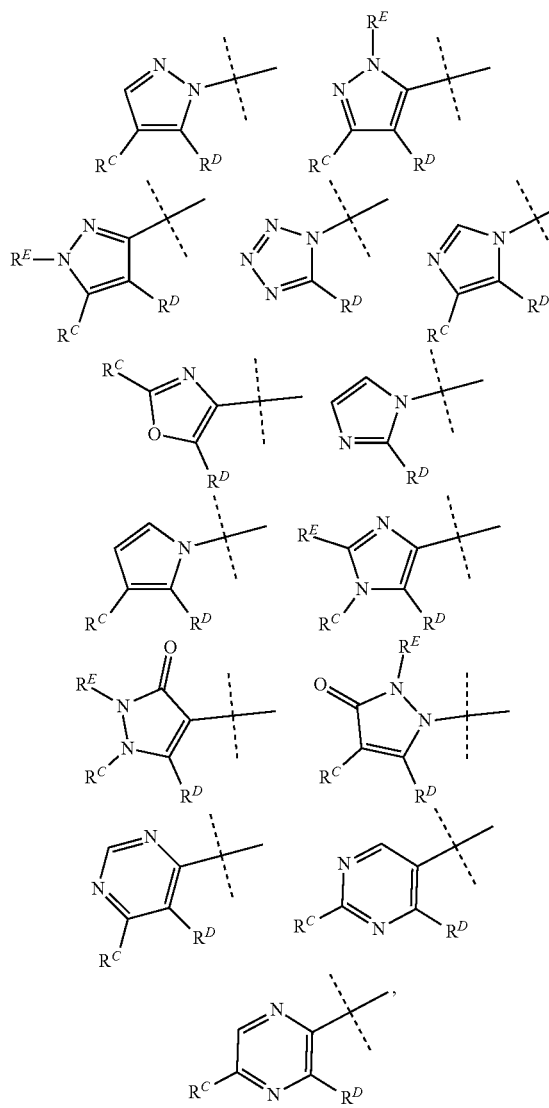

and when Ring B is $C_2$-$C_{10}$ heterocycloalkylene, Ring C is substituted or unsubstituted arylene, $L^2$ is absent, $L^1$ is $C_1$-$C_6$ alkylene, $R^C$ is —$CH_3$ and $R^A$ is —$CO_2H$ or —$CO_2R^B$, then Ring A has the structure of one of:

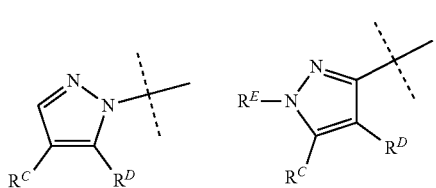

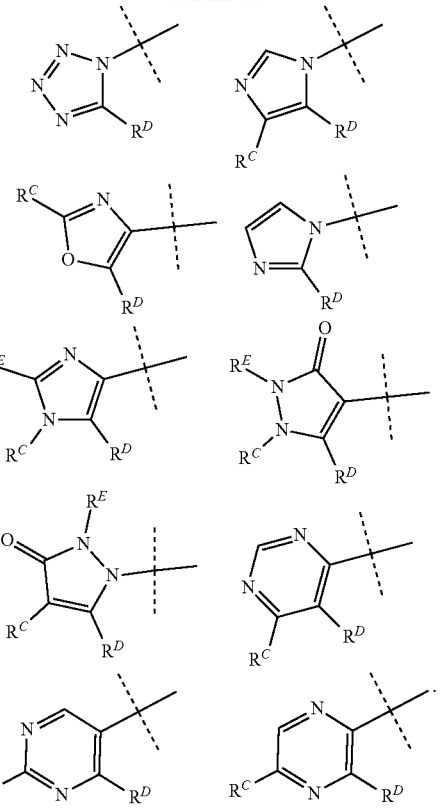

Other compounds of the invention have the structures indicated by the numbered embodiment and claims herein.

DETAILED DESCRIPTION OF THE INVENTION

Definitions

As used herein and unless otherwise stated or implied by context, terms that are used herein have the meanings defined below. Unless otherwise contraindicated or implied, e.g., by including mutually exclusive elements or options, in these definitions and throughout this specification, the terms "a" and "an" mean one or more and the term "or" means and/or where permitted by context. Thus, as used in the specification and the appended claims, the singular forms "a," "an" and "the" include plural referents unless the context clearly dictates otherwise.

At various locations in the present disclosure, e.g., in any disclosed embodiments or in the claims, reference is made to compounds, compositions, or methods that "comprise" one or more specified components, elements or steps. Invention embodiments also specifically include those compounds, compositions, compositions or methods that are or that consist of or that consist essentially of those specified components, elements or steps. The terms "comprising", "consist of" and "consist essentially of" have their normally accepted meanings under U.S. patent law unless otherwise specifically stated. The term "comprised of" is used interchangeably with the term "comprising" and are stated as equivalent terms. For example, disclosed compositions, devices, articles of manufacture or methods that "comprise" a component or step are open and they include or read on those compositions or methods plus an additional component(s) or step(s). Similarly, disclosed compositions, devices, articles of manufacture or methods that "consist of" a component or step are closed and they would not include or read on those compositions or methods having appreciable amounts of an additional component(s) or an additional step(s). Furthermore, use of the term "including" as well as other forms, such as "include", "includes," and "included," is not limiting. The section headings used herein are for organizational purposes only and are not to be construed as limiting the subject matter described. Unless otherwise indicated, conventional methods of mass spectroscopy, NMR, HPLC, protein chemistry, biochemistry, recombinant DNA techniques and pharmacology are employed.

"Bond" or "single bond" as used herein means a chemical bond between two atoms, or two moieties when the atoms joined by the bond are considered to be part of larger substructure. As explicitly stated or implied by context, when a group described herein is a bond, the referenced group is absent thereby allowing a bond to be formed between the remaining identified groups.

"Membered ring" as used herein means any cyclic structure. The term "membered" is meant to denote the number of skeletal atoms that constitute the ring. Thus, by way of example and not limitation, those membered rings include cyclohexyl, pyridinyl, pyranyl and thiopyranyl, which are 6-membered rings and cyclopentyl, pyrrolyl, furanyl, and thienyl, which are 5-membered rings.

"Moiety" as used herein means a specific segment, fragment or functional group of a molecule or compound. Chemical moieties are sometimes indicated as chemical entities that are embedded in or appended (i.e., a substituent or variable group) to a molecule or compound.

"Alkyl" as used herein is a collection of carbon atoms that are covalently linked together in normal, secondary, tertiary or cyclic arrangements, i.e., in a linear, branched, cyclic arrangement or some combination thereof. An alkyl substituent to a structure is that chain of carbon atoms that is covalently attached to the structure through a $sp^3$ carbon of the substituent. The alkyl substituents, as used herein, contains one or more saturated moieties or groups and may additionally contain unsaturated alkyl moieties or groups, i.e., the substituent may comprise one, two, three or more independently selected double bonds or triple bonds of a combination thereof, typically one double or one triple bond if such unsaturated alkyl moieties or groups are present.

Unsaturated alkyl moieties or groups include moieties or groups as described below for alkenyl, alkynyl, cycloalkyl, and aryl moieties. Saturated alkyl moieties contain saturated carbon atoms ($sp^3$) and no aromatic, $sp^2$ or sp carbon atoms. The number of carbon atoms in an alkyl moiety or group can vary and typically is 1 to about 50, e.g., about 1-30 or about 1-20, unless otherwise specified, e.g., $C_{1-8}$ alkyl or C1-C8 alkyl means an alkyl moiety containing 1, 2, 3, 4, 5, 6, 7 or 8 carbon atoms and $C_{1-6}$ alkyl or C1-C6 means an alkyl moiety containing 1, 2, 3, 4, 5 or 6 carbon atoms.

When an alkyl substituent, moiety or group is specified, species may include methyl, ethyl, 1-propyl (n-propyl), 2-propyl (iso-propyl, —CH(CH$_3$)$_2$), 1-butyl (n-butyl), 2-methyl-1-propyl (iso-butyl, —CH$_2$CH(CH$_3$)$_2$), 2-butyl (sec-butyl, —CH(CH$_3$)CH$_2$CH$_3$), 2-methyl-2-propyl (t-butyl, —C(CH$_3$)$_3$), amyl, isoamyl, sec-amyl and other linear, cyclic and branch chain alkyl moieties. Unless otherwise specified, alkyl groups can contain species and groups described below for cycloalkyl, alkenyl, alkynyl groups, aryl groups, arylalkyl groups, alkylaryl groups and the like.

Cycloalkyl as used here is a monocyclic, bicyclic or tricyclic ring system composed of only carbon atoms. The term "cycloalkyl" encompasses a monocyclic or polycyclic aliphatic, non-aromatic radical, wherein each of the atoms forming the ring (i.e. skeletal atoms) is a carbon atom. The number of carbon atoms in an cycloalkyl substituent, moiety or group can vary and typically is 3 to about 50, e.g., about 1-30 or about 1-20, unless otherwise specified, e.g., $C_{3-8}$ alkyl or $C_3$-$C_8$ alkyl means an cycloalkyl substituent, moiety or group containing 3, 4, 5, 6, 7 or 8 carbon atoms and $C_{3-6}$ alkyl or $C_3$-$C_6$ means an cycloalkyl substituent, moiety or group containing 3, 4, 5 or 6 carbon atoms. Cycloalkyl substituents, moieties or groups will typically have 3, 4, 5, 6, 7, 8, 9, 10, 11, 12, 13, 14, 15, 16, 17, 18, 19 or 20 carbon atoms and may contain exo or endo-cyclic double bonds or endo-cyclic triple bonds or a combination of both wherein the endo-cyclic double or triple bonds, or the combination of both, do not form a cyclic conjugated system of 4n+2 electrons; wherein the bicyclic ring system may share one (i.e., spiro ring system) or two carbon atoms and the tricyclic ring system may share a total of 2, 3 or 4 carbon atoms, typically 2 or 3.

Unless otherwise specified, cycloalkyl substituents, moieties or groups can contain moieties and groups described for alkenyl, alkynyl, aryl, arylalkyl, alkylaryl and the like and can contain one or more other cycloalkyl moieties. Thus, cycloalkyls may be saturated, or partially unsaturated. Cycloalkyls may be fused with an aromatic ring, and the points of attachment to the aromatic ring are at a carbon or carbons of the cycloalkyl substituent, moiety or group that is not an aromatic ring carbon atom. Cycloalkyl groups include groups having from 3 to 10 ring atoms. Cycloalkyl substituents, moieties or groups include cyclopropyl, cyclopentyl, cyclohexyl, adamantly or other cyclic all carbon containing moieties. Cycloalkyls further include cyclobutyl, cyclopentenyl, cyclohexenyl, cycloheptyl and cyclooctyl. Cycloalkyl groups may be substituted or unsubstituted. Depending on the substituent structure, a cycloalkyl substituent can be a monoradical or a diradical (i.e., an cycloalkylene, such as, but not limited to, cyclopropan-1,1-diyl, cyclobutan-1,1-diyl, cyclopentan-1,1-diyl, cyclohexan-1,1-diyl, cyclohexan-1,4-diyl, cycloheptan-1,1-diyl, and the like). When cycloalkyl is used as a Markush group (i.e., a substituent) the cycloalkyl is attached to a Markush formula with which it is associated through a carbon involved in a cyclic carbon ring system carbon of the cycloalkyl group that is not an aromatic carbon.

"Alkylamine" as used herein means an —N(alkyl)$_x$H$_y$ group, moiety or substituent where x and y are independently selected from the group x=1, y=1 and x=2, y=0. Alkylamine includes those —N(alkyl)$_x$H$_y$ groups wherein x=2 and y=0 and the alkyl groups taken together with the nitrogen atom to which they are attached form a cyclic ring system.

"Heteroalkylene" as used herein means an alkylene (i.e. alkanediyl) group, moiety or substituent in which one or more skeletal atoms of the alkyl are selected from an atom other than carbon, e.g., oxygen, nitrogen, sulfur, phosphorus or combinations thereof. Heteroalkylene includes $C_1$-$C_6$ heteroalkylene or $C_1$-$C_4$ heteroalkylene. Exemplary heteroalkylenes include, but are not limited to, —OCH$_2$—, —OCH(CH$_3$)—, —OC(CH$_3$)$_2$—, —OCH$_2$CH$_2$—, —CH$_2$O—, —CH(CH$_3$)O—, C(CH$_3$)$_2$O—, —CH$_2$CH$_2$O—, —CH$_2$OCH$_2$—, —CH$_2$OCH$_2$CH$_2$—, —CH$_2$CH$_2$OCH$_2$—, —SCH$_2$—, —SCH(CH$_3$)—, —SC(CH$_3$)$_2$—, —SCH$_2$CH$_2$—, —CH$_2$S—, —CH(CH$_3$)S—, —C(CH$_3$)$_2$S—, —CH$_2$CH$_2$S—, —CH$_2$SCH$_2$—, —CH$_2$SCH$_2$CH$_2$—, —CH$_2$CH$_2$SCH$_2$—, —S(=O)$_2$CH$_2$—, —S(=O)$_2$CH(CH$_3$)—, —S(=O)$_2$C(CH$_3$)$_2$—, —S(=O)$_2$CH$_2$CH$_2$—, —CH$_2$S(=O)$_2$—, —CH(CH$_3$)S(=O)$_2$—, —C(CH$_3$)$_2$S(=O)$_2$—, —CH$_2$CH$_2$S(=O)$_2$—, —CH$_2$S(=O)$_2$CH$_2$—, —CH$_2$S(=O)$_2$CH$_2$CH$_2$—, CH$_2$CH$_2$S(=O)$_2$CH$_2$—, —NHCH$_2$—, —NHCH(CH$_3$)—, —NHC(CH$_3$)$_2$—, —NHCH$_2$CH$_2$—, —CH$_2$NH—, —CH(CH$_3$)NH—, —C(CH$_3$)$_2$NH—, —CH$_2$CH$_2$NH—, —CH$_2$NHCH$_2$—, —CH$_2$NHCH$_2$CH$_2$—, —CH$_2$CH$_2$NHCH$_2$—, and the like.

"Carboxylic acid bioisostere" as used herein means a functional group, moiety or substituent that exhibits similar physical, biological and/or chemical properties as a carboxylic acid moiety. By way of example and not limitation, carboxylic acid bioisosteres include,

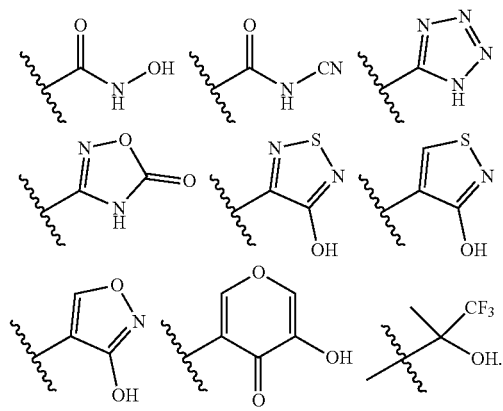

"Alkenyl" as used herein means a substituent, moiety or group that comprises one or more double bond moities (e.g., —CH=CH—) or 1, 2, 3, 4, 5 or 6 or more, typically 1, 2 or 3 such moieties and can include an aryl moiety or group such as benzene, and additionally comprises linked normal, secondary, tertiary or cyclic carbon atoms, i.e., linear, branched, cyclic or any combination thereof unless the alkenyl moiety is a vinyl moiety (e.g., —CH=CH$_2$). An alkenyl moiety, group or substituent with multiple double bonds may have the double bonds arranged contiguously (i.e. a 1,3 butadienyl moiety) or non-contiguously with one or more intervening saturated carbon atoms or a combination thereof, provided that a cyclic, contiguous arrangement of double bonds do not form a cyclically conjugated system of 4n+2 electrons (i.e., aromatic). The number of carbon atoms in an alkenyl group or moiety can vary and typically is 2 to about 50, e.g., about 2-30 or about 2-20, unless otherwise specified, e.g., $C_{2-8}$ alkenyl or $C_{2-8}$ alkenyl means an alkenyl moiety containing 2, 3, 4, 5, 6, 7 or 8 carbon atoms and $C_{2-6}$ alkenyl or $C_{2-6}$ alkenyl means an alkenyl moiety containing 2, 3, 4, 5 or 6 carbon atoms. Alkenyl moieties or groups will typically have 2, 3, 4, 5, 6, 7, 8, 9, 10, 11, 12, 13, 14, 15, 16, 17, 18, 19 or 20 carbon atoms.

When an alkenyl moiety, group or substituent is specified, species include, by way of example and not limitation, any of the alkyl or cycloalkyl, groups moieties or substituents described herein that has one or more double bonds, methylene (=CH$_2$), methylmethylene (=CH—CH$_3$), ethylmethylene (=CH—CH$_2$—CH$_3$), =CH—CH$_2$—CH$_2$—CH$_3$, vinyl (—CH=CH$_2$), allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl and other linear, cyclic and branched chained all carbon containing moieties containing at least one double bond. When alkenyl is used as a Markush group (i.e., a substituent) the alkenyl is attached to a Markush formula with which it is associated through an unsaturated carbon of a double bond of the alkenyl moiety or group unless specified otherwise.

"Alkynyl" as used herein means a substituent, moiety or group that comprises one or more triple bond moieties (i.e., —C≡C—), e.g., 1, 2, 3, 4, 5, 6 or more, typically 1 or 2 triple bonds, optionally comprising 1, 2, 3, 4, 5, 6 or more double bonds, with the remaining bonds (if present) being single bonds and comprising linked normal, secondary, tertiary or cyclic carbon atoms, i.e., linear, branched, cyclic or any combination thereof, unless the alkynyl moiety is ethynyl. The number of carbon atoms in an alkenyl moiety or group can vary and typically is 2 to about 50, e.g., about 2-30 or about 2-20, unless otherwise specified, e.g., $C_{2-8}$ alkynyl or C2-8 alkynyl means an alkynyl moiety containing 2, 3, 4, 5, 6, 7 or 8 carbon atoms. Alkynyl groups will typically have 2, 3, 4, 5, 6, 7, 8, 9, 10, 11, 12, 13, 14, 15, 16, 17, 18, 19 or 20 carbon atoms.

When an alkynyl moiety or group is specified, species include, by way of example and not limitation, any of the alkyl moieties, groups or substituents described herein that has one or more double bonds, ethynyl, propynyl, butynyl, iso-butynyl, 3-methyl-2-butynyl, 1-pentynyl, cyclopentynyl, 1-methyl-cyclopentynyl, 1-hexynyl, 3-hexynyl, cyclohexynyl and other linear, cyclic and branched chained all carbon containing moieties containing at least one triple bond. When an alkynyl is used as a Markush group (i.e., a substituent) the alkynyl is attached to a Markush formula with which it is associated through one of the unsaturated carbons of the alkynyl functional group.

"Aromatic" as used herein refers to a planar ring having a delocalized pi-electron system containing 4n+2 pi electrons, where n is a positive integer. Aromatic rings can be formed from five, six, seven, eight, nine, ten, or more than ten atoms. Aromatics are optionally substituted. The term "aromatic" includes both carboxylic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

"Aryl" as used here means an aromatic ring system or a fused ring system with no ring heteroatoms comprising 1, 2, 3 or 4 to 6 rings, typically 1 to 3 rings, wherein the rings are composed of only carbon atoms; and refers to a cyclically conjugated system of 4n+2 electrons (Huckel rule), typically 6, 10 or 14 electrons some of which may additionally participate in exocyclic conjugation (cross-conjugated (e.g., quinone). Aryl substituents, moieties or groups are typically formed by five, six, seven, eight, nine, or more than nine, carbon atoms. Aryl substituents, moieties or groups are optionally substituted. Exemplary aryls include $C_6$-$C_{10}$ aryls such as phenyl and naphthalenyl and phenanthryl. Depending on the structure, an aryl group can be a monoradical or a diradical (i.e., an arylene group). Exemplary arylenes include, but are not limited to, phenyl-1,2-ene, phenyl-1,3-ene, and phenyl-1,4-ene. When aryl is used as a Markush group (i.e., a substituent) the aryl is attached to a Markush formula with which it is associated through an aromatic carbon of the aryl group.

"Arylalkyl" as used herein means a substituent, moiety or group where an aryl moiety is bonded to an alkyl moiety, i.e., -alkyl-aryl, where alkyl and aryl groups are as described above, e.g., —CH$_2$—C$_6$H$_5$ or —CH$_2$CH(CH$_3$)—C$_6$H$_5$. When arylalkyl is used as a Markush group (i.e., a substituent) the alkyl moiety of the arylalkyl is attached to a Markush formula with which it is associated through a sp$^3$ carbon of the alkyl moiety.

"Alkylaryl" as used herein means a substituent, moiety or group where an alkyl moiety is bonded to an aryl moiety, i.e., -aryl-alkyl, where aryl and alkyl groups are as described above, e.g., —C$_6$H$_4$—CH$_3$ or —C$_6$H$_4$—CH$_2$CH(CH$_3$). When alkylaryl is used as a Markush group (i.e., a substituent) the aryl moiety of the alkylaryl is attached to a Markush formula with which it is associated through a sp$^2$ carbon of the aryl moiety.

"Substituted alkyl", "substituted cycloalkyl", "substituted alkenyl", "substituted alkynyl", substituted alkylaryl", "substituted arylalkyl", "substituted heterocycle", "substituted aryl" and the like as used herein mean an alkyl, alkenyl, alkynyl, alkylaryl, arylalkyl heterocycle, aryl or other group or moiety as defined or disclosed herein that has a substituent(s) that replaces a hydrogen atom(s) or a substituent(s) that interrupts a carbon atom chain. Alkenyl and alkynyl groups that comprise a substituent(s) are optionally substituted at a carbon that is one or more methylene moieties removed from the double bond.

"Optionally substituted alkyl", "optionally substituted alkenyl", "optionally substituted alkynyl", "optionally substituted alkylaryl", "optionally substituted arylalkyl", "optionally substituted heterocycle", "optionally substituted aryl", "optionally substituted heteroaryl", "optionally substituted alkylheteroaryl", "optionally substituted heteroarylalkyl" and the like as used herein mean an alkyl, alkenyl, alkynyl, alkylaryl, arylalkyl heterocycle, aryl, heteroaryl, alkylheteroaryl, heteroarylalkyl, or other substituent, moiety or group as defined or disclosed herein that has a substituent(s) that optionally replaces a hydrogen atom(s) or a substituent(s) that interrupts a carbon atom chain. Such substituents are as described herein. For a phenyl moiety, the arrangement of any two substituents present on the aromatic ring can be ortho (o), meta (m), or para (p). An optionally substituted fluoroalkyl is an alkyl or cycloalkyl moiety, typically a linear alkyl, wherein one or more hydrogen atoms is replaced by fluorine and at least one other atom other than carbon and fluorine.

An optionally substituted or substituted substituent, moiety or group includes those having one or more additional group(s) that replace its hydrogen atom(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, nitro, haloalkyl, fluoroalkyl, fluoroalkoxy, and amino, including mono- and di-substituted amino groups, and the protected derivatives thereof. By way of example and not limitation an optional substituent(s) may be halide, —CN, —NO$_2$, or LsRs, wherein each Ls is independently selected from a bond, —O—, —C(=O)—, —C(=O)O—, —S—, —S(=O)—, —S(=O)$_2$—, —NH—, —NHC(=O)—, —C(=O)NH—, S(=O)$_2$NH—, —NHS(=O)$_2$, —OC(=O)NH—, —NHC(=O)O—, or —(C$_1$-C$_6$ alkylene)-; and each Rs is selected from —H, alkyl, fluoroalkyl, heteroalkyl, cycloalkyl, aryl, heteroaryl, or heterocycloalkyl. The protecting groups that may form the protective derivatives of the above substituents may be found in sources such as Greene and Wuts, above. Optional substituents include those selected from the group consisting of halogen, —CN, —NH$_2$, —OH, —N(CH$_3$)$_2$, alkyl, fluoroalkyl, heteroalkyl, cycloalkyl, heterocycloalkyl, aryl, heteroaryl, alkoxy, aryloxy, alkylthio, arylthio, alkylsulfoxide, arylsulfoxide, alkylsulfone, and arylsulfone, those selected from the group consisting of halogen, —CN, —NH$_2$, —OH, NH(CH$_3$), —N(CH$_3$)$_2$, —CO$_2$H, —CO$_2$ alkyl, —C(=O)NH$_2$, —C(=O)NHalkyl, —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, —S-alkyl and —S(=O)$_2$ alkyl or those selected from the group consisting of halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. Typically, an optionally substituted, substituent, moiety or group is substituted with one or two of the preceding groups, or more typically with one of the preceding groups. An optional substituent on an aliphatic carbon atom (acyclic or cyclic, saturated or unsaturated carbon atoms, excluding aromatic carbon atoms) further includes oxo (=O).

"Heterocycle" or "heterocyclic" as used herein means a cycloalkyl or aromatic ring system wherein one or more, typically 1, 2 or 3, but not all of the carbon atoms comprising the ring system are replaced by a heteroatom which is an atom other than carbon, including, N, O, S, Se, B, Si, P, typically N, O or S wherein two or more heteroatoms may be adjacent to each other or separated by one or more carbon atoms, typically 1-17 carbon atoms, 1-7 atoms or 1-3 atoms. Heterocycles includes heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms.

Non-aromatic heterocyclic, substituents, moieties or groups (also known as heterocycloalkyls) have at least 3 atoms in their ring system, and aromatic heterocyclic groups have at least 5 atoms in their ring system and include benzo-fused ring systems. Heterocyclics with 3, 4, 5, 6 and 10 atoms include aziridinyl azetidinyl, thiazolyl, pyridyl and quinolinyl, respectively. Nonaromatic heterocyclic substituents, moieties or groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3azabicyclo[4.1.0]heptanyl, 3H-indolyl and quinolizinyl. Aromatic heterocyclic includes, by way of example and not limitation, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzo-thiophenyl, benzothiazolyl, benzoxazolyl, quinazolinyl, quinoxalinyl, naphthyridinyl, and furopyridinyl. Non-aromatic heterocycles may be substituted with one or two oxo (=O) moieties, and includes pyrrolidin-2-one.

When heterocycle is used as a Markush group (i.e., a substituent) the heterocycle is attached to a Markush formula with which it is associated through a carbon or a heteroatom of the heterocycle, where such an attachment does not result in an unstable or disallowed formal oxidation state of that carbon or heteroatom. A heterocycle that is C-linked is bonded to a molecule through a carbon atom include moieties such as —(CH$_2$)$_n$-heterocycle where n is 1, 2 or 3 or —C<heterocycle where C<represents a carbon atom in a heterocycle ring. A heterocycle that is N-linked is a nitrogen containing heterocycle that is bonded a heterocycle ring nitrogen sometimes described as —N<heterocycle where N<represents a nitrogen atom in a heterocycle ring. Thus, nitrogen-containing heterocycles may be C-linked or N-linked and include pyrrole substituents, which may be pyrrol-1-yl (N-linked) or pyrrol-3-yl (C-linked), imidazole substituents, which may be imidazol-1-yl or imidazol-3-yl (both N-linked) or imidazol-2-yl, imidazol-4-yl or imidazol-5-yl (all C-linked).

"Heteroaryl" as used herein means an aryl ring system wherein one or more, typically 1, 2 or 3, but not all of the carbon atoms comprising the aryl ring system are replaced by a heteroatom which is an atom other than carbon, including, N, O, S, Se, B, Si, P, typically, oxygen (—O—), nitrogen (—NX—) or sulfur (—S—) where X is —H, a protecting group or C$_{1-6}$ optionally substituted alkyl, wherein the heteroatom participates in the conjugated system either through pi-bonding with an adjacent atom in the ring system or through a lone pair of electrons on the heteroatom and may be optionally substituted on one or more carbons or heteroatoms, or a combination of both, in a manner which retains the cyclically conjugated system.

Heterocycles and heteroaryls, include, by way of example and not limitation, heterocycles and heteroaryls described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. 1960, 82:5545-5473 particularly 5566-5573). Examples of heteroaryls include by way of example and not limitation pyridyl, thiazolyl, pyrimidinyl, furanyl, thienyl, pyrrolyl, pyrazolyl, purinyl, imidazolyl, benzofuranyl, indolyl, isoindolyl, quinolinyl, isoquinolinyl, benzimidazolyl, pyridazinyl, pyrazinyl, benzothiopyran, benzotriazine, isoxazolyl, pyrazolopyrimidinyl, quinoxalinyl, thiadiazolyl, triazolyl and the like. Heterocycles that are not heteroaryls include, by way of example and not limitation, tetrahydrothiophenyl, tetrahydrofuranyl, indolenyl, piperidinyl, pyrrolidinyl, 2-pyrrolidonyl, tetrahydroquinolinyl, tetrahydroisoquinolinyl, decahydroquinolinyl, octahydroisoquinolinyl, 2H-pyrrolyl, 3H-indolyl, 4H-quinolizinyl, imidazolidinyl, imidazolinyl, pyrazolidinyl, piperazinyl, quinuclidinyl, morpholinyl, oxazolidinyl and the like.

Other heteroaryls include, by way of example and not limitation, the following moieties:

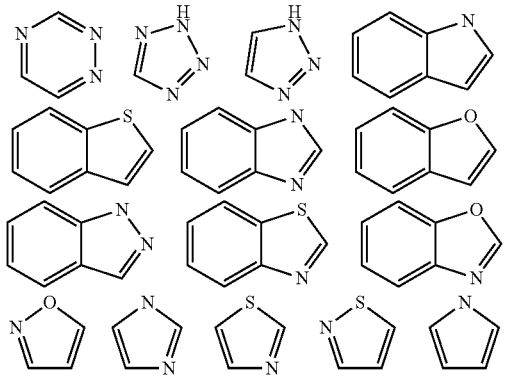

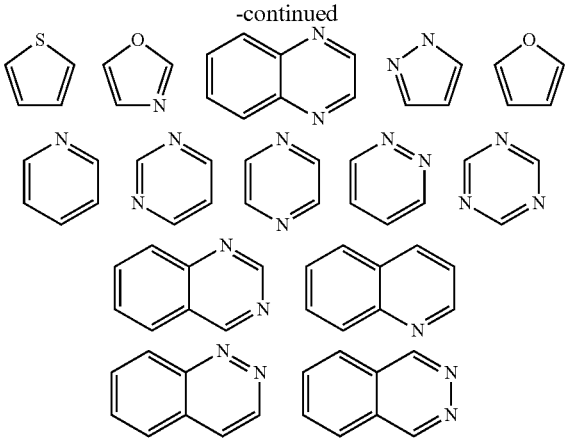

Monocyclic heteroaryls include, by way of example and not limitation, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Heteroaryls include those substituents, moieties or groups containing 0-3 N atoms, 1-3 N atoms or 0-3 N atoms, 0-1 O atoms and 0-1 S atoms. A heteroaryl may be monocyclic or bicyclic. The ring system of a heteroaryls ring typically contains 1-9 carbons (i.e., C$_1$-C$_9$ heteroaryl). Monocyclic heteroaryls include C$_1$-C$_5$ heteroaryls. Monocyclic heteroaryls include those having 5-membered or 6-membered ring systems. Bicyclic heteroaryls include C$_6$-C$_9$ heteroaryls. Depending on the structure, a heteroaryl group can be a monoradical or a diradical (i.e., a heteroarylene group).

"Heterocycloalkyl" or "heteroalicyclic" as used herein means a cycloalkyl group, moiety or substituent wherein at least on carbon of the cycloalkyl chain is replaces with a heteroatom selected from the group consisting of nitrogen, oxygen and sulfur. The heterocycloalkyl may be fused with an aryl or heteroaryl. Heterocycloalkyls, also referred to as non-aromatic heterocycles, include by way of example and not limitation:

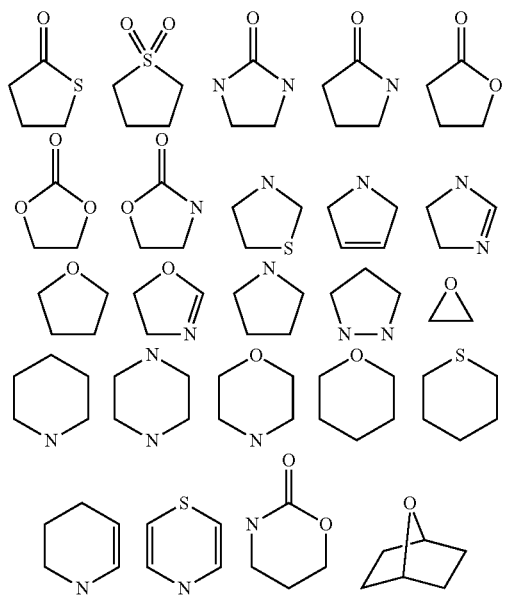

Heterocycloalkyl includes, by way of example and not limitation, oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. Heteroalicyclics further includes all ring forms of carbohydrates, including but not limited to monosaccharides, disaccharides and oligosaccharides. Typically, a heterocycloalkyl is a $C_2$-$C_{10}$ heterocycloalkyl and includes $C_4$-$C_{10}$ heterocycloalkyl. A heterocycloalkyl may contain 0-2 N atoms, 0-2 O atoms or 0-1 S atoms.

"Heteroarylalkyl" as used herein means a substituent, moiety or group where a heteroaryl moiety is bonded to an alkyl moiety, i.e., -alkyl-heteroaryl, where alkyl and heteroaryl groups are as described above. When heteroarylalkyl is used as a Markush group (i.e., a substituent) the alkyl moiety of the heteroarylalkyl is attached to a Markush formula with which it is associated through a $sp^3$ carbon of the alkyl moiety.

"Alkylheteroaryl" as used herein means a substituent, moiety or group where a heteroaryl moiety is bonded to an alkyl moiety, i.e., -heteroaryl-alkyl, where heteroaryl and alkyl groups are as described above. When heteroarylalkyl is used as a Markush group (i.e., a substituent) the heteroaryl moiety of the heteroarylalkyl is attached to a Markush formula with which it is associated through a $sp^2$ carbon or heteroatom of the alkyl moiety.

"Halogen" or "halo" as used herein means fluorine, chlorine, bromine or iodine.

"Haloalkyl" as used herein means an alkyl substituent moiety or group in which one or more of its hydrogen atoms are replaced by one or more independently selected halide atoms. Haloalkyl includes $C_1$-$C_4$ haloalkyl. Example but non-limiting $C_1$-$C_4$ haloalkyls are —$CH_2Cl$, $CH_2Br$, —$CH_2I$, —$CHBrCl$, —$CHCl$—$CH_2Cl$ and —$CHCl$—$CH_2I$.

"Haloalkylene" as used herein means an alkylene substituent, moiety or group in which one or more hydrogen atoms are replaced by one or more halide atoms. Haloalkylene includes $C_1$-$C_6$ haloalkylenes or $C_1$-$C_4$ haloalkylenes.

"Fluoroalkyl" as used herein means an alkyl in which one or more hydrogen atoms are replaced by a fluorine atom. Fluoroalkyl includes $C_1$-$C_6$ and $C_1$-$C_4$ fluoroalkyls. Example but non-limiting fluoroalkyls include —$CH_3F$, —$CH_2F_2$ and —$CF_3$ and perfluroalkyls.

"Fluoroalkylene" as used herein means an alkylene in which one or more hydrogen atoms are replaced by a fluorine atom. Fluoroalkylene includes $C_1$-$C_6$ fluoroalkylenes or $C_1$-$C_4$ fluoroalkylenes.

The term "heteroalkyl" refers to an alkyl group in which one or more skeletal atoms of the alkyl are selected from an atom other than carbon, e.g., oxygen, nitrogen, sulfur, phosphorus or combinations thereof. In one aspect, a heteroalkyl is a C1-C6 heteroalkyl.

"Protecting group" as used here means a moiety that prevents or reduces the ability of the atom or functional group to which it is linked from participating in unwanted reactions. Non-limiting examples are for —$OR^{PR}$, wherein $R^{PR}$ is a protecting group for the oxygen atom found in a hydroxyl, while for —$C(O)$—$OR^{PR}$, $R^{PR}$ may be a carboxylic acid protecting group; for —$SR^{PR}$, $R^{PR}$ may be a protecting group for sulfur in thiols and for —$NHR^{PR}$ or —$N(R^{PR})_2$—, at least one of $R^{PR}$ is a nitrogen atom protecting group for primary or secondary amines. Hydroxyl, amine, ketones and other reactive groups may require protection against reactions taking place elsewhere in the molecule. The protecting groups for oxygen, sulfur or nitrogen atoms are usually used to prevent unwanted reactions with electrophilic compounds, such as acylating agents. Typical protecting groups for atoms or functional groups are given in Greene (1999), "Protective groups in organic synthesis, $3^{rd}$ ed.", Wiley Interscience.

"Ester" as used herein means a substituent, moiety or group that contains a —C(O)—O— structure (i.e., ester functional group) wherein the carbon atom of the structure is not directly connected to another heteroatom and is directly connected to —H or another carbon atom. Typically, esters comprise or consist of an organic moiety containing 1-50 carbon atoms, 1-20 carbon atoms or 1-8 carbon atoms and 0 to 10 independently selected heteroatoms (e.g., O, S, N, P, Si), typically 0-2 where the organic moiety is bonded through the —C(O)—O— structure and include ester moieties such as organic moiety-C(O)—O—. The organic moiety usually comprises one or more of any of the organic groups described herein, e.g., $C_{1-20}$ alkyl moieties, $C_{2-20}$ alkenyl moieties, $C_{2-20}$ alkynyl moieties, aryl moieties, $C_{3-8}$ heterocycles or substituted derivatives of any of these, e.g., comprising 1, 2, 3, 4 or more substituents, where each substituent is independently chosen. Exemplary, non-limiting substitutions for hydrogen or carbon atoms in these organic groups are as described above for substituted alkyl and other substituted moieties and are independently chosen. The substitutions listed above are typically substituents that one can use to replace one or more carbon atoms, e.g., —O— or —C(O)—, or one or more hydrogen atom, e.g., halogen, —$NH_2$ or —OH. Exemplary esters include by way of example and not limitation, one or more independently selected acetate, propionate, isopropionate, isobutyrate, butyrate, valerate, isovalerate, caproate, isocaproate, hexanoate, heptanoate, octanoate, phenylacetate esters or benzoate esters. When ester is used as a Markush group (i.e., a substituent) the single bonded oxygen of the ester functional group is attached to a Markush formula with which it is associated.

"Acetal", "thioacetal", "ketal", "thioketal" and the like as used herein means a moiety, group or substituent comprising or consisting of a carbon to which is bonded two of the same or different heteroatoms wherein the heteroatoms are independently selected S and O. For acetal the carbon has two bonded oxygen atoms, a hydrogen atom and an organic moiety. For ketal, the carbon has two bonded oxygen atoms and two independently selected organic moieties where the organic moiety is as described herein alkyl or optionally substituted alkyl group. For thioacetals and thioketals one or both of the oxygen atoms in acetal or ketal, respectively, is replaced by sulfur. The oxygen or sulfur atoms in ketals and thioketals are sometimes linked by an optionally substituted alkyl moiety. Typically, the alkyl moiety is an optionally substituted $C_{1-8}$ alkyl or branched alkyl structure such as —$C(CH_3)_2$—, —$CH(CH_3)$—, —$CH_2$—, —$CH_2$—$CH_2$—, —$C[(C_2$-$C_4$ alkyl$)_2]_{1, 2, 3}$- or —$[CH(C_2$-$C_4$ alkyl$)]_{1, 2, 3}$-. Some of these moieties can serve as protecting groups for an aldehyde or ketone include, by way of example and not limitation, acetals for aldehydes and ketals for ketones and contain —O—$CH_2$—$CH_2$—$CH_2$—O— or —O—$CH_2$—$CH_2$—O— moieties that form a spiro ring with the carbonyl carbon, and can be removed by chemical synthesis methods or by metabolism in cells or biological fluids.

"Ether" as used herein means an organic moiety, group or substituent that comprises or consists of 1, 2, 3, 4 or more —O— moieties, usually 1 or 2, wherein no two —O— moieties are immediately adjacent (i.e., directly attached) to each other. Typically, ethers comprise an organic moiety containing 1-50 carbon atoms, 1-20 carbon atoms or 1-8 carbon atoms and 0 to 10 independently selected heteroatoms (e.g., O, S, N, P, Si), typically 0-2. An ether moiety, group or substituent includes organic moiety-O— wherein the organic moiety is as described herein for alkyl or optionally substituted alkyl group. When ether is used as a Markush group (i.e., a substituent) the oxygen of the ether functional group is attached to a Markush formula with which it is associated. When ether is a used as substituent in a Markush group it is sometimes designated as an "alkoxy" group. Alkoxy includes C1-C4 ether substituents such as, by way of example and not limitation, methoxy, ethoxy, propoxy, iso-propoxy and butoxy. Ether further includes those substituents, moieties or groups that contain one (excluding ketal) or more —OCH$_2$CH$_2$O—, moieties in sequence (i.e., polyethylene or PEG moieties).

"Carbonate" as used here means a substituent, moiety or group that contains a —O—C(=O)—O— structure (i.e., carbonate functional group). Typically, carbonate groups as used here comprise or consist of an organic moiety containing 1-50 carbon atoms, 1-20 carbon atoms or 1-8 carbon atoms and 0 to 10 independently selected heteroatoms (e.g., O, S, N, P, Si), typically 0-2, bonded through the —O—C(=O)—O— structure, e.g., organic moiety-O—C(=O)—O—. When carbonate is used as a Markush group (i.e., a substituent) one of the singly bonded oxygen atoms of the carbonate functional group is attached to a Markush formula with which it is associated.

"Carbamate" or "urethane" as used here means a substituent, moiety or group that contains a —O—C(=O)N(R$^{PR}$)—, —O—C(=O)N(R$^{PR}$)$_2$, —O—C(=O)NH(optionally substituted alkyl) or —O—C(=O)N(optionally substituted alkyl)$_2$-structure (i.e., carbamate functional group) where R$^{PR}$ and optionally substituted alkyl are independently selected and R$^{PR}$ are independently —H, a protecting group or an organic moiety as described for ester, alkyl or optionally substituted alkyl. Typically, carbamate groups as used here comprise or consist of an organic moiety containing about 1-50 carbon atoms, 1-20 carbon atoms or 1-8 carbon atoms and 0 to 10 independently selected heteroatoms (e.g., O, S, N, P, Si), typically 0-2, bonded through the —O—C(=O)—NR$^{PR}$— structure, e.g., organic moiety-O—C(=O)—NR$^{PR}$— or —O—C(=O)—NR$^{PR}$-organic moiety. When carbamate is used as a Markush group (i.e., a substituent) the singly bonded oxygen (O-linked) or nitrogen (N-linked) of the carbamate functional group is attached to a Markush formula with which it is associated. The linkage of the carbamate substituent is either explicitly stated (N- or O-linked) or implicit in the context to which this substituent is referred.

For any substituent group or moiety described by a given range of carbon atoms, the designated range means that any individual number of carbon atoms is described. Thus, reference to, e.g., "C1-C4 optionally substituted alkyl", "C2-6 alkenyl optionally substituted alkenyl", "C3-C8 optionally substituted heterocycle" specifically means that a 1, 2, 3 or 4 carbon optionally substituted alkyl moiety as defined herein is present, or a 2, 3, 4, 5 or 6 carbon alkenyl, or a 3, 4, 5, 6, 7 or 8 carbon moiety comprising a heterocycle or optionally substituted alkenyl moiety as defined herein is present. All such designations are expressly intended to disclose all of the individual carbon atom groups and thus "C1-C4 optionally substituted alkyl" includes, e.g., 3 carbon alkyl, 4 carbon substituted alkyl and 4 carbon alkyl, including all positional isomers and the like are disclosed and can be expressly referred to or named. For esters, carbonates and carbamates defined by a given range of carbon atoms, the designated range includes the carbonyl carbon of the respective functional group. Thus a C1 ester refers to a formate ester and a C2 ester refers to an acetate ester. The organic substitutents, moieties and groups described herein, and for other any other moieties described herein, usually will exclude unstable moieties except where such unstable moieties are transient species that one can use to make a compound with sufficient chemical stability for the one or more of the uses described herein. Substituents, moieties or groups by operation of the definitions herein that results in those having a pentavalent carbon are specifically excluded.

"LPA-dependent", "LPA-mediated" or like terms as used herein means a disease or condition whose etiology, progression or persistence is effected by in whole or in part by signaling through one or more lysophosphatidic acid receptor subtypes, including by way of example and not limitation lysophosphatidic acid receptor subtypes 1-6 (LPARs). LPA-dependent or LPA-mediated diseases and conditions include but not limited to fibrosis of organs (e.g., liver, kidney, lung, heart and the like), liver diseases (e.g., acute hepatitis, chronic hepatitis, liver fibrosis, liver cirrhosis, portal hypertension, regenerative failure, nonalcoholic steatohepatitis (NASH), liver hypofunction, hepatic blood flow disorder, and the like), cell proliferative disease (e.g., cancers, including but not limited to solid tumor, solid tumor metastasis, vascular fibroma, myeloma, multiple myeloma, Kaposi's sarcoma, leukemia, chronic lymphocytic leukemia (CLL), invasive metastasis of cancer cell, and the like), inflammatory disease (e.g., psoriasis, nephropathy, pneumonia and the like), gastrointestinal tract disease (e.g., irritable bowel syndrome (IBS), inflammatory bowel disease (IBD), abnormal pancreatic secretion, and the like), renal disease, urinary tract-associated disease (e.g., benign prostatic hyperplasia or symptoms associated with neuropathic bladder disease), spinal cord tumor, hernia of intervertebral disk, spinal canal stenosis, symptoms derived from diabetes, lower urinary tract disease (e.g., obstruction of lower urinary tract, and the like), inflammatory disease of lower urinary tract (e.g., dysuria, frequent urination, and the like), pancreas disease, abnormal angiogenesis-associated disease (e.g., arterial obstruction and the like), scleroderma, brain-associated disease (e.g., cerebral infarction, cerebral hemorrhage, and the like), nervous system diseases (e.g., neuropathic pain, peripheral neuropathy, pruritus and the like), ocular disease (e.g., age-related macular degeneration (AMD), diabetic retinopathy, proliferative vitreo-retinopathy (PVR), cicatricial pemphigoid, glaucoma filtration surgery scarring, and the like).

"LPA1R selective agents", LPA1R selective compounds" and like terms as used herein means agents or compounds that interact with the lysophosphatidic acid subtype 1 receptor in preference to the lysophosphatidic acid receptor 2-6. Typically, that preference is manifested by 10-fold stronger binding affinity of the agent to LPA1R in comparison to other known LPARs as measured by experimentally determined K$_D$ values.

"Pharmaceutically acceptable formulation" as used herein means a composition comprising an active pharmaceutical ingredient, such as a compound having the formula of I-VI in addition to one or more pharmaceutically acceptable excipients or refers to a composition prepared from an active pharmaceutical ingredient and one or more pharmaceutically acceptable excipients, wherein the composition is suitable for administration to a subject, such as a human or an animal, in need thereof. For a pharmaceutically acceptable formulation to be suitable for administration to a human the formulation must have biological activity for treating or preventing a disease or condition disclosed herein or an expectation must exist that the formulation would have a desired activity towards an "intent to treat" disease or condition. Typically, the "intent to treat" disease or condition is a lysophosphatidic acid receptor-mediated condition or disease. More typically the disease or condition to be treated or prevented is a lysophosphatidic acid lysophosphatidic acid type 1 receptor-mediated disease or condition. A pharmaceutically acceptable formulation that is suitable for administration to an animal does not necessarily require a biological activity for treating or preventing a disease or condition, and may be administered to the animal in order to evaluate a potential pharmacological or biological activity of a Formula I-XII compound. Those formulations must therefore be suitable for treating or preventing a disease or condition disclosed herein in an animal in need thereof or is suitable for evaluating a pharmacological or biological activity of a Formula I-XII compound. Compositions that are suitable only for use in vitro assays or which contain a vehicle, component or excipient in an amount not permitted in a drug product are specifically excluded from the definition of a pharmaceutically acceptable formulation.

The pharmaceutically acceptable formulation may be comprised of, or be prepared from, one, two or more Formula I-XII compounds, typically one or two, and one or more pharmaceutically acceptable excipients. More typically, the formulations will consist essentially of or consist of a single Formula I-XII compound and one or more pharmaceutically acceptable excipients. Other formulations may be comprised of, consist essentially of, or consist of one, two or more Formula I-XII compounds and one two or more compounds in current use for treating lysophosphatidic acid lysophosphatidic acid type 1 receptor-mediated disease or condition disclosed herein and one or more pharmaceutically acceptable excipients. Typically those formulations will consist essentially of or consist of a single Formula I-XII compound, a single compound in current use for treating a lysophosphatidic acid lysophosphatidic acid type 1 receptor-mediated disease or condition and one or more pharmaceutically acceptable excipients.

"Solid formulation" as used herein refers to a pharmaceutically acceptable formulation comprising at least one Formula I-XII compound and one or more pharmaceutically acceptable excipients in solid form(s) wherein the formulation is in a unit dosage form suitable for administration of a solid. The dosage units include tablets, capsules, caplets, gelcaps, suspensions and other dosage units typically associated with parenteral or enteral (oral) administration of a solid.

"Liquid formulation" as used herein refers to a pharmaceutically acceptable formulation wherein at least one Formula I-XII compound has been admixed or contacted with one or more pharmaceutically acceptable excipients, wherein at least one of the excipients is in liquid form in proportions required for a liquid formulation, i.e., such that a majority of the mass amount of the Formula I-XII compound(s) is dissolved into the non-solid excipient. Dosage units containing a liquid formulation include syrups, gels, ointments and other dosage units typically associated with parenteral or enteral administration of a pharmaceutical formulation to a subject in need thereof in liquid form.

"Prevent, "preventing" and like terms as used herein takes on its normal and customary meaning in the medical arts and therefore does not require that each instance to which the term refers be avoided with certainty.

Numbered Embodiments

The following embodiments exemplify the invention and are not meant to limit the invention in any manner. In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, stereoselective synthesis and/or the separation of stereoisomers by chiral chromatographic columns. The methods and formulations described herein include the use of pharmaceutically acceptable salts of compounds having the structure of Formulas (I-VI), as well as active metabolites of these compounds having the same type of activity. In some situations, compounds may exist as tautomers. All tautomers are included within the scope of the compounds presented herein. In specific embodiments, the compounds described herein will exist as salts, including pharmaceutically acceptable salts. The salt forms include inorganic addition salts such as $F^-$ $Cl^-$, $Br^-$, $I^-$ and sulfate salts and organic addition salts such as mesylate, besylate, tosylate, citrate, succinate, fumarate and malonate. In other embodiments, the compounds described herein exist as quaternary ammonium salts.

1. A compound of Formula I having the structure

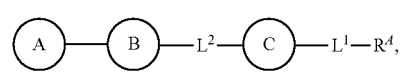

Formula I or a pharmaceutically acceptable salt or prodrug thereof,
wherein $R^A$ is $-CO_2H$, $-CO_2R^B$, $-CN$, tetrazolyl, $-C(=O)NH_2$, $-C(=O)NHR^B$, $-C(=O)NHSO_2R^B$ or $-C(=O)NHCH_2CH_2SO_3H$ or a carboxylic acid isostere;

$L^1$ is absent or substituted or unsubstituted $C_1$-$C_6$ alkylene, substituted or unsubstituted $C_1$-$C_6$ fluoroalkylene, substituted or unsubstituted $C_3$-$C_8$ cycloalkylene, substituted or unsubstituted $C_1$-$C_6$ heteroalkylene, or $-UV-Z-$, wherein $-UV-$ is defined by $-OW-$, $-WO-$, $-N(R^J)W-$, $-WN(R^J)-$, $-N(R^J)C(=O)-$, $-SW-$, $-S(=O)_nW-$, or $-C(=O)N(R^J)-$, wherein W is substituted or unsubstituted $C_1$-$C_3$ alkylene, or W is $-C(R^L)_2-$; Z is substituted or unsubstituted $C_1$-$C_6$ alkylene, substituted or unsubstituted $C_3$-$C_8$ cycloalkylene, or $C_1$-$C_6$ fluoroalkylene or Z is $-C(R^L)_2-$; and n is 0, 1, or 2;

$L^2$ is absent, or substituted or unsubstituted $C_1$-$C_6$ alkylene, substituted or unsubstituted $C_3$-$C_8$ cycloalkylene, $C_1$-$C_6$ fluoroalkylene, substituted or unsubstituted $C_3$-$C_8$ cycloalkylene, substituted or unsubstituted $C_1$-$C_6$ heteroalkylene, $-O-$, $-S-$, $-SO-$, $-SO_2-$, $-NR^J-$, $-C(=O)-$, or $-C(=O)N(R^J)-$;

wherein $R^B$ is substituted or unsubstituted $C_1$-$C_4$ alkyl, or has the structure of one of:

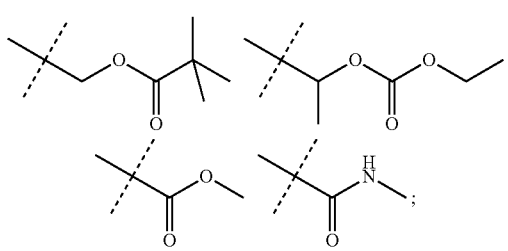

Ring A is a 5 or 6 membered heteroarene having the structure of one of:

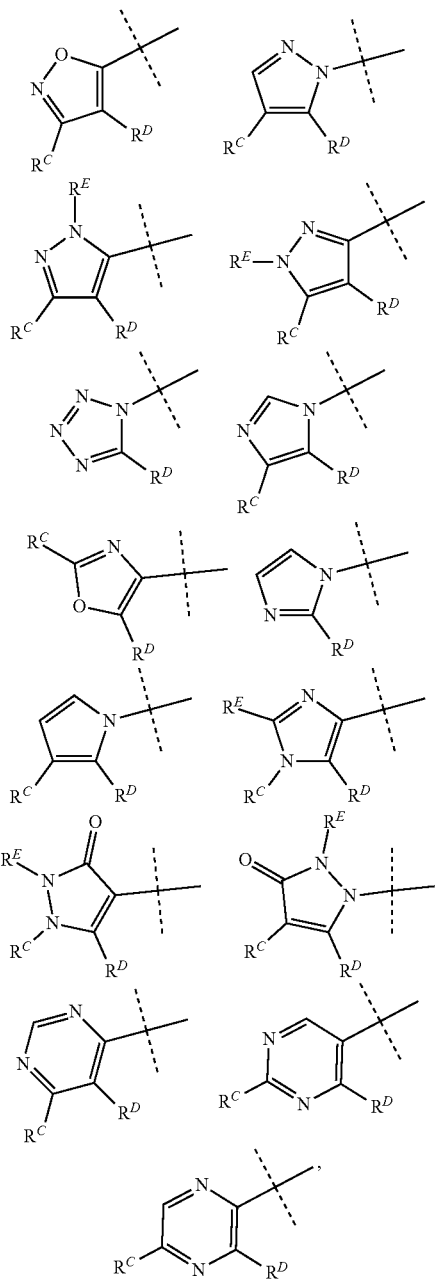

wherein the dashed line indicates the point of attachment of Ring A to Ring B;

wherein one of $R^C$ and $R^D$ is —H, —CN, —F, —Cl, —Br, —I, —OC$_1$-C$_4$ alkyl, C$_1$-C$_4$ alkyl, C$_3$-C$_6$ cycloalkyl, or C$_1$-C$_4$ fluoroalkyl, and the other $R^C$ or $R^D$ is —NR$^F$C(=O)XCH(R$^G$)—CY, —N(R$^F$)C(=O)XC(R$^G$)$_2$—CY, or —NR$^F$C(=O)X—CY, —C(=O)—N(R$^F$)—CH(R$^G$)X—CY, or —C(=O)—N(R$^F$)—C(R$^G$)$_2$X—CY, wherein X is absent, —O—, —NH— or —CH$_2$—;

$R^E$ is —H, —C$_1$-C$_4$ alkyl or —C$_1$-C$_4$ fluoroalkyl, $R^F$ is —H or C$_1$-C$_4$ alkyl, and $R^G$ is independently selected $R^E$ or one $R^G$ is C$_1$-C$_4$ alkyl and is taken together with CY and the the carbon atom to which $R^G$ and CY is attached to define a substituted or unsubstituted carbocycle or substituted or unsubstituted heterocycle and the other $R^G$, if present, is as defined for $R^E$;

wherein CY is substituted or unsubstituted C$_1$-C$_6$ alkyl, substituted or unsubstituted C$_3$-C$_{10}$ cycloalkyl, substituted or unsubstituted C$_2$-C$_{10}$ heterocycloalkyl, substituted or unsubstituted aryl, or substituted or unsubstituted heteroaryl, wherein if CY is substituted then CY is substituted with 1, 2, or 3 independently selected $R^H$, $R^H$ is independently —H, halogen, —CN, —NO$_2$, —OH, —OR$^J$, —SR$^J$, —S(=O)R$^J$, —S(=O)$_2$R$^J$, —N(R$^J$)S(=O)$_2$R$^J$, —S(=O)$_2$N(R$^L$)$_2$, —C(=O)R$^J$, OC(=O)R$^J$, —CO$_2$R$^J$, —OCO$_2$R$^J$, —N(R$^L$)$_2$, —C(=O)N(R$^L$)$_2$, —OC(=O)N(R$^L$)$_2$, N(R$^J$)C(=O)N(R$^L$)$_2$, —N(R$^J$)C(=O)R$^J$, —N(R$^J$)C(=O)OR$^J$, C$_1$-C$_4$ alkyl, C$_1$-C$_4$ fluoroalkyl, C$_1$-C$_4$ fluoroalkoxy, C$_1$-C$_4$ alkoxy, or C$_1$-C$_4$ heteroalkyl, wherein each $R^J$ is independently substituted or unsubstituted C$_1$-C$_6$ alkyl, substituted or unsubstituted C$_1$-C$_6$ heteroalkyl, substituted or unsubstituted C$_1$-C$_6$ fluoroalkyl, substituted or unsubstituted C$_3$-C$_6$ cycloalkyl, substituted or unsubstituted heterocycloalkyl, substituted or unsubstituted aryl, substituted or unsubstituted heteroaryl, —C$_1$-C$_4$ alkylene-(substituted or unsubstituted C$_3$-C$_6$ cycloalkyl), —C$_1$-C$_4$ alkylene-(substituted or unsubstituted heterocycloalkyl), —C$_1$-C$_4$ alkylene-(substituted or unsubstituted aryl), and —C$_1$-C$_4$ alkylene-(substituted or unsubstituted heteroaryl), and wherein each $R^L$ is independently —H, C$_1$-C$_6$ alkyl, C$_1$-C$_6$ heteroalkyl, C$_1$-C$_6$ fluoroalkyl, substituted or unsubstituted C$_3$-C$_6$ cycloalkyl, substituted or unsubstituted heterocycloalkyl, substituted or unsubstituted aryl, substituted or unsubstituted heteroaryl, —C$_1$-C$_4$ alkylene-(substituted or unsubstituted C$_3$-C$_6$ cycloalkyl), —C$_1$-C$_4$ alkylene-(substituted or unsubstituted heterocycloalkyl), —C$_1$-C$_4$ alkylene(substituted or unsubstituted aryl), or —C$_1$-C$_4$ alkylene-(substituted or unsubstituted heteroaryl), or when $R^H$ is —S(=O)$_2$N(R$^L$)$_2$, —N(R$^L$)$_2$, —C(=O)N(R$^L$)$_2$, —OC(=O)N(R$^L$)$_2$ or —N(R$^J$)C(=O)N(R$^L$)$_2$, each $R^L$ is independently —H or C$_1$-C$_6$ alkyl, or the $R^L$ groups independently are C$_1$-C$_6$ alkyl which are taken together with the N atom to which they are attached to define a substituted or unsubstituted heterocycle, or when W or Z is —C(R$^L$)$_2$— each $R^L$ is independently —H, C$_1$-C$_6$ alkyl, or the $R^L$ groups independently are C$_1$-C$_6$ alkyl which are taken together with the carbon atom to which they are attached to define a carbocycle;

Ring B is substituted or unsubstituted C$_3$-C$_{10}$ cycloalkylene, substituted or unsubstituted C$_2$-C$_{10}$ heterocycloalkylene, substituted or unsubstituted arylene, or substituted or unsubstituted heteroarylene, where if ring B is substituted then ring B is substituted with 1, 2, or 3 independently selected $R^H$, wherein $R^H$ is as previously defined; and Ring C is absent or substituted or unsubstituted C$_3$-C$_{10}$ cycloalkylene, substituted or unsubstituted C$_2$-C$_{10}$ heterocycloalkylene, substituted or unsubstituted arylene, or substituted or unsubstituted heteroarylene, wherein if ring C is substituted then ring C is substituted with 1, 2, or 3 independently selected $R^H$, wherein $R^H$ is as previously defined, wherein when Ring B is substituted or unsubstituted arylene, Ring C is absent, L$^2$ is absent, L$^1$ is —UV—Z, wherein —UV— is —N(R$^J$)C(=O)—, wherein $R^F$ is —H, $R^D$ is —N(R$^F$)C(=O)XCH(R$^G$)—CY, wherein X is —O—, $R^G$ is —CH$_3$ and $R^F$ is —H, and $R^C$ is —H, —CH$_3$ or —CF$_3$, or when Ring B is substituted or unsubstituted arylene and Ring C is substituted or unsubstituted arylene or is substituted or unsubstituted C$_3$-C$_{10}$ cycloalkylene, or Ring B is substituted or unsubstituted C$_3$-C$_{10}$ cycloalkylene and Ring C is substituted or unsubstituted arylene, L² is absent, L¹ is C₁-C₆ alkylene, and $R^C$ is —H or —CH₃ and $R^A$ is —CO₂H or —CO₂R$^B$, then Ring A has the structure of one of:

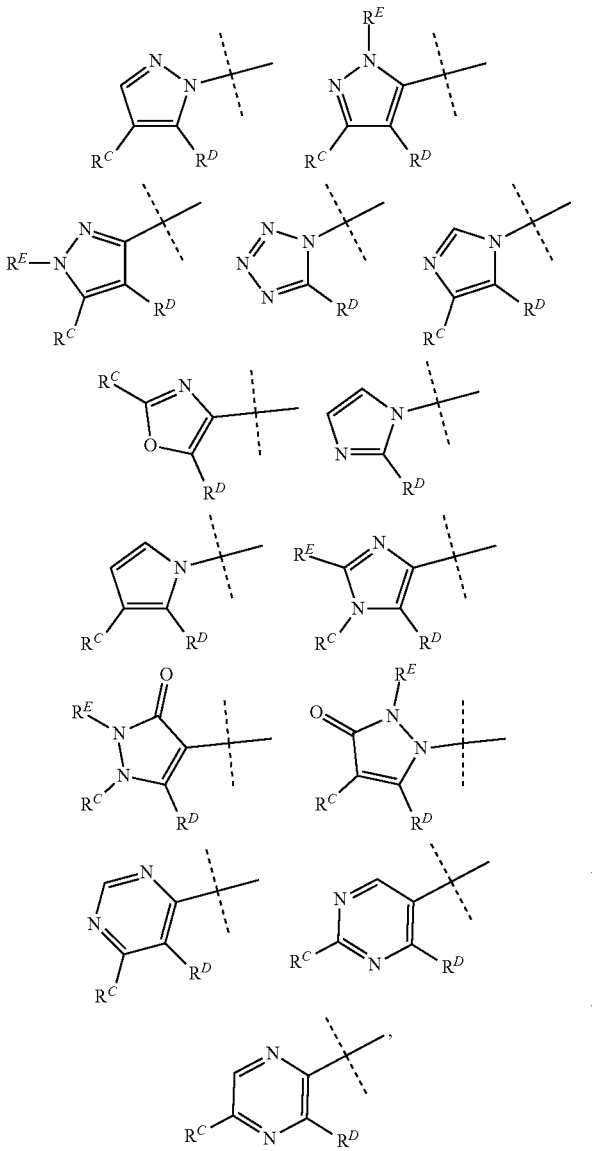

and when Ring B is C₂-C₁₀ heterocycloalkylene, Ring C is substituted or unsubstituted arylene, L² is absent, L¹ is C₁-C₆ alkylene, $R^C$ is —CH₃ and $R^A$ is —CO₂H or —CO₂R$^B$, then Ring A has the structure of one of:

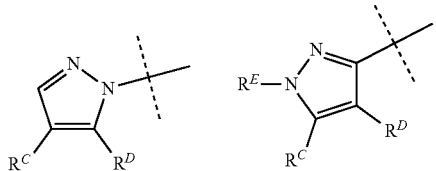

-continued

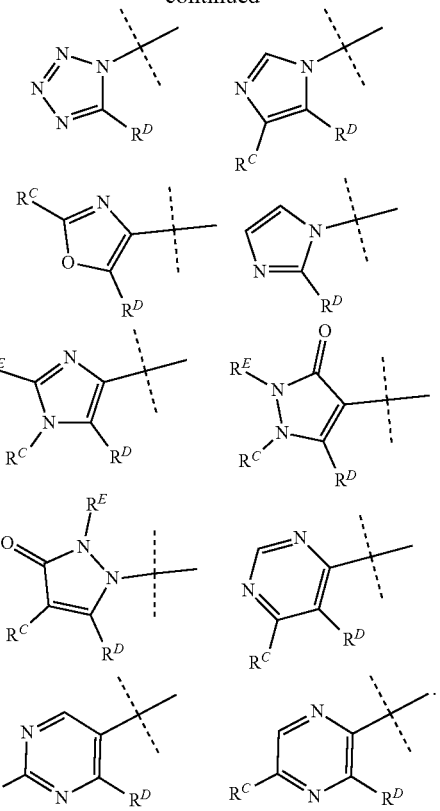

In some embodiments $R^C$ is —H, —CN, —F, —Cl, —Br, —I, —OC₁-C₄ alkyl, C₁-C₄ alkyl, C₃-C₆ cycloalkyl, or C₁-C₄ fluoroalkyl and $R^D$ is —N(R$^F$)—C(=O)XCH(R$^G$)—CY, —N(R$^F$)₂—C(=O)XC(R$^G$)₂—CY or —N(R$^F$)—C(=O)X—CY, wherein $R^F$ and each $R^G$ independently are —H or C₁-C₄alkyl.

In some embodiments $R^A$ is —CO₂H, —CO₂R$^B$, —CN, tetrazolyl, —C(=O)NH₂, —C(=O)NHR$^B$, C(=O)NHSO₂R$^B$ or —C(=O)NHCH₂CH₂SO₃H or a carboxylic acid isostere.

In preferred embodiments $R^A$ is —CO₂H, —CO₂R$^B$, —CN, or —C(=O)NHSO₂R$^B$, wherein $R^B$ is substituted or unsubstituted C₁-C₄ alkyl or has the structure of one of:

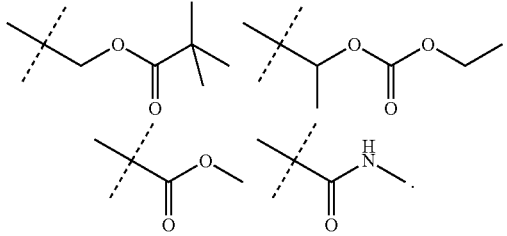

In some embodiments L¹ is absent or substituted or unsubstituted C₁-C₆ alkylene, C₁-C₆ fluoroalkylene, or substituted or unsubstituted C₁-C₆ heteroalkylene.

In some preferred embodiments L¹ is absent or substituted or unsubstituted C₁-C₆ alkylene or —UV—Z—, wherein —UV— is defined by —OW—, —WO—, —N(R$^J$)W—, —WN(R$^J$)—, —N(R$^J$)C(=O)—, —SW—, —S(=O)ₙW—, or —C(=O)N(R$^J$)—, wherein W is substituted or unsubstituted $C_1$-$C_3$ alkylene, Z is substituted or unsubstituted $C_1$-$C_6$ alkylene or $C_1$-$C_6$ fluoroalkylene; and n is 0, 1, or 2.

In particularly preferred embodiments $L^1$ is —$CH_2$—,

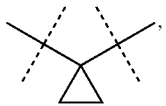

dimethylmethane (i.e., —$C(CH_3)_2$—), or —UV—Z— wherein —UV— is defined by —WO—, —WN($R^J$)—, or —C(=O)N($R^J$)—, wherein W is substituted or unsubstituted $C_1$-$C_3$ alkylene; and Z is substituted or unsubstituted $C_1$-$C_6$ alkylene.

In some embodiments $L^2$ is absent, or substituted or unsubstituted $C_1$-$C_6$ alkylene, $C_1$-$C_6$ fluoroalkylene, substituted or unsubstituted $C_1$-$C_6$ heteroalkylene, —O—, —S—, —S(=O)—, S(=O)$_2$—, —N($R^B$)—, or —C(=O)—.

In some preferred embodiments $L^2$ is absent, —O—, —S—, —S(=O)—, S(=O)$_2$—, —N($R^J$)—, or —C(=O)—.

In some embodiments Ring A is a 5 or 6 membered heteroarene having one of the structures of:

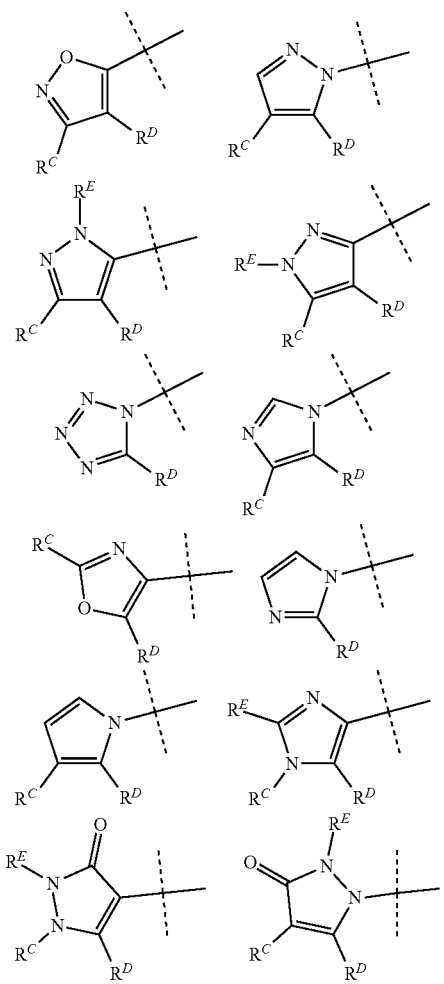

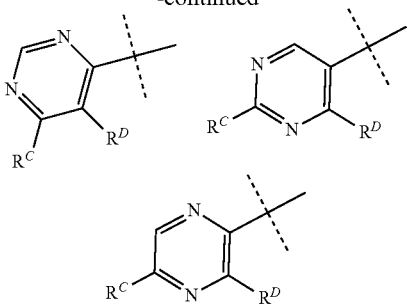

In some embodiments, Formula I compounds have $R^C$ defined as —H, —CN, —F, —Cl, —Br, —I, —O$C_1$-$C_4$ alkyl, $C_1$-$C_4$ alkyl, $C_3$-$C_6$ cycloalkyl, or $C_1$-$C_4$ fluoroalkyl.

In more preferred embodiments, Formula I compounds have $R^C$ defined as —H, —F, —CN, —$CH_3$, or —$CF_3$.

In some embodiments, Formula I compounds have $R^D$ defined as —N($R^F$)C(=O)—XCH($R^G$)—CY, —N($R^F$)C(=O)XC($R^G$)$_2$—CY, or —N($R^F$)C(=O)X—CY, wherein X is absent, —O—, —NH— or —$CH_2$—, wherein $R^F$ is —H or $C_1$-$C_4$ alkyl and X, CY and $R^G$ are as previously defined.

In more preferred embodiments, Formula I compounds have $R^D$ defined as —N($R^F$)C(=O)OCH($R^G$)—CY, —N($R^F$)C(=O)NHC($R^G$)—CY, or —N($R^F$)C(=O)$CH_2$—CY, wherein $R^F$ is —H or $C_1$-$C_4$ alkyl and X, CY and $R^G$ are as previously defined.

In some embodiments, Formula I compounds have $R^E$ defined as —H or $C_1$-$C_4$ alkyl, $C_1$-$C_6$ cycloalkyl or $C_1$-$C_4$ fluoroalkyl.

In more preferred embodiments, Formula I compounds have $R^E$ defined as —H, —$CH_3$, cyclopropyl or —$CF_3$.

In some embodiments, Formula I compounds have $R^F$ defined as H, $C_1$-$C_4$ alkyl or $C_3$-$C_6$cycloalkyl.

In more preferred embodiments, Formula I compounds have $R^F$ defined as —H.

In some embodiments of Formula I compounds one $R^G$ is —$C_1$-$C_4$ alkyl and is taken together with CY and the the carbon atom to which $R^G$ and CY is attached to define a substituted or unsubstituted carbocycle or a substituted or unsubstituted heterocycle and the other $R^G$, if present is —H.

In other embodiments of Formula I compounds $R^G$ is independently —H or $C_1$-$C_4$ alkyl.

In some embodiments of Formula I compounds Ring B is substituted or unsubstituted $C_3$-$C_{10}$ cycloalkylene, substituted or unsubstituted $C_2$-$C_{10}$ heterocycloalkylene, a substituted or unsubstituted arylene, or substituted or unsubstituted heteroarylene, wherein if ring B is substituted then ring B is substituted with 1, 2, or 3 independently selected $R^H$.

In some embodiments of Formula I compounds Ring C is substituted or unsubstituted $C_3$-$C_{10}$ cycloalkylene, substituted or unsubstituted $C_2$-$C_{10}$ heterocycloalkylene, a substituted or unsubstituted arylene, or substituted or unsubstituted heteroarylene, wherein if ring C is substituted then ring C is substituted with 1, 2, or 3 independently selected $R^H$.

In some embodiments of Formula I compounds CY is substituted or unsubstituted $C_1$-$C_6$alkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl, wherein if CY is substituted then CY is substituted with 1, 2, or 3 independently selected $R^H$.

In some preferred embodiments Ring A has the structure of one of:

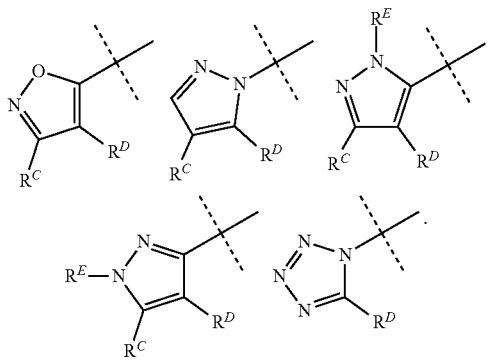

Particularly preferred Formula I compounds have Ring B and Ring C each independently defined as 1,4-substituted aryl or heteroaryl, $R^A$ is —$CO_2H$, $R^C$ is —F or —CN, $R^D$ is —$NR^FC(=O)OCH(R^G)$—CY, $R^E$ is —$CH_3$, and $R^F$, $R^G$, and CY are as previously defined.

Other particularly preferred Formula I compounds have Ring B defined as 1,4-substituted aryl or heteroaryl, $L^1$ is —UV—Z— wherein —UV— is defined by —WO—, —WN($R^J$)—, or —C(=O)N($R^J$)—, wherein W is $CH_2$, Z is substituted or unsubstituted $C_1$-$C_6$ alkylene, $R^A$ is —$CO_2H$, $R^D$ is —N($R^F$)C(=O)OCH($R^G$)—CY, $R^E$ is —$CH_3$, and $R^C$, $R^F$, $R^G$, and CY are as previously defined.

2. The compound of embodiment 1 wherein Ring A has the structure of one of:

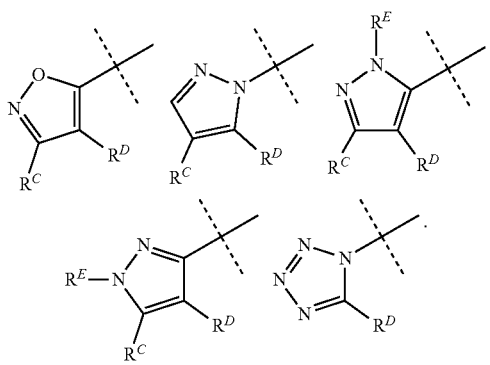

3. The compound of embodiment 1 or 2 wherein $R^C$ is —H, —CN, —F, —$CH_3$, or —$CF_3$.

4. The compound of embodiment 1, 2 or 3 wherein $R^C$ is —F or —CN.

5. The compound of embodiment 1, 2, 3 or 4 wherein $L^2$, is absent.

6 The compound of embodiment 1, 2, 3, 4 or 5 wherein $L^1$, when present, is a geminally substituted alkyl, cycloalkyl or heterocycloalkyl group, or is UV—Z—,
wherein —UV— is defined by —OW—, —WO—, —N($R^J$)W—, —WN($R^J$)—, —N($R^J$)C(=O)—, —SW—, —S(=O)$_n$W—, or —C(=O)N($R^J$)—, wherein W is substituted or unsubstituted $C_1$-$C_3$ alkylene or W is —C($R^L$)$_2$—, wherein $R^L$ independently are —H or $C_1$-$C_4$ alkyl or the two $R^L$ are independently $C_1$-$C_4$ alkyl taken together with the carbon to which $R^L$ is attached to define a carbocycle, Z is substituted or unsubstituted $C_1$-$C_6$ alkylene or $C_1$-$C_6$ fluoroalkylene; and n is 0, 1, or 2.

7. The compound of embodiments 6 wherein $L^1$, when present, is —$CH_2$—,

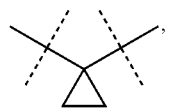

or dimethylmethane, or —UV—Z— wherein —UV— is defined by —WO—, —WN($R^J$)—, or —C(=O)N($R^J$)—, wherein W is —$CH_2$—, Z is substituted or unsubstituted $C_1$-$C_6$ alkylene.

8. The compound of any one of embodiments 1-7 wherein $R^F$ is —H.

9. The compound of any one of embodiments 1-8 wherein $R^G$ is —$CH_3$.

10. The compound of any one of embodiments 1-9 wherein CY is substituted or unsubstituted substituted phenyl.

11. The compound of any one of embodiments 1-10 wherein $R^H$ is —H, halogen, —CN, —$NO_2$, —OH, —$OR^J$, —$SR^J$, —S(=O)$R^J$, —S(=O)$_2R^J$, —N($R^L$)$_2$, $C_1$-$C_4$ alkyl, $C_1$-$C_4$ fluoroalkyl, $C_1$-$C_4$ fluoroalkoxy, $C_1$-$C_4$ alkoxy, and $C_1$-$C_4$ heteroalkyl.

12. The compound of any one of embodiments 1-11 wherein $R^H$ are independently selected from —H, halogen or substituted or unsubstituted $C_1$-$C_4$ alkyl or substituted $C_1$-$C_4$ alkoxy.

13. The compound of any one of embodiments 1-12 wherein $R^H$ is independently —H, —Cl, —F, —$CH_3$, —$CF_3$, —$OCH_3$ or —$OCF_3$.

14. A compound of Formula II having the structure:

Formula II

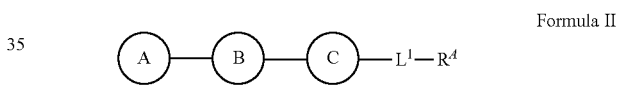

or a pharmaceutically acceptable salt or prodrug thereof
wherein $R^A$ is —$CO_2H$, —$CO_2R^B$, —CN, tetrazolyl, —C(=O)$NH_2$, —C(=O)$NHR^B$, C(=O)$NHSO_2R^B$ or —C(=O)$NHCH_2CH_2SO_3H$ or a carboxylic acid isostere,
$R^B$ is optionally substituted $C_1$-$C_4$ alkyl or has the structure of one of:

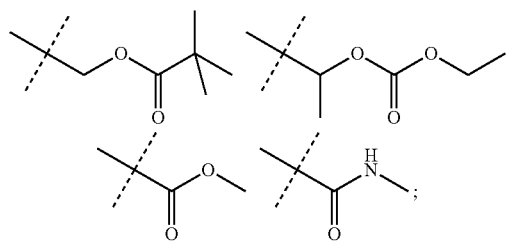

$L^1$ is absent or optionally substituted $C_1$-$C_6$ alkylene; optionally substituted $C_1$-$C_6$ fluoroalkylene, or optionally substituted $C_1$-$C_6$ heteroalkylene or —UV—Z—, wherein —UV— is defined by —OW—, —WO—, —N($R^J$)W—, —WN($R^J$)—, —N($R^J$)C(=O)—, —SW—, —S(=O)$_n$W—, or —C(=O)N($R^J$)—, wherein W is optionally substituted $C_1$-$C_3$ alkylene or W is —C($R^L$)$_2$—, Z is optionally substituted $C_1$-$C_6$ alkylene or $C_1$-$C_6$ fluoroalkylene or Z is —C($R^L$)$_2$—; and n is 0, 1, or 2;

Ring A is a 5 or 6 membered heteroarene having the structure of one of:

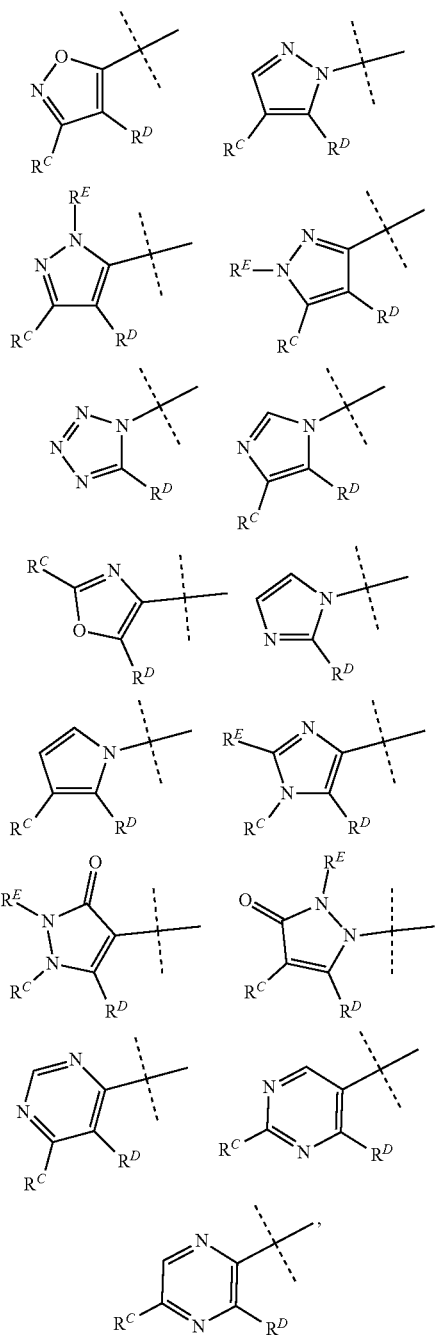

wherein $R^C$ is —H, —CN, —F, —Cl, —Br, —I, —O$C_1$-$C_4$ alkyl, $C_1$-$C_4$ alkyl, $C_3$-$C_6$ cycloalkyl, or $C_1$-$C_4$ fluoroalkyl;

$R^D$ is —N($R^F$)C(=O)XCH($R^G$)—CY, —N($R^F$)C(=O)XC($R^G$)$_2$—CY, or —N($R^F$)C(=O)X—CY; where X is absent, —O—, —NH— or —$CH_2$—;

$R^E$ is —H or $C_1$-$C_4$ alkyl, $C_1$-$C_6$ cycloalkyl or $C_1$-$C_4$ fluoroalkyl;

$R^F$ is —H, $C_1$-$C_4$ alkyl or $C_1$-$C_6$ cycloalkyl;

$R^G$ is independently selected $R^E$, or one of $R^G$ is $C_1$-$C_4$ alkyl and is taken together with CY and the carbon atom to which $R^G$ and CY are attached to define a substituted or unsubstituted carbocycle or a substituted or unsubstituted heterocycle and the other $R^G$, if present, is as defined for $R^E$;

Ring B is optionally substituted $C_3$-$C_{10}$ cycloalkylene, optionally substituted $C_2$-$C_{10}$ heterocycloalkylene, optionally substituted arylene, or optionally substituted heteroarylene, where if ring B is substituted then ring B is substituted with 1, 2, or 3 independently selected $R^H$;

Ring C is absent or optionally substituted $C_3$-$C_{10}$ cycloalkylene, optionally substituted $C_2$-$C_{10}$ heterocycloalkylene, optionally substituted arylene, or optionally substituted heteroarylene, wherein if ring C is substituted then ring C is substituted with 1, 2, or 3 independently selected $R^H$;

CY is optionally substituted $C_1$-$C_6$ alkyl, optionally substituted $C_3$-$C_{10}$ cycloalkyl, optionally substituted $C_2$-$C_{10}$ heterocycloalkyl, optionally substituted aryl, or optionally substituted heteroaryl, wherein if CY is substituted then CY is substituted with 1, 2, or 3 independently selected $R^H$, or wherein each $R^H$ is independently selected —H, halogen, —CN, —NO$_2$, —OH, —O$R^J$, —S$R^J$, —S(=O)$R^J$, —S(=O)$_2$$R^J$, —N($R^J$)S(=O)$_2$$R^J$, —S(=O)$_2$N($R^L$)$_2$, —C(=O)$R^J$, —OC(=O)$R^J$, —C(=O)O$R^J$, —OC(=O)O$R^J$, —N($R^L$)$_2$, —C(=O)N($R^L$)$_2$, —OC(=O)N($R^L$)$_2$, —N($R^J$)C(=O)N($R^L$)$_2$, —N($R^J$)C(=O)$R^J$, —N($R^J$)C(=O)O$R^J$, $C_1$-$C_4$ alkyl, $C_1$-$C_4$ fluoroalkyl, $C_1$-$C_4$ fluoroalkoxy, $C_1$-$C_4$ alkoxy, or $C_1$-$C_4$ heteroalkyl, and wherein $R^J$ is optionally substituted $C_1$-$C_6$ alkyl, optionally substituted $C_1$-$C_6$ heteroalkyl, optionally substituted $C_1$-$C_6$ fluoroalkyl, optionally substituted $C_3$-$C_6$ cycloalkyl, optionally substituted heterocycloalkyl, optionally substituted aryl, optionally substituted heteroaryl, —$C_1$-$C_4$ alkylene-(optionally substituted $C_3$-$C_6$ cycloalkyl), —$C_1$-$C_4$ alkylene-(optionally substituted heterocycloalkyl), —$C_1$-$C_4$ alkylene-(substituted or unsubstituted aryl), or —$C_1$-$C_4$ alkylene-(optionally substituted heteroaryl), and each $R^L$ is independently —H, optionally substituted $C_1$-$C_6$ alkyl, optionally substituted $C_1$-$C_6$ heteroalkyl, optionally substituted $C_1$-$C_6$ fluoroalkyl, optionally substituted $C_3$-$C_6$ cycloalkyl, optionally substituted heterocycloalkyl, optionally substituted aryl, optionally substituted heteroaryl, —$C_1$-$C_4$ alkylene-(optionally substituted $C_3$-$C_6$ cycloalkyl), —$C_1$-$C_4$ alkylene-(optionally substituted heterocycloalkyl), —$C_1$-$C_4$ alkylene-(optionally substituted aryl), or —$C_1$-$C_4$ alkylene-(optionally substituted heteroaryl), or when $R^H$ is —S(=O)$_2$N($R^L$)$_2$, —N($R^L$)$_2$, —C(=O)N($R^L$)$_2$, —OC(=O)N($R^L$)$_2$ or —N($R^J$)C(=O)N($R^L$)$_2$, each $R^L$ is independently —H or $C_1$-$C_6$ alkyl, or the $R^L$ groups independently are $C_1$-$C_6$ alkyl which are taken together with the N atom to which they are attached to define an optionally substituted heterocycle, or when W or Z is —C($R^L$)$_2$—, each $R^L$ is independently —H or $C_1$-$C_6$ alkyl, or the $R^L$ groups independently are $C_1$-$C_6$ alkyl which are taken together with the carbon atom to which they are attached to define a carbocycle;

wherein when Ring B is substituted or unsubstituted arylene, Ring C is absent, $L^1$ is —UV—Z, wherein —UV— is —N($R^J$)C(=O)—, wherein $R^J$ is —H, $R^D$ is —N($R^F$)C(=O)XCH($R^G$)—CY, wherein X is —O—, $R^G$ is —CH$_3$ and $R^F$ is —H, and $R^C$ is —H, —CH$_3$ or —CF$_3$, or when Ring B is substituted or unsubstituted arylene and Ring C is substituted or unsubstituted arylene or is substituted or unsubstituted $C_3$-$C_{10}$ cycloalkylene, or Ring B is substituted or unsubstituted $C_3$-$C_{10}$ cycloalkylene and Ring C is substituted or unsubstituted arylene and $L^1$ is $C_1$-$C_6$ alkylene, and $R^C$ is —H or —$CH_3$ and $R^A$ is —$CO_2H$ or —$CO_2R^B$, then Ring A has the structure of one of:

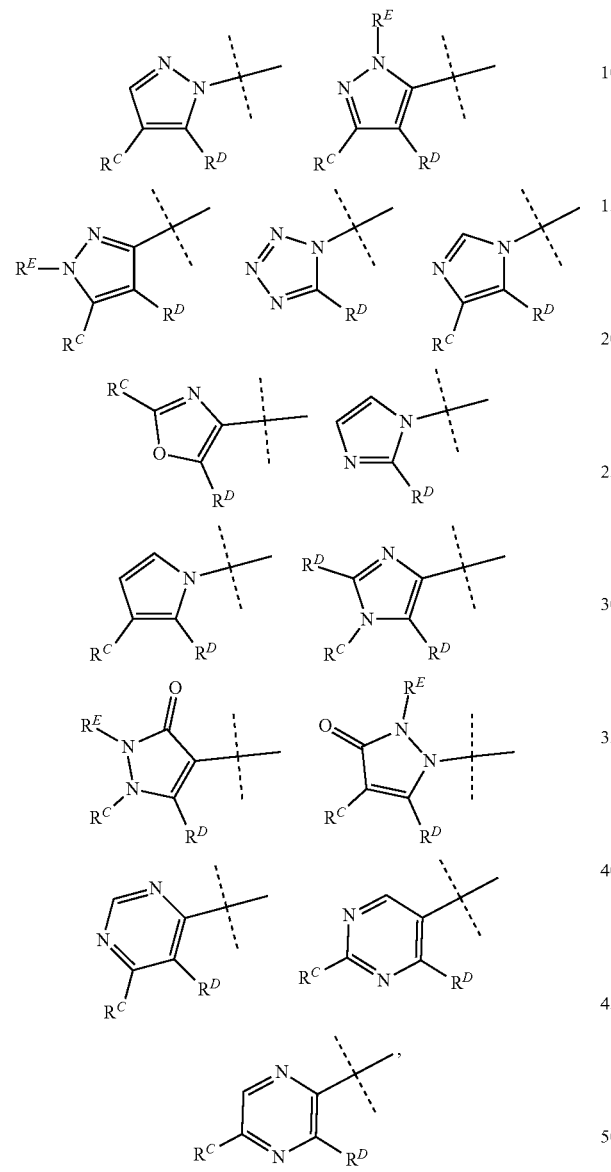

and when Ring B is $C_2$-$C_{10}$ heterocycloalkylene, Ring C is substituted or unsubstituted arylene, $L^1$ is $C_1$-$C_6$ alkylene, $R^C$ is —$CH_3$ and $R^A$ is —$CO_2H$ or —$CO_2R^B$, then Ring A has the structure of one of:

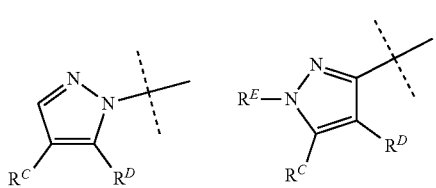

-continued

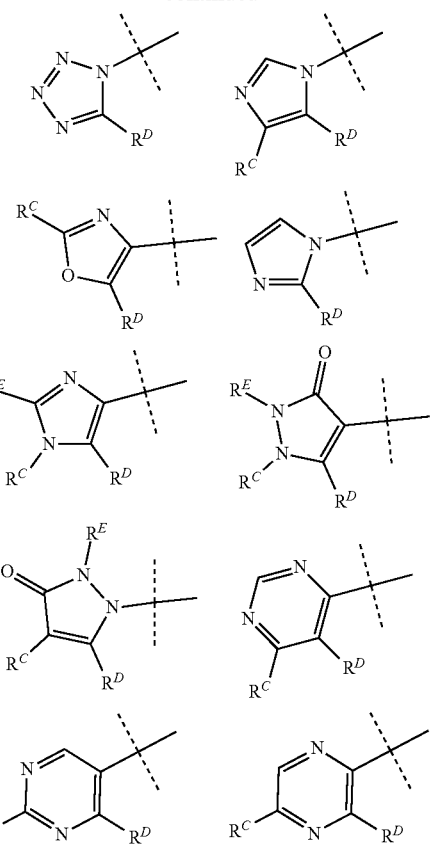

In preferred embodiments Ring A has the structure of one of:

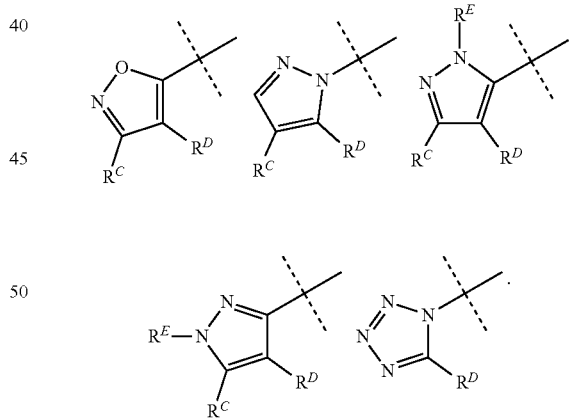

Particularly preferred Formula II compounds have Ring B and Ring C defined each as 1,4-substituted aryl or heteroaryl, $R^A$ is $CO_2H$, and $R^D$ is —N($R^F$)C(=O)OCH($R^G$)—CY.

Particularly preferred Formula II compounds have Ring B defined as 1,4-substituted aryl or heteroaryl, $L^1$ is —UV—Z—, wherein —UV— is defined by —WO—, —WN($R^J$)—, or —C(=O)N($R^J$)—, wherein W is —$CH_2$—, Z is substituted or unsubstituted $C_1$-$C_6$ alkylene, $R^A$ is —$CO_2H$, $R^D$ is —N($R^F$)C(=O)OCH($R^G$)—CY.

15. A compound of Formula III having the structure:

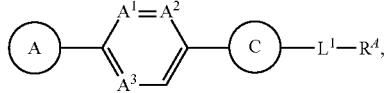

Formula III or a pharmaceutically acceptable salt or prodrug thereof, wherein $R^A$ is —CO$_2$H, —CO$_2$R$^B$, —CN, tetrazolyl, —C(=O)NH$_2$, —C(=O)NHR$^B$, C(=O)NHSO$_2$R$^B$ or —C(=O)NHCH$_2$CH$_2$SO$_3$H or a carboxylic acid isostere;

$R^B$ is substituted or unsubstituted $C_1$-$C_4$ alkyl or has the structure of one of

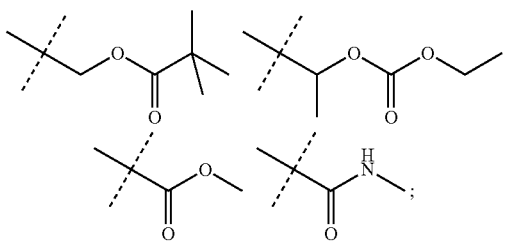

$L^1$ is absent or is substituted or unsubstituted $C_1$-$C_6$ alkylene, $C_1$-$C_6$ fluoroalkylene; or substituted or unsubstituted $C_1$-$C_6$ heteroalkylene or —UV—Z— wherein —UV— is defined by —OW—, —WO—, —N(R$^J$)W—, —WN(R$^J$)—, —N(R$^J$)C(=O)—, —SW—, —S(=O)$_n$W—, or —C(=O)N(R$^J$)—, wherein W is substituted or unsubstituted $C_1$-$C_3$ alkylene or W is —C(R$^L$)$_2$—, Z is substituted or unsubstituted $C_1$-$C_6$ alkylene or $C_1$-$C_6$ fluoroalkylene; and n is 0, 1, or 2;

Ring A is a 5-6 membered heteroarenes having one the structure of one of:

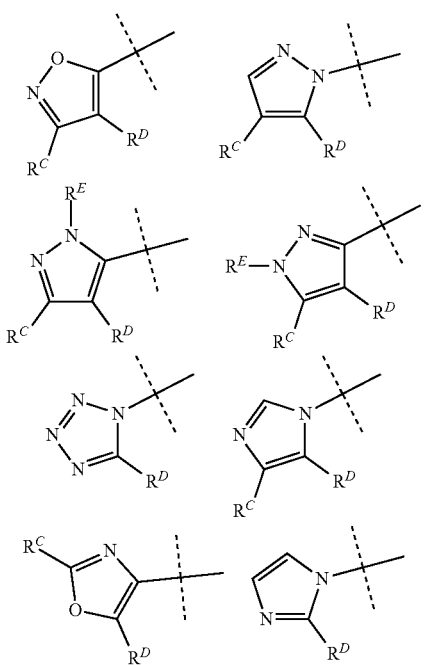

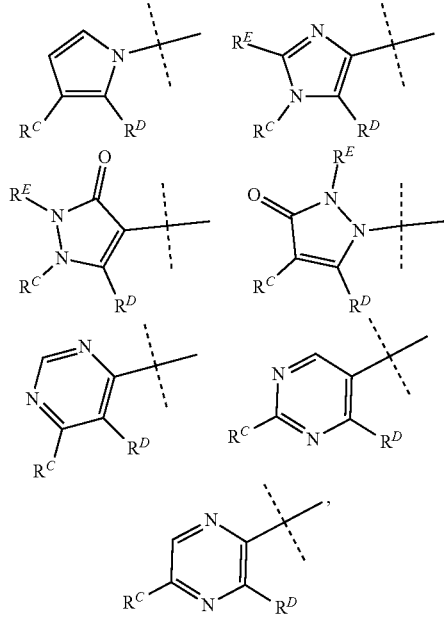

wherein R$^C$ is —H, —CN, —F, —Cl, —Br, —I, —OC$_1$-C$_4$ alkyl, $C_1$-$C_4$ alkyl, $C_3$-$C_6$ cycloalkyl, or $C_1$-$C_4$ fluoroalkyl;

R$^D$ is —N(R$^F$)C(=O)XCH(R$^G$)—CY, —N(R$^F$)C(=O)XC(R$^G$)$_2$—CY, or —N(R$^F$)C(=O)X—CY. wherein X is absent, —O—, —NH— or —CH$_2$—;

R$^E$ is —H or $C_1$-$C_4$ alkyl, $C_1$-$C_6$ cycloalkyl or $C_1$-$C_4$ fluoroalkyl;

R$^F$—H, $C_1$-$C_4$ alkyl or $C_1$-$C_6$ cycloalkyl;

R$^G$ is independently selected R$^E$, or one R$^G$ is —C$_1$-$C_4$ alkyl and is taken together with CY and the the carbon atom to which R$^G$ and CY is attached to define a substituted or unsubstituted carbocycle or a substituted or unsubstituted heterocycle and the other R$^G$, if present, is as defined for R$^E$;

A$^1$, A$^2$ and A$^3$ are independently =NH—, —N=, =CH— or —CH=,

Ring C is absent or substituted or unsubstituted $C_3$-$C_{10}$ cycloalkylene, substituted or unsubstituted $C_2$-$C_{10}$ heterocycloalkylene, substituted or unsubstituted arylene, or substituted or unsubstituted heteroarylene, wherein if ring C is substituted then ring C is substituted with 1, 2, or 3 independently selected R$^H$;

CY is substituted or unsubstituted $C_1$-$C_6$ alkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl, wherein if CY is substituted then CY is substituted with 1, 2, or 3 R$^H$;

wherein each R$^H$ is independently —H, halogen, —CN, —NO$_2$, —OH, —OR$^J$, —SR$^J$, —S(=O)R$^J$, —S(=O)$_2$R$^J$, —N(R$^J$)S(=O)$_2$R$^J$, —S(=O)$_2$N(R$^L$)$_2$, —C(=O)R$^J$, —OC(=O)R$^J$, —C(=O)OR$^J$, —OC(=O)OR$^J$, —N(R$^L$)$_2$, —C(=O)N(R$^L$)$_2$, —OC(=O)N(R$^L$)$_2$, N(R$^J$)C(=O)N(R$^L$)$_2$, —N(R$^J$)C(=O)R$^J$, —NR$^J$C(=O)OR$^J$, $C_1$-$C_4$ alkyl, $C_1$-$C_4$ fluoroalkyl, $C_1$-$C_4$ fluoroalkoxy, $C_1$-$C_4$ alkoxy, or $C_1$-$C_4$ heteroalkyl;

each R$^J$ is independently substituted or unsubstituted $C_1$-$C_6$ alkyl, substituted or unsubstituted $C_1$-$C_6$ heteroalkyl, substituted or unsubstituted $C_1$-$C_6$ fluoroalkyl, substituted or unsubstituted $C_3$-$C_6$ cycloalkyl, substituted or unsubstituted heterocycloalkyl, substituted or unsubstituted aryl, substituted or unsubstituted heteroaryl, —$C_1$-$C_4$ alkylene-(substituted or unsubstituted C$_3$-C$_6$ cycloalkyl), —C$_1$-C$_4$ alkylene-(substituted or unsubstituted heterocycloalkyl), —C$_1$-C$_4$ alkylene-(substituted or unsubstituted aryl), or C$_1$-C$_4$ alkylene-(substituted or unsubstituted heteroaryl);

each R$^L$ is independently —H, substituted or unsubstituted C$_1$-C$_6$ alkyl, substituted or unsubstituted C$_1$-C$_6$ heteroalkyl, substituted or unsubstituted C$_1$-C$_6$ fluoroalkyl, substituted or unsubstituted cycloalkyl, a substituted or unsubstituted heterocycloalkyl, substituted or unsubstituted aryl, substituted or unsubstituted heteroaryl, —C$_1$-C$_4$ alkylene-(substituted or unsubstituted cycloalkyl), —C$_1$-C$_4$ alkylene-(substituted or unsubstituted heterocycloalkyl), —C$_1$-C$_4$ alkylene(substituted or unsubstituted aryl), or —C$_1$-C$_4$ alkylene-(substituted or unsubstituted heteroaryl), or when R$^H$ is —S(=O)$_2$N(R$^L$)$_2$, —N(R$^L$)$_2$, —C(=O)N(R$^L$)$_2$, —OC(=O)N(R$^L$)$_2$ or N(R$^J$)C(=O)N(R$^L$)$_2$, each R$^L$ is independently —H or C$_1$-C$_6$ alkyl, or the R$^L$ groups independently are C$_1$-C$_6$ alkyl which are taken together with the N atom to which they are attached to define a substituted or unsubstituted heterocycle, or when W or Z is —C(R$^L$)$_2$—, each R$^L$ is independently —H or C$_1$-C$_6$ alkyl, or the R$^L$ groups independently are C$_1$-C$_6$ alkyl which are taken together with the carbon atom to which they are attached to define a carbocycle;

wherein when A$^1$, A$^2$ and A$^3$ are =CH— or —CH=, Ring C is absent, L$^1$ is —UV—Z, wherein —UV— is —N(R$^J$)C(=O)—, wherein R$^J$ is —H, R$^D$ is —N(R$^F$)C(=O)XCH(R$^G$)—CY, wherein X is —O—, R$^G$ is —CH$_3$ and R$^F$ is —H, and R$^C$ is —H, —CH$_3$ or —CF$_3$, or when Ring C is substituted or unsubstituted arylene or substituted or unsubstituted C$_3$-C$_{10}$ cycloalkylene and R$^C$ is —H or —CH$_3$ and R$^A$ is —CO$_2$H or —CO$_2$R$^B$, then Ring A has the structure of one of:

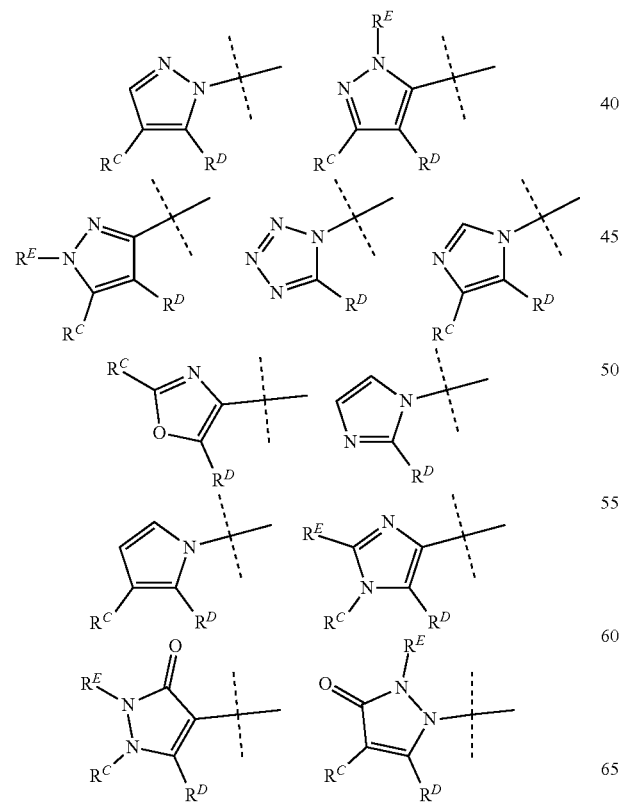

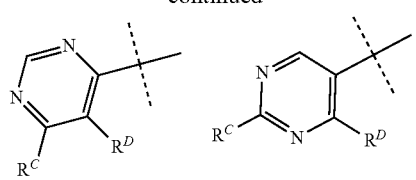

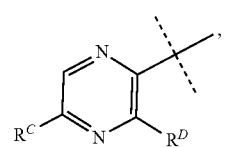

and when Ring C is substituted or unsubstituted arylene, L$^1$ is C$_1$-C$_6$ alkylene, R$^C$ is —CH$_3$ and R$^A$ is —CO$_2$H or —CO$_2$R$^B$.

then Ring A has the structure of one of:

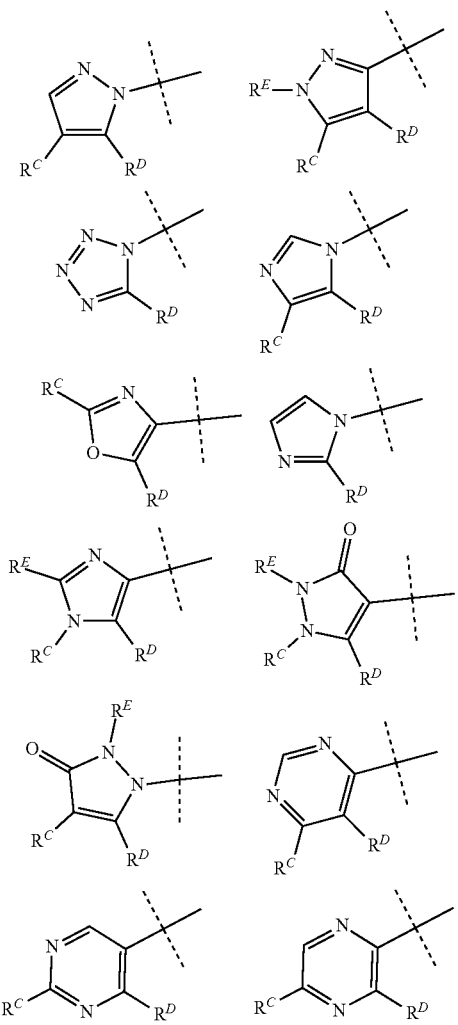

In preferred embodiments Ring A has the structure of one of:

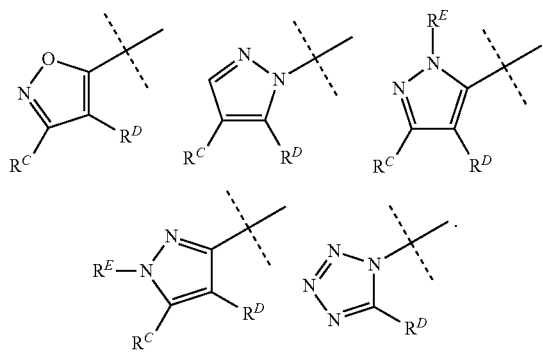

Particularly preferred Formula III compounds have Ring C is defined as 1,4-substituted phenyl or pyridyl, $R^A$ is —CO$_2$H, and $R^D$ is —N(R$^F$)C(=O)OCH(R$^G$)—CY; L$^1$ is —UV—Z— wherein —UV— is defined by —WO—, —WN(R$^J$)—, or —C(=O)N(R$^J$)—, wherein W is —CH$_2$—, Z is substituted or unsubstituted C$_1$-C$_6$ alkylene, $R^A$ is —CO$_2$H, and $R^D$ is —N(R$^F$)C(=O)OCH(R$^G$)—CY.

16. A compound of Formula IV having the structure:

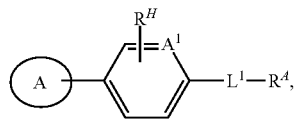

Formula IV or a pharmaceutically acceptable salt or prodrug thereof, wherein $R^A$ is —CO$_2$H, —CO$_2$R$^B$, —CN, tetrazolyl, —C(=O)NH$_2$, —C(=O)NHR$^B$, —C(=O)NHSO$_2$R$^B$ or —C(=O)NHCH$_2$CH$_2$SO$_3$H or a carboxylic acid isostere;

$R^B$ is optionally substituted —C$_1$-C$_4$ alkyl or has the structure of one of:

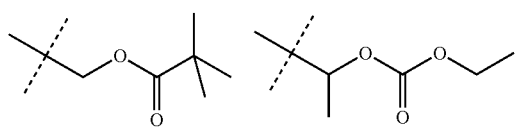

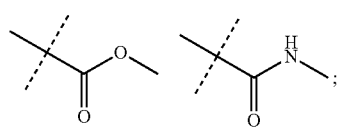

L$^1$ is —UV—Z—, wherein —UV— is defined by —OW—, —WO—, —N(R$^J$)W—, —WN(R$^J$)—, —N(R$^J$)C(=O)—, —SW—, —S(=O)$_n$W—, or —C(=O)N(R$^J$)—, wherein W is substituted or unsubstituted C$_1$-C$_3$ alkylene or W is —C(R$^L$)$_2$—, Z is substituted or unsubstituted C$_1$-C$_6$ alkylene or substituted or unsubstituted C$_1$-C$_6$ fluoroalkylene or Z is —C(R$^L$)$_2$—; and n is 0, 1, or 2;

A$^1$ is independently =N— or =CH—;

Ring A is a 5 or 6 membered heteroarene having one of the structures of:

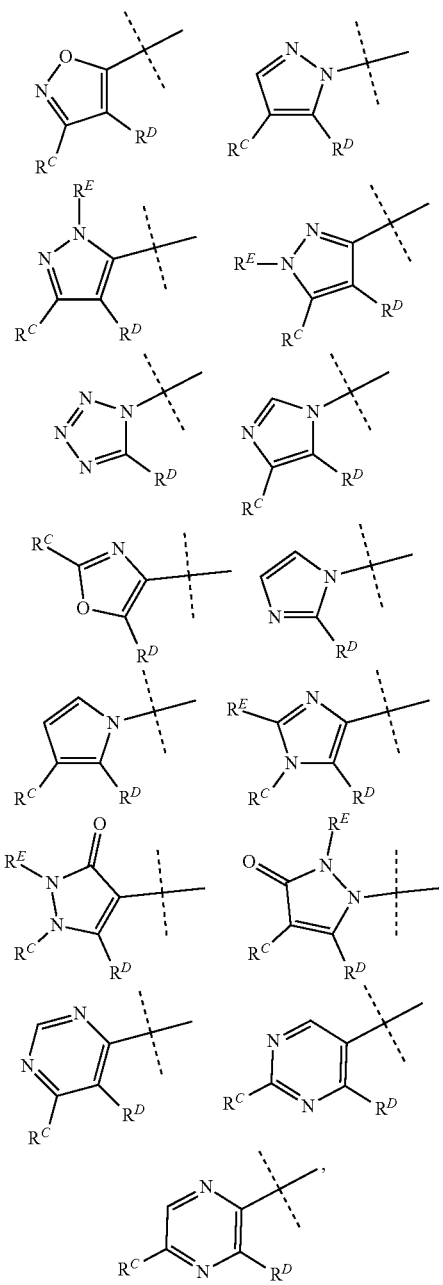

wherein R$^C$ is —H, —CN, —F, —Cl, —Br, —I, —OC$_1$-C$_4$ alkyl, C$_1$-C$_4$ alkyl, C$_3$-C$_6$ cycloalkyl, or C$_1$-C$_4$ fluoroalkyl;

R$^D$ is —N(R$^F$)C(=O)XCH(R$^G$)—CY, —N(R$^F$)C(=O)XC(R$^G$)$_2$—CY, or —N(R$^F$)C(=O)X—CY, wherein X is absent, —O—, —NH— or —CH$_2$—;

R$^E$ is —H or C$_1$-C$_4$ alkyl, C$_3$-C$_6$ cycloalkyl or C$_1$-C$_4$ fluoroalkyl;

R$^F$ is —H, C$_1$-C$_4$ alkyl or C$_3$-C$_6$ cycloalkyl;

R$^G$ is independently selected R$^E$, or one R$^G$ is —C$_1$-C$_4$ alkyl and is taken together with CY and the carbon atom to which R$^G$ and CY is attached to define a substituted or unsubstituted carbocycle or a substituted or unsubstituted heterocycle, and the other R$^G$, if present, is as defined for R$^E$;

CY is C$_1$-C$_6$ alkyl, a substituted or unsubstituted C$_3$-C$_{10}$ cycloalkyl, a substituted or unsubstituted C$_2$-C$_{10}$ heterocycloalkyl, a substituted or unsubstituted aryl, or a substituted or unsubstituted heteroaryl, wherein if CY is substituted then CY is substituted with 1, 2, or 3 $R^H$;

wherein each $R^H$ is independently —H, halogen, —CN, —NO$_2$, —OH, —OR$^J$, —SR$^J$, —S(=O)R, —S(=O)$_2$R$^J$, —N(R$^J$)S(=O)$_2$R$^J$, —S(=O)$_2$N(R$^L$)$_2$, —C(=O)R, —OC(=O)R$^J$, —C(=O)$^O$R$^J$, —OC(=O)OR$^J$, —N(R$^L$)$_2$, —C(=O)N(R$^L$)$_2$, —OC(=O)N(R$^L$)$_2$, N(R$^J$)C(=O)N(R$^L$)$_2$, —N(R$^J$)C(=O)R$^J$, —N(R$^J$)C(=O)OR$^J$, C$_1$-C$_4$ alkyl, C$_1$-C$_4$ fluoroalkyl, C$_1$-C$_4$ fluoroalkoxy, C$_1$-C$_4$ alkoxy, or C$_1$-C$_4$ heteroalkyl;

wherein $R^J$ is independently substituted or unsubstituted C$_1$-C$_6$ alkyl, substituted or unsubstituted C$_1$-C$_6$ heteroalkyl, substituted or unsubstituted C$_1$-C$_6$ fluoroalkyl, substituted or unsubstituted C$_3$-C$_6$ cycloalkyl, substituted or unsubstituted heterocycloalkyl, substituted or unsubstituted aryl, substituted or unsubstituted heteroaryl, —C$_1$-C$_4$ alkylene-(substituted or unsubstituted C$_3$-C$_6$ cycloalkyl), —C$_1$-C$_4$ alkylene-(substituted or unsubstituted heterocycloalkyl), —C$_1$-C$_4$ alkylene-(substituted or unsubstituted aryl), or C$_1$-C$_4$ alkylene-(substituted or unsubstituted heteroaryl); and each $R^L$ is independently —H, substituted or unsubstituted C$_1$-C$_6$ alkyl, substituted or unsubstituted C$_1$-C$_6$ heteroalkyl, substituted or unsubstituted C$_1$-C$_6$ fluoroalkyl, substituted or unsubstituted cycloalkyl, substituted or unsubstituted heterocycloalkyl, substituted or unsubstituted aryl, substituted or unsubstituted heteroaryl, —C$_1$-C$_4$ alkylene-(substituted or unsubstituted C$_3$-C$_6$ cycloalkyl), —C$_1$-C$_4$ alkylene-(substituted or unsubstituted heterocycloalkyl), —C$_1$-C$_4$ alkylene-(substituted or unsubstituted aryl), or —C$_1$-C$_4$ alkylene-(substituted or unsubstituted heteroaryl), or when $R^H$ is —S(=O)$_2$N(R$^L$)$_2$, —N(R$^L$)$_2$, —C(=O)N(R$^L$)$_2$, —OC(=O)N(R$^L$)$_2$ or —N(R$^J$)C(=O)N(R$^L$)$_2$, each $R^L$ is independently —H or C$_1$-C$_6$ alkyl, or the $R^L$ groups independently are C$_1$-C$_6$ alkyl which are taken together with the N atom to which they are attached to define a substituted or unsubstituted heterocycle, or when W or Z is —C(R$^L$)$_2$—, each $R^L$ is independently —H or C$_1$-C$_6$ alkyl, or the $R^L$ groups independently are C$_1$-C$_6$ alkyl which are taken together with the carbon atom to which they are attached to define a carbocycle, or when $R^H$ is —S(=O)$_2$N(R$^L$)$_2$, —N(R$^L$)$_2$, —C(=O)N(R$^L$)$_2$, —OC(=O)N(R$^L$)$_2$ or —N(R$^J$)C(=O)N(R$^L$)$_2$, each $R^L$ is independently is —H or C$_1$-C$_6$ alkyl, or the $R^L$ groups independently are C$_1$-C$_6$ alkyl which are taken together with the N atom to which they are attached to define a substituted or unsubstituted heterocycle, or when W is —C(R$^L$)$_2$—, each $R^L$ is independently —H, C$_1$-C$_6$ alkyl, or the $R^L$ groups independently are C$_1$-C$_6$ alkyl which are taken together with the carbon atom to which they are attached to define a carbocycle;

wherein A$^1$ is =CH—, L$^1$ is —UV—Z, wherein —UV— is —N(R$^J$)C(=O)—, wherein R$^J$ is —H, R$^D$ is —N(R$^F$)—C(=O)XCH(R$^G$)—CY, wherein X is —O—, R$^G$ is —CH$_3$ and R$^F$ is —H, and R$^C$ is —H, —CH$_3$ or —CF$_3$, and R$^C$ is —H or —CH$_3$ and R$^A$ is —CO$_2$H or CO$_2$R$^B$. then Ring A has the structure of one of:

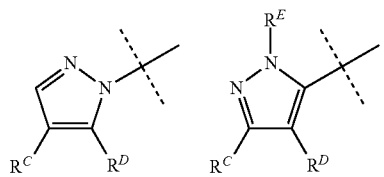

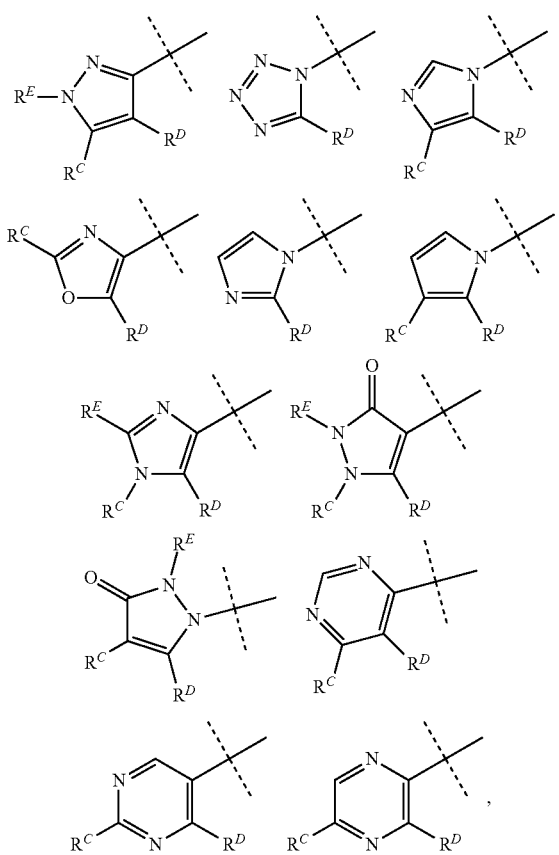

In preferred embodiments Ring A has the structure of one of:

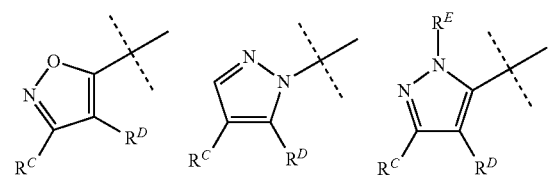

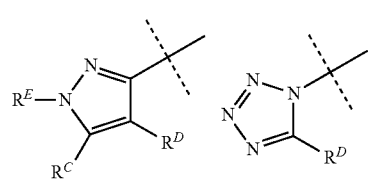

Particularly preferred Formula IV compounds have L$^1$ defined as —UV—Z—, wherein —UV— is defined by —WO—, —WN(R$^J$)—, or —C(=O)N(R$^J$)—, wherein W is —CH$_2$—, Z is substituted or unsubstituted C$_1$-C$_6$ alkylene, R$^A$ is —CO$_2$H, and R$^D$ is —N(R$^F$)C(=O)OCH(R$^G$)—CY.

17. A compound of Formula V having the structure:

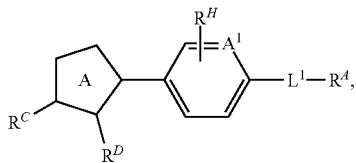

Formula V or a pharmaceutically acceptable salt or prodrug thereof, wherein $R^A$ is —CO$_2$H, —CO$_2$R$^B$, —CN, tetrazolyl, —C(=O)NH$_2$, —C(=O)NHR$^B$, C(=O)NHSO$_2$R$^B$ or —C(=O)NHCH$_2$CH$_2$SO$_3$H or a carboxylic acid isostere, wherein $R^B$ is optionally substituted C$_1$-C$_4$ alkyl or has the structure of one of

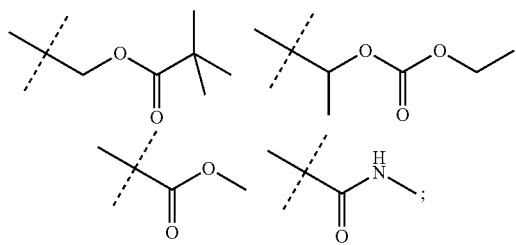

$L^1$ is —UV—Z—, wherein —UV— is defined by —OW—, —WO—, —N(R$^J$)W—, —WN(R$^J$)—, —N(R$^J$)C(=O)—, —SW—, —S(=O)$_n$W—, or —C(=O)N(R$^J$)—, wherein W is substituted or unsubstituted C$_1$-C$_3$ alkylene or W is —C(R$^L$)$_2$—, Z is substituted or unsubstituted C$_1$-C$_6$ alkylene or substituted or unsubstituted C$_1$-C$_6$ fluoroalkylene or Z is —C(R$^L$)$_2$—; and n is 0, 1, or 2;

$A^1$ is =N— or =CH—;

Ring A is a 5 membered heteroarene having the structure of one of:

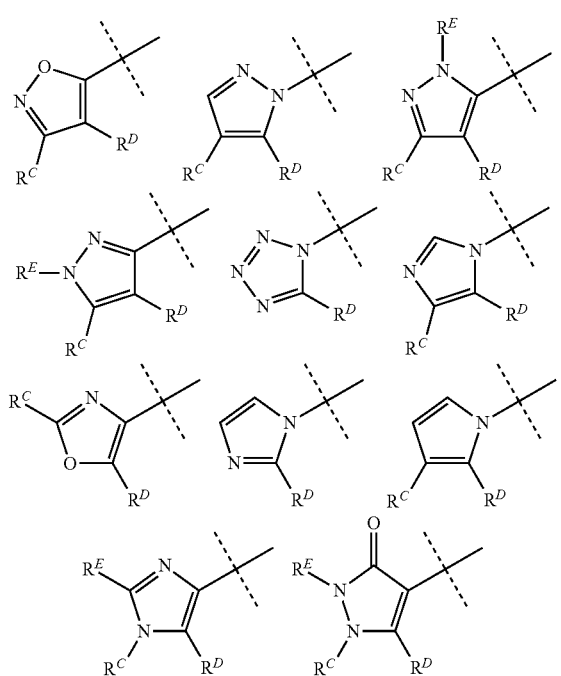

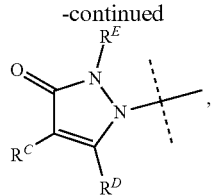

wherein $R^C$ is —H, —CN, —F, —Cl, —Br, —I, —OC$_1$-C$_4$ alkyl, C$_1$-C$_4$ alkyl, C$_3$-C$_6$ cycloalkyl, or C$_1$-C$_4$ fluoroalkyl;

$R^D$ is —N(R$^F$)C(=O)XCH(R$^G$)—CY, —N(R$^F$)C(=O)XC(R$^G$)$_2$—CY, or —N(R$^F$)C(=O)X—CY; wherein X is absent, —O—, —NH— or —CH$_2$—;

$R^E$ is —H or C$_1$-C$_4$ alkyl, C$_3$-C$_6$ cycloalkyl or C$_1$-C$_4$ fluoroalkyl;

$R^F$ is —H, C$_1$-C$_4$ alkyl or —C$_3$-C$_6$ cycloalkyl;

$R^G$ is independently selected $R^E$, or one $R^G$ is —C$_1$-C$_4$ alkyl and is taken together with CY and the carbon atom to which $R^G$ and CY is attached to define a substituted or unsubstituted carbocycle or a substituted or unsubstituted heterocycle, and the other $R^G$, if present, is as defined for $R^E$;

CY is substituted or unsubstituted C$_1$-C$_6$ alkyl, substituted or unsubstituted C$_3$-C$_{10}$ cycloalkyl, substituted or unsubstituted C$_2$-C$_{10}$ heterocycloalkyl, substituted or unsubstituted aryl, or a substituted or unsubstituted heteroaryl, wherein if CY is substituted then CY is substituted with 1, 2, or 3 independently selected $R^H$;

$R^H$ is independently —H, halogen, —CN, —NO$_2$, —OH, —OR$^J$, —SR$^J$, —S(=O)R$^J$, —S(=O)$_2$R$^J$, —N(R$^J$)S(=O)$_2$R$^J$, —S(=O)$_2$N(R$^L$)$_2$, —C(=O)R$^J$, —OC(=O)R$^J$, —C(=O)OR$^J$, —OC(=O)OR$^J$, —N(R$^L$)$_2$, —C(=O)N(R$^L$)$_2$, —OC(=O)N(R$^L$)$_2$, NR$^J$C(=O)N(R$^L$)$_2$, —NR$^J$C(=O)R$^J$, —NR$^J$C(=O)OR$^J$, C$_1$-C$_4$ alkyl, C$_1$-C$_4$ fluoroalkyl, C$_1$-C$_4$ fluoroalkoxy, C$_1$-C$_4$ alkoxy, and C$_1$-C$_4$ heteroalkyl;

wherein each $R^J$ is independently substituted or unsubstituted C$_1$-C$_6$ alkyl, substituted or unsubstituted C$_1$-C$_6$ heteroalkyl, substituted or unsubstituted C$_1$-C$_6$ fluoroalkyl, substituted or unsubstituted C$_3$-C$_6$ cycloalkyl, substituted or unsubstituted heterocycloalkyl, substituted or unsubstituted aryl, substituted or unsubstituted heteroaryl, —C$_1$-C$_4$ alkylene-(substituted or unsubstituted C$_3$-C$_6$ cycloalkyl), —C$_1$-C$_4$ alkylene-(substituted or unsubstituted heterocycloalkyl), —C$_1$-C$_4$ alkylene-(substituted or unsubstituted aryl), or C$_1$-C$_4$ alkylene-(substituted or unsubstituted heteroaryl);

wherein each $R^L$ is independently —H, substituted or unsubstituted C$_1$-C$_6$ alkyl, substituted or unsubstituted C$_1$-C$_6$ heteroalkyl, substituted or unsubstituted C$_1$-C$_6$ fluoroalkyl, substituted or unsubstituted C$_3$-C$_6$ cycloalkyl, substituted or unsubstituted heterocycloalkyl, substituted or unsubstituted aryl, substituted or unsubstituted heteroaryl, —C$_1$-C$_4$ alkylene-(substituted or unsubstituted C$_3$-C$_6$ cycloalkyl), —C$_1$-C$_4$ alkylene-(substituted or unsubstituted heterocycloalkyl), —C$_1$-C$_4$ alkylene(substituted or unsubstituted aryl), or —C$_1$-C$_4$ alkylene-(substituted or unsubstituted heteroaryl), or when $R^H$ is —S(=O)$_2$N(R$^L$)$_2$, —N(R$^L$)$_2$, —C(=O)N(R$^L$)$_2$, —OC(=O)N(R$^L$)$_2$ or —N(R$^J$)C(=O)N(R$^L$)$_2$, each $R^L$ is independently —H or C$_1$-C$_6$ alkyl, or the $R^L$ groups independently are C$_1$-C$_6$ alkyl which are taken together with the N atom to which they are attached to define a substituted or unsubstituted heterocycle, or when W or Z is —C(R$^L$)$_2$—, each R$^L$ is independently —H or C$_1$-C$_6$ alkyl, or the R$^L$ groups independently are C$_1$-C$_6$ alkyl which are taken together with the carbon atom to which they are attached to define a carbocycle.

wherein when A$^1$ is =CH—, L$^1$ is —UV—Z, wherein —UV— is —N(R$^J$)C(=O)—, and R$^C$ is —H, —CH$_3$ or —CF$_3$, then Ring A has the structure of one of:

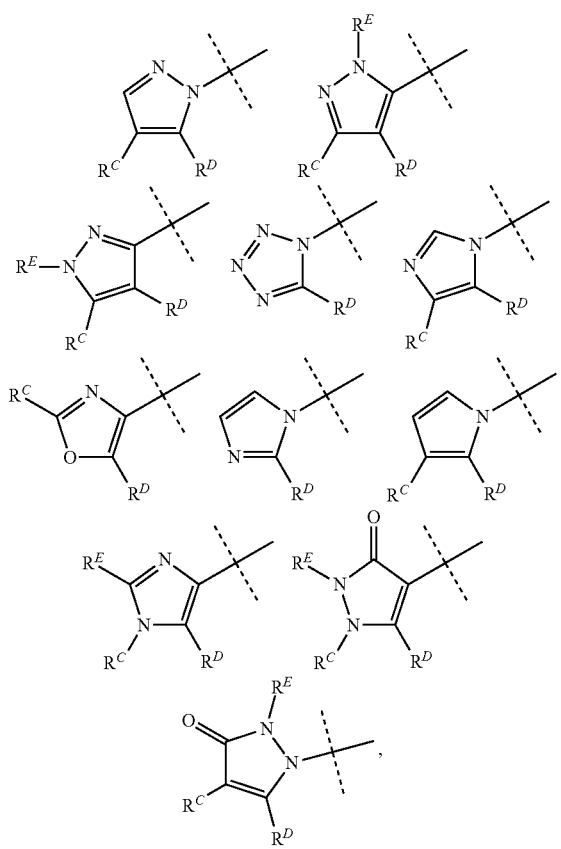

Particularly preferred Formula V compounds have L$^1$ defined as UV—Z— wherein —UV— is defined by —WO—, —WN(R$^J$)—, or —C(=O)N(R$^J$)—, wherein W is —CH$_2$—, Z is substituted or unsubstituted C$_1$-C$_6$ alkylene, R$^A$ is —CO$_2$H, and R$^D$ is —N(R$^F$)C(=O)OCH(R$^G$)—CY.

18. A compound of Formula VI having the structure:

Formula VI

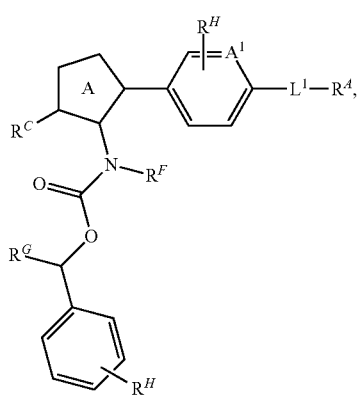

or a pharmaceutically acceptable salt or prodrug thereof, wherein R$^A$ is —CO$_2$H, —CO$_2$R$^B$, —CN, tetrazolyl, —C(=O)NH$_2$, —C(=O)NHR$^B$, —C(=O)NHSO$_2$R$^B$ or —C(=O)NHCH$_2$CH$_2$SO$_3$H or a carboxylic acid isostere, wherein R$^B$ is optionally substituted C$_1$-C$_4$ alkyl or has the structure of one of:

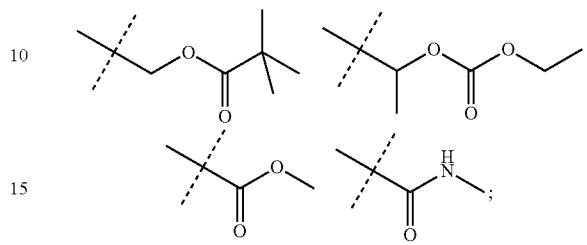

L$^1$ is UV—Z— wherein —UV— is defined by —OW—, —WO—, —N(R$^J$)W—, —WN(R$^J$)—, —N(R$^J$)C(=O)—, —SW—, —S(=O)$_n$W—, or —C(=O)N(R$^J$)—, wherein W is substituted or unsubstituted C$_1$-C$_3$ alkylene or W is —C(R$^L$)$_2$—, Z is substituted or unsubstituted C$_1$-C$_6$ alkylene or substituted or unsubstituted C$_1$-C$_6$ fluoroalkylene or Z is —C(R$^L$)$_2$—; and n is 0, 1, or 2;

A$^1$ is independently =N— or =CH—;

Ring A is a 5 membered heteroarene having one of the structures of:

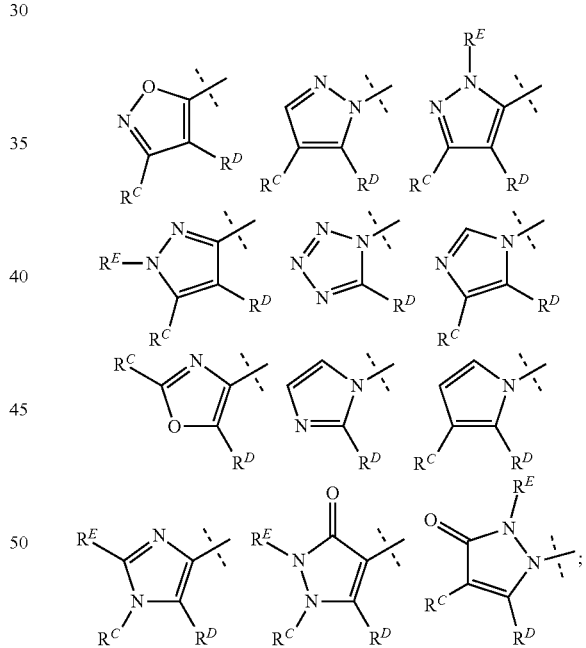

wherein R$^C$ is defined as —H, —CN, —F, —Cl, —Br, —I, —OC$_1$-C$_4$ alkyl, C$_1$-C$_4$ alkyl, C$_3$-C$_6$ cycloalkyl, or C$_1$-C$_4$ fluoroalkyl;

wherein R$^D$ is the —N(R$^F$)C(=O)CH(R$^G$)—CY substituent of Formula VI wherein CY is phenyl substituted with one R$^H$;

R$^G$ is independently selected R$^E$, or one R$^G$ is —C$_1$-C$_4$ alkyl and is taken together with CY and the carbon atom to which R$^G$ and CY is attached to define a substituted or unsubstituted carbocycle or a substituted or unsubstituted heterocycle, and the other R$^G$, if present, is as defined for R$^E$;

$R^F$ is —H, —$C_1$-$C_4$ alkyl or —$C_3$-$C_6$ cycloalkyl;

$R^H$ is independently selected from —H, halogen, —CN, —$NO_2$, —OH, —$OR^J$, —$SR^J$, —S(=O)$R^J$, —S(=O)$_2R^J$, —N($R^J$)S(=O)$_2R^J$, —S(=O)$_2$N($R^L$)$_2$, —C(=O)R, OC(=O)$R^J$, —$CO_2R^J$, —OC(=O)OR, —N($R^J$)$_2$, —C(=O)N($R^L$)$_2$, —OC(=O)N($R^L$)$_2$, N($R^J$)C(=O)N($R^L$)$_2$, —N($R^J$)C(=O)R, —N($R^J$)C(=O)$OR^J$, $C_1$-$C_4$ alkyl, $C_1$-$C_4$ fluoroalkyl, $C_1$-$C_4$ fluoroalkoxy, $C_1$-$C_4$ alkoxy, and $C_1$-$C_4$ heteroalkyl;

wherein $R^J$ is substituted or unsubstituted $C_1$-$C_6$ alkyl, substituted or unsubstituted $C_1$-$C_6$ heteroalkyl, substituted or unsubstituted $C_1$-$C_6$ fluoroalkyl, substituted or unsubstituted $C_3$-$C_6$ cycloalkyl, substituted or unsubstituted heterocycloalkyl, substituted or unsubstituted aryl, a substituted or unsubstituted heteroaryl, —$C_1$-$C_4$ alkylene-(substituted or unsubstituted $C_3$-$C_6$ cycloalkyl), —$C_1$-$C_4$ alkylene-(substituted or unsubstituted heterocycloalkyl), —$C_1$-$C_4$ alkylene-(substituted or unsubstituted aryl), or $C_1$-$C_4$ alkylene-(substituted or unsubstituted heteroaryl);

wherein each $R^L$ is independently —H, substituted or unsubstituted $C_1$-$C_6$ alkyl, substituted or unsubstituted $C_1$-$C_6$ heteroalkyl, substituted or unsubstituted $C_1$-$C_6$ fluoroalkyl, substituted or unsubstituted $C_3$-$C_6$ cycloalkyl, substituted or unsubstituted heterocycloalkyl, substituted or unsubstituted aryl, substituted or unsubstituted heteroaryl, —$C_1$-$C_4$ alkylene-(substituted or unsubstituted cycloalkyl), —$C_1$-$C_4$ alkylene-(substituted or unsubstituted heterocycloalkyl), —$C_1$-$C_4$ alkylene(substituted or unsubstituted aryl), or —$C_1$-$C_4$ alkylene-(substituted or unsubstituted heteroaryl), or when $R^H$ is —S(=O)$_2$N($R^L$)$_2$, —N($R^L$)$_2$, —C(=O)N($R^L$)$_2$, —OC(=O)N($R^L$)$_2$ or N($R^J$)C(=O)N($R^L$)$_2$, each $R^L$ is independently —H or $C_1$-$C_6$ alkyl, or the $R^L$ groups independently are $C_1$-$C_6$ alkyl which are taken together with the N atom to which they are attached to define a substituted or unsubstituted heterocycle, or when W or Z is —C($R^L$)$_2$—, each $R^L$ is independently —H or $C_1$-$C_6$ alkyl, or the $R^L$ groups independently are $C_1$-$C_6$ alkyl which are taken together with the carbon atom to which they are attached to define a carbocycle.

In preferred embodiments Ring A has the structure of one of:

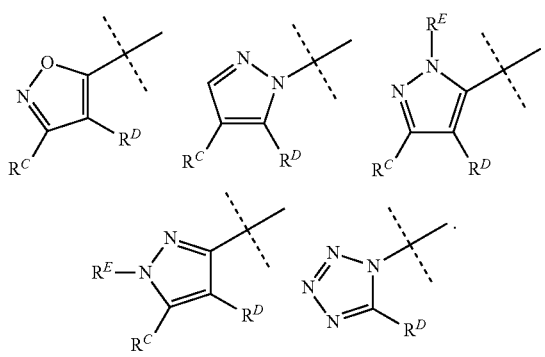

Particularly preferred Formula VI compounds have $L^1$ as —UV—Z— wherein —UV— is —C(=O)NH—, —$CH_2$O— or —$CH_2$NH—, Z is substituted —CH—, and $R^A$ is —$CO_2$H.

19. A compound of Formula VII having the structure of:

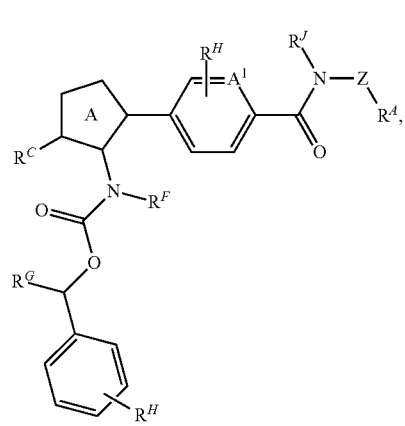

Formula VII or a pharmaceutically acceptable salt or prodrug thereof, wherein $R^A$ is —$CO_2$H, —$CO_2R^B$, —CN, tetrazolyl, —C(=O)$NH_2$, —C(=O)$NHR^B$, —C(=O)$NHSO_2R^B$ or —C(=O)$NHCH_2CH_2SO_3$H or a carboxylic acid isostere;

$R^B$ is optionally substituted $C_1$-$C_4$ alkyl or has the structure of one of:

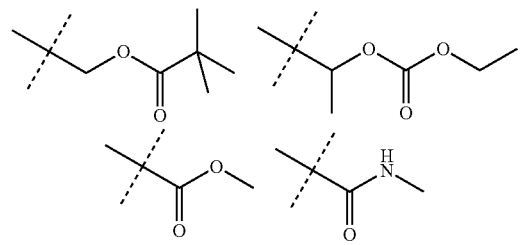

$A^1$ is independently =N— or =CH—;
Ring A has the structure of one of:

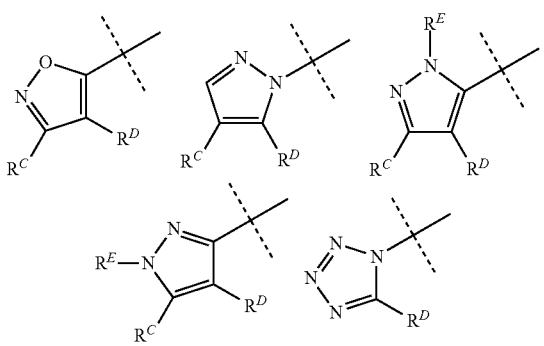

$R^C$ is —H, —CN, —F, —Cl, —Br, —I, —O$C_1$-$C_4$ alkyl, $C_1$-$C_4$ alkyl, $C_3$-$C_6$ cycloalkyl, or $C_1$-$C_4$ fluoroalkyl;

wherein $R^D$ is the —N($R^F$)C(=O)CH($R^G$)—CY substituent of Formula VII wherein CY is phenyl substituted with one $R^H$;

$R^E$, $R^F$ and $R^G$ independently are —H or $C_1$-$C_4$ alkyl;
Z is —C($R^L$)$_2$—;
$R^H$ is independently —H, halogen, —CN, —$NO_2$, —OH, —$OR^J$, —$SR^J$, —S(=O)$R^J$, —S(=O)$_2$R, —N($R^J$) S(=O)$_2R^J$, —S(=O)$_2$N($R^L$)$_2$, —C(=O)$R^J$, —OC(=O) $R^J$, —$CO_2R^J$, —OC$O_2R^J$, —N($R^L$)$_2$, —C(=O)N($R^L$)$_2$, —OC(=O)N($R^L$)$_2$, $NR^J$C(=O)N($R^L$)$_2$, —$NR^J$C(=O)$R^J$, —NR$^J$C(=O)OR$^J$, C$_1$-C$_4$ alkyl, C$_1$-C$_4$ fluoroalkyl, C$_1$-C$_4$ fluoroalkoxy, C$_1$-C$_4$ alkoxy, and C$_1$-C$_4$ heteroalkyl;

R$^J$ is substituted or unsubstituted C$_1$-C$_6$ alkyl, substituted or unsubstituted C$_1$-C$_6$ heteroalkyl, C$_1$-C$_6$ fluoroalkyl, substituted or unsubstituted C$_3$-C$_6$ cycloalkyl, substituted or unsubstituted heterocycloalkyl, substituted or unsubstituted aryl, substituted or unsubstituted heteroaryl, —C$_1$-C$_4$ alkylene-(substituted or unsubstituted C$_3$-C$_6$ cycloalkyl), —C$_1$-C$_4$ alkylene-(substituted or unsubstituted heterocycloalkyl), —C$_1$-C$_4$ alkylene-(substituted or unsubstituted aryl), or C$_1$-C$_4$ alkylene-(substituted or unsubstituted heteroaryl);

R$^L$ is —H, substituted or unsubstituted C$_1$-C$_6$ alkyl, substituted or unsubstituted C$_1$-C$_6$ heteroalkyl, substituted or unsubstituted C$_1$-C$_6$ fluoroalkyl, substituted or unsubstituted C$_3$-C$_6$ cycloalkyl, substituted or unsubstituted heterocycloalkyl, substituted or unsubstituted aryl, substituted or unsubstituted heteroaryl, —C$_1$-C$_4$ alkylene-(substituted or unsubstituted C$_3$-C$_6$ cycloalkyl), —C$_1$-C$_4$ alkylene-(substituted or unsubstituted heterocycloalkyl), —C$_1$-C$_4$ alkylene(substituted or unsubstituted aryl), or —C$_1$-C$_4$ alkylene-(substituted or unsubstituted heteroaryl), or when R$^H$ is —S(=O)$_2$N(R$^L$)$_2$, —N(R$^L$)$_2$, —C(=O)N(R$^L$)$_2$, —OC(=O)N(R$^L$)$_2$ or —N(R$^J$)C(=O)N(R$^L$)$_2$, each R$^L$ is independently —H or C$_1$-C$_6$ alkyl, or the R$^L$ groups independently are C$_1$-C$_6$ alkyl which are taken together with the N atom to which they are attached to define a substituted or unsubstituted heterocycle, or each R$^L$ in Z is independently —H or C$_1$-C$_6$ alkyl, or the R$^L$ groups independently are C$_1$-C$_6$ alkyl which are taken together with the carbon atom to which they are attached to define a carbocycle.

In some embodiments, Formula VII compounds have R$^F$ defined as —H, C$_1$-C$_4$ alkyl or C$_1$-C$_6$ cycloalkyl and each R$^H$R$^J$ and R$^L$ are as previously defined;

In particularly preferred Formula VII compounds R$^A$ is —CO$_2$H.

20. A compound of Formula VIII having the structure:

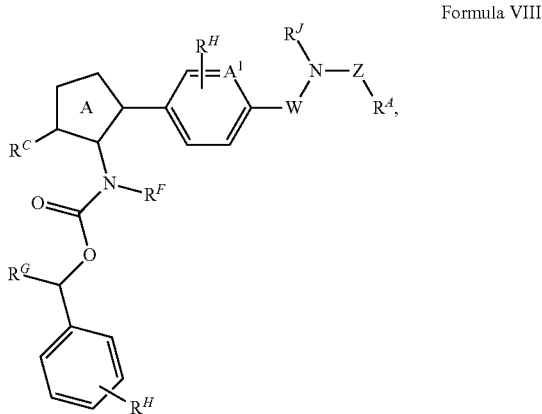

Formula VIII or a pharmaceutically acceptable salt or prodrug thereof,
wherein R$^A$ is —CO$_2$H, —CO$_2$R$^B$, —CN, tetrazolyl, —C(=O)NH$_2$, —C(=O)NHR$^B$, —C(=O)NHSO$_2$R$^B$ or —C(=O)NHCH$_2$CH$_2$SO$_3$H or a carboxylic acid isostere;

R$^B$ is optionally substituted C$_1$-C$_4$ alkyl or has the structure of one of:

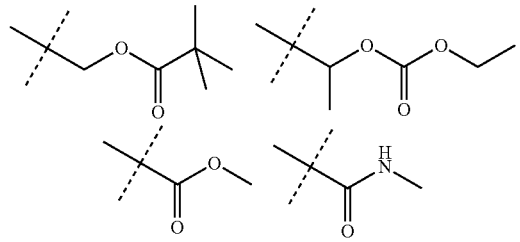

A$^1$ is =N— or =CH—;
Ring A has the structure of one of:

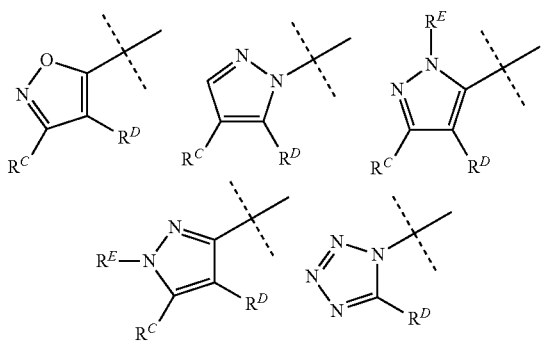

R$^C$—H, —CN, —F, —Cl, —Br, —I, —OC$_1$-C$_4$ alkyl, C$_1$-C$_4$ alkyl, C$_3$-C$_6$ cycloalkyl, or C$_1$-C$_4$ fluoroalkyl;
wherein R$^D$ is the —N(R$^F$)C(=O)CH(R$^G$)—CY substituent of Formula VII wherein CY is phenyl substituted with one R$^H$;

R$^F$ and R$^E$ independently are —H or C$_1$-C$_4$ alkyl or C$_3$-C$_6$ cycloalkyl;

R$^G$ is —H or C$_1$-C$_4$ alkyl or is C$_1$-C$_4$ alkyl that is taken together with the the R$^H$ phenyl moiety of the Ring A R$^D$ substituent and the carbon atom to which R$^G$ and said phenyl moiety is attached to define a carbocycle;

W is —C(R$^L$)$_2$—;
Z is —C(R$^L$)$_2$—;
R$^H$ is —H, halogen, —CN, —NO$_2$, —OH, —OR$^J$, —SR$^J$, —S(=O)R$^J$, —S(=O)$_2$R$^J$, —N(R$^J$)S(=O)$_2$R, —S(=O)$_2$N(R$^L$)$_2$, —C(=O)R$^J$, —OC(=O)R$^J$, —CO$_2$R$^J$, —OCO$_2$R$^J$, —N(R$^L$)$_2$, —C(=O)N(R$^L$)$_2$, —OC(=O)N(R$^L$)$_2$, NR$^J$C(=O)N(R$^L$)$_2$, —NR$^J$C(=O)R$^J$, —NR$^J$C(=O)OR$^J$, C$_1$-C$_4$ alkyl, C$_1$-C$_4$ fluoroalkyl, C$_1$-C$_4$ fluoroalkoxy, C$_1$-C$_4$ alkoxy, and C$_1$-C$_4$ heteroalkyl;

R$^J$ is substituted or unsubstituted C$_1$-C$_6$ alkyl, substituted or unsubstituted C$_1$-C$_6$ heteroalkyl, is substituted or unsubstituted C$_1$-C$_6$ fluoroalkyl, substituted or unsubstituted C$_3$-C$_6$ cycloalkyl, substituted or unsubstituted heterocycloalkyl, substituted or unsubstituted aryl, substituted or unsubstituted heteroaryl, —C$_1$-C$_4$ alkylene-(substituted or unsubstituted C$_3$-C$_6$ cycloalkyl), —C$_1$-C$_4$ alkylene-(substituted or unsubstituted heterocycloalkyl), —C$_1$-C$_4$ alkylene-(substituted or unsubstituted aryl), or C$_1$-C$_4$ alkylene-(substituted or unsubstituted heteroaryl);

R$^L$ independently are —H, substituted or unsubstituted C$_1$-C$_6$ alkyl, substituted or unsubstituted C$_1$-C$_6$ heteroalkyl, substituted or unsubstituted C$_1$-C$_6$ fluoroalkyl, substituted or unsubstituted C$_3$-C$_6$ cycloalkyl, substituted or unsubstituted heterocycloalkyl, substituted or unsubstituted aryl, substituted or unsubstituted heteroaryl, —C$_1$-C$_4$ alkylene-(substituted or unsubstituted C$_3$-C$_6$ cycloalkyl), —C$_1$-C$_4$ alkylene- (substituted or unsubstituted heterocycloalkyl), —C₁-C₄ alkylene(substituted or unsubstituted aryl), or —C₁-C₄ alkylene-(substituted or unsubstituted heteroaryl), or when $R^H$ is —S(=O)₂N($R^L$)₂, —N($R^L$)₂, —C(=O)N($R^L$)₂, —OC(=O)N($R^L$)₂ or —N($R^J$)C(=O)N($R^L$)₂, each $R^L$ is independently —H or C₁-C₆ alkyl, or the $R^L$ groups independently are C₁-C₆ alkyl which are taken together with the N atom to which they are attached to define a substituted or unsubstituted heterocycle, or each $R^L$ is in W or Z independently —H or C₁-C₆ alkyl, or the $R^L$ groups independently are C₁-C₆ alkyl which are taken together with the carbon atom to which they are attached to define a carbocycle.

In some embodiments, Formula VIII compounds have $R^F$ defined as —H, C₁-C₄ alkyl or C₃-C₆ cycloalkyl.

In particularly preferred Formula VIII compounds $R^A$ is —CO₂H and $R^J$ is —H.

21. A compound of Formula IX having the structure:

Formula IX

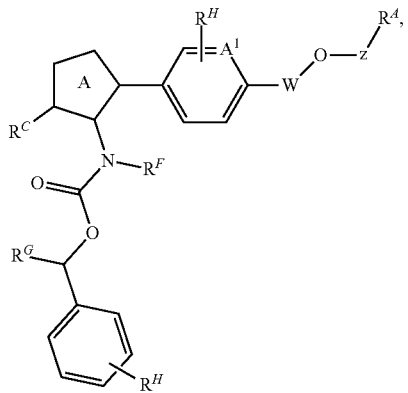

or a pharmaceutically acceptable salt or prodrug thereof, wherein $R^A$ is —CO₂H, —CO₂$R^B$, —CN, tetrazolyl, —C(=O)NH₂, —C(=O)NH$R^B$, C(=O)NHSO₂$R^B$ or —C(=O)NHCH₂CH₂SO₃H or a carboxylic acid isostere;

$R^B$ is optionally substituted C₁-C₄ alkyl or has the structure of one of:

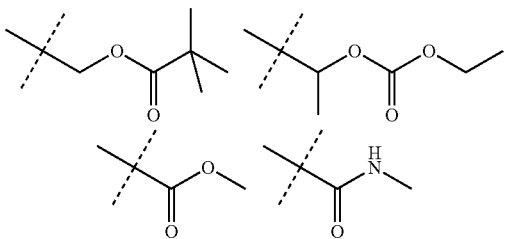

Ring has the structure of one of:

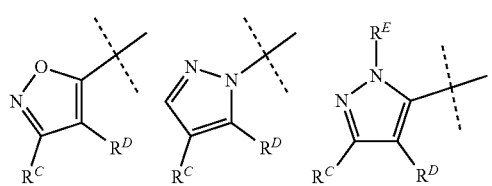

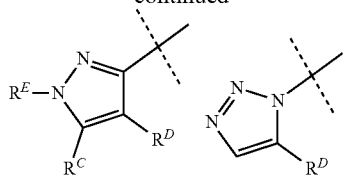

$R^C$—H, —CN, —F, —Cl, —Br, —I, —OC₁-C₄ alkyl, C₁-C₄ alkyl, C₃-C₆ cycloalkyl, or C₁-C₄ fluoroalkyl;

wherein $R^D$ is the —N($R^F$)C(=O)CH($R^G$)—CY substituent in Formula IX wherein CY is phenyl substituted with one $R^H$;

$R^E$, $R^F$ and $R^G$ independently are —H, C₁-C₄ alkyl or C₁-C₆ cycloalkyl or $R^E$ and $R^F$ independently are —H, C₁-C₄ alkyl or C₁-C₆ cycloalkyl and $R^G$ is C₁-C₄ alkyl that is taken together with the the $R^H$ phenyl moiety of the Ring A $R^D$ substituent and the carbon atom to which $R^G$ and said phenyl moiety is attached to define a carbocycle;

$R^H$ is independently —H, halogen, —CN, —NO₂, —OH, —O$R^J$, —S$R^J$, —S(=O)$R^J$, —S(=O)₂R, —N($R^J$)S(=O)₂$R^J$, —S(=O)₂N($R^L$)₂, —C(=O)R, —OC(=O)$R^J$, —CO₂$R^J$, —OCO₂$R^J$, —N($R^L$)₂, —C(=O)N($R^L$)₂, —OC(=O)N($R^L$)₂, N$R^J$C(=O)N($R^L$)₂, —N$R^J$C(=O)$R^J$, —N$R^J$C(=O)O$R^J$, C₁-C₄ alkyl, C₁-C₄ fluoroalkyl, C₁-C₄ fluoroalkoxy, C₁-C₄ alkoxy, and C₁-C₄ heteroalkyl;

$R^J$ is substituted or unsubstituted C₁-C₆ alkyl, substituted or unsubstituted C₁-C₆ heteroalkyl, substituted or unsubstituted C₁-C₆ fluoroalkyl, substituted or unsubstituted C₃-C₆ cycloalkyl, substituted or unsubstituted heterocycloalkyl, substituted or unsubstituted aryl, substituted or unsubstituted heteroaryl, —C₁-C₄ alkylene-(substituted or unsubstituted C₃-C₆ cycloalkyl), —C₁-C₄ alkylene-(substituted or unsubstituted heterocycloalkyl), —C₁-C₄ alkylene-(substituted or unsubstituted aryl), or C₁-C₄ alkylene-(substituted or unsubstituted heteroaryl);

W is —C($R^L$)₂—;
Z is —C($R^L$)₂—;

$R^L$ independently are —H, substituted or unsubstituted C₁-C₆ alkyl, substituted or unsubstituted C₁-C₆ heteroalkyl, substituted or unsubstituted C₁-C₆ fluoroalkyl, substituted or unsubstituted C₃-C₆ cycloalkyl, substituted or unsubstituted heterocycloalkyl, substituted or unsubstituted aryl, substituted or unsubstituted heteroaryl, —C₁-C₄ alkylene-(substituted or unsubstituted C₃-C₆ cycloalkyl), —C₁-C₄ alkylene-(substituted or unsubstituted heterocycloalkyl), —C₁-C₄ alkylene(substituted or unsubstituted aryl), or —C₁-C₄ alkylene-(substituted or unsubstituted heteroaryl), or each $R^L$ in W or Z independently are C₁-C₆ alkyl which are taken together with the carbon atom to which they are attached to define a carbocycle.

In preferred Formula IX compounds $R^A$ is —CO₂H.

22. A compound of Formula X having the structure:

Formula X

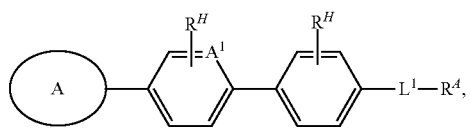

or a pharmaceutically acceptable salt or prodrug thereof, wherein $R^A$ is —CO₂H, —CO₂$R^B$, —CN, tetrazolyl, —C(=O)NH₂, —C(=O)NH$R^B$, C(=O)NHSO₂$R^B$ or —C(=O)NHCH₂CH₂SO₃H or a carboxylic acid isostere;

$R^B$ is optionally substituted $C_1$-$C_4$ alkyl or has the structure of one of:

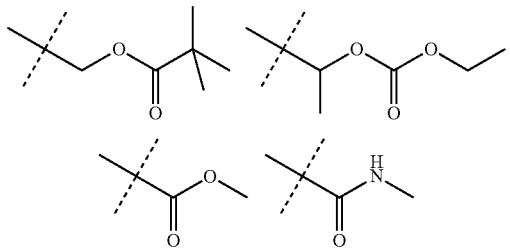

$L^1$ is absent or optionally substituted $C_1$-$C_6$ alkylene; $C_1$-$C_6$ fluoroalkylene; or optionally substituted $C_1$-$C_6$ heteroalkylene or $L^1$, when present is —$CH_2$—,

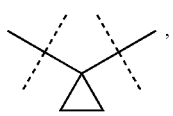

or disubstituted dimethylmethane.

$A^1$ is =N— or =CH—;

Ring A has the structure of one of:

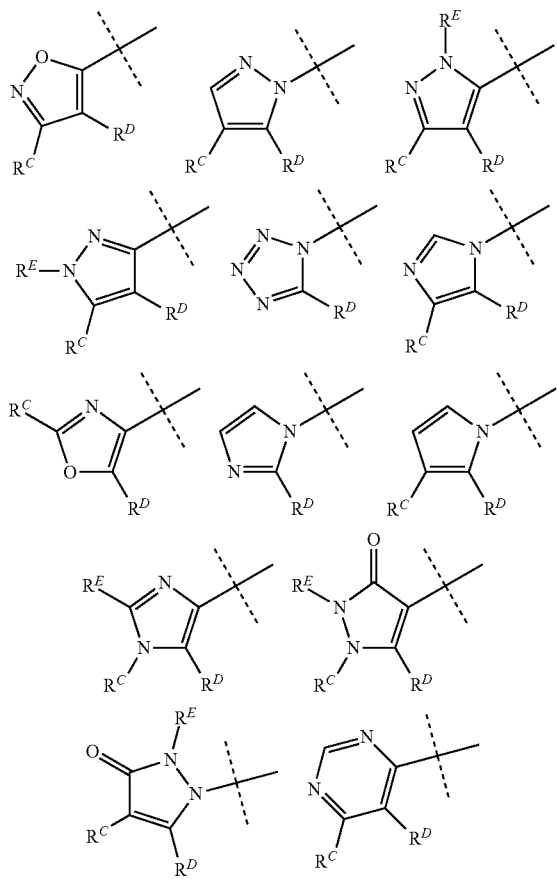

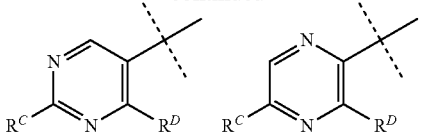

$R^C$ is —H, —CN, —F, —Cl, —Br, —I, —$OC_1$-$C_4$ alkyl, $C_1$-$C_4$ alkyl, $C_3$-$C_6$ cycloalkyl, or $C_1$-$C_4$ fluoroalkyl;

$R^D$ is —$NR^F$C(=O)XCH($R^G$)—CY, —$NR^F$C(=O)XC($R^G$)$_2$—CY, or —$NR^F$C(=O)X—CY; where X is absent, —O—, —NH— or —$CH_2$—;

$R^E$, $R^F$ and $R^G$ independently are —H or $C_1$-$C_4$ alkyl or $C_3$-$C_6$ cycloalkyl or $R^E$ and $R^F$ independently are —H, $C_1$-$C_4$ alkyl or $C_1$-$C_6$ cycloalkyl and one $R^G$ is $C_1$-$C_4$ alkyl and is taken together with CY and the carbon atom to which $R^G$ and CY are attached to define a substituted or unsubstituted carbocycle or a substituted or unsubstituted heterocycle, and the other $R^G$, if present, is as defined for $R^E$;

$R^H$ is —H, halogen, —CN, —$NO_2$, —OH, —$OR^J$, —$SR^J$, —S(=O)$R^J$, —S(=O)$_2R^J$, —N($R^J$)S(=O)$_2$R, —S(=O)$_2$N($R^L$)$_2$, —C(=O)$R^J$, —OC(=O)$R^J$, —$CO_2R^J$, —$OCO_2R^J$, —N($R^L$)$_2$, —C(=O)N($R^L$)$_2$, —OC(=O)N($R^L$)$_2$, $NR^J$C(=O)N($R^L$)$_2$, —$NR^J$C(=O)$R^J$, —$NR^J$C(=O)$OR^J$, $C_1$-$C_4$ alkyl, $C_1$-$C_4$ fluoroalkyl, $C_1$-$C_4$ fluoroalkoxy, $C_1$-$C_4$ alkoxy, and $C_1$-$C_4$ heteroalkyl;

$R^J$ is substituted or unsubstituted $C_1$-$C_6$ alkyl, substituted or unsubstituted $C_1$-$C_6$ heteroalkyl, substituted or unsubstituted $C_1$-$C_6$ fluoroalkyl, substituted or unsubstituted $C_3$-$C_6$ cycloalkyl, substituted or unsubstituted heterocycloalkyl, substituted or unsubstituted aryl, substituted or unsubstituted heteroaryl, —$C_1$-$C_4$ alkylene-(substituted or unsubstituted $C_3$-$C_6$ cycloalkyl), —$C_1$-$C_4$ alkylene-(substituted or unsubstituted heterocycloalkyl), —$C_1$-$C_4$ alkylene-(substituted or unsubstituted aryl), or $C_1$-$C_4$ alkylene-(substituted or unsubstituted heteroaryl);

$R^L$ independently are —H, substituted or unsubstituted $C_1$-$C_6$ alkyl, substituted or unsubstituted $C_1$-$C_6$ heteroalkyl, substituted or unsubstituted $C_1$-$C_6$ fluoroalkyl, substituted or unsubstituted $C_3$-$C_6$ cycloalkyl, substituted or unsubstituted heterocycloalkyl, substituted or unsubstituted aryl, substituted or unsubstituted heteroaryl, —$C_1$-$C_4$ alkylene-(substituted or unsubstituted $C_3$-$C_6$ cycloalkyl), —$C_1$-$C_4$ alkylene-(substituted or unsubstituted heterocycloalkyl), —$C_1$-$C_4$ alkylene(substituted or unsubstituted aryl), or —$C_1$-$C_4$ alkylene-(substituted or unsubstituted heteroaryl), or when $R^H$ is —S(=O)$_2$N($R^L$)$_2$, —N($R^L$)$_2$, —C(=O)N($R^L$)$_2$, —OC(=O)N($R^L$)$_2$ or —N($R^J$)C(=O)N($R^L$)$_2$, each $R^L$ is independently —H or $C_1$-$C_6$ alkyl, or the $R^L$ groups independently are $C_1$-$C_6$ alkyl which are taken together with the N atom to which they are attached to define a substituted or unsubstituted heterocycle;

CY is substituted or unsubstituted $C_1$-$C_6$ alkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl, wherein if CY is substituted then CY is substituted with 1, 2, or 3 $R^H$, wherein when $L^1$ is not absent and $R^C$ is —H or —$CH_3$ and $R^A$ is —$CO_2$H or —$CO_2R^B$, then Ring A has the structure of one of:

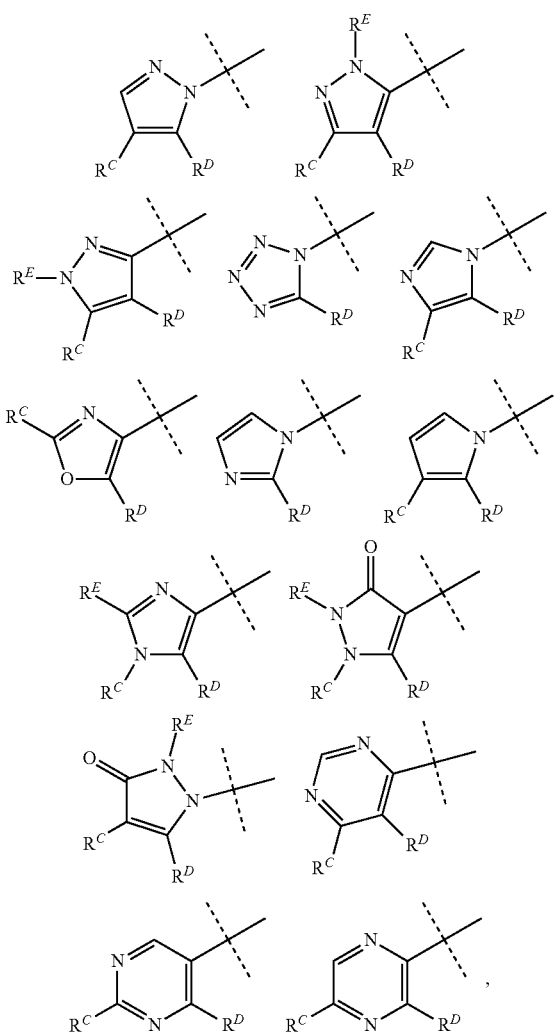

In preferred embodiments Ring A has the structure of one of:

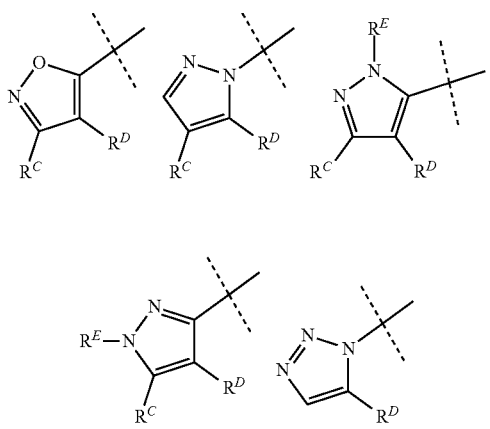

23. A compound of Formula XI having the structure:

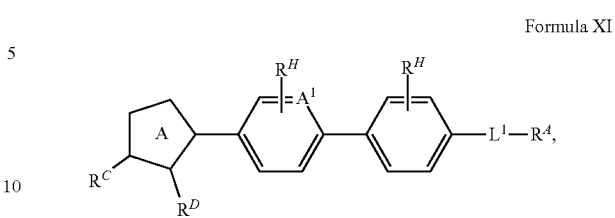

Formula XI or a pharmaceutically acceptable salt or prodrug thereof, wherein $R^A$ is —CO$_2$H, —CO$_2$R$^B$, —CN, tetrazolyl, —C(=O)NH$_2$, —C(=O)NHR$^B$, —C(=O)NHSO$_2$R$^B$ or —C(=O)NHCH$_2$CH$_2$SO$_3$H or a carboxylic acid isostere; $R^B$ is optionally substituted C$_1$-C$_4$ alkyl or has the structure of one of:

$L^1$ is absent or optionally substituted C$_1$-C$_6$ alkylene; C$_1$-C$_6$ fluoroalkylene; or optionally substituted C$_1$-C$_6$ heteroalkylene or $L^1$, when present is —CH$_2$—, or disubstituted dimethylmethane.
$A^1$ is =N— or =CH—;
Ring A has the structure of one of:

$R^C$ is —H, —CN, —F, —Cl, —Br, —I, —OC$_1$-C$_4$ alkyl, C$_1$-C$_4$ alkyl, C$_3$-C$_6$ cycloalkyl, or C$_1$-C$_4$ fluoroalkyl;
$R^D$ is —N(R$^F$)C(=O)XCH(R$^G$)—CY, —N(R$^F$)C(=O)XC(R$^G$)$_2$—CY, or —N(R$^F$)C(=O)X—CY; where X is absent, —O—, —NH— or —CH$_2$—;
$R^E$, $R^F$ and $R^G$ independently are —H or C$_1$-C$_4$ alkyl or C$_3$-C$_6$ cycloalkyl or $R^E$ and $R^F$ independently are —H or C$_1$-C$_4$ alkyl or C$_1$-C$_6$ cycloalkyl and one $R^G$ is C$_1$-C$_4$ alkyl and is taken together with CY and carbon atom to which $R^G$ and CY are attached to define a substituted or unsubstituted carbocycle or a substituted or unsubstituted heterocycle, and the other $R^G$, if present, is as defined for $R^E$;

$R^H$ is —H, halogen, —CN, —NO$_2$, —OH, —OR$^J$, —SR$^J$, —S(═O)R$^J$, —S(═O)$_2$R$^J$, —N(R$^J$)S(═O)$_2$R, —S(═O)$_2$N(R$^L$)$_2$, —C(═O)R$^J$, —OC(═O)R$^J$, —CO$_2$R$^J$, —OCO$_2$R$^J$, —N(R$^L$)$_2$, —C(═O)N(R$^L$)$_2$, —OC(═O)N(R$^L$)$_2$, NR$^J$C(═O)N(R$^L$)$_2$, —NR$^J$C(═O)R$^J$, —NR$^J$C(═O)OR$^J$, C$_1$-C$_4$ alkyl, C$_1$-C$_4$ fluoroalkyl, C$_1$-C$_4$ fluoroalkoxy, C$_1$-C$_4$ alkoxy, and C$_1$-C$_4$ heteroalkyl;

$R^J$ is substituted or unsubstituted C$_1$-C$_6$ alkyl, substituted or unsubstituted C$_1$-C$_6$ heteroalkyl, substituted or unsubstituted C$_1$-C$_6$ fluoroalkyl, substituted or unsubstituted C$_3$-C$_6$ cycloalkyl, substituted or unsubstituted heterocycloalkyl, substituted or unsubstituted aryl, substituted or unsubstituted heteroaryl, —C$_1$-C$_4$ alkylene-(substituted or unsubstituted C$_3$-C$_6$ cycloalkyl), —C$_1$-C$_4$ alkylene-(substituted or unsubstituted heterocycloalkyl), —C$_1$-C$_4$ alkylene-(substituted or unsubstituted aryl), or C$_1$-C$_4$ alkylene-(substituted or unsubstituted heteroaryl);

$R^L$ independently are —H, substituted or unsubstituted C$_1$-C$_6$ alkyl, substituted or unsubstituted C$_1$-C$_6$ heteroalkyl, substituted or unsubstituted C$_1$-C$_6$ fluoroalkyl, substituted or unsubstituted C$_3$-C$_6$ cycloalkyl, substituted or unsubstituted heterocycloalkyl, substituted or unsubstituted aryl, substituted or unsubstituted heteroaryl, —C$_1$-C$_4$ alkylene-(substituted or unsubstituted C$_3$-C$_6$ cycloalkyl), —C$_1$-C$_4$ alkylene-(substituted or unsubstituted heterocycloalkyl), —C$_1$-C$_4$ alkylene(substituted or unsubstituted aryl), or —C$_1$-C$_4$ alkylene-(substituted or unsubstituted heteroaryl), or when $R^H$ is —S(═O)$_2$N(R$^L$)$_2$, —N(R$^L$)$_2$, —C(═O)N(R$^L$)$_2$, —OC(═O)N(R$^L$)$_2$ or —N(R$^J$)C(═O)N(R$^L$)$_2$, each $R^L$ is independently —H or C$_1$-C$_6$ alkyl, or the $R^L$ groups independently are C$_1$-C$_6$ alkyl which are taken together with the N atom to which they are attached to define a substituted or unsubstituted heterocycle, CY is C$_1$-C$_6$ alkyl, a substituted or unsubstituted C$_3$-C$_{10}$ cycloalkyl, a substituted or unsubstituted C$_2$-C$_{10}$ heterocycloalkyl, a substituted or unsubstituted aryl, or a substituted or unsubstituted heteroaryl, wherein if CY is substituted then CY is substituted with 1, 2, or 3 $R^H$, wherein when $L^1$ is not absent and $R^C$ is —H or —CH$_3$ and $R^A$ is —CO$_2$H or —CO$_2$R$^B$, then Ring A has the structure of one of:

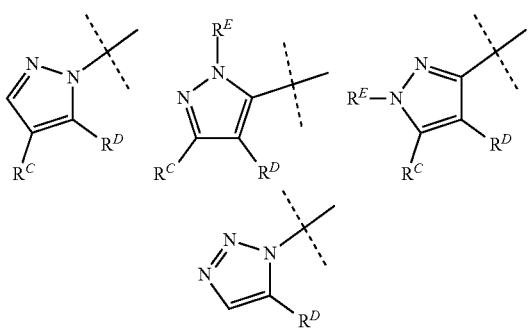

In particularly preferred Formula XI compounds $R^A$ is —CO$_2$H, and $R^D$ is —NR$^F$C(═O)OCH(R$^G$)—CY.

24. A compound of Formula XII having the structure:

Formula XII

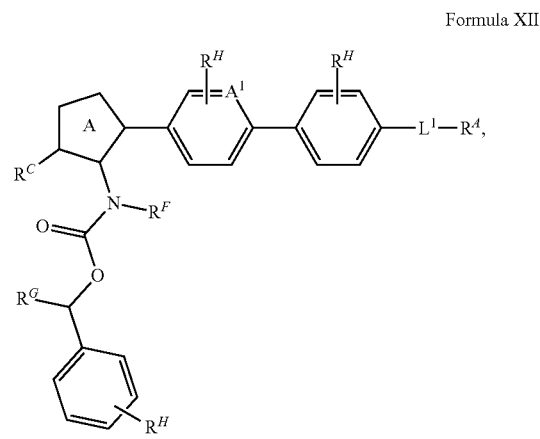

or a pharmaceutically acceptable salt or prodrug thereof, wherein $R^A$ is —CO$_2$H, —CO$_2$R$^B$, —CN, tetrazolyl, —C(═O)NH$_2$, —C(═O)NHR$^B$, C(═O)NHSO$_2$R$^B$ or —C(═O)NHCH$_2$CH$_2$SO$_3$H or a carboxylic acid isostere;

$R^B$ is optionally substituted C$_1$-C$_4$ alkyl or has the structure of one of:

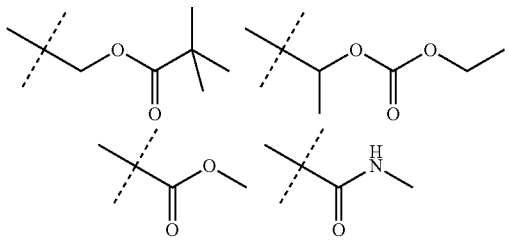

$L^1$ is absent or optionally substituted C$_1$-C$_6$ alkylene; C$_1$-C$_6$ fluoroalkylene; or optionally substituted C$_1$-C$_6$ heteroalkylene, or $L^1$, when present is —CH$_2$—,

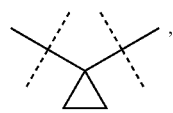

or disubstituted dimethylmethane.

$A^1$ is ═N— or ═CH—;

Ring A has the structure of one of:

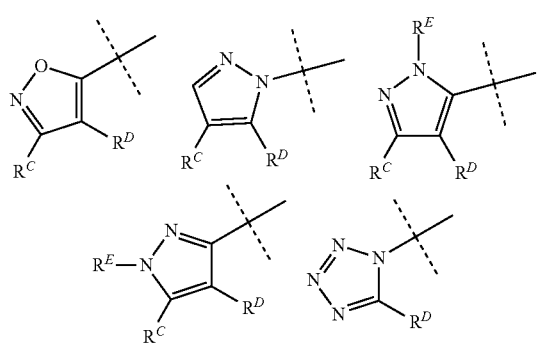

$R^C$ is —H, —CN, —F, —Cl, —Br, —I, —OC$_1$-C$_4$ alkyl, C$_1$-C$_4$ alkyl, C$_3$-C$_6$ cycloalkyl, or C$_1$-C$_4$ fluoroalkyl;

wherein $R^D$ is the —N(R$^F$)C(═O)CH(R$^G$)—CY substituent in Formula XII wherein CY is phenyl substituted with one R$^H$;

$R^E$, $R^F$ and $R^G$ independently are —H or C$_1$-C$_4$ alkyl or C$_3$-C$_6$ cycloalkyl or $R^E$ and $R^F$ independently are —H or C$_1$-C$_4$ alkyl or C$_1$-C$_6$ cycloalkyl and one $R^G$ is —C$_1$-C$_4$ alkyl and is taken together with the $R^H$ phenyl moiety of the Ring A $R^D$ substituent and the carbon atom to which $R^G$ and said phenyl moiety is attached to define a substituted or unsubstituted carbocycle or a substituted or unsubstituted heterocycle, and the other $R^G$, if present, is as defined for $R^E$;

$R^H$ is —H, halogen, —CN, —NO$_2$, —OH, —OR$^J$, —SR$^J$, —S(═O)R$^J$, —S(═O)$_2$R$^J$, —N(R$^J$)S(═O)$_2$R$^J$, —S(═O)$_2$N(R$^L$)$_2$, —C(═O)R$^J$, —OC(═O)R$^J$, —CO$_2$R$^J$, —OCO$_2$R$^J$, —N(R$^L$)$_2$, —C(═O)N(R$^L$)$_2$, —OC(═O)N(R$^L$)$_2$, NR$^J$C(═O)N(R$^L$)$_2$, —NR$^J$C(═O)R$^J$, —NR$^J$C(═O)OR$^J$, C$_1$-C$_4$ alkyl, C$_1$-C$_4$ fluoroalkyl, C$_1$-C$_4$ fluoroalkoxy, C$_1$-C$_4$ alkoxy, and C$_1$-C$_4$ heteroalkyl;

$R^J$ is substituted or unsubstituted C$_1$-C$_6$ alkyl, substituted or unsubstituted C$_1$-C$_6$ heteroalkyl, substituted or unsubstituted C$_1$-C$_6$ fluoroalkyl, substituted or unsubstituted C$_3$-C$_6$ cycloalkyl, substituted or unsubstituted heterocycloalkyl, substituted or unsubstituted aryl, substituted or unsubstituted heteroaryl, —C$_1$-C$_4$ alkylene-(substituted or unsubstituted C$_3$-C$_6$ cycloalkyl), —C$_1$-C$_4$ alkylene-(substituted or unsubstituted heterocycloalkyl), —C$_1$-C$_4$ alkylene-(substituted or unsubstituted aryl), or C$_1$-C$_4$ alkylene-(substituted or unsubstituted heteroaryl);

$R^L$ independently are —H, substituted or unsubstituted C$_1$-C$_6$ alkyl, substituted or unsubstituted C$_1$-C$_6$ heteroalkyl, substituted or unsubstituted C$_1$-C$_6$ fluoroalkyl, substituted or unsubstituted C$_3$-C$_6$ cycloalkyl, substituted or unsubstituted heterocycloalkyl, substituted or unsubstituted aryl, substituted or unsubstituted heteroaryl, —C$_1$-C$_4$ alkylene-(substituted or unsubstituted C$_3$-C$_6$ cycloalkyl), —C$_1$-C$_4$ alkylene-(substituted or unsubstituted heterocycloalkyl), —C$_1$-C$_4$ alkylene(substituted or unsubstituted aryl), or —C$_1$-C$_4$ alkylene-(substituted or unsubstituted heteroaryl), or when $R^H$ is —S(═O)$_2$N(R$^L$)$_2$, —N(R$^L$)$_2$, —C(═O)N(R$^L$)$_2$, —OC(═O)N(R$^L$)$_2$ or —N(R$^J$)C(═O)N(R$^L$)$_2$, each $R^L$ is independently —H or C$_1$-C$_6$ alkyl, or the $R^L$ groups independently are C$_1$-C$_6$ alkyl which are taken together with the N atom to which they are attached to define a substituted or unsubstituted heterocycle, wherein when $L^1$ is not absent and $R^C$ is —H or —CH$_3$ and $R^A$ is —CO$_2$H or —CO$_2$R$^B$, then Ring A has the structure of one

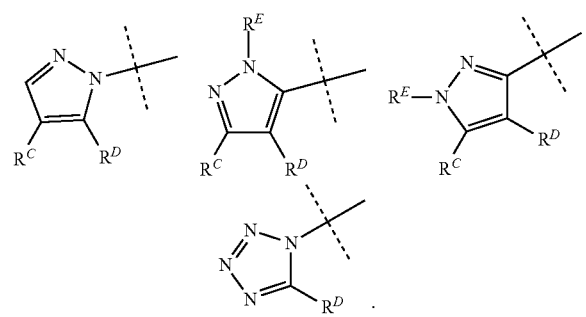

In particularly preferred Formula XII compounds $R^A$ is —CO$_2$H.

25. A composition comprising, essentially consisting of or consisting of one or more compounds of Formula I-XII and one or more excipients.

In preferred embodiments the composition comprises, consists essentially of, or consists of one compound of Formula I-XII and one or more excipients.

In other preferred embodiments the composition is a pharmaceutically acceptable formulation comprising, consisting essentially of, or consisting of one compound of Formula I-XII and one or more pharmaceutically acceptable excipients.

26. A compound of Formula I-XII or a pharmaceutically acceptable salt or prodrug thereof wherein the binding affinity of the compound to lysophosphatidic acid receptor-1 (LPA1R) is between about 10 μM and 1 μM or less 27. The compound of embodiment 19 wherein the compound is a selective lysophosphatidic acid receptor-1 (LPA1R) compound.

28. A compound of Formula I-XII or a pharmaceutically acceptable salt, or prodrug thereof wherein the compound is a selective lysophosphatidic acid receptor-1 (LPA1R) compound.

29. The compound of embodiment 20, 21 or 22 wherein the compound is a selective lysophosphatidic acid receptor-1 (LPA1R) compound wherein the binding affinity (i.e., $K_D$) of the LPA1R compound is between about 1 μM and 1 μM or less. In preferred embodiments the $K_D$ is 100 nM or less, more preferably 10 nM or less.

30. A compound of Table 1.

31. The compound of embodiment 30 wherein the compound is 1-(4-{4-[1-(2-Chloro-phenyl)-ethoxycarbonylamino]-3-methyl-isoxazol-5-yl}-benzoylamino)-cyclopropane-carboxylic acid, 2-(4-{4-[1-(2-Chloro-phenyl)-ethoxycarbonylamino]-3-methyl-isoxazol-5-yl}-benzoylamino)-indan-2-carboxylic acid, 2-(S)-(4-{4-[(R,S)-1-(2-Chloro-phenyl)-ethoxy-carbonylamino]-3-methyl-isoxazol-5-yl}-benzoylamino) phenyl acetic acid, 2-(R)-(4-{4-[(R,S)-1-(2-Chloro-phenyl)-ethoxycarbonylamino]-3-methyl-isoxazol-5-yl}-benzoylamino) phenyl propanoic acid, 2(R)-[[4-[3-methyl-4-((R)-1-phenylethoxycarbonylamino)isoxazol-5-yl]benzoyl]amino]-3-phenyl-propanoic acid, 2(S)-[[4-[3-methyl-4-((R)-phenylethoxycarbonyl-amino)isoxazol-5-yl]benzoyl]amino]-3-phenyl-propanoic acid, (R)-2-{4-[3-Methyl-4-((S)-1-phenyl-ethoxycarbonylamino)-isoxazol-5-yl]-benzoylamino}-3-phenyl-propionic acid, (S)-2-{4-[3-Methyl-4-((S)-1-phenyl-ethoxycarbonylamino)-isoxazol-5-yl]-benzoylamino}-3-phenyl-propionic acid, (R)-2-(4-{4-[(R)-1-(2-Chloro-phenyl)-ethoxycarbonylamino]-3-methyl-isoxazol-5-yl}-benzoylamino)-3-phenyl-propionic acid, (R)-2-(4-{4-[(R)-1-(2-Chloro-phenyl)-ethoxycarbonylamino]-3-methyl-isoxazol-5-yl}-benzoylamino)-3-(4-fluoro-phenyl)-propionic acid, (R)-3-(4-Chloro-phenyl)-2-(4-{4-[(R)-1-(2-chloro-phenyl)-ethoxycarbonylamino]-3-methyl-isoxazol-5-yl}-benzoylamino)-propionic acid (R)-2-(4-{4-[(R)-1-(2-Chloro-phenyl)-ethoxycarbonylamino]-3-methyl-isoxazol-5-yl}-benzoylamino)-3-(3,4-difluoro-phenyl)-propionic acid, (R)-3-(2-Chloro-phenyl)-2-(4-{4-[(R)-1-(2-chloro-phenyl)-ethoxycarbonylamino]-3-methyl-isoxazol-5-yl}-benzoylamino)-propionic acid (R)-3-(4-Bromo-phenyl)-2-(4-{4-[(R)-1-(2-chloro-phenyl)-ethoxycarbonylamino]-3-methyl-isoxazol-5-yl}-benzoylamino)-propionic acid, (R)-2-(4-{4-[(R)-1-(2-Chloro-phenyl)-ethoxycarbonylamino]-3-methyl-isoxazol-5-yl}-benzoylamino)-3-(2-fluoro-phenyl)-propionic acid, (R)-2-(4-{4-[(R)-1-(2-Chloro-phenyl)-ethoxycarbonylamino]-3-methyl-isoxazol-5-yl}-benzoylamino)-3-p-tolyl-propionic acid, (R)-2-(4-{4-[(R)-

1-(2-Chloro-phenyl)-ethoxycarbonylamino]-3-methyl-isoxazol-5-yl}-benzoylamino)-3-(4-trifluoromethyl-phenyl)-propionic acid, (R)-2-(4-{4-[(R)-1-(2-Chloro-phenyl)-ethoxycarbonylamino]-3-methyl-isoxazol-5-yl}-benzoylamino)-3-(4-cyano-phenyl)-propionic acid, (R)-2-(4-{4-[(R)-1-(2-chloro-phenyl)-ethoxycarbonylamino]-3-methyl-isoxazol-5-yl}-benzoylamino)-3-cyclopropyl-propionic acid, 32. The compound of embodiment 30 wherein the compound is (R)-2-[[4-[2,5-dimethyl-4-((R)-1-phenylethoxycarbonylamino)pyrazol-3-yl]benzoyl]amino]-3-phenyl-propanoic acid, (R)-2-[[4-[2,5-dimethyl-4-((R)-1-phenylethoxycarbonylamino)pyrazol-3-yl]benzoyl]amino]-3-(4-fluorophenyl)propanoic acid, (R)-3-(4-bromophenyl)-2-[[4-[2,5-dimethyl-4-((R)-1-phenylethoxycarbonyl-amino)pyrazol-3-yl]benzoyl]amino]propanoic acid, (R)-3-(4-chlorophenyl)-2-[[4-[2,5-dimethyl-4-((R)-1-phenylethoxycarbonyl-amino)pyrazol-3-yl]benzoyl]amino]propanoic acid or (R)-3-(3,4-difluorophenyl)-2-[[4-[2,5-dimethyl-4-((R)-1-phenylethoxycarbonyl-amino)pyrazol-3-yl]benzoyl]amino] propanoic acid.

33. The compound of embodiment 30 wherein the compound is 2-[4-[4-[2,5-dimethyl-4-(1-phenylethoxycarbonylamino) pyrazol-3-yl]phenyl]phenyl]acetic, 2-[4-[4-[4-[1-(2-chloro-phenyl)ethoxycarbonylamino]-2,5-dimethyl-pyrazol-3-yl]phenyl]phenyl]acetic acid, 2-[4-[4-[4-[1-(2-fluorophenyl)ethoxycarbonylamino]-2,5-dimethyl-pyrazol-3-yl]phenyl]-phenyl] acetic acid, 2-[4-[4-[4-[1-(2,6-difluorophenyl)ethoxycarbonylamino]-2,5-dimethyl-pyrazol-3-yl]-phenyl]phenyl]acetic acid, 2-[4-[4-[4-[1-(2-methoxyphenyl)ethoxycarbonyl-amino]-2,5-di-methyl-pyrazol-3-yl]phenyl]phenyl]acetic acid, 1-[4-[4-[2,5-dimethyl-4-(1-phenylethoxy-carbonylamino)pyrazol-3-yl]phenyl]phenyl]cyclopropanecarboxylic acid, 1-[4-[6-[2,5-di-methyl-4-(1-phenylethoxycarbonylamino)pyrazol-3-yl]-3-pyridyl]phenyl]cyclo-propane carboxylic acid, 1-[4-[4-[4-[1-(2-chlorophenyl)ethoxycarbonylamino]-2,5-dimethyl-pyrazol-3-yl]phenyl]phenyl]cyclopropanecarboxylic acid, 1-[4-[4-[4-[1-(2-fluorophenyl)-ethoxycarbonyl-amino]-2,5-dimethyl-pyrazol-3-yl]phenyl]phenyl]cyclopropanecarboxylic acid, 1-[4-[4-[4-[1-(2,6-difluorophenyl)ethoxycarbonylamino]-2,5-dimethyl-pyrazol-3-yl]phenyl]phenyl]cyclopropanecarboxylic acid, 1-[4-[4-[4-[1-(2-methoxyphenyl)ethoxy-carbonylamino]-2,5-dimethyl-pyrazol-3-yl]phenyl]phenyl]cyclopropanecarboxylic acid, 2-[4-[4-[2,5-dimethyl-4-(1-phenyl-ethoxycarbonylamino)pyrazol-3-yl]phenyl]phenyl]-2-methyl-propanoic acid, 2-[4-[4-[4-[1-(2-chlorophenyl)ethoxycarbonylamino]-2,5-dimethyl-pyrazol-3-yl]phenyl]phenyl]-2-methyl-propanoic acid, 2-[4-[4-[4-[1-(2-fluorophenyl)ethoxycarbonyl-amino]-2,5-dimethyl-pyrazol-3-yl]phenyl]phenyl]-2-methyl-propanoic acid, 2-[4-[4-[4-[1-(2,6-difluorophenyl)ethoxycarbonyl-amino]-2,5-dimethyl-pyrazol-3-yl]phenyl]phenyl]-2-methyl-propanoic acid or 2-[4-[4-[4-[1-(2-methoxyphenyl)ethoxycarbonylamino]-2,5-dimethyl-pyrazol-3-yl]phenyl]-phenyl]-2-methyl-propanoic acid.

34. The compound of embodiment 30 wherein the compound is (R)-2-[[4-[1,5-dimethyl-4-((R)-1-phenylethoxycarbonylamino)pyrazol-3-yl]benzoyl]amino]-3-phenyl-propanoic acid, (R)-2-[[4-[1,5-dimethyl-4-((R)-1-phenylethoxycarbonylamino)pyrazol-3-yl]benzoyl]amino]-3-(4-fluorophenyl)propanoic acid, (R)-3-(4-bromophenyl)-2-[[4-[1,5-dimethyl-4-((R)-1-phenylethoxycarbonyl-amino)pyrazol-3-yl]benzoyl]amino]propanoic acid, ((R)-3-(4-chlorophenyl)-2-[[4-[1,5-dimethyl-4-((R)-1-phenylethoxycarbonyl-amino)pyrazol-3-yl]benzoyl]amino]propanoic acid or (R)-3-(3,4-difluorophenyl)-2-[[4-[1,5-dimethyl-4-((R)-1-phenylethoxycarbonyl-amino)pyrazol-3-yl]benzoyl]amino] propanoic acid.

35. The compound of embodiment 30 wherein the compound is (R)-2-(4-{5-[(R)-1-(2-Chloro-phenyl)-ethoxycarbonylamino]-4-methyl-pyrazol-1-yl}-benzoylamino)-3-phenyl-propionic acid.

36. The compound of embodiment 30 wherein the compound is (R)-2-{4-[3-Methyl-4-((R)-1-phenyl-ethoxycarbonylamino)-isoxazol-5-yl]-benzylamino}-3-phenyl-propionic acid, (R)-3-(2-Fluoro-phenyl)-2-{4-[3-methyl-4-((R)-1-phenyl-ethoxycarbonylamino)-isoxazol-5-yl]-benzylamino}-propionic acid, (R)-2-{4-[3-Methyl-4-((R)-1-phenyl-ethoxycarbonylamino)-isoxazol-5-yl]-benzylamino}-3-(4-trifluoromethyl-phenyl)-propionic acid, (R)-3-Cyclopropyl-2-{4-[3-methyl-4-((R)-1-phenyl-ethoxycarbonylamino)-isoxazol-5-yl]-benzylamino}-propionic acid, (R)-3-(2-Chloro-phenyl)-2-{4-[3-methyl-4-((R)-1-phenyl-ethoxycarbonylamino)-isoxazol-5-yl]-benzylamino}-propionic acid, (R)-3-(4-Chloro-phenyl)-2-{4-[3-methyl-4-((R)-1-phenyl-ethoxycarbonylamino)-isoxazol-5-yl]-benzylamino}-propionic acid, (R)-2-(4-{4-[(R)-1-(2-Chloro-phenyl)-ethoxycarbonylamino]-3-methyl-isoxazol-5-yl}-benzylamino)-3-phenyl-propionic acid, (R)-2-(4-{4-[(R)_1-(2-Chloro-phenyl)-ethoxycarbonylamino]-3-methyl-isoxazol-5-yl}-benzylamino)-3-(2-fluoro-phenyl)-propionic acid, (R)-2-(4-{4-[(R)-1-(2-Chloro-phenyl)-ethoxycarbonylamino]-3-methyl-isoxazol-5-yl}-benzylamino)-3-(4-trifluoromethyl-phenyl)-propionic acid, (R)-3-(2-Chloro-phenyl)-2-(4-{4-[(R)-1-(2-chloro-phenyl)-ethoxycarbonylamino]-3-methyl-isoxazol-5-yl}-benzylamino)-propionic acid or (R)-2-(4-{4-[(R)-1-(2-Chloro-phenyl)-ethoxycarbonylamino]-3-methyl-isoxazol-5-yl}-benzylamino)-3-cyclopropyl-propionic acid.

37. The compound of embodiment 30 wherein the compound is 2-{4-[3-Methyl-4-((R)-1-phenyl-ethoxycarbonylamino)-isoxazol-5-yl]-benzyloxy}-3-phenyl-propionic acid, 2-{4-[3-Methyl-4-((R)-1-phenyl-ethoxycarbonylamino)-isoxazol-5-yl]-benzyloxy}-3-phenyl-propionic acid, (RS)-3-Cyclopropyl-2-{4-[3-methyl-4-((R)-1-phenyl-ethoxycarbonylamino)-isoxazol-5-yl]-benzyloxy}-propionic acid or (RS)-3-Cyclopropyl-2-{4-[3-methyl-4-((R)-1-phenyl-ethoxycarbonylamino)-isoxazol-5-yl]-benzyloxy}-propionic acid.

38. The compound of embodiment 30 wherein the compound is 2-[4-[4-[5-[1-(2-chlorophenyl)ethoxycarbonylamino]-4-cyano-pyrazol-1-yl]phenyl]phenyl]acetic acid, (R)-1-[4-[4-[1,5-dimethyl-4-(1-phenylethoxycarbonylamino)pyrazol-3-yl]phenyl]phenyl]cyclo-propane carboxylic acid, (R)-1-[4-[4-[2,5-dimethyl-4-(1-phenylethoxycarbonylamino)pyrazol-3-yl]phenyl]phenyl]cyclopropane carboxylic acid, (R)-1-(4'-{5-[1-(2-Chloro-phenyl)-ethoxycarbonyl-amino]-4-fluoro-pyrazol-1-yl}-3-fluoro-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-2-fluoro-biphenyl-4-yl)-cyclo-propanecarboxylic acid, (R)-1-(2-Chloro-4'-{5-[1-(2-chloro-phenyl)-ethoxycarbonylamino]-4-fluoro-pyrazol-1-yl}-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-2-methyl-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-biphenyl-4-yl)-cyclopropanecarboxylic acid, (R)-1-{4'-[5-(1-Phenyl-ethoxycarbonylamino)-4-trifluoromethyl-pyrazol-1-yl]-biphenyl-4-yl}-cyclopropanecarboxylic acid, (R)-1-{2-Fluoro-4'-[5-(1-phenyl-ethoxycarbonylamino)-4-trifluoromethyl-pyrazol-1-yl]-biphenyl-4-yl}- cyclopropanecarboxylic acid or (R)-1-(4-{5-[5-(1-Phenyl-ethoxycarbonylamino)-pyrazol-1-yl]-pyridin-2-yl}-phenyl)-cyclopropanecarboxylic acid.

39. The compound of embodiment 30 wherein the compound is 2-[[4-[3-methyl-4-(1-phenylethoxycarbonylamino)isoxazol-5-yl]benzoyl]amino]-3-phenyl-propanoic acid, 3-cyclopropyl-2-[[4-[3-methyl-4-(1-phenylethoxycarbonylamino)isoxazol-5-yl]benzoyl]amino]-propanoic acid, 2-[[4-[3-methyl-4-(1-phenylethoxycarbonylamino)isoxazol-5-yl]benzoyl]-amino]-3-phenoxy-propanoic acid, 2-[[4-[3-methyl-4-(1-phenylethoxycarbonylamino)-isoxazol-5-yl]benzoyl]amino]-4-phenyl-butanoic acid, 2-[[4-[4-[1-(2-chlorophenyl)ethoxy-carbonylamino]-3-methyl-isoxazol-5-yl]benzoyl]amino]-3-phenyl-propanoic acid, 2-[[4-[4-[1-(2-chlorophenyl)ethoxycarbonylamino]-3-methyl-isoxazol-5-yl]benzoyl]amino]-3-cyclopropylpropanoic acid, 2-[[4-[4-[1-(2-chlorophenyl)ethoxycarbonylamino]-3-methyl-isoxazol-5-yl]-benzoyl]amino]-4-phenyl-butanoic acid, 2-[[4-[4-[1-(2-chlorophenyl)ethoxycarbonylamino]-3-methyl-isoxazol-5-yl]benzoyl]amino]-3-phenoxy-propanoic acid, 2-[[4-[4-[1-(2-fluorophenyl)-ethoxycarbonylamino]-3-methyl-isoxazol-5-yl]benzoyl]amino]-4-phenyl-butanoic acid, 2-[[4-[4-[1-(2-fluorophenyl)ethoxycarbonylamino]-3-methyl-isoxazol-5-yl]benzoyl]amino]-3-phenoxy-propanoic acid, 3-cyclopropyl-2-[[4-[4-[1-(2-fluorophenyl)ethoxycarbonylamino]-3-methyl-isoxazol-5-yl]benzoyl]amino]propanoic acid, 2-[[4-[4-[1-(2-fluorophenyl)ethoxy-carbonylamino]-3-methyl-isoxazol-5-yl]benzoyl]amino]-3-phenyl-propanoic acid, 3-(4-methoxyphenyl)-2-[[4-[3-methyl-4-(1-phenylethoxycarbonylamino)isoxazol-5-yl]benzoyl]-amino]propanoic acid, 3-(4-fluorophenyl)-2-[[4-[3-methyl-4-(1-phenylethoxycarbonylamino)-isoxazol-5-yl]benzoyl]amino]propanoic acid, 3-(2,6-difluorophenyl)-2-[[4-[3-methyl-4-(1-phenylethoxycarbonylamino)isoxazol-5-yl]benzoyl]amino]propanoic acid, 3-(3-cyano-phenyl)-2-[[4-[3-methyl-4-(1-phenylethoxycarbonylamino)isoxazol-5-yl]benzoyl]amino]-propanoic acid, 3-(2-chlorophenyl)-2-[[4-[3-methyl-4-(1-phenylethoxycarbonylamino)-isoxazol-5-yl]benzoyl]amino]propanoic acid, 3-(4-chlorophenyl)-2-[[4-[3-methyl-4-(1-phenylethoxycarbonylamino)isoxazol-5-yl]benzoyl]amino]propanoic acid, 2-[[4-[3-methyl-4-(1-phenylethoxycarbonylamino)isoxazol-5-yl]benzoyl]amino]-3-[4-(trifluoromethyl)phenyl]-propanoic acid, 3-(4-hydroxyphenyl)-2-[[4-[3-methyl-4-(1-phenylethoxycarbonylamino)-isoxazol-5-yl]benzoyl]amino]propanoic acid, 3-(3,4-difluorophenyl)-2-[[4-[3-methyl-4-(1-phenylethoxycarbonylamino)isoxazol-5-yl]benzoyl]amino]propanoic acid, 3-(4-bromo-phenyl)-2-[[4-[3-methyl-4-(1-phenylethoxycarbonylamino)isoxazol-5-yl]benzoyl]amino]-propanoic acid, 2-[[4-[3-methyl-4-(1-phenylethoxycarbonylamino)isoxazol-5-yl]benzoyl]-amino]-3-[4-(trifluoromethoxy)phenyl]propanoic acid, 2-[[4-[4-[1-(2-chlorophenyl)ethoxy-carbonylamino]-3-methyl-isoxazol-5-yl]benzoyl]amino]-3-(4-methoxyphenyl)propanoic acid, 2-[[4-[4-[1-(2-chlorophenyl)ethoxycarbonylamino]-3-methyl-isoxazol-5-yl]benzoyl]amino]-3-(4-fluorophenyl)propanoic acid, 2-[[4-[4-[1-(2-chlorophenyl)ethoxycarbonylamino]-3-methyl-isoxazol-5-yl]benzoyl]amino]-3-(2,6-difluorophenyl)propanoic acid, 2-[[4-[4-[1-(2-chloro-phenyl)ethoxycarbonylamino]-3-methyl-isoxazol-5-yl]benzoyl]amino]-3-(3-cyanophenyl)-propanoic acid, 3-(2-chlorophenyl)-2-[[4-[4-[1-(2-chlorophenyl)ethoxycarbonylamino]-3-methyl-isoxazol-5-yl]benzoyl]amino]propanoic acid, 3-(4-chlorophenyl)-2-[[4-[4-[1-(2-chlorophenyl)ethoxycarbonylamino]-3-methyl-isoxazol-5-yl]benzoyl]amino]propanoic acid, 2-[[4-[4-[1-(2-chlorophenyl)ethoxycarbonylamino]-3-methyl-isoxazol-5-yl]benzoyl]amino]-3-[4-(trifluoromethyl)phenyl] propanoic acid, 2-[[4-[4-[1-(2-chlorophenyl) ethoxycarbonylamino]-3-methyl-isoxazol-5-yl]benzoyl]amino]-3-(4-hydroxyphenyl)propanoic acid, 3-(4-bromo-phenyl)-2-[[4-[4-[1-(2-chlorophenyl)ethoxycarbonylamino]-3-methyl-isoxazol-5-yl]benzoyl]-amino]propanoic acid, 2-[[4-[4-[1-(2-chlorophenyl)ethoxycarbonylamino]-3-methyl-isoxazol-5-yl]benzoyl]amino]-3-(3,4-difluorophenyl)propanoic acid, 2-[[4-[4-[1-(2-chlorophenyl)-ethoxycarbonylamino]-3-methyl-isoxazol-5-yl]benzoyl]amino]-3-[4-(trifluoromethoxy)-phenyl]propanoic acid, 2-[[4-[4-[1-(2-fluorophenyl)ethoxycarbonylamino]-3-methyl-isoxazol-5-yl]benzoyl]amino]-3-(4-methoxyphenyl)propanoic acid, 3-(4-fluorophenyl)-2-[[4-[4-[1-(2-fluorophenyl)ethoxycarbonylamino]-3-methyl-isoxazol-5-yl]benzoyl]amino]propanoic acid, 3-(2,6-difluorophenyl)-2-[[4-[4-[1-(2-fluorophenyl)ethoxycarbonylamino]-3-methyl-isoxazol-5-yl]benzoyl]amino]propanoic acid, 3-(3-cyanophenyl)-2-[[4-[4-[1-(2-fluorophenyl)ethoxy-carbonylamino]-3-methyl-isoxazol-5-yl]benzoyl]amino]propanoic acid, 3-(2-chlorophenyl)-2-[[4-[4-[1-(2-fluorophenyl)ethoxycarbonylamino]-3-methyl-isoxazol-5-yl]benzoyl]-amino]propanoic acid, 3-(4-chlorophenyl)-2-[[4-[4-[1-(2-fluorophenyl)ethoxycarbonylamino]-3-methyl-isoxazol-5-yl]benzoyl]amino]propanoic acid, 2-[[4-[4-[1-(2-fluorophenyl)ethoxy-carbonylamino]-3-methyl-isoxazol-5-yl]benzoyl]amino]-3-[4-(trifluoromethyl)phenyl]-propanoic acid, 2-[[4-[4-[1-(2-fluorophenyl)ethoxycarbonylamino]-3-methyl-isoxazol-5-yl]benzoyl]amino]-3-(4-hydroxyphenyl) propanoic acid, 3-(3,4-difluorophenyl)-2-[[4-[4-[1-(2-fluorophenyl)ethoxycarbonylamino]-3-methyl-isoxazol-5-yl]benzoyl]amino]propanoic acid, 3-(4-bromophenyl)-2-[[4-[4-[1-(2-fluorophenyl)ethoxycarbonylamino]-3-methyl-isoxazol-5-yl]benzoyl]amino]propanoic acid, 2-[[4-[4-[1-(2-fluorophenyl)ethoxycarbonylamino]-3-methyl-isoxazol-5-yl]benzoyl]amino]-3-[4-(trifluoromethoxy)phenyl] propanoic acid, (±)-(4-{4-[1-(2-Chloro-phenyl)-ethoxycarbonyl-amino]-3-methyl-isoxazol-5-yl}-benzoylamino)-acetic acid, (+)-2-(4-{4-[1-(2-Chloro-phenyl)-ethoxycarbonylamino]-3-methyl-isoxazol-5-yl}-benzoylamino)-2-methyl-propionic acid, (±)-2-(4-{4-[1-(2-Chloro-phenyl)-ethoxycarbonylamino]-3-methyl-isoxazol-5-yl}-benzoylamino)-propionic acid, (±)-2-(4-{4-[1-(2-Chloro-phenyl)-ethoxycarbonylamino]-3-methyl-isoxazol-5-yl}-benzoylamino)-3-hydroxy-propionic acid, (±)-1-(4-{4-[1-(2-Chloro-phenyl)ethoxycarbonyl-amino]-3-methyl-isoxazol-5-yl}-benzoyl)-pyrrolidine-2-carboxylic acid or (±)-2-(4-{4-[1-(2-Chloro-phenyl)-ethoxycarbonylamino]-3-methyl-isoxazol-5-yl}-benzoylamino)-propionic acid.

40. The compound of embodiment 30 wherein the compound is 2-{p-[3-Fluoro-4-(1-phenylethoxycarbonylamino)-5-isoxazolyl]benzoylamino}-3-phenylpropionic acid, 2-(p-{4-[1-(o-Chlorophenyl)ethoxycarbonylamino]-3-fluoro-5-isoxazolyl}benzoylamino)-3-phenyl-propionic acid, 3-Cyclopropyl-2-{p-[3-fluoro-4-(1-phenylethoxycarbonylamino)-5-isoxazolyl]-benzoylamino}propionic acid, 2-(p-{4-[1-(o-Chlorophenyl)ethoxycarbonylamino]-3-fluoro-5-isoxazolyl}benzoylamino)-3-cyclopropylpropionic acid, 2-[({p-[3-Fluoro-4-(1-phenylethoxy-carbonylamino)-5-isoxazolyl]phenyl}methyl)amino]-3-phenylpropionic acid, 2-{[(p-{4-[1-(o-Chlorophenyl)ethoxycarbonylamino]-3-fluoro-5-isoxazolyl}phenyl)methyl]amino}-3-phenylpropionic acid, 3-Cyclopropyl-2-[({p-[3-fluoro-4-(1-phenylethoxycarbonylamino)-5-isoxazolyl]phenyl}methyl)amino]propionic acid, 2-{[(p-{4-[1-(o-Chlorophenyl)ethoxycarbonyl-amino]-3-fluoro-5-isoxazolyl}phenyl)

methyl]amino}-3-cyclopropylpropionic acid, 2-({p-[3-Fluoro-4-(1-phenylethoxycarbonylamino)-5-isoxazolyl]phenyl}methoxy)-3-phenylpropionic acid, 2-[(p-{4-[1-(o-Chlorophenyl)ethoxycarbonylamino]-3-fluoro-5-isoxazolyl}phenyl)-methoxy]-3-phenylpropionic acid, 3-Cyclopropyl-2-({p-[3-fluoro-4-(1-phenylethoxycarbonylamino)-5-isoxazolyl]phenyl}methoxy) propionic acid or 2-[(p-{4-[1-(o-Chlorophenyl)ethoxy-carbonylamino]-3-fluoro-5-isoxazolyl}phenyl)methoxy]-3-cyclopropylpropionic acid.

41. The compound of embodiment 30 wherein the compound is 2-Benzyl-3-{5-[3-fluoro-4-(1-phenylethoxycarbonylamino)-5-isoxazolyl]-2-pyridylamino}propionic acid, 2-Benzyl-3-(5-{4-[1-(o-chlorophenyl)ethoxycarbonylamino]-3-fluoro-5-isoxazolyl}-2-pyridyl-amino) propionic acid, 2-(Cyclopropylmethyl)-3-{5-[3-fluoro-4-(1-phenylethoxycarbonyl-amino)-5-isoxazolyl]-2-pyridylamino}propionic acid, 3-(5-{4-[1-(o-Chlorophenyl)ethoxy-carbonylamino]-3-fluoro-5-isoxazolyl}-2-pyridylamino)-2-(cyclopropylmethyl)propionic acid, 2-Benzyl-3-{5-[3-fluoro-4-(1-phenylethoxycarbonylamino)-5-isoxazolyl]-2-pyridyloxy}-propionic acid, 2-Benzyl-3-(5-{4-[1-(o-chlorophenyl)ethoxycarbonylamino]-3-fluoro-5-isoxazolyl}-2-pyridyloxy)propionic acid 2-Benzyl-3-(5-{4-[1-(o-chlorophenyl)ethoxycarbonyl-amino]-3-fluoro-5-isoxazolyl}-2-pyridyloxy) propionic acid, 2-(Cyclopropylmethyl)-3-{5-[3-fluoro-4-(1-phenylethoxycarbonyl-amino)-5-isoxazolyl]-2-pyridyloxy}propionic acid, 3-(5-{4-[1-(o-Chlorophenyl)ethoxy-carbonylamino]-3-fluoro-5-isoxazolyl}-2-pyridyloxy)-2-(cyclo-propylmethyl)propionic acid, 2-{5-[3-Fluoro-4-(1-phenylethoxycarbonylamino)-5-isoxazolyl]-2-pyridylamino}-3-phenyl-propionic acid, 2-(5-{4-[1-(o-Chlorophenyl)ethoxycarbonylamino]-3-fluoro-5-isoxazolyl}-2-pyridylamino)-3-phenylpropionic acid, 3-Cyclopropyl-2-{5-[3-fluoro-4-(1-phenylethoxy-carbonylamino)-5-isoxazolyl]-2-pyridylamino}propionic acid, 2-(5-{4-[1-(o-Chlorophenyl)-ethoxycarbonylamino]-3-fluoro-5-isoxazolyl}-2-pyridylamino)-3-cyclopropyl-propionic acid, 2-{5-[3-Fluoro-4-(1-phenylethoxycarbonylamino)-5-isoxazolyl]-2-pyridyloxy}-3-phenyl-propionic acid, 2-(5-{4-[1-(o-Chlorophenyl)ethoxycarbonylamino]-3-fluoro-5-isoxazolyl}-2-pyridyloxy)-3-phenylpropionic acid, 3-Cyclopropyl-2-{5-[3-fluoro-4-(1-phenyl-ethoxy-carbonylamino)-5-isoxazolyl]-2-pyridyloxy}propionic acid, 2-(5-{4-[1-(o-Chloro-phenyl)-ethoxycarbonylamino]-3-fluoro-5-isoxazolyl}-2-pyridyloxy)-3-cyclopropylpropionic acid, 2-{p-[3-fluoro-4-(1-phenylethoxycarbonylamino)-5-isoxazolyl]benzoylamino}-3-phenylpropionic acid, 2-(p-{4-[1-(o-chlorophenyl)ethoxycarbonylamino]-3-fluoro-5-isoxazolyl}benzoyl-amino)-3-phenylpropionic acid, 3-cyclopropyl-2-{p-[3-fluoro-4-(1-phenylethoxycarbonyl-amino)-5-isoxazolyl]benzoylamino}propionic acid, 2-(p-{4-[1-(o-chlorophenyl)ethoxy-carbonylamino]-3-fluoro-5-isoxazolyl}benzoylamino)-3-cyclopropylpropionic acid, 2-[({p-[3-fluoro-4-(1-phenylethoxycarbonylamino)-5-isoxazolyl]phenyl}methyl)amino]-3-phenyl-propionic acid, 2-{[(p-{4-[1-(o-chlorophenyl)ethoxycarbonylamino]-3-fluoro-5-isoxazolyl}-phenyl)methyl]amino}-3-phenylpropionic acid, 3-cyclopropyl-2-[({p-[3-fluoro-4-(1-phenyl-ethoxycarbonylamino)-5-isoxazolyl]phenyl}methyl)amino] propionic acid, 2-{[(p-{4-[1-(o-chlorophenyl)ethoxycarbonylamino]-3-fluoro-5-isoxazolyl}phenyl)methyl]amino}-3-cyclopropylpropionic acid, 2-({p-[3-fluoro-4-(1-phenylethoxycarbonylamino)-5-isoxazolyl]phenyl}methoxy)-3-phenylpropionic acid, 2-[(p-{4-[1-(o-chlorophenyl)ethoxycarbonyl-amino]-3-fluoro-5-isoxazolyl}phenyl) methoxy]-3-phenylpropionic acid, 3-cyclopropyl-2-({p-[3-fluoro-4-(1-phenylethoxycarbonylamino)-5-isoxazolyl]phenyl}methoxy) propionic acid, 2-[(p-{4-[1-(o-chlorophenyl)ethoxycarbonylamino]-3-fluoro-5-isoxazolyl}phenyl) methoxy]-3-cyclopropylpropionic acid, 2-benzyl-3-{5-[3-fluoro-4-(1-phenylethoxycarbonylamino)-5-isoxazolyl]-2-pyridylamino}propionic acid, 2-benzyl-3-(5-{4-[1-(o-chlorophenyl)ethoxy-carbonylamino]-3-fluoro-5-isoxazolyl}-2-pyridylamino)propionic acid, 2-(cyclopropyl-methyl)-3-{5-[3-fluoro-4-(1-phenylethoxycarbonylamino)-5-isoxazolyl]-2-pyridylamino}-propionic acid, 3-(5-{4-[1-(o-chlorophenyl)ethoxycarbonylamino]-3-fluoro-5-isoxazolyl}-2-pyridyl-amino)-2-(cyclopropylmethyl)propionic acid, 2-benzyl-3-{5-[3-fluoro-4-(1-phenylethoxy-carbonylamino)-5-isoxazolyl]-2-pyridyloxy}propionic acid, 2-benzyl-3-(5-{4-[1-(o-chloro-phenyl)ethoxycarbonylamino]-3-fluoro-5-isoxazolyl}-2-pyridyloxy) propionic acid, 2-(cyclo-propylmethyl)-3-{5-[3-fluoro-4-(1-phenylethoxycarbonylamino)-5-isoxazolyl]-2-pyridyloxy}-propionic acid, 3-(5-{4-[1-(o-chlorophenyl)ethoxycarbonylamino]-3-fluoro-5-isoxazolyl}-2-pyridyloxy)-2-(cyclopropylmethyl)propionic acid, 2-{5-[3-fluoro-4-(1-phenylethoxycarbonyl-amino)-5-isoxazolyl]-2-pyridylamino}-3-phenylpropionic acid, 2-(5-{4-[1-(o-chlorophenyl)-ethoxycarbonylamino]-3-fluoro-5-isoxazolyl}-2-pyridylamino)-3-phenylpropionic acid, 3-cyclopropyl-2-{5-[3-fluoro-4-(1-phenylethoxycarbonylamino)-5-isoxazolyl]-2-pyridylamino}-propionic acid, 2-(5-{4-[1-(o-chlorophenyl)ethoxycarbonylamino]-3-fluoro-5-isoxazolyl}-2-pyridylamino)-3-cyclopropylpropionic acid, 2-{5-[3-fluoro-4-(1-phenylethoxycarbonylamino)-5-isoxazolyl]-2-pyridyloxy}-3-phenylpropionic acid, 2-(5-{4-[1-(o-chlorophenyl)ethoxy-carbonylamino]-3-fluoro-5-isoxazolyl}-2-pyridyloxy)-3-phenyl-propionic acid, 3-cyclopropyl-2-{5-[3-fluoro-4-(1-phenylethoxycarbonylamino)-5-isoxazolyl]-2-pyridyloxy}propionic acid or 2-(5-{4-[1-(o-chlorophenyl)ethoxycarbonylamino]-3-fluoro-5-isoxazolyl}-2-pyridyloxy)-3-cyclopropylpropionic acid.

42. The compound of embodiment 30 wherein the compound is 2-{p-[3-Cyano-4-(1-phenylethoxycarbonylamino)-5-isoxazolyl]benzoylamino}-3-phenylpropionic acid, 2-(p-{4-[1-(o-Chlorophenyl)ethoxycarbonylamino]-3-cyano-5-isoxazolyl}benzoylamino)-3-phenyl-propionic acid, 2-{p-[3-Cyano-4-(1-phenylethoxycarbonylamino)-5-isoxazolyl]benzoyl-amino}-3-cyclopropylpropionic acid, 2-(p-{4-[1-(o-Chlorophenyl)ethoxycarbonylamino]-3-cyano-5-isoxazolyl}benzoylamino)-3-cyclopropylpropionic acid, 2-[({p-[3-Cyano-4-(1-phenylethoxycarbonylamino)-5-isoxazolyl]phenyl}methyl)amino]-3-phenylpropionic acid, 2-{[(p-{4-[1-(o-Chlorophenyl)ethoxycarbonylamino]-3-cyano-5-isoxazolyl}phenyl)methyl]-amino}-3-phenylpropionic acid, 2-[({p-[3-Cyano-4-(1-phenylethoxycarbonylamino)-5-isoxazolyl]phenyl}methyl)amino]-3-cyclopropylpropionic acid, 2-{[(p-{4-[1-(o-Chlorophenyl)-ethoxycarbonylamino]-3-cyano-5-isoxazolyl}phenyl) methyl]amino}-3-cyclopropylpropionic acid, 2-({p-[3-Cyano-4-(1-phenylethoxycarbonylamino)-5-isoxazolyl]phenyl}methoxy)-3-phenylpropionic acid, 2-[(p-{4-[1-(o-Chlorophenyl)ethoxycarbonylamino]-3-cyano-5-isoxazolyl}phenyl)methoxy]-3-phenylpropionic acid, 2-({p-[3-Cyano-4-(1-phenylethoxycarbonyl-amino)-5-isoxazolyl]phenyl}methoxy)-3-cyclopropylpropionic acid or 2-[(p-{4-[1-(o-Chloro-phenyl)ethoxycarbonylamino]-3-cyano-5-isoxazolyl}phenyl)methoxy]-3-cyclopropylpropionic acid.

43. A compound of embodiment 30 wherein the compound is 2-Benzyl-3-{5-[3-cyano-4-(1-phenylethoxycarbonylamino)-5-isoxazolyl]-2-pyridylamino}propionic acid, 2-Benzyl-3-(5-{4-[1-(o-chlorophenyl)ethoxycarbonylamino]-3-cyano-5-isoxazolyl}-2-pyridylamino)-propionic acid, 3-{5-[3-Cyano-4-(1-phenylethoxycarbonylamino)-5-isoxazolyl]-2-pyridyl-amino}-2-(cyclopropylmethyl)propionic acid, 3-(5-{4-[1-(o-Chlorophenyl)ethoxycarbonyl-amino]-3-cyano-5-isoxazolyl}-2-pyridylamino)-2-(cyclopropylmethyl) propionic acid, 2-Benzyl-3-{5-[3-cyano-4-(1-phenylethoxycarbonylamino)-5-isoxazolyl]-2-pyridyloxy}propionic acid, 2-Benzyl-3-(5-{4-[1-(o-chlorophenyl)ethoxycarbonylamino]-3-cyano-5-isoxazolyl}-2-pyridyloxy)propionic acid, 3-{5-[3-Cyano-4-(1-phenylethoxycarbonylamino)-5-isoxazolyl]-2-pyridyloxy}-2-(cyclopropylmethyl)propionic acid, 3-(5-{4-[1-(o-Chlorophenyl)ethoxycarbonyl-amino]-3-cyano-5-isoxazolyl}-2-pyridyloxy)-2-(cyclopropylmethyl)propionic acid, 2-{5-[3-Cyano-4-(1-phenylethoxycarbonylamino)-5-isoxazolyl]-2-pyridylamino}-3-phenylpropionic acid, 2-(5-{4-[1-(o-Chlorophenyl)ethoxycarbonylamino]-3-cyano-5-isoxazolyl}-2-pyridyl-amino)-3-phenylpropionic acid, 2-{5-[3-Cyano-4-(1-phenylethoxycarbonylamino)-5-isoxazolyl]-2-pyridylamino}-3-cyclopropylpropionic acid, 2-(5-{4-[1-(o-Chlorophenyl)ethoxy-carbonylamino]-3-cyano-5-isoxazolyl}-2-pyridylamino)-3-cyclopropylpropionic acid, 2-{5-[3-Cyano-4-(1-phenylethoxycarbonylamino)-5-isoxazolyl]-2-pyridyloxy}-3-phenylpropionic acid, 2-(5-{4-[1-(o-Chlorophenyl)ethoxycarbonylamino]-3-cyano-5-isoxazolyl}-2-pyridyloxy)-3-phenylpropionic acid, 2-{5-[3-Cyano-4-(1-phenylethoxycarbonylamino)-5-isoxazolyl]-2-pyridyloxy}-3-cyclopropylpropionic acid, 2-(5-{4-[1-(o-Chlorophenyl)ethoxycarbonylamino]-3-cyano-5-isoxazolyl}-2-pyridyloxy)-3-cyclopropylpropionic acid, 2-{p-[3-cyano-4-(1-phenyl-ethoxycarbonylamino)-5-isoxazolyl]benzoylamino}-3-phenylpropionic acid, 2-(p-{4-[1-(o-chlorophenyl)ethoxycarbonylamino]-3-cyano-5-isoxazolyl}benzoylamino)-3-phenylpropionic acid, 2-{p-[3-cyano-4-(1-phenylethoxycarbonylamino)-5-isoxazolyl]benzoylamino}-3-cyclopropylpropionic acid, 2-(p-{4-[1-(o-chlorophenyl)ethoxycarbonylamino]-3-cyano-5-isoxazolyl}benzoylamino)-3-cyclopropylpropionic acid, 2-[({p-[3-cyano-4-(1-phenylethoxy-carbonylamino)-5-isoxazolyl]phenyl}methyl)amino]-3-phenylpropionic acid, 2-{[(p-{4-[1-(o-chlorophenyl)ethoxycarbonylamino]-3-cyano-5-isoxazolyl}phenyl)methyl]amino}-3-phenyl-propionic acid, 2-[({p-[3-cyano-4-(1-phenylethoxycarbonylamino)-5-isoxazolyl]phenyl}-methyl)amino]-3-cyclopropylpropionic acid, 2-{[(p-{4-[1-(o-chlorophenyl)ethoxycarbonyl-amino]-3-cyano-5-isoxazolyl}phenyl)methyl]amino}-3-cyclopropylpropionic acid, 2-({p-[3-cyano-4-(1-phenylethoxycarbonylamino)-5-isoxazolyl]phenyl}methoxy)-3-phenylpropionic acid, 2-[(p-{4-[1-(o-chlorophenyl)ethoxycarbonylamino]-3-cyano-5-isoxazolyl}phenyl)-methoxy]-3-phenylpropionic acid, 2-({p-[3-cyano-4-(1-phenylethoxycarbonylamino)-5-isoxazolyl]phenyl}methoxy)-3-cyclopropylpropionic acid, 2-[(p-{4-[1-(o-chlorophenyl)ethoxy-carbonylamino]-3-cyano-5-isoxazolyl}phenyl)methoxy]-3-cyclopropylpropionic acid, 2-benzyl-3-{5-[3-cyano-4-(1-phenylethoxycarbonylamino)-5-isoxazolyl]-2-pyridylamino}-propionic acid, 2-benzyl-3-(5-{4-[1-(o-chlorophenyl)ethoxycarbonylamino]-3-cyano-5-isoxazolyl}-2-pyridylamino)propionic acid, 3-{5-[3-cyano-4-(1-phenylethoxycarbonylamino)-5-isoxazolyl]-2-pyridylamino}-2-(cyclopropylmethyl) propionic acid, 3-(5-{4-[1-(o-chlorophenyl)ethoxycarbonylamino]-3-cyano-5-isoxazolyl}-2-pyridylamino)-2-(cyclopropylmethyl)-propionic acid, 2-benzyl-3-{5-[3-cyano-4-(1-phenylethoxycarbonylamino)-5-isoxazolyl]-2-pyridyloxy}propionic acid, 2-benzyl-3-(5-{4-[1-(o-chlorophenyl)ethoxycarbonylamino]-3-cyano-5-isoxazolyl}-2-pyridyloxy) propionic acid, 3-{5-[3-cyano-4-(1-phenylethoxycarbonyl-amino)-5-isoxazolyl]-2-pyridyloxy}-2-(cyclopropylmethyl)propionic acid, 3-(5-{4-[1-(o-chloro-phenyl)ethoxycarbonylamino]-3-cyano-5-isoxazolyl}-2-pyridyloxy)-2-(cyclopropylmethyl)-propionic acid, 2-{5-[3-cyano-4-(1-phenylethoxycarbonylamino)-5-isoxazolyl]-2-pyridyl-amino}-3-phenylpropionic acid, 2-(5-{4-[1-(o-chlorophenyl)ethoxycarbonylamino]-3-cyano-5-isoxazolyl}-2-pyridylamino)-3-phenylpropionic acid, 2-{5-[3-cyano-4-(1-phenylethoxy-carbonylamino)-5-isoxazolyl]-2-pyridylamino}-3-cyclopropylpropionic acid, 2-(5-{4-[1-(o-chlorophenyl)ethoxycarbonylamino]-3-cyano-5-isoxazolyl}-2-pyridylamino)-3-cyclopropyl-propionic acid, 2-{5-[3-cyano-4-(1-phenylethoxycarbonylamino)-5-isoxazolyl]-2-pyridyloxy}-3-phenylpropionic acid, 2-(5-{4-[1-(o-chlorophenyl)ethoxycarbonylamino]-3-cyano-5-isoxazolyl}-2-pyridyloxy)-3-phenylpropionic acid, 2-{5-[3-cyano-4-(1-phenylethoxycarbonyl-amino)-5-isoxazolyl]-2-pyridyloxy}-3-cyclopropylpropionic acid or 2-(5-{4-[1-(o-chlorophenyl)-ethoxycarbonylamino]-3-cyano-5-isoxazolyl}-2-pyridyloxy)-3-cyclopropylpropionic acid.

44. A compound of embodiment 30 wherein the compound is 2-Benzyl-3-{5-[3-methyl-4-(1-phenylethoxycarbonylamino)-5-isoxazolyl]-2-pyridylamino}propionic acid, 2-Benzyl-3-(5-{4-[1-(o-chlorophenyl)ethoxycarbonylamino]-3-methyl-5-isoxazolyl}-2-pyridylamino)-propionic acid, 2-(Cyclopropylmethyl)-3-{5-[3-methyl-4-(1-phenylethoxycarbonylamino)-5-isoxazolyl]-2-pyridylamino}propionic acid, 3-(5-{4-[1-(o-Chlorophenyl)ethoxycarbonylamino]-3-methyl-5-isoxazolyl}-2-pyridylamino)-2-(cyclopropylmethyl)propionic acid, 2-Benzyl-3-{5-[3-methyl-4-(1-phenylethoxycarbonylamino)-5-isoxazolyl]-2-pyridyloxy}propionic acid, 2-Benzyl-3-(5-{4-[1-(o-chlorophenyl)ethoxycarbonylamino]-3-methyl-5-isoxazolyl}-2-pyridyl-oxy)propionic acid, 2-(Cyclopropylmethyl)-3-{5-[3-methyl-4-(1-phenylethoxycarbonylamino)-5-isoxazolyl]-2-pyridyloxy}propionic acid, 3-(5-{4-[1-(o-Chlorophenyl)ethoxycarbonylamino]-3-methyl-5-isoxazolyl}-2-pyridyloxy)-2-(cyclopropylmethyl)propionic acid, 2-{5-[3-Methyl-4-(1-phenylethoxycarbonylamino)-5-isoxazolyl]-2-pyridylamino}-3-phenylpropionic acid, 2-(5-{4-[1-(o-Chlorophenyl)ethoxycarbonylamino]-3-methyl-5-isoxazolyl}-2-pyridylamino)-3-phenylpropionic acid, 2-(5-{4-[1-(o-Chlorophenyl)ethoxycarbonylamino]-3-methyl-5-isoxazolyl}-2-pyridylamino)-3-cyclopropylpropionic acid, 2-{5-[3-Methyl-4-(1-phenylethoxy-carbonylamino)-5-isoxazolyl]-2-pyridyloxy}-3-phenylpropionic acid, 2-(5-{4-[1-(o-Chloro-phenyl)ethoxycarbonylamino]-3-methyl-5-isoxazolyl}-2-pyridyloxy)-3-phenylpropionic acid, 3-Cyclopropyl-2-{5-[3-methyl-4-(1-phenylethoxycarbonylamino)-5-isoxazolyl]-2-pyridyl-oxy}propionic acid, 2-(5-{4-[1-(o-Chlorophenyl)ethoxycarbonylamino]-3-methyl-5-isoxazolyl}-2-pyridyloxy)-3-cyclopropylpropionic acid, 2-benzyl-3-{5-[3-methyl-4-(1-phenyl-ethoxycarbonylamino)-5-isoxazolyl]-2-pyridylamino}propionic acid, 2-benzyl-3-(5-{4-[1-(o-chlorophenyl)ethoxycarbonylamino]-3-methyl-5-isoxazolyl}-2-pyridylamino)propionic acid, 2-(cyclopropylmethyl)-3-{5-[3-methyl-4-(1-phenylethoxycarbonylamino)-5-isoxazolyl]-2-pyridylamino}propionic acid, 3-(5-{4-[1-(o-chlorophenyl)

ethoxycarbonylamino]-3-methyl-5-isoxazolyl}-2-pyridylamino)-2-(cyclopropylmethyl)propionic acid, 2-benzyl-3-{5-[3-methyl-4-(1-phenylethoxycarbonylamino)-5-isoxazolyl]-2-pyridyloxy}propionic acid, 2-benzyl-3-(5-{4-[1-(o-chlorophenyl)ethoxycarbonylamino]-3-methyl-5-isoxazolyl}-2-pyridyloxy) propionic acid, 2-(cyclopropylmethyl)-3-{5-[3-methyl-4-(1-phenylethoxycarbonylamino)-5-isoxazolyl]-2-pyridyloxy}propionic acid, 3-(5-{4-[1-(o-chlorophenyl)ethoxycarbonylamino]-3-methyl-5-isoxazolyl}-2-pyridyloxy)-2-(cyclopropylmethyl) propionic acid, 2-{5-[3-methyl-4-(1-phenyl-ethoxycarbonylamino)-5-isoxazolyl]-2-pyridylamino}-3-phenylpropionic acid, 2-(5-{4-[1-(o-chlorophenyl)ethoxycarbonylamino]-3-methyl-5-isoxazolyl}-2-pyridylamino)-3-phenyl-propionic acid, 3-cyclopropyl-2-{5-[3-methyl-4-(1-phenylethoxycarbonylamino)-5-isoxazolyl]-2-pyridylamino}propionic acid, 2-(5-{4-[1-(o-chlorophenyl)ethoxycarbonylamino]-3-methyl-5-isoxazolyl}-2-pyridylamino)-3-cyclopropylpropionic acid, 2-{5-[3-methyl-4-(1-phenylethoxy-carbonylamino)-5-isoxazolyl]-2-pyridyloxy}-3-phenylpropionic acid, 2-(5-{4-[1-(o-chloro-phenyl)ethoxycarbonylamino]-3-methyl-5-isoxazolyl}-2-pyridyloxy)-3-phenylpropionic acid, 3-cyclopropyl-2-{5-[3-methyl-4-(1-phenylethoxycarbonylamino)-5-isoxazolyl]-2-pyridyloxy}-propionic acid, 2-(5-{4-[1-(o-chlorophenyl)ethoxycarbonylamino]-3-methyl-5-isoxazolyl}-2-pyridyloxy)-3-cyclopropylpropionic acid, 3-{p-[3-methyl-4-(1-phenylethoxycarbonylamino)-5-isoxazolyl]benzoylamino}-4-phenylbutyric acid, 4-cyclopropyl-3-{p-[3-methyl-4-(1-phenyl-ethoxycarbonylamino)-5-isoxazolyl]benzoylamino}butyric acid, 3-[({p-[3-methyl-4-(1-phenyl-ethoxycarbonylamino)-5-isoxazolyl]phenyl}methyl)amino]-4-phenylbutyric acid, 4-cyclo-propyl-3-[({p-[3-methyl-4-(1-phenylethoxycarbonylamino)-5-isoxazolyl]phenyl}methyl)-amino]butyric acid, 3-({p-[3-methyl-4-(1-phenylethoxycarbonylamino)-5-isoxazolyl]phenyl}-methoxy)-4-phenylbutyric acid, 4-cyclopropyl-3-({p-[3-methyl-4-(1-phenylethoxycarbonyl-amino)-5-isoxazolyl]phenyl}methoxy) butyric acid, 3-{5-[3-methyl-4-(1-phenylethoxycarbonyl-amino)-5-isoxazolyl]-2-pyridylamino}-4-phenylbutyric acid, 4-cyclopropyl-3-{5-[3-methyl-4-(1-phenylethoxycarbonylamino)-5-isoxazolyl]-2-pyridylamino}butyric acid, 3-{5-[3-methyl-4-(1-phenylethoxycarbonylamino)-5-isoxazolyl]-2-pyridyloxy}-4-phenylbutyric acid, 4-cyclo-propyl-3-{5-[3-methyl-4-(1-phenylethoxycarbonylamino)-5-isoxazolyl]-2-pyridyloxy}butyric acid.

45. A compound of embodiment 30 wherein the compound is 2-[[4-[1,5-dimethyl-4-(1-phenylethoxycarbonylamino)pyrazol-3-yl]benzoyl]amino]-3-(4-methoxyphenyl)propanoic acid, 2-[[4-[1,5-dimethyl-4-(1-phenylethoxycarbonylamino) pyrazol-3-yl]benzoyl]amino]-3-(4-fluorophenyl)propanoic acid, 3-(2,6-difluorophenyl)-2-[[4-[1,5-dimethyl-4-(1-phenylethoxy-carbonylamino) pyrazol-3-yl]benzoyl]amino]propanoic acid, 3-(3-cyanophenyl)-2-[[4-[1,5-dimethyl-4-(1-phenylethoxycarbonylamino) pyrazol-3-yl]benzoyl]amino] propanoic acid, 3-(2-chlorophenyl)-2-[[4-[1,5-dimethyl-4-(1-phenylethoxycarbonylamino) pyrazol-3-yl]benzoyl]-amino]propanoic acid, 3-(4-chlorophenyl)-2-[[4-[1,5-dimethyl-4-(1-phenylethoxycarbonyl-amino)pyrazol-3-yl]benzoyl]amino]propanoic acid, 2-[4-[1,5-dimethyl-4-(1-phenylethoxy-carbonylamino)pyrazol-3-yl]benzoyl]amino]-3-[4-(trifluoromethyl)phenyl]propanoic acid, 2-[[4-[1,5-dimethyl-4-(1-phenylethoxycarbonylamino) pyrazol-3-yl]benzoyl]amino]-3-(4-hydroxyphenyl)propanoic acid, 3-(3,4-difluorophenyl)-2-[[4-[1,5-dimethyl-4-(1-phenylethoxy-carbonylamino)pyrazol-3-yl]benzoyl]amino]propanoic acid, 3-(4-bromophenyl)-2-[[4-[1,5-dimethyl-4-(1-phenylethoxycarbonylamino)pyrazol-3-yl]benzoyl]amino] propanoic acid, 2-[[4-[1,5-dimethyl-4-(1-phenylethoxycarbonylamino) pyrazol-3-yl]benzoyl]amino]-3-[4-(trifluoro-methoxy)phenyl]propanoic acid, 2-[[4-[4-[1-(2-chlorophenyl)ethoxycarbonylamino]-1,5-dimethyl-pyrazol-3-yl]benzoyl]amino]-3-(4-methoxyphenyl) propanoic acid, 2-[[4-[4-[1-(2-chlorophenyl)ethoxycarbonylamino]-1,5-dimethyl-pyrazol-3-yl]benzoyl]amino]-3-(4-fluoro-phenyl)propanoic acid, 2-[[4-[4-[1-(2-chlorophenyl)ethoxycarbonylamino]-1,5-dimethyl-pyrazol-3-yl]benzoyl]amino]-3-(2,6-difluorophenyl)propanoic acid, 2-[[4-[4-[1-(2-chloro-phenyl)ethoxycarbonylamino]-1,5-dimethyl-pyrazol-3-yl]benzoyl]amino]-3-(3-cyanophenyl)-propanoic acid, 3-(2-chlorophenyl)-2-[[4-[4-[1-(2-chlorophenyl)ethoxycarbonylamino]-1,5-dimethyl-pyrazol-3-yl]benzoyl]amino]propanoic acid, 3-(4-chlorophenyl)-2-[[4-[4-[1-(2-chlorophenyl)ethoxycarbonylamino]-1,5-dimethyl-pyrazol-3-yl]benzoyl]amino]propanoic acid, 2-[[4-[4-[1-(2-chlorophenyl)ethoxycarbonylamino]-1,5-dimethyl-pyrazol-3-yl]benzoyl]-amino]-3-[4-(trifluoromethyl)phenyl] propanoic acid, 2-[[4-[4-[1-(2-chlorophenyl)ethoxy-carbonylamino]-1,5-dimethyl-pyrazol-3-yl]benzoyl] amino]-3-(4-hydroxyphenyl)propanoic acid, 2-[[4-[4-[1-(2-chlorophenyl)ethoxycarbonylamino]-1,5-dimethyl-pyrazol-3-yl]benzoyl]-amino]-3-(3,4-difluorophenyl)propanoic acid, 3-(4-bromophenyl)-2-[[4-[4-[1-(2-chloro-phenyl)ethoxycarbonylamino]-1,5-dimethyl-pyrazol-3-yl]benzoyl]amino]propanoic acid, 2-[[4-[4-[1-(2-chlorophenyl)ethoxy-carbonylamino]-1,5-dimethyl-pyrazol-3-yl]benzoyl]amino]-3-[4-(trifluoromethoxy)phenyl]propanoic acid, 2-[[4-[4-[1-(2-fluorophenyl)ethoxycarbonyl-amino]-1,5-dimethyl-pyrazol-3-yl]benzoyl]amino]-3-(4-methoxyphenyl) propanoic acid, 3-(4-fluorophenyl)-2-[[4-[4-[1-(2-fluoro-phenyl)ethoxycarbonylamino]-1,5-dimethyl-pyrazol-3-yl]benzoyl]amino]propanoic acid, 3-(2,6-difluorophenyl)-2-[[4-[4-[1-(2-fluorophenyl)ethoxy-carbonylamino]-1,5-dimethyl-pyrazol-3-yl]benzoyl]amino]propanoic acid, 3-(3-cyanophenyl)-2-[[4-[4-[1-(2-fluorophenyl) ethoxycarbonylamino]-1,5-dimethyl-pyrazol-3-yl]benzoyl] amino]-propanoic acid, 3-(2-chlorophenyl)-2-[[4-[4-[1-(2-fluorophenyl)ethoxycarbonylamino]-1,5-dimethyl-pyrazol-3-yl]benzoyl]amino]propanoic acid, 3-(4-chlorophenyl)-2-[[4-[4-[1-(2-fluorophenyl)ethoxycarbonylamino]-1,5-dimethyl-pyrazol-3-yl]benzoyl]amino]propanoic acid, 2-[[4-[4-[1-(2-fluorophenyl)ethoxycarbonylamino]-1,5-dimethyl-pyrazol-3-yl]benzoyl]amino]-3-[4-(trifluoromethyl)phenyl]propanoic acid, 2-[[4-[4-[1-(2-fluorophenyl)ethoxy-carbonyl-amino]-1,5-dimethyl-pyrazol-3-yl]benzoyl]amino]-3-(4-hydroxyphenyl)propanoic acid, 3-(3,4-difluorophenyl)-2-[[4-[4-[1-(2-fluorophenyl)ethoxycarbonylamino]-1,5-dimethyl-pyrazol-3-yl]benzoyl]amino]propanoic acid, 3-(4-bromophenyl)-2-[[4-[4-[1-(2-fluorophenyl)ethoxy-carbonylamino]-1,5-dimethyl-pyrazol-3-yl]benzoyl]amino]propanoic acid, 2-[[4-[4-[1-(2-fluorophenyl)ethoxycarbonylamino]-1,5-dimethyl-pyrazol-3-yl]benzoyl]amino]-3-[4-(trifluoromethoxy)phenyl]propanoic acid, 2-{p-[1-methyl-5-methyl-4-(1-phenylethoxy-carbonylamino)-1 h-pyrazol-3-yl]benzoylamino}-3-phenylpropionic acid, 3-cyclopropyl-2-{p-[1-methyl-5-methyl-4-(1-phenylethoxycarbonylamino)-1 h-pyrazol-3-yl]benzoylamino}-propionic acid, 2-(p-{4-[1-(o-chlorophenyl)ethoxycarbonylamino]-1-methyl-5-methyl-1 h-pyrazol-3-yl}benzoylamino)-3-phenylpropionic acid, 2-(p-{4-[1-(o-chlorophenyl)ethoxy-carbonylamino]-1-methyl-5-methyl-1 h-pyrazol-3-yl}benzoylamino)-3-cyclopropylpropionic acid, 2-[({p-[1-methyl-5-methyl-4-(1-phenylethoxycarbonylamino)-1 h-pyrazol-3-yl]phenyl}-methyl)amino]-3-phenylpropionic acid, 3-cyclopropyl-2-[({p-[1-methyl-5-methyl-4-(1-phenyl-ethoxycarbonylamino)-1 h-pyrazol-3-yl]phenyl}methyl)amino]propionic acid, 2-{[(p-{4-[1-(o-chlorophenyl)ethoxycarbonylamino]-1-methyl-5-methyl-1 h-pyrazol-3-yl}phenyl)methyl]-amino}-3-phenylpropionic acid, 2-{[(p-{4-[1-(o-chlorophenyl)ethoxycarbonylamino]-1-methyl-5-methyl-1 h-pyrazol-3-yl}phenyl)methyl amino}-3-cyclopropylpropionic acid, 2-({p-[1-methyl-5-methyl-4-(1-phenylethoxycarbonylamino)-1 h-pyrazol-3-yl]phenyl}methoxy)-3-phenyl-propionic acid, 3-cyclopropyl-2-({p-[1-methyl-5-methyl-4-(1-phenylethoxycarbonylamino)-1 h-pyrazol-3-yl]phenyl}methoxy) propionic acid, 2-[(p-{4-[1-(o-chlorophenyl)ethoxycarbonyl-amino]-1-methyl-5-methyl-1h-pyrazol-3-yl}phenyl) methoxy]-3-phenylpropionic acid, 2-[(p-{4-[1-(o-chlorophenyl)ethoxycarbonylamino]-1-methyl-5-methyl-1 h-pyrazol-3-yl}phenyl)-methoxy]-3-cyclopropylpropionic acid, 3-{p-[1-methyl-5-methyl-4-(1-phenylethoxycarbonyl-amino)-1 h-pyrazol-3-yl]benzoylamino}-4-phenylbutyric acid, 4-cyclopropyl-3-{p-[1-methyl-5-methyl-4-(1-phenylethoxycarbonylamino)-1 h-pyrazol-3-yl] benzoylamino}butyric acid, 3-[({p-[1-methyl-5-methyl-4-(1-phenylethoxycarbonylamino)-1 h-pyrazol-3-yl] phenyl}methyl)amino]-4-phenylbutyric acid, 4-cyclopropyl-3-[({p-[1-methyl-5-methyl-4-(1-phenylethoxycarbonyl-amino)-1 h-pyrazol-3-yl]phenyl}methyl) amino]butyric acid, 3-({p-[1-methyl-5-methyl-4-(1-phenylethoxycarbonylamino)-1h-pyrazol-3-yl]phenyl}methoxy)-4-phenylbutyric acid or 4-cyclopropyl-3-({p-[1-methyl-5-methyl-4-(1-phenylethoxycarbonylamino)-1 h-pyrazol-3-yl]phenyl}methoxy)butyric acid.

46. A compound of embodiment 30 wherein the compound is 2-[4-[4-[4-cyano-5-(1-phenylethoxycarbonylamino)pyrazol-1-yl]phenyl]phenyl]acetic acid, 1-[4-[4-[4-cyano-5-(1-phenylethoxycarbonylamino)pyrazol-1-yl]phenyl]phenyl]cyclopropanecarboxylic acid, 1-[4-[4-[5-[1-(2-chlorophenyl)ethoxycarbonylamino]-4-cyano-pyrazol-1-yl]phenyl]phenyl]cyclo-propanecarboxylic acid, 2-[4-[4-[4-cyano-5-(1-phenylethoxycarbonylamino) pyrazol-1-yl]phenyl]phenyl]-2-methyl-propanoic acid, 2-[4-[4-[5-[1-(2-chlorophenyl)ethoxycarbonyl-amino]-4-cyano-pyrazol-1-yl]phenyl]phenyl]-2-methyl-propanoic acid, 1-{4'-[4-Fluoro-5-(1-phenylethoxycarbonylamino)-1H-pyrazol-1-yl]-4-biphenylyl}cyclopropanecarboxylic acid, 1-(4'-{5-[1-(o-Chlorophenyl)ethoxycarbonylamino]-4-fluoro-1H-pyrazol-1-yl}-4-biphenylyl)-cyclopropanecarboxylic acid, 1-{3-Fluoro-4'-[4-fluoro-5-(1-phenylethoxycarbonylamino)-1H-pyrazol-1-yl]-4-biphenylyl}cyclopropanecarboxylic acid, 1-(4'-{5-[1-(o-Chlorophenyl)ethoxy-carbonylamino]-4-fluoro-1H-pyrazol-1-yl}-3-fluoro-4-biphenylyl) cyclopropanecarboxylic acid, 1-{2-Fluoro-4'-[4-fluoro-5-(1-phenylethoxycarbonylamino)-1H-pyrazol-1-yl]-4-biphenylyl}-cyclopropanecarboxylic acid, 1-(4'-{5-[1-(o-Chlorophenyl)ethoxycarbonylamino]-4-fluoro-1H-pyrazol-1-yl}-2-fluoro-4-biphenylyl)cyclopropanecarboxylic acid, 1-(2-Chloro-4'-{5-[1-(o-chlorophenyl)ethoxycarbonylamino]-4-fluoro-1H-pyrazol-1-yl}-4-biphenylyl)cyclopropane-carboxylic acid, 1-(4-{p-[4-Fluoro-5-(1-phenylethoxycarbonylamino)-1H-pyrazol-1-yl]-phenyl}tolyl) cyclopropanecarboxylic acid, 1-[4-(p-{5-[1-(o-Chlorophenyl)ethoxycarbonyl-amino]-4-fluoro-1H-pyrazol-1-yl}phenyl)tolyl]cyclopropanecarboxylic acid, 1-(p-{5-[5-(1-Phenylethoxycarbonylamino)-1H-pyrazol-1-yl]-2-pyridyl}phenyl)cyclopropanecarboxylic acid, 1-[p-(5-{5-[1-(o-Chlorophenyl)ethoxycarbonylamino]-1H-pyrazol-1-yl}-2-pyridyl)-phenyl]cyclopropanecarboxylic acid, 1-(p-{5-[4-Methyl-5-(1-phenylethoxycarbonylamino)-1H-pyrazol-1-yl]-2-pyridyl}phenyl)cyclopropanecarboxylic acid, 1-[p-(5-{5-[1-(o-Chloro-phenyl)ethoxycarbonylamino]-4-methyl-1H-pyrazol-1-yl}-2-pyridyl)phenyl] cyclopropane-carboxylic acid, 1-(2-Fluoro-4-{5-[5-(1-phenylethoxycarbonylamino)-1H-pyrazol-1-yl]-2-pyridyl}phenyl)cyclopropanecarboxylic acid, 1-[4-(5-{5-[1-(o-Chlorophenyl)ethoxycarbonyl-amino]-1H-pyrazol-1-yl}-2-pyridyl)-2-fluorophenyl]cyclopropanecarboxylic acid, 1-(3-Fluoro-4-{5-[5-(1-phenylethoxycarbonylamino)-1H-pyrazol-1-yl]-2-pyridyl}phenyl)cyclopropane-carboxylic acid, 1-[4-(5-{5-[1-(o-Chlorophenyl)ethoxycarbonylamino]-1H-pyrazol-1-yl}-2-pyridyl)-3-fluorophenyl]cyclopropanecarboxylic acid, 1-(p-{5-[4-Methyl-5-(1-phenylethoxy-carbonylamino)-1H-pyrazol-1-yl]-2-pyridyl}phenyl)cyclopropanecarboxylic acid, 1-(p-{5-[4-Methyl-5-(1-phenylethoxycarbonylamino)-1H-pyrazol-1-yl]-2-pyridyl}phenyl)cyclopropane-carboxylic acid, 1-[p-(5-{5-[1-(o-Chlorophenyl)ethoxycarbonylamino]-4-methyl-1H-pyrazol-1-yl}-2-pyridyl)phenyl] cyclopropanecarboxylic acid, 1-(2-Fluoro-4-{5-[4-methyl-5-(1-phenyl-ethoxycarbonylamino)-1H-pyrazol-1-yl]-2-pyridyl}phenyl)cyclopropanecarboxylic acid, 1-[4-(5-{5-[1-(o-Chlorophenyl)ethoxycarbonylamino]-4-methyl-1H-pyrazol-1-yl}-2-pyridyl)-2-fluorophenyl] cyclopropanecarboxylic acid, 1-(3-Fluoro-4-{5-[4-methyl-5-(1-phenylethoxy-carbonylamino)-1H-pyrazol-1-yl]-2-pyridyl}phenyl)cyclopropanecarboxylic acid, 1-[4-(5-{5-[1-(o-Chlorophenyl)ethoxycarbonylamino]-4-methyl-1H-pyrazol-1-yl}-2-pyridyl)-3-fluoro-phenyl]cyclopropanecarboxylic acid, 1-(p-{5-[4-Fluoro-5-(1-phenylethoxycarbonylamino)-1H-pyrazol-1-yl]-2-pyridyl}phenyl)cyclopropanecarboxylic acid, 1-[p-(5-{5-[1-(o-Chloro-phenyl)ethoxycarbonylamino]-4-fluoro-1H-pyrazol-1-yl}-2-pyridyl)phenyl]cyclopropane-carboxylic acid, 1-(2-Fluoro-4-{5-[4-fluoro-5-(1-phenylethoxycarbonylamino)-1H-pyrazol-1-yl]-2-pyridyl}phenyl)cyclopropanecarboxylic acid, 1-[4-(5-{5-[1-(o-Chlorophenyl)ethoxy-carbonylamino]-4-fluoro-1H-pyrazol-1-yl}-2-pyridyl)-2-fluorophenyl]cyclopropanecarboxylic acid, 1-(3-Fluoro-4-{5-[4-fluoro-5-(1-phenylethoxycarbonylamino)-1H-pyrazol-1-yl]-2-pyridyl}phenyl) cyclopropanecarboxylic acid, 1-[4-(5-{5-[1-(o-Chlorophenyl)ethoxycarbonyl-amino]-4-fluoro-1H-pyrazol-1-yl}-2-pyridyl)-3-fluorophenyl] cyclopropanecarboxylic acid, 1-(p-{5-[4-Cyano-5-(1-phenylethoxycarbonylamino)-1H-pyrazol-1-yl]-2-pyridyl}phenyl)cyclo-propanecarboxylic acid, 1-[p-(5-{5-[1-(o-Chlorophenyl)ethoxycarbonylamino]-4-cyano-1H-pyrazol-1-yl}-2-pyridyl)phenyl]cyclopropanecarboxylic acid, 1-(4-{5-[4-Cyano-5-(1-phenyl-ethoxycarbonylamino)-1H-pyrazol-1-yl]-2-pyridyl}-2-fluorophenyl)cyclopropanecarboxylic acid, 1-[4-(5-{5-[1-(o-Chlorophenyl)ethoxycarbonylamino]-4-cyano-1H-pyrazol-1-yl}-2-pyridyl)-2-fluorophenyl]cyclopropanecarboxylic acid, 1-(4-{5-[4-Cyano-5-(1-phenylethoxy-carbonylamino)-1H-pyrazol-1-yl]-2-pyridyl}-3-fluorophenyl)cyclopropane-carboxylic acid or 1-[4-(5-{5-[1-(o-Chlorophenyl)ethoxycarbonylamino]-4-cyano-1H-pyrazol-1-yl}-2-pyridyl)-3-fluoro-phenyl]cyclopropanecarboxylic acid.

47. A compound of embodiment 30 wherein the compound is 3-phenyl-2-[[4-[5-(1-phenylethoxycarbonylamino) oxazol-4-yl]benzoyl]amino]propanoic acid, 3-cyclopropyl-2-[[4-[5-(1-phenylethoxycarbonylamino)oxazol-4-yl]

benzoyl]amino]propanoic acid, 4-phenyl-2-[[4-[5-(1-phenylethoxycarbonylamino)oxazol-4-yl]benzoyl]amino]butanoic acid, 3-phenoxy-2-[[4-[5-(1-phenylethoxycarbonylamino)oxazol-4-yl]benzoyl]amino]propanoic acid, 3-Phenyl-2-[({p-[5-(1-phenylethoxycarbonylamino)-1,3-oxazol-4-yl]phenyl}methyl)-amino]propionic acid, 3-Cyclopropyl-2-[({p-[5-(1-phenylethoxycarbonylamino)-1,3-oxazol-4-yl]phenyl}-methyl)amino]propionic acid, 3-Phenyl-2-({p-[5-(1-phenylethoxycarbonyl-amino)-1,3-oxazol-4-yl]phenyl}methoxy)propionic acid, 4-Phenyl-3-({p-[5-(1-phenylethoxy-carbonylamino)-1,3-oxazol-4-yl]phenyl}methoxy)butyric acid or 4-Cyclopropyl-3-({p-[5-(1-phenylethoxycarbonyl-amino)-1,3-oxazol-4-yl]phenyl}methoxy)butyric acid.

48. A compound of embodiment 30 wherein the compound is 2-[[4-[1-methyl-5-(1-phenylethoxycarbonylamino)imidazol-4-yl]benzoyl]amino]-3-phenyl-propanoic acid, 3-cyclopropyl-2-[[4-[1-methyl-5-(1-phenylethoxycarbonylamino)imidazol-4-yl]benzoyl]-amino]propanoic acid, 2-[[4-[1-methyl-5-(1-phenylethoxycarbonylamino)imidazol-4-yl]benzoyl]amino]-4-phenyl-butanoic acid, 2-[[4-[1-methyl-5-(1-phenylethoxycarbonyl-amino)imidazol-4-yl]benzoyl]amino]-3-phenoxy-propanoic acid, 2-[({p-[1-Methyl-5-(1-phenylethoxycarbonylamino)-1H-imidazol-4-yl]phenyl}methyl)amino]-3-phenylpropionic acid, 3-Cyclopropyl-2-[({p-[1-methyl-5-(1-phenylethoxycarbonylamino)-1H-imidazol-4-yl]phenyl}methyl)amino]propionic acid, 2-({p-[1-Methyl-5-(1-phenylethoxycarbonylamino)-1H-imidazol-4-yl]phenyl}methoxy)-3-phenylpropionic acid, 3-Cyclopropyl-2-({p-[1-methyl-5-(1-phenylethoxycarbonylamino)-1H-imidazol-4-yl]phenyl}methoxy)propionic acid, 3-[({p-[1-Methyl-5-(1-phenylethoxycarbonylamino)-1H-imidazol-4-yl]phenyl}methyl)amino]-4-phenylbutyric acid, 4-Cyclopropyl-3-[({p-[1-methyl-5-(1-phenylethoxycarbonylamino)-1H-imidazol-4-yl]phenyl}methyl)amino]butyric acid, 3-({p-[1-Methyl-5-(1-phenylethoxycarbonyl-amino)-1H-imidazol-4-yl]phenyl}methoxy)-4-phenylbutyric acid or 4-Cyclopropyl-3-({p-[1-methyl-5-(1-phenylethoxycarbonylamino)-1H-imidazol-4-yl]phenyl}methoxy)butyric acid.

49. A compound of embodiment 30 wherein the compound is 2-[[4-[1,2-dimethyl-3-oxo-5-(1-phenylethoxycarbonylamino)pyrazol-4-yl]benzoyl]amino]-3-phenyl-propanoic acid, 3-cyclopropyl-2-[[4-[1,2-dimethyl-3-oxo-5-(1-phenylethoxycarbonylamino)pyrazol-4-yl]benzoyl]amino]propanoic acid, 2-[[4-[1,2-dimethyl-3-oxo-5-(1-phenylethoxycarbonyl-amino)pyrazol-4-yl]benzoyl]amino]-4-phenyl-butanoic acid, 2-[[4-[1,2-dimethyl-3-oxo-5-(1-phenylethoxycarbonylamino)pyrazol-4-yl]benzoyl]amino]-3-phenoxy-propanoic acid, 2-[({p-[1,2-Dimethyl-3-oxo-5-(1-phenylethoxycarbonylamino)-1,2-dihydropyrazol-4-yl]-phenyl}-methyl)amino]-3-phenylpropionic acid, 3-Cyclopropyl-2-[({p-[1,2-dimethyl-3-oxo-5-(1-phenylethoxycarbonylamino)-1,2-dihydropyrazol-4-yl]phenyl}methyl)amino]propionic acid, 2-({p-[1,2-Dimethyl-3-oxo-5-(1-phenylethoxycarbonylamino)-1,2-dihydropyrazol-4-yl]-phenyl}methoxy)-3-phenylpropionic acid, 3-Cyclopropyl-2-({p-[1,2-dimethyl-3-oxo-5-(1-phenylethoxycarbonylamino)-1,2-dihydropyrazol-4-yl]phenyl}methoxy)propionic acid, 3-[({p-[1,2-Dimethyl-3-oxo-5-(1-phenylethoxycarbonylamino)-1,2-dihydropyrazol-4-yl]-phenyl}-methyl)amino]-4-phenylbutyric acid, 4-Cyclopropyl-3-[({p-[1,2-dimethyl-3-oxo-5-(1-phenyl-ethoxycarbonylamino)-1,2-dihydropyrazol-4-yl]phenyl}methyl)amino]butyric acid, 3-({p-[1,2-Dimethyl-3-oxo-5-(1-phenylethoxycarbonylamino)-1,2-dihydropyrazol-4-yl]-phenyl}-methoxy)-4-phenylbutyric acid or 4-Cyclopropyl-3-({p-[1,2-dimethyl-3-oxo-5-(1-phenylethoxy-carbonylamino)-1,2-dihydropyrazol-4-yl]phenyl}methoxy)butyric acid.

50. A compound of embodiment 30 wherein the compound is 3-phenyl-2-[[4-[5-(1-phenylethoxycarbonylamino)pyrimidin-4-yl]benzoyl]amino]propanoic acid, 3-cyclopropyl-2-[[4-[5-(1-phenylethoxycarbonylamino)pyrimidin-4-yl]benzoyl]amino]propanoic acid, 4-phenyl-2-[[4-[5-(1-phenylethoxycarbonylamino)pyrimidin-4-yl]benzoyl]amino]butanoic acid, 3-phenoxy-2-[[4-[5-(1-phenylethoxycarbonylamino)pyrimidin-4-yl]benzoyl]amino]-propanoic acid, 3-Phenyl-2-[({p-[5-(1-phenylethoxycarbonylamino)-4-pyrimidinyl]phenyl}-methyl)-amino]propionic acid, 3-Cyclopropyl-2-[({p-[5-(1-phenylethoxycarbonylamino)-4-pyrimidinyl]-phenyl}methyl)amino]propionic acid, 3-Phenyl-2-({p-[5-(1-phenylethoxy-carbonylamino)-4-pyrimidinyl]phenyl}methoxy) propionic acid, 3-Cyclopropyl-2-({p-[5-(1-phenylethoxycarbonyl-amino)-4-pyrimidinyl]phenyl}methoxy)propionic acid, 4-Phenyl-3-[({p-[5-(1-phenylethoxy-carbonyl-4-pyrimidinyl]phenyl}methyl)amino]butyric acid, 4-Cyclopropyl-3-[({p-[5-(1-phenylethoxycarbonylamino)-4-pyrimidinyl]phenyl}methyl)amino]-butyric acid, 4-Phenyl-3-({p-[5-(1-phenylethoxycarbonylamino)-4-pyrimidinyl]phenyl}-methoxy)butyric acid, 4-Cyclopropyl-3-({p-[5-(1-phenylethoxycarbonylamino)-4-pyrimidinyl]phenyl}methoxy)butyric acid, 2-[[4-[6-methyl-5-(1-phenylethoxycarbonyl-amino)pyrimidin-4-yl]benzoyl]amino]-3-phenyl-propanoic acid, 3-cyclopropyl-2-[[4-[6-methyl-5-(1-phenylethoxycarbonylamino)-pyrimidin-4-yl]benzoyl]amino]propanoic acid, 2-[[4-[6-methyl-5-(1-phenylethoxycarbonyl-amino)pyrimidin-4-yl]benzoyl]amino]-4-phenyl-butanoic acid or 2-[[4-[6-methyl-5-(1-phenyl-ethoxycarbonylamino)pyrimidin-4-yl]benzoyl]-amino]-3-phenoxy-propanoic acid.

51. A compound of embodiment 30 wherein the compound is 3-phenyl-2-[[4-[4-(1-phenylethoxycarbonylamino)pyrimidin-5-yl]benzoyl]amino]propanoic acid, 3-cyclopropyl-2-[[4-[4-(1-phenylethoxycarbonylamino)pyrimidin-5-yl]benzoyl]amino]propanoic acid, 4-phenyl-2-[[4-[4-(1-phenylethoxycarbonylamino)pyrimidin-5-yl]benzoyl]amino]butanoic acid or 3-phenoxy-2-[[4-[4-(1-phenylethoxycarbonylamino)pyrimidin-5-yl]benzoyl]amino]-propanoic acid, 52. A compound of embodiment 30 wherein the compound is 3-phenyl-2-[[4-[3-(1-phenylethoxycarbonylamino)pyrazin-2-yl]benzoyl]amino]propanoic acid, 3-cyclopropyl-2-[[4-[3-(1-phenylethoxycarbonylamino)pyrazin-2-yl]benzoyl]amino]propanoic acid, 4-phenyl-2-[[4-[3-(1-phenylethoxycarbonylamino)pyrazin-2-yl]benzoyl]amino]butanoic acid or 3-phenoxy-2-[[4-[3-(1-phenylethoxycarbonylamino)pyrazin-2-yl]benzoyl]amino]propanoic acid.

53. A compound of embodiment 30 wherein the compound is 1-{p-[3-Methyl-4-(1-phenylethoxycarbonylamino)-5-isoxazolyl]phenyl}-4-piperidinecarboxylic acid, (1-{p-[3-Methyl-4-(1-phenylethoxycarbonylamino)-5-isoxazolyl]phenyl}-4-piperidyl)acetic acid, 1-(1-{p-[3-Methyl-4-(1-phenylethoxycarbonylamino)-5-isoxazolyl]phenyl}-4-piperidyl)cyclo-propanecarboxylic acid, [1-(1-{p-[3-Methyl-4-(1-phenylethoxycarbonylamino)-5-isoxazolyl]-phenyl}-4-piperidyl)cyclopropyl]acetic acid, 1-{5-[3-Methyl-4-(1-phenylethoxycarbonyl-amino)-5-isoxazolyl]-2-pyridyl}-4-piperidinecarboxylic acid, (1-{5-[3-Methyl-4-(1-phenyl-ethoxycarbonylamino)-5-isoxazolyl]-

2-pyridyl}-4-piperidyl)acetic acid, 1-(1-{5-[3-Methyl-4-(1-phenylethoxycarbonylamino)-5-isoxazolyl]-2-pyridyl}-4-piperidyl)cyclopropanecarboxylic acid, [1-(1-{5-[3-Methyl-4-(1-phenylethoxycarbonylamino)-5-isoxazolyl]-2-pyridyl}-4-piperidyl)cyclopropyl]acetic acid, 1-{p-[3-Fluoro-4-(1-phenylethoxycarbonylamino)-5-isoxazolyl]phenyl}-4-piperidinecarboxylic acid, (1-{p-[3-Fluoro-4-(1-phenylethoxycarbonyl-amino)-5-isoxazolyl]phenyl}-4-piperidyl)acetic acid, 1-(1-{p-[3-Fluoro-4-(1-phenylethoxycarbonylamino)-5-isoxazolyl]phenyl}-4-piperidyl) cyclopropanecarboxylic acid, [1-(1-{p-[3-Fluoro-4-(1-phenylethoxycarbonylamino)-5-isoxazolyl]phenyl}-4-piperidyl)cyclopropyl]acetic acid, 1-{5-[3-Fluoro-4-(1-phenylethoxycarbonylamino)-5-isoxazolyl]-2-pyridyl}-4-piperidine-carboxylic acid, (1-{5-[3-Fluoro-4-(1-phenylethoxycarbonylamino)-5-isoxazolyl]-2-pyridyl}-4-piperidyl)acetic acid, 1-(1-{5-[3-Fluoro-4-(1-phenylethoxycarbonylamino)-5-isoxazolyl]-2-pyridyl}-4-piperidyl)cyclopropanecarboxylic acid, [1-(1-{5-[3-Fluoro-4-(1-phenylethoxy-carbonylamino)-5-isoxazolyl]-2-pyridyl}-4-piperidyl)cyclopropyl]acetic acid, 1-{p-[3-Cyano-4-(1-phenylethoxycarbonylamino)-5-isoxazolyl]phenyl}-4-piperidinecarboxylic acid, (1-{p-[3-Cyano-4-(1-phenylethoxycarbonylamino)-5-isoxazolyl]phenyl}-4-piperidyl)acetic acid, 1-(1-{p-[3-Cyano-4-(1-phenylethoxycarbonylamino)-5-isoxazolyl]phenyl}-4-piperidyl)cyclo-propanecarboxylic acid, [1-(1-{p-[3-Cyano-4-(1-phenylethoxycarbonylamino)-5-isoxazolyl]-phenyl}-4-piperidyl)cyclopropyl]acetic acid, 1-{5-[3-Cyano-4-(1-phenylethoxycarbonyl-amino)-5-isoxazolyl]-2-pyridyl}-4-piperidinecarboxylic acid, (1-{5-[3-Cyano-4-(1-phenyl-ethoxycarbonylamino)-5-isoxazolyl]-2-pyridyl}-4-piperidyl)acetic acid, 1-(1-{5-[3-Cyano-4-(1-phenylethoxycarbonylamino)-5-isoxazolyl]-2-pyridyl}-4-piperidyl)cyclopropanecarboxylic acid, [1-(1-{5-[3-Cyano-4-(1-phenylethoxycarbonylamino)-5-isoxazolyl]-2-pyridyl}-4-piperidyl)cyclopropyl]acetic acid, 1-{p-[5-(1-Phenylethoxycarbonylamino)-1H-pyrazol-1-yl]phenyl}-4-piperidinecarboxylic acid, (1-{p-[5-(1-Phenylethoxycarbonylamino)-1H-pyrazol-1-yl]phenyl}-4-piperidyl)acetic acid, 1-(1-{p-[5-(1-Phenylethoxycarbonylamino)-1H-pyrazol-1-yl]phenyl}-4-piperidyl)cyclopropanecarboxylic acid, [1-(1-{p-[5-(1-Phenylethoxycarbonyl-amino)-1H-pyrazol-1-yl]phenyl}-4-piperidyl)cyclopropyl]acetic acid, 1-{5-[5-(1-Phenylethoxy-carbonylamino)-1H-pyrazol-1-yl]-2-pyridyl}-4-piperidinecarboxylic acid, (1-{5-[5-(1-Phenyl-ethoxycarbonylamino)-1H-pyrazol-1-yl]-2-pyridyl}-4-piperidyl)acetic acid, 1-(1-{5-[5-(1-Phenylethoxycarbonylamino)-1H-pyrazol-1-yl]-2-pyridyl}-4-piperidyl)cyclopropanecarboxylic acid, [1-(1-{5-[5-(1-Phenylethoxycarbonylamino)-1H-pyrazol-1-yl]-2-pyridyl}-4-piperidyl)-cyclopropyl]acetic acid, 1-{p-[4-Methyl-5-(1-phenylethoxycarbonylamino)-1H-pyrazol-1-yl]phenyl}-4-piperidinecarboxylic acid, (1-{p-[4-Methyl-5-(1-phenylethoxycarbonylamino)-1H-pyrazol-1-yl]phenyl}-4-piperidyl)acetic acid, 1-(1-{p-[4-Methyl-5-(1-phenylethoxy-carbonylamino)-1H-pyrazol-1-yl]phenyl}-4-piperidyl)cyclopropanecarboxylic acid, [1-(1-{p-[4-Methyl-5-(1-phenylethoxycarbonylamino)-1H-pyrazol-1-yl]phenyl}-4-piperidyl)cyclopropyl-]acetic acid, 1-{5-[4-Methyl-5-(1-phenylethoxycarbonylamino)-1H-pyrazol-1-yl]-2-pyridyl}-4-piperidinecarboxylic acid, (1-{5-[4-Methyl-5-(1-phenylethoxycarbonylamino)-1H-pyrazol-1-yl]-2-pyridyl}-4-piperidyl)acetic acid, 1-(1-{5-[4-Methyl-5-(1-phenylethoxycarbonylamino)-1H-pyrazol-1-yl]-2-pyridyl}-4-piperidyl)cyclopropanecarboxylic acid, [1-(1-{5-[4-Methyl-5-(1-phenylethoxycarbonylamino)-1H-pyrazol-1-yl]-2-pyridyl}-4-piperidyl)cyclopropyl]acetic acid, 1-{p-[4-Fluoro-5-(1-phenylethoxycarbonylamino)-1H-pyrazol-1-yl]phenyl}-4-piperidine-carboxylic acid, (1-{p-[4-Fluoro-5-(1-phenylethoxycarbonylamino)-1H-pyrazol-1-yl]phenyl}-4-piperidyl)acetic acid, 1-(1-{p-[4-Fluoro-5-(1-phenylethoxycarbonylamino)-1H-pyrazol-1-yl]phenyl}-4-piperidyl)cyclopropanecarboxylic acid, [1-(1-{p-[4-Fluoro-5-(1-phenylethoxy-carbonylamino)-1H-pyrazol-1-yl]phenyl}-4-piperidyl)cyclopropyl]acetic acid, 1-{5-[4-Fluoro-5-(1-phenylethoxycarbonylamino)-1H-pyrazol-1-yl]-2-pyridyl}-4-piperidinecarboxylic acid, (1-{5-[4-Fluoro-5-(1-phenylethoxycarbonylamino)-1H-pyrazol-1-yl]-2-pyridyl}-4-piperidyl)acetic acid, 1-(1-{5-[4-Fluoro-5-(1-phenylethoxycarbonylamino)-1H-pyrazol-1-yl]-2-pyridyl}-4-piperidyl)cyclopropanecarboxylic acid, [1-(1-{5-[4-Fluoro-5-(1-phenylethoxycarbonylamino)-1H-pyrazol-1-yl]-2-pyridyl}-4-piperidyl)cyclopropyl]acetic acid, 1-{p-[4-Cyano-5-(1-phenyl-ethoxycarbonylamino)-1H-pyrazol-1-yl]phenyl}-4-piperidinecarboxylic acid, (1-{p-[4-Cyano-5-(1-phenylethoxycarbonylamino)-1H-pyrazol-1-yl]phenyl}-4-piperidyl)acetic acid, 1-(1-{p-[4-Cyano-5-(1-phenylethoxycarbonylamino)-1H-pyrazol-1-yl]phenyl}-4-piperidyl)cyclopropane-carboxylic acid, [1-(1-{p-[4-Cyano-5-(1-phenylethoxycarbonylamino)-1H-pyrazol-1-yl]-phenyl}-4-piperidyl)cyclopropyl]acetic acid, 1-{5-[4-Cyano-5-(1-phenylethoxycarbonyl-amino)-1H-pyrazol-1-yl]-2-pyridyl}-4-piperidinecarboxylic acid, (1-{5-[4-Cyano-5-(1-phenyl-ethoxycarbonylamino)-1H-pyrazol-1-yl]-2-pyridyl}-4-piperidyl)acetic acid, 1-(1-{5-[4-Cyano-5-(1-phenylethoxycarbonylamino)-1H-pyrazol-1-yl]-2-pyridyl}-4-piperidyl)cyclopropane-carboxylic acid or [1-(1-{5-[4-Cyano-5-(1-phenylethoxycarbonylamino)-1H-pyrazol-1-yl]-2-pyridyl}-4-piperidyl)cyclopropyl]acetic acid.

54. A pharmaceutically acceptable formulation comprising, consisting essentially of, or consisting of a compound of Table 1 and one or more pharmaceutically acceptable excipients.

55. A pharmaceutically acceptable formulation comprising, consisting essentially of, or consisting of a compound of embodiment 31 and one or more pharmaceutically acceptable excipients.

56. A pharmaceutically acceptable formulation comprising, consisting essentially of, or consisting of a compound of embodiment 32 and one or more pharmaceutically acceptable excipients.

57. A pharmaceutically acceptable formulation comprising, consisting essentially of, or consisting of a compound of embodiment 33 and one or more pharmaceutically acceptable excipients.

58. A pharmaceutically acceptable formulation comprising, consisting essentially of, or consisting of a compound of embodiment 34 and one or more pharmaceutically acceptable excipients.

59. A pharmaceutically acceptable formulation comprising, consisting essentially of, or consisting of a compound of embodiment 35 and one or more pharmaceutically acceptable excipients.

60. A pharmaceutically acceptable formulation comprising, consisting essentially of, or consisting of a compound of embodiment 36 and one or more pharmaceutically acceptable excipients.

61. A pharmaceutically acceptable formulation comprising, consisting essentially of, or consisting of a compound of embodiment 37 and one or more pharmaceutically acceptable excipients.

62. A pharmaceutically acceptable formulation comprising, consisting essentially of, or consisting of a compound of embodiment 38 and one or more pharmaceutically acceptable excipients.

63. A pharmaceutically acceptable formulation comprising, consisting essentially of, or consisting of a compound of embodiment 39 and one or more pharmaceutically acceptable excipients.

64. A pharmaceutically acceptable formulation comprising, consisting essentially of, or consisting of a compound of embodiment 40 and one or more pharmaceutically acceptable excipients.

65. A pharmaceutically acceptable formulation comprising, consisting essentially of, or consisting of a compound of embodiment 41 and one or more pharmaceutically acceptable excipients.

66. A pharmaceutically acceptable formulation comprising, consisting essentially of, or consisting of a compound of embodiment 42 and one or more pharmaceutically acceptable excipients.

67. A pharmaceutically acceptable formulation comprising, consisting essentially of, or consisting of a compound of embodiment 43 and one or more pharmaceutically acceptable excipients.

68. A pharmaceutically acceptable formulation comprising, consisting essentially of, or consisting of a compound of embodiment 44 and one or more pharmaceutically acceptable excipients.

69. A pharmaceutically acceptable formulation comprising, consisting essentially of, or consisting of a compound of embodiment 45 and one or more pharmaceutically acceptable excipients.

70. A pharmaceutically acceptable formulation comprising, consisting essentially of, or consisting of a compound of embodiment 46 and one or more pharmaceutically acceptable excipients.

71. A pharmaceutically acceptable formulation comprising, consisting essentially of, or consisting of a compound of embodiment 47 and one or more pharmaceutically acceptable excipients.

72. A pharmaceutically acceptable formulation comprising, consisting essentially of, or consisting of a compound of embodiment 48 and one or more pharmaceutically acceptable excipients.

73. A pharmaceutically acceptable formulation comprising, consisting essentially of, or consisting of a compound of embodiment 49 and one or more pharmaceutically acceptable excipients.

74. A pharmaceutically acceptable formulation comprising, consisting essentially of, or consisting of a compound of embodiment 50 and one or more pharmaceutically acceptable excipients.

75. A pharmaceutically acceptable formulation comprising, consisting essentially of, or consisting of a compound of embodiment 51 and one or more pharmaceutically acceptable excipients.

76. A pharmaceutically acceptable formulation comprising, consisting essentially of, or consisting of a compound of embodiment 52 and one or more pharmaceutically acceptable excipients.

77. A pharmaceutically acceptable formulation comprising, consisting essentially of, or consisting of a compound of embodiment 53 and one or more pharmaceutically acceptable excipients.

78. A method comprising administering an effective amount of a Formula I-XII compound to a subject having a LPA-dependent or LPA-mediated disease or condition.

79. The method of embodiment 78 wherein the LPA-dependent or LPA-mediated disease or condition is a disease with fibrosis of the organs.

80. The method of embodiment 79 wherein the fibrosis is of the liver, kidney, lung, heart, eye and the like.

81. The method of embodiment 78 wherein the LPA-dependent or LPA-mediated disease or condition is chronic pain 82. The method of embodiment 78 wherein the LPA-dependent or LPA-mediated disease or condition is pruritus.

83. The method of embodiment 78 wherein the LPA-mediated disease is a proliferative disease including cancer (solid tumor, solid tumor metastasis, vascular fibroma, myeloma, multiple myeloma, Kaposi's sarcoma, leukemia, chronic lymphocytic leukemia (CLL) and the like) and invasive metastasis of cancer cell, including ovarian, breast and triple negative breast cancer and the like, 84. The method of embodiment 78 wherein the LPA-mediated disease is an inflammatory disease including psoriasis, nephropathy, pneumonia and the like, 85. The method of embodiment 78 wherein the LPA-mediated disease is a gastrointestinal disease such as inflammatory bowel disease, 86. The method of embodiment 78 wherein the LPA-mediated disease is an ocular disease including age-related macular degeneration (AMD), diabetic retinopathy, proliferative vitreoretinopathy (PVR), cicatricial pemphigoid, glaucoma filtration surgery scarring, uveitis and the like, 87. The method of embodiment 78 wherein the LPA-mediated disease is a liver disease including acute hepatitis, chronic hepatitis, liver fibrosis, liver cirrhosis, cholestatic pruritus, portal hypertension, regenerative failure, nonalcoholic steatohepatitis (NASH), liver hypofunction, hepatic blood flow disorder, and the like, 88. The method of embodiment 78 wherein the LPA-mediated disease is a renal disease including chronic kidney disease, end stage renal disease, uremic pruritus, nephropathy including diabetic nephropathy and the like, 89. The method of embodiment 78 wherein the LPA-mediated disease is a skin disease including scleroderma, skin scarring, atopic dermatitis, psoriasis and the like, 90. The method of any one of embodiments 78-89 wherein the subject is a human.

91. The method of any one of embodiments 78-90 wherein the compound is selected from Table 1.

92. The method of any one of embodiments 78-90 wherein the compound is 1-(4-{4-[1-(2-Chloro-phenyl)-ethoxycarbonylamino]-3-methyl-isoxazol-5-yl}-benzoylamino)-cyclo-propanecarboxylic acid, 2-(4-{4-[1-(2-Chloro-phenyl)-ethoxycarbonyl-amino]-3-methyl-isoxazol-5-yl}-benzoylamino)-indan-2-carboxylic acid, 2-(S)-(4-{4-[(R,S)-1-(2-Chloro-phenyl)-ethoxycarbonylamino]-3-methyl-isoxazol-5-yl}-benzoylamino) phenyl acetic acid, 2-(R)-(4-{4-[(R,S)-1-(2-Chloro-phenyl)-ethoxycarbonylamino]-3-methyl-isoxazol-5-yl}-benzoylamino) phenyl propanoic acid, 2(R)-[[4-[3-methyl-4-((R)-1-phenyl-ethoxycarbonylamino)isoxazol-5-yl]benzoyl]amino]-3-phenyl-propanoic acid, 2(S)-[[4-[3-methyl-4-((R)-phenylethoxycarbonyl-amino)isoxazol-5-yl]benzoyl]amino]-3-phenyl-propanoic acid, (R)-2-{4-[3-Methyl-4-((S)-1-phenyl-ethoxycarbonylamino)-isoxazol-5-yl]-benzoylamino}-3-phenyl-propionic acid, (S)-2-{4-[3-Methyl-4-((S)-1-phenyl-ethoxycarbonylamino)-isoxazol-5-yl]-benzoylamino}-3-phenyl-propionic acid, (R)-2-(4-{4-[(R)-1-(2-Chloro-phenyl)-ethoxycarbonylamino]-3-methyl-isoxazol-5-yl}-benzoylamino)-3-phenyl-propionic acid, (R)-2-(4-{4-[(R)-1-(2-Chloro-phenyl)-ethoxycarbonylamino]-3-methyl-isoxazol-5-yl}-benzoylamino)-3-(4-fluoro-phenyl)-propionic acid, (R)-3-(4-Chloro-phenyl)-2-(4-{4-[(R)-1-(2-chloro-phenyl)-ethoxycarbonylamino]-3-methyl-isoxazol-5-yl}-benzoylamino)-propionic acid, (R)-2-(4-{4-[(R)-1-(2-Chloro-phenyl)-ethoxycarbonylamino]-3-methyl-isoxazol-5-yl}-benzoylamino)-3-(3,4-difluoro-phenyl)-propionic acid, (R)-3-(2-Chloro-phenyl)-2-(4-{4-[(R)-1-(2-chloro-phenyl)-ethoxycarbonylamino]-3-methyl-isoxazol-5-yl}-benzoylamino)-propionic acid, (R)-3-(4-Bromo-phenyl)-2-(4-{4-[(R)-1-(2-chloro-phenyl)-ethoxycarbonylamino]-3-methyl-isoxazol-5-yl}-benzoylamino)-propionic acid, (R)-2-(4-{4-[(R)-1-(2-Chloro-phenyl)-ethoxycarbonylamino]-3-methyl-isoxazol-5-yl}-benzoylamino)-3-(2-fluoro-phenyl)-propionic acid, (R)-2-(4-{4-[(R)-1-(2-Chloro-phenyl)-ethoxycarbonylamino]-3-methyl-isoxazol-5-yl}-benzoylamino)-3-p-tolyl-propionic acid, (R)-2-(4-{4-[(R)-1-(2-Chloro-phenyl)-ethoxycarbonylamino]-3-methyl-isoxazol-5-yl}-benzoylamino)-3-(4-trifluoromethyl-phenyl)-propionic acid, (R)-2-(4-{4-[(R)-1-(2-Chloro-phenyl)-ethoxycarbonylamino]-3-methyl-isoxazol-5-yl}-benzoylamino)-3-(4-cyano-phenyl)-propionic acid, (R)-2-(4-{4-[(R)-1-(2-chloro-phenyl)-ethoxycarbonylamino]-3-methyl-isoxazol-5-yl}-benzoylamino)-3-cyclopropyl-propionic acid, (R)-2-[[4-[2,5-dimethyl-4-((R)-1-phenylethoxycarbonylamino)pyrazol-3-yl]benzoyl]amino]-3-phenyl-propanoic acid, (R)-2-[[4-[2,5-dimethyl-4-((R)-1-phenylethoxycarbonylamino)pyrazol-3-yl]benzoyl]amino]-3-(4-fluorophenyl)propanoic acid, (R)-3-(4-bromophenyl)-2-[[4-[2,5-dimethyl-4-((R)-1-phenylethoxycarbonyl-amino)pyrazol-3-yl]benzoyl]amino]propanoic acid, (R)-3-(4-chlorophenyl)-2-[[4-[2,5-dimethyl-4-((R)-1-phenylethoxycarbonyl-amino)pyrazol-3-yl]benzoyl]amino]propanoic acid, (R)-3-(3,4-difluorophenyl)-2-[[4-[2,5-dimethyl-4-((R)-1-phenylethoxycarbonyl-amino)pyrazol-3-yl]benzoyl]amino]propanoic acid, (R)-2-[[4-[1,5-dimethyl-4-((R)-1-phenylethoxycarbonylamino)pyrazol-3-yl]benzoyl]amino]-3-phenyl-propanoic acid, (R)-2-[[4-[1,5-dimethyl-4-((R)-1-phenylethoxycarbonylamino)pyrazol-3-yl]benzoyl]amino]-3-(4-fluorophenyl)propanoic acid, (R)-3-(4-bromophenyl)-2-[[4-[1,5-dimethyl-4-((R)-1-phenylethoxycarbonyl-amino) pyrazol-3-yl]benzoyl]amino]propanoic acid, ((R)-3-(4-chlorophenyl)-2-[[4-[1,5-dimethyl-4-((R)-1-phenylethoxycarbonyl-amino)pyrazol-3-yl]benzoyl]amino]propanoic acid, (R)-3-(3,4-difluorophenyl)-2-[[4-[1,5-dimethyl-4-((R)-1-phenylethoxycarbonyl-amino)pyrazol-3-yl]benzoyl]amino]propanoic acid, (R)-2-(4-{5-[(R)-1-(2-Chloro-phenyl)-ethoxycarbonylamino]-4-methyl-pyrazol-1-yl}-benzoylamino)-3-phenyl-propionic acid, (R)-2-{4-[3-Methyl-4-((R)-1-phenyl-ethoxycarbonylamino)-isoxazol-5-yl]-benzylamino}-3-phenyl-propionic acid, (R)-3-(2-Fluoro-phenyl)-2-{4-[3-methyl-4-((R)-1-phenyl-ethoxycarbonylamino)-isoxazol-5-yl]-benzylamino}-propionic acid, (R)-2-{4-[3-Methyl-4-((R)-1-phenyl-ethoxycarbonylamino)-isoxazol-5-yl]-benzylamino}-3-(4-trifluoromethyl-phenyl)-propionic acid, (R)-3-Cyclopropyl-2-{4-[3-methyl-4-((R)-1-phenyl-ethoxycarbonylamino)-isoxazol-5-yl]-benzylamino}-propionic acid, (R)-3-(2-Chloro-phenyl)-2-{4-[3-methyl-4-((R)-1-phenyl-ethoxycarbonylamino)-isoxazol-5-yl]-benzylamino}-propionic acid, (R)-3-(4-Chloro-phenyl)-2-{4-[3-methyl-4-((R)-1-phenyl-ethoxycarbonylamino)-isoxazol-5-yl]-benzylamino}-propionic acid, (R)-2-(4-{[(R)-1-(2-Chloro-phenyl)-ethoxycarbonylamino]-3-methyl-isoxazol-5-yl}-benzylamino)-3-phenyl-propionic acid, (R)-2-(4-{4-[(R)_1-(2-Chloro-phenyl)-ethoxycarbonylamino]-3-methyl-isoxazol-5-yl}-benzylamino)-3-(2-fluoro-phenyl)-propionic acid, (R)-2-(4-{4-[(R)-1-(2-Chloro-phenyl)-ethoxycarbonylamino]-3-methyl-isoxazol-5-yl}-benzylamino)-3-(4-trifluoromethyl-phenyl)-propionic acid, (R)-3-(2-Chloro-phenyl)-2-(4-{4-[(R)-1-(2-chloro-phenyl)-ethoxycarbonylamino]-3-methyl-isoxazol-5-yl}-benzylamino)-propionic acid, (R)-2-(4-{4-[(R)-1-(2-Chloro-phenyl)-ethoxycarbonylamino]-3-methyl-isoxazol-5-yl}-benzylamino)-3-cyclopropyl-propionic acid, 2-{4-[3-Methyl-4-((R)-1-phenyl-ethoxycarbonylamino)-isoxazol-5-yl]-benzyloxy}-3-phenyl-propionic acid, 2-{4-[3-Methyl-4-((R)-1-phenyl-ethoxycarbonylamino)-isoxazol-5-yl]-benzyloxy}-3-phenyl-propionic acid, (RS)-3-Cyclopropyl-2-{4-[3-methyl-4-((R)-1-phenyl-ethoxycarbonylamino)-isoxazol-5-yl]-benzyloxy}-propionic acid, (RS)-3-Cyclopropyl-2-{4-[3-methyl-4-((R)-1-phenyl-ethoxycarbonylamino)-isoxazol-5-yl]-benzyloxy}-propionic acid, 2-[4-[4-[5-[1-(2-chlorophenyl)ethoxycarbonylamino]-4-cyano-pyrazol-1-yl]phenyl]phenyl]acetic acid, (R)-1-[4-[4-[1,5-dimethyl-4-(1-phenylethoxycarbonylamino)pyrazol-3-yl]phenyl]phenyl-cyclopropane carboxylic acid, (R)-1-[4-[4-[2,5-dimethyl-4-(1-phenylethoxycarbonylamino)-pyrazol-3-yl]phenyl]phenyl]cyclopropane carboxylic acid, (R)-1-(4'-{5-[1-(2-Chloro-phenyl)-ethoxycarbonyl-amino]-4-fluoro-pyrazol-1-yl}-3-fluoro-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-2-fluoro-biphenyl-4-yl)-cyclo-propanecarboxylic acid, (R)-1-(2-Chloro-4'-{5-[1-(2-chloro-phenyl)-ethoxycarbonylamino]-4-fluoro-pyrazol-1-yl}-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-2-methyl-biphenyl-4-yl)-cyclopropanecarboxylic acid, (R)-1-(4'-{5-[1-(2-Chloro-phenyl)-ethoxy-carbonylamino]-4-fluoro-pyrazol-1-yl}-biphenyl-4-yl)-cyclopropanecarboxylic acid, (R)-1-{4'-[5-(1-Phenyl-ethoxycarbonylamino)-4-trifluoromethyl-pyrazol-1-yl]-biphenyl-4-yl}-cyclo-propanecarboxylic acid, (R)-1-{2-Fluoro-4'-[5-(1-phenyl-ethoxycarbonylamino)-4-trifluoro-methyl-pyrazol-1-yl]-biphenyl-4-yl}-cyclopropanecarboxylic acid, (R)-1-(4-{5-[5-(1-Phenyl-ethoxycarbonylamino)-pyrazol-1-yl]-pyridin-2-yl}-phenyl)-cyclopropanecarboxylic acid, 93. The method of any one of embodiments 78-90 wherein the compound is selected from embodiment 31.
94. The method of any one of embodiments 78-90 wherein the compound is selected from embodiment 32.
95. The method of any one of embodiments 78-90 wherein the compound is selected from embodiment 33.
96. The method of any one of embodiments 78-90 wherein the compound is selected from embodiment 34.
97. The method of any one of embodiments 78-90 wherein the compound is selected from embodiment 35.
98. The method of any one of embodiments 78-90 wherein the compound is selected from embodiment 36.
99. The method of any one of embodiments 78-90 wherein the compound is selected from embodiment 37.
100. The method of any one of embodiments 78-90 wherein the compound is selected from embodiment 38.
101. The method of any one of embodiments 78-90 wherein the compound is selected from embodiment 39.
102. The method of any one of embodiments 78-90 wherein the compound is selected from embodiment 40.
103. The method of any one of embodiments 78-90 wherein the compound is selected from embodiment 41.
104. The method of any one of embodiments 78-90 wherein the compound is selected from embodiment 42.

105. The method of any one of embodiments 78-90 wherein the compound is selected from embodiment 43.

106. The method of any one of embodiments 78-90 wherein the compound is selected from embodiment 44.

107. The method of any one of embodiments 78-90 wherein the compound is selected from embodiment 45.

108. The method of any one of embodiments 78-90 wherein the compound is selected from embodiment 46.

109. The method of any one of embodiments 78-90 wherein the compound is selected from embodiment 47.

110. The method of any one of embodiments 78-90 wherein the compound is selected from embodiment 48.

111. The method of any one of embodiments 78-90 wherein the compound is selected from embodiment 49.

112. The method of any one of embodiments 78-90 wherein the compound is selected from embodiment 50.

113. The method of any one of embodiments 78-90 wherein the compound is selected from embodiment 51.

114. The method of any one of embodiments 78-90 wherein the compound is selected from embodiment 52.

115. The method of any one of embodiments 78-90 wherein the compound is selected from embodiment 53.

116. A composition comprising, consisting essentially of or consisting of one or more compounds of Formula (I-XII) and one or more agents currently used to treat a LPA-dependent or LPA-mediated disease or a disease or condition described herein.

117. A pharmaceutically acceptable formulation comprising, consisting essentially of or consisting of one or more compounds of Formula (I-XII), one or more agents currently used to treat a LPA-dependent or LPA-mediated disease and one or more pharmaceutically acceptable excipients.

118. A method comprising administering in combination with or co-administrating a compound of Formula (I-XII) to a subject with a LPA-dependent or LPA-mediated disease or condition and a currently used agent to treat a LPA-dependent or LPA-mediated disease The one or more additional therapeutically active agents other than compounds of Formula (I-XII) are selected from: corticosteroids, immunosuppressants, analgesics, anti-cancer agents, anti-inflammatories, chemokine receptor antagonists, bronchodilators, leukotriene receptor antagonists, leukotriene formation inhibitors, platelet activating factor receptor antagonists, monoacylglycerol kinase inhibitors, phospholipase $A_1$ inhibitors, phospholipase $A_2$ inhibitors, and lysophospholipase D (lysoPLD) inhibitors, autotaxin inhibitors, decongestants, mast cell stabilizers, antihistamines, mucolytics, anticholinergics, antitussives, expectorants, and β-2 agonists.

In preferred embodiments the currently used agent(s) are selected from those described in the Merck Index known to affect lysophosphatidic acid receptor signaling. In other preferred embodiments the Formula (I-XII) compound is selected from Table 1.

In other embodiments, therapies which combine a compound of Formula (I-XII), with currently used agents that act on differing signalling pathways to the LPA synthesis or signalling pathway so as to provide complementary clinical outcomes, are encompassed herein for treating LPA-dependent or LPA-mediated diseases or conditions.

Examples of additional therapeutic agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, trastuzumab, BAY 11-7082, PKC412, or PD 184352, Taxol™ (paclitaxel), and analogs of Taxol™, such as Taxotere™, U0126, PD98059, PD184352, PD0325901, ARRY-142886, SB239063, SP600 125, BAY 43-9006, wortmannin, or LY294002, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; amino glutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; deazaguanine; deazaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spiro germanium hydrochloride; spiromustine; spiroplatin; streptonigrin; streptozotocin; sulofenur; talisomycin; tecogalan sodium; tegafur; teloxantrone hydrochloride; temoporfm; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, mechloroethamine, cyclophosphamide, chlorambucil, meiphalan, etc.), ethylenimine, hexamethlymelamine, thiotepa, busulfan), carmustine, lomusitne, semustine, streptozocin, ortriazenes, dacarbazine, methotrexate, fluorouracil, floxouridine, Cytarabine, mercaptopurine, thioguanine, pentostatin, hydroxyprogesterone caproate, megestrol acetate, medroxyprogesterone acetate, estrogens, diethlystilbestrol, ethinyl estradiol, tamoxifen), testosterone propionate, fluoxymesterone, flutamide, leuprolide, cisplatin, carboblatin, mitoxantrone), procarbazine, mitotane, amino glutethimide, Erbulozole, Dolastatin 10, Mivobulin isethionate, Vincristine, NSC-639829, Discodermolide, ABT-751, Altorhyrtin A and Altorhyrtin C), Spongistatins 1-9, Cemadotin hydrochloride, Epothilone A, Epothilone B, Epothilone C, Epothilone D, Epothilone E, Epothilone F, Epothilone B N-oxide, Epothilone AN-oxide, 16-aza-epothilone B, 21aminoepothilone B, 21-hydroxyepothilone D, 26-fluoroepothilone, Auristatin PE, Soblidotin, Cryptophycin 52, Vitilevuamide, Tubulysin A, Canadensol, Centaureidin, Oncocidin Al Fijianolide B, Laulimalide, Narcosine, Nascapine, Hemiasterlin, Vanadocene acetylacetonate, Indanocine Eleutherobins (such as Desmethyleleutherobin, Desacetyleleutherobin, Isoeleutherobin A, and Z-Eleutherobin), Caribaeoside, Caribaeolin, Halichondrin B, Diazonamide A, Taccalonolide A, Diozostatin, (−)-Phenylahistin, Myoseverin B, Resverastatin phosphate sodium, Aprepitant, *cannabis*, marinol, dronabinol, erythropoetin-α, Filgrastim, rituximab, natalizumab, cyclophosphamide, penicillamine, cyclosporine, nitrosoureas, cisplatin, carboplatin, oxaliplatin, methotrexate, azathioprine, mercaptopurine, pyrimidine analogues, protein synthesis inhibitors, dactinomycin, anthracyclines, mitomycin C, bleomycin, mithramycin, Atgam® Thymoglobuline®, OKT3®, basiliximab, daclizumab, cyclosporin, tacrolimus, sirolimus, Interferons, opioids, infliximab, etanercept, adalimumab, golimumab, leflunomide, sulfasalazine, hydroxychloroquinine, minocycline, rapamicin, mycophenolic acid, mycophenolate mofetil, FTY720, Cyclosporin A (CsA) or tacrolimus (FK506), aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, valdecoxib, parecoxib, etoricoxib, lumiracoxib, betamethasone, prednisone, alclometasone, aldosterone, amcinonide, beclomethasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, ulobetasol, pioglitazone, clofibrate, fenofibrate gemfibrozil, folic acid, isbogrel, ozagrel, ridogrel, dazoxiben, lovastatin, simvastatin, pravastatin, fluvastatin, atorvastatin, nisvastatin, and rosuvastatin, edaravone, vitamin C, TROLOX™, citicoline and minicycline, (2R)-2-propyloctanoic acid, propranolol, nadolol, timolol, pindolol, labetalol, metoprolol, atenolol, esmolol and acebutolol, memantine, traxoprodil, tirofiban lamifiban, argatroban, enalapril, cyclandelate, losartan, valsartan, candesartan, irbesartan, telmisartan, olmesartan mepyramine (pyrilamine), antazoline, diphenhydramine, carbinoxamine, doxylamine, clemastine, dimenhydrinate, pheniramine, chlorphenamine (chlorpheniramine), dexchlorpheniramine, brompheniramine, triprolidine, cetirizine, cyclizine, chlorcyclizine, hydroxyzine, meclizine, loratadine, desloratidine, promethazine, alimemazine (trimeprazine), cyproheptadine, azatadine, ketotifen, acrivastine, astemizole, cetirizine, mizolastine, terfenadine, azelastine, epinastine, levocabastine, olopatadine, levocetirizine, fexofenadine, rupatadine, bepotastine), mucolytics, anticholinergics, antitussives, analgesics, expectorants, albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, pranlukast, tomelukast, zafirlukast, ambrisentan, bosentan, enrasentan, sitaxsentan, tezosentan, iloprost, treprostinil, pirfenidone, epinephrine, isoproterenol, orciprenaline, xanthines, zileuton.

119. The method of embodiments 116-118 wherein the subject is a human.

120. The method of embodiments 116-119 wherein the Formula I-XII compound(s) are selected from Table 1.

121. The method of embodiments 116-119 wherein the Formula I-XII compound(s) are selected from the group consisting of 1-(4-{4-[1-(2-Chloro-phenyl)-ethoxycarbonylamino]-3-methyl-isoxazol-5-yl}-benzoylamino)-cyclopropanecarboxylic acid, 2-(4-{4-[1-(2-Chloro-phenyl)-ethoxycarbonylamino]-3-methyl-isoxazol-5-yl}-benzoylamino)-indan-2-carboxylic acid, 2-(S)-(4-{4-[(R,S)-1-(2-Chloro-phenyl)-ethoxycarbonylamino]-3-methyl-isoxazol-5-yl}-benzoylamino) phenyl acetic acid, 2-(R)-(4-{4-[(R,S)-1-(2-Chloro-phenyl)-ethoxycarbonylamino]-3-methyl-isoxazol-5-yl}-benzoylamino) phenyl propanoic acid, 2(R)-[[4-[3-methyl-4-((R)-1-phenylethoxycarbonylamino)isoxazol-5-yl]benzoyl]amino]-3-phenyl-propanoic acid, 2(S)-[[4-[3-methyl-4-((R)-phenylethoxycarbonyl-amino)isoxazol-5-yl]benzoyl]amino]-3-phenyl-propanoic acid, (R)-2-{4-[3-Methyl-4-((S)-1-phenyl-ethoxycarbonylamino)-isoxazol-5-yl]-benzoylamino}-3-phenyl-propionic acid, (S)-2-{4-[3-Methyl-4-((S)-1-phenyl-ethoxycarbonylamino)-isoxazol-5-yl]-benzoylamino}-3-phenyl-propionic acid, (R)-2-(4-{4-[(R)-1-(2-Chloro-phenyl)-ethoxycarbonylamino]-3-methyl-isoxazol-5-yl}-benzoylamino)-3-phenyl-propionic acid, (R)-2-(4-{4-[(R)-1-(2-Chloro-phenyl)-ethoxycarbonylamino]-3-methyl-isoxazol-5-yl}-benzoylamino)-3-(4-fluoro-phenyl)-propionic acid, (R)-3-(4-Chloro-phenyl)-2-(4-{4-[(R)-1-(2-chloro-phenyl)-ethoxycarbonylamino]-3-methyl-isoxazol-5-yl}-benzoylamino)-propionic acid, (R)-2-(4-{4-[(R)-1-(2-Chloro-phenyl)-ethoxycarbonylamino]-3-methyl-isoxazol-5-yl}-benzoylamino)-3-(3,4-difluoro-phenyl)-propionic acid, (R)-3-(2-Chloro-phenyl)-2-(4-{4-[(R)-1-(2-chloro-phenyl)-ethoxycarbonylamino]-3-methyl-isoxazol-5-yl}-benzoylamino)-propionic acid, (R)-3-(4-Bromo-phenyl)-2-(4-{4-[(R)-1-(2-chloro-phenyl)-ethoxycarbonylamino]-3-methyl-isoxazol-5-yl}-benzoylamino)-propionic acid, (R)-2-(4-{4-[(R)-1-(2-Chloro-phenyl)-ethoxycarbonylamino]-3-methyl-isoxazol-5-yl}-benzoylamino)-3-(2-fluoro-phenyl)-propionic acid, (R)-2-(4-{4-[(R)-1-(2-Chloro-phenyl)-ethoxycarbonylamino]-3-methyl-isoxazol-5-yl}-benzoylamino)-3-p-tolyl-propionic acid, (R)-2-(4-{4-[(R)-1-(2-Chloro-phenyl)-ethoxycarbonylamino]-3-methyl-isoxazol-5-yl}-benzoylamino)-3-(4-trifluoromethyl-phenyl)-propionic acid, (R)-2-(4-{4-[(R)-1-(2-Chloro-phenyl)-ethoxycarbonylamino]-3-methyl-isoxazol-5-yl}-benzoylamino)-3-(4-cyano-phenyl)-propionic acid, (R)-2-

(4-{4-[(R)-1-(2-chloro-phenyl)-ethoxycarbonylamino]-3-methyl-isoxazol-5-yl}-benzoylamino)-3-cyclopropyl-propionic acid, (R)-2-[[4-[2,5-dimethyl-4-((R)-1-phenylethoxycarbonylamino)pyrazol-3-yl]benzoyl]amino]-3-phenyl-propanoic acid, (R)-2-[[4-[2,5-dimethyl-4-((R)-1-phenylethoxycarbonylamino)pyrazol-3-yl]benzoyl]amino]-3-(4-fluorophenyl)propanoic acid, (R)-3-(4-bromophenyl)-2-[[4-[2,5-dimethyl-4-((R)-1-phenylethoxycarbonyl-amino)pyrazol-3-yl]benzoyl]amino]propanoic acid, (R)-3-(4-chlorophenyl)-2-[[4-[2,5-dimethyl-4-((R)-1-phenylethoxycarbonyl-amino)pyrazol-3-yl]benzoyl]amino]propanoic acid, (R)-3-(3,4-difluorophenyl)-2-[[4-[2,5-dimethyl-4-((R)-1-phenylethoxycarbonyl-amino) pyrazol-3-yl]benzoyl]amino] propanoic acid, (R)-2-[[4-[1,5-dimethyl-4-((R)-1-phenylethoxycarbonylamino)pyrazol-3-yl]benzoyl]amino]-3-phenyl-propanoic acid, (R)-2-[[4-[1,5-dimethyl-4-((R)-1-phenylethoxycarbonylamino)pyrazol-3-yl]benzoyl]amino]-3-(4-fluorophenyl)propanoic acid, (R)-3-(4-bromophenyl)-2-[[4-[1,5-dimethyl-4-((R)-1-phenylethoxycarbonyl-amino)pyrazol-3-yl]benzoyl]amino]propanoic acid, (R)-3-(4-chlorophenyl)-2-[[4-[1,5-dimethyl-4-((R)-1-phenylethoxycarbonyl-amino)pyrazol-3-yl]benzoyl]amino]propanoic acid, (R)-3-(3,4-difluorophenyl)-2-[[4-[1,5-dimethyl-4-((R)-1-phenylethoxycarbonyl-amino)pyrazol-3-yl]benzoyl]amino] propanoic acid, (R)-2-(4-{5-[(R)-1-(2-Chloro-phenyl)-ethoxycarbonylamino]-4-methyl-pyrazol-1-yl}-benzoylamino)-3-phenyl-propionic acid, (R)-2-{4-[3-Methyl-4-((R)-1-phenyl-ethoxycarbonylamino)-isoxazol-5-yl]-benzylamino}-3-phenyl-propionic acid, (R)-3-(2-Fluoro-phenyl)-2-{4-[3-methyl-4-((R)-1-phenyl-ethoxycarbonylamino)-isoxazol-5-yl]-benzylamino}-propionic acid, (R)-2-{4-[3-Methyl-4-((R)-1-phenyl-ethoxycarbonylamino)-isoxazol-5-yl]-benzylamino}-3-(4-trifluoromethyl-phenyl)-propionic acid, (R)-3-Cyclopropyl-2-{4-[3-methyl-4-((R)-1-phenyl-ethoxycarbonylamino)-isoxazol-5-yl]-benzylamino}-propionic acid, (R)-3-(2-Chloro-phenyl)-2-{4-[3-methyl-4-((R)-1-phenyl-ethoxycarbonylamino)-isoxazol-5-yl]-benzylamino}-propionic acid, (R)-3-(4-Chloro-phenyl)-2-{4-[3-methyl-4-((R)-1-phenyl-ethoxycarbonylamino)-isoxazol-5-yl]-benzylamino}-propionic acid, (R)-2-(4-{4-[(R)-1-(2-Chloro-phenyl)-ethoxycarbonylamino]-3-methyl-isoxazol-5-yl}-benzylamino)-3-phenyl-propionic acid, (R)-2-(4-{4-[(R)_1-(2-Chloro-phenyl)-ethoxycarbonylamino]-3-methyl-isoxazol-5-yl}-benzylamino)-3-(2-fluoro-phenyl)-propionic acid, (R)-2-(4-{4-[(R)-1-(2-Chloro-phenyl)-ethoxycarbonylamino]-3-methyl-isoxazol-5-yl}-benzylamino)-3-(4-trifluoromethyl-phenyl)-propionic acid, (R)-3-(2-Chloro-phenyl)-2-(4-{4-[(R)-1-(2-chloro-phenyl)-ethoxycarbonylamino]-3-methyl-isoxazol-5-yl}-benzylamino)-propionic acid, (R)-2-(4-{4-[(R)-1-(2-Chloro-phenyl)-ethoxycarbonylamino]-3-methyl-isoxazol-5-yl}-benzylamino)-3-cyclopropyl-propionic acid, 2-{4-[3-Methyl-4-((R)-1-phenyl-ethoxycarbonylamino)-isoxazol-5-yl]-benzyloxy}-3-phenyl-propionic acid, 2-{4-[3-Methyl-4-((R)-1-phenyl-ethoxycarbonylamino)-isoxazol-5-yl]-benzyloxy}-3-phenyl-propionic acid, (RS)-3-Cyclopropyl-2-{4-[3-methyl-4-((R)-1-phenyl-ethoxycarbonylamino)-isoxazol-5-yl]-benzyloxy}-propionic acid, (RS)-3-Cyclopropyl-2-{4-[3-methyl-4-((R)-1-phenyl-ethoxycarbonylamino)-isoxazol-5-yl]-benzyloxy}-propionic acid, 2-[4-[4-[5-[1-(2-chlorophenyl)ethoxycarbonylamino]-4-cyano-pyrazol-1-yl]phenyl]phenyl]acetic acid, (R)-1-[4-[4-[1,5-dimethyl-4-(1-phenylethoxycarbonylamino)pyrazol-3-yl]phenyl]phenyl]cyclo-propane carboxylic acid, (R)-1-[4-[4-[2,5-dimethyl-4-(1-phenylethoxycarbonylamino)pyrazol-3-yl]phenyl]phenyl]-cyclopropane carboxylic acid, (R)-1-(4'-{5-[1-(2-Chloro-phenyl)-ethoxycarbonyl-amino]-4-fluoro-pyrazol-1-yl}-3-fluoro-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-2-fluoro-biphenyl-4-yl)-cyclo-propanecarboxylic acid, (R)-1-(2-Chloro-4'-{5-[1-(2-chloro-phenyl)-ethoxycarbonylamino]-4-fluoro-pyrazol-1-yl}-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-2-methyl-biphenyl-4-yl)-cyclopropane-carboxylic acid, (R)-1-(4'-{5-[1-(2-Chloro-phenyl)-ethoxycarbonylamino]-4-fluoro-pyrazol-1-yl}-biphenyl-4-yl)-cyclopropanecarboxylic acid, (R)-1-{4'-[5-(1-Phenyl-ethoxycarbonyl-amino)-4-trifluoromethyl-pyrazol-1-yl]-biphenyl-4-yl}-cyclopropanecarboxylic acid, (R)-1-{2-Fluoro-4'-[5-(1-phenyl-ethoxycarbonylamino)-4-trifluoromethyl-pyrazol-1-yl]-biphenyl-4-yl}-cyclopropanecarboxylic acid, (R)-1-(4-{5-[5-(1-Phenyl-ethoxycarbonylamino)-pyrazol-1-yl]-pyridin-2-yl}-phenyl)-cyclopropanecarboxylic acid, 122. The method of embodiments 116-119 wherein the Formula I-XII compound(s) are selected from embodiment 31.

123. The method of embodiments 116-119 wherein the Formula I-XII compound(s) are selected from embodiment 32.

124. The method of embodiments 116-119 wherein the Formula I-XII compound(s) are selected from embodiment 33.

125. The method of embodiment 116-119 wherein the Formula I-XII compound(s) are selected from embodiment 34.

126. The method of embodiment 116-119 wherein the Formula I-XII compound(s) are selected from embodiment 35.

127. The method of embodiment 116-119 wherein the Formula I-XII compound(s) are selected from embodiment 36.

128. The method of embodiment 116-119 wherein the Formula I-XII compound(s) are selected from embodiment 37.

129. The method of embodiment 116-119 wherein the Formula I-XII compound(s) are selected from embodiment 38.

130. The method of embodiment 116-119 wherein the Formula I-XII compound(s) are selected from embodiment 39.

131. The method of embodiment 116-119 wherein the Formula I-XII compound(s) are selected from embodiment 40.

132. The method of embodiment 116-119 wherein the Formula I-XII compound(s) are selected from embodiment 41.

133. The method of embodiment 116-119 wherein the Formula I-XII compound(s) are selected from embodiment 42.

134. The method of embodiment 116-119 wherein the Formula I-XII compound(s) are selected from embodiment 43.

135. The method of embodiment 116-119 wherein the Formula I-XII compound(s) are selected from embodiment 44.

136. The method of embodiment 116-119 wherein the Formula I-XII compound(s) are selected from embodiment 45.

137. The method of embodiment 116-119 wherein the Formula I-XII compound(s) are selected from embodiment 46.

138. The method of embodiment 116-119 wherein the Formula I-XII compound(s) are selected from embodiment 47.

139. The method of embodiment 116-119 wherein the Formula I-XII compound(s) are selected from embodiment 48.

140. The method of embodiment 116-119 wherein the Formula I-XII compound(s) are selected from embodiment 49.

141. The method of embodiment 116-119 wherein the Formula I-XII compound(s) are selected from embodiment 50.

142. The method of embodiment 116-119 wherein the Formula I-XII compound(s) are selected from embodiment 51.

143. The method of embodiment 116-119 wherein the Formula I-XII compound(s) are selected from embodiment 52.

144. The method of embodiment 116-119 wherein the Formula I-XII compound(s) are selected from embodiment 53.

145. The composition of embodiment 116 where the currently used agent is a mast cell stabilizing agent 146. The composition of embodiment 116 where the currently used agent is a platelet activating factor receptor antagonist, 147. The composition of embodiment 145 where the mast cell stabilizing agent is cromoglicate, nedocromil, azelastine, bepotastine, epinastine, ketotifen, olopatadine and rupatadine.

148. The composition of embodiment 146 where the platelet activating factor receptor antagonist is rupatadine, SM-12502, CV-3988 and WEB 2170.

1A. A compound wherein the compound has the structure of Formula I

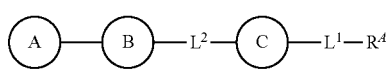

Formula I or a pharmaceutically acceptable salt or prodrug thereof, wherein $R^A$ is —$CO_2H$, —$CO_2R^B$, —CN, tetrazolyl, —C(=O)$NH_2$, —C(=O)$NHR^B$, —C(=O)$NHSO_2R^B$ or —C(=O)$NHCH_2CH_2SO_3H$ or a carboxylic acid isostere; wherein $R^B$ is —H or —$C_1$-$C_4$ alkyl, or has the structure of one of:

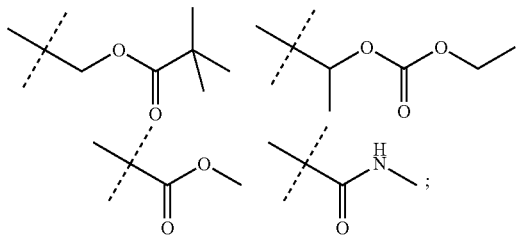

$L^1$ is absent or substituted or unsubstituted $C_1$-$C_6$ alkylene, substituted or unsubstituted $C_3$-$C_6$ cycloalkylene, $C_1$-$C_6$ fluoroalkylene, substituted or unsubstituted $C_1$-$C_6$ heteroalkylene, or —UV—Z—, wherein —UV— is defined by —OW—, —WO—, —N($R^J$)W—, —WN($R^J$)—, —N($R^J$)C(=O)—, —SW—, —S(=O)$_n$W— or —C(=O)N($R^J$)—, wherein W is substituted or unsubstituted $C_1$-$C_3$ alkylene or substituted or unsubstituted $C_3$-$C_6$ cycloalkylene or W is —C($R^L$)$_2$—, and wherein Z is substituted or unsubstituted $C_1$-$C_6$ alkylene, substituted or unsubstituted $C_3$-$C_6$cycloalkylene, or $C_1$-$C_6$ fluoroalkylene or Z is —C($R^L$)$_2$—; wherein n is 0, 1, or 2;

$L^2$ is absent, or substituted or unsubstituted $C_1$-$C_6$ alkylene, substituted or unsubstituted $C_3$-$C_6$ cycloalkylene, $C_1$-$C_6$ fluoroalkylene, substituted or unsubstituted $C_1$-$C_6$ heteroalkylene, —O—, —S—, —S(=O)—, —S(=O)$_2$—, —N($R^J$)—, —C(=O)—, or —C(=O)N($R^J$)—;

Ring A is a 5-6 membered heteroarene selected from one of:

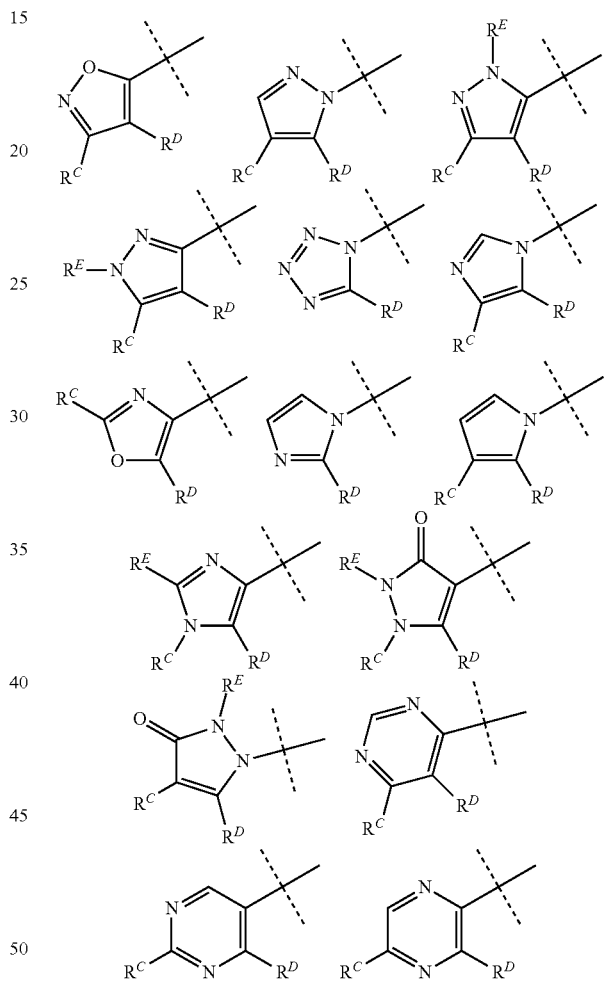

wherein the dashed line indicates the point of attachment of Ring A to Ring B; wherein one of $R^C$ and $R^D$ is —H, —CN, —F, —Cl, —Br, —I, —O$C_1$-$C_4$ alkyl, —$C_1$-$C_4$ alkyl, —$C_3$-$C_6$ cycloalkyl, or —$C_1$-$C_4$ fluoroalkyl, and the other $R^C$ or $R^D$ is —N($R^F$)—C(=O)XCH($R^G$)—CY, —N($R^F$)—C(=O)XC($R^G$)$_2$—CY, —N($R^F$)—C(=O)X—CY, —C(=O)—N($R^F$)—CH($R^G$)X—CY, —C(=O)—N($R^F$)—C($R^G$)$_2$X—CY, or —C(=O)X—N($R^F$)—X—CY, wherein X is absent, —O—, —NH— or —$CH_2$—;

$R^E$ is —H, —$C_1$-$C_4$ alkyl or —$C_1$-$C_4$ fluoroalkyl; $R^F$ is —H or $C_1$-$C_4$ alkyl; $R^G$ is independently selected $R^E$, or one $R^G$ is —$C_1$-$C_4$ alkyl and is taken together with the carbon atom to which $R^G$ is attached and the carbon or heteroatom to which CY is attached to define a substituted or unsubstituted carbocycle or a substituted or unsubstituted heterocycle, and the other $R^G$, if present, is as defined for $R^E$;

CY is substituted or unsubstituted $C_1$-$C_6$ alkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl, wherein if CY is substituted then CY is substituted with 1, 2, or 3 independently selected $R^H$;

wherein each $R^H$ is independently selected from —H, halogen, —CN, —NO$_2$, —OH, —OR$^J$, —SR$^J$, —S(=O) R$^J$, —S(=O)$_2$R$^J$, —N(R$^J$)S(=O)$_2$R$^J$, —S(=O)$_2$N(R$^L$)$_2$, —C(=O)R$^J$, OC(=O)R$^J$, —CO$_2$R$^J$, —OCO$_2$R$^J$, —N(R$^L$)$_2$, —C(=O)N(R$^L$)$_2$, —OC(=O)N(R$^L$)$_2$, —N(R$^J$)C(=O)N(R$^L$)$_2$, —N(R$^J$)C(=O)R$^J$, —N(R$^J$)C(=O)OR$^J$, $C_1$-$C_4$ alkyl, $C_1$-$C_4$ fluoroalkyl, $C_1$-$C_4$ fluoroalkoxy, $C_1$-$C_4$ alkoxy, and $C_1$-$C_4$ heteroalkyl, wherein each $R^J$ is independently substituted or unsubstituted $C_1$-$C_6$ alkyl, substituted or unsubstituted $C_1$-$C_6$ heteroalkyl, $C_1$-$C_6$ fluoroalkyl, substituted or unsubstituted $C_3$-$C_6$ cycloalkyl, substituted or unsubstituted heterocycloalkyl, substituted or unsubstituted aryl, substituted or unsubstituted heteroaryl, —$C_1$-$C_4$ alkylene-(substituted or unsubstituted $C_3$-$C_6$ cycloalkyl), —$C_1$-$C_4$ alkylene-(substituted or unsubstituted heterocycloalkyl), —$C_1$-$C_4$ alkylene-(substituted or unsubstituted aryl), or —$C_1$-$C_4$ alkylene-(substituted or unsubstituted heteroaryl);

wherein each $R^L$ is independently —H, substituted or unsubstituted $C_1$-$C_6$ alkyl, substituted or unsubstituted $C_1$-$C_6$ heteroalkyl, $C_1$-$C_6$ fluoroalkyl, substituted or unsubstituted $C_3$-$C_6$ cycloalkyl, substituted or unsubstituted heterocycloalkyl, substituted or unsubstituted aryl, substituted or unsubstituted heteroaryl, —$C_1$-$C_4$ alkylene-(substituted or unsubstituted cycloalkyl), —$C_1$-$C_4$ alkylene-(substituted or unsubstituted heterocycloalkyl), —$C_1$-$C_4$ alkylene(substituted or unsubstituted aryl), or —$C_1$-$C_4$ alkylene-(substituted or unsubstituted heteroaryl), or when $R^H$ is —S(=O)$_2$N(R$^L$)$_2$, —N(R$^L$)$_2$, —C(=O)N(R$^L$)$_2$, —OC(=O)N(R$^L$)$_2$ or —N(R$^F$)C(=O)N(R$^L$)$_2$, each $R^L$ is independently —H or $C_1$-$C_6$ alkyl, or the $R^L$ groups independently are $C_1$-$C_6$ alkyl which are taken together with the N atom to which they are attached to define a substituted or unsubstituted heterocycle, or when W is —C(R$^L$)$_2$— or Z is —C(R$^L$)$_2$—, each $R^L$ is independently —H, $C_1$-$C_6$ alkyl, or the $R^L$ groups independently are $C_1$-$C_6$ alkyl which are taken together with the carbon atom to which they are attached to define a carbocycle;

Ring B is substituted or unsubstituted $C_3$-$C_{10}$ cycloalkylene, substituted or unsubstituted $C_2$-$C_{10}$ heterocycloalkylene, substituted or unsubstituted arylene, or substituted or unsubstituted heteroarylene, where if ring B is substituted then ring B is substituted with 1, 2, or 3 independently selected $R^H$, wherein $R^H$ is as previously defined;

Ring C is absent or substituted or unsubstituted $C_3$-$C_{10}$ cycloalkylene, substituted or unsubstituted $C_2$-$C_{10}$ heterocycloalkylene, substituted or unsubstituted arylene, or substituted or unsubstituted heteroarylene, where if ring C is substituted then ring C is substituted with 1, 2, or 3 independently selected $R^H$, wherein $R^H$ is as previously defined, wherein when Ring B is substituted or unsubstituted arylene, Ring C is absent, $L^2$ is absent, $L^1$ is —UV—Z—, wherein —UV— is —N(R$^J$)C(=O)—, wherein $R^J$ is —H, $R^D$ is —N(R$^F$)—C(=O)XCH(R$^G$)—CY, wherein X is —O—, $R^G$ is —CH$_3$ and $R^F$ is —H, and $R^C$ is —H, —CH$_3$ or —CF$_3$, or when Ring B is substituted or unsubstituted arylene and Ring C is substituted or unsubstituted arylene or is substituted or unsubstituted $C_3$-$C_{10}$ cycloalkylene, or Ring B is substituted or unsubstituted $C_3$-$C_{10}$ cycloalkylene and Ring C is substituted or unsubstituted arylene, $L^2$ is absent, $L^1$ is $C_1$-$C_6$ alkylene, and $R^C$ is —H or —CH$_3$ and $R^A$ is —CO$_2$H or CO$_2$R$^B$.

then Ring A has the structure of one of:

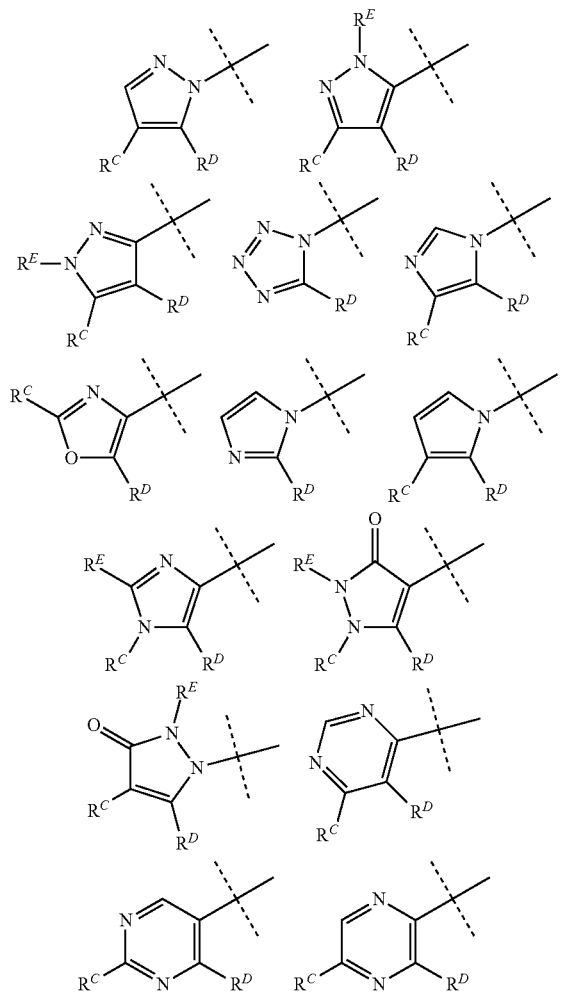

and when Ring B is $C_2$-$C_{10}$ heterocycloalkylene, Ring C is substituted or unsubstituted arylene, $L^2$ is absent, $L^1$ is $C_1$-$C_6$ alkylene, $R^C$ is —CH$_3$ and $R^A$ is —CO$_2$H or CO$_2$R$^B$, then Ring A has the structure of one of:

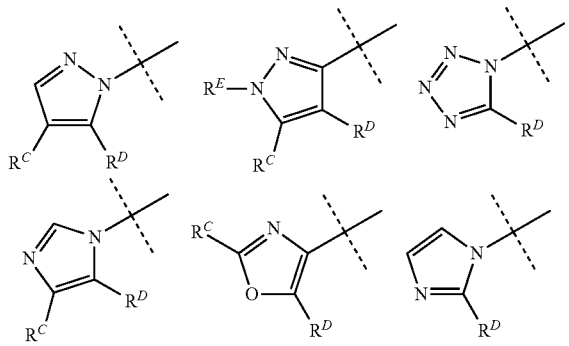

-continued

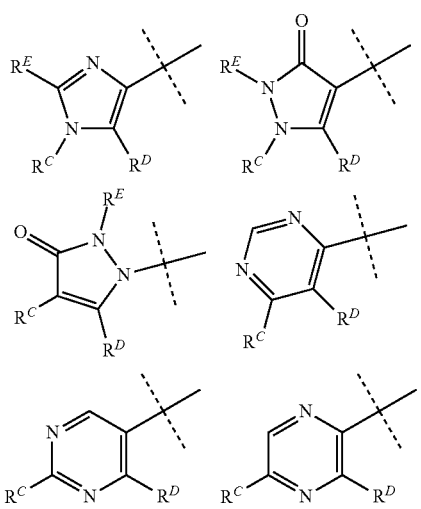

2A. The compound of embodiment 1A wherein $R^C$ is —H, —CN, —F, —Cl, —Br, —I, —OC$_1$-C$_4$ alkyl, —C$_1$-C$_4$ alkyl, —C$_3$-C$_6$ cycloalkyl, or —C$_1$-C$_4$ fluoroalkyl and $R^D$ is —N(R$^F$)—C(=O)XCH(R$^G$)—CY, N(R$^F$)—C(=)XC(R$^G$)$_2$—CY, —N(R$^F$)—C(=O)X—CY, wherein R$^F$ and each R$^G$ independently are —H or C$_1$-C$_4$ alkyl.

3A. The compound of embodiment 2A wherein Ring A is selected from one of:

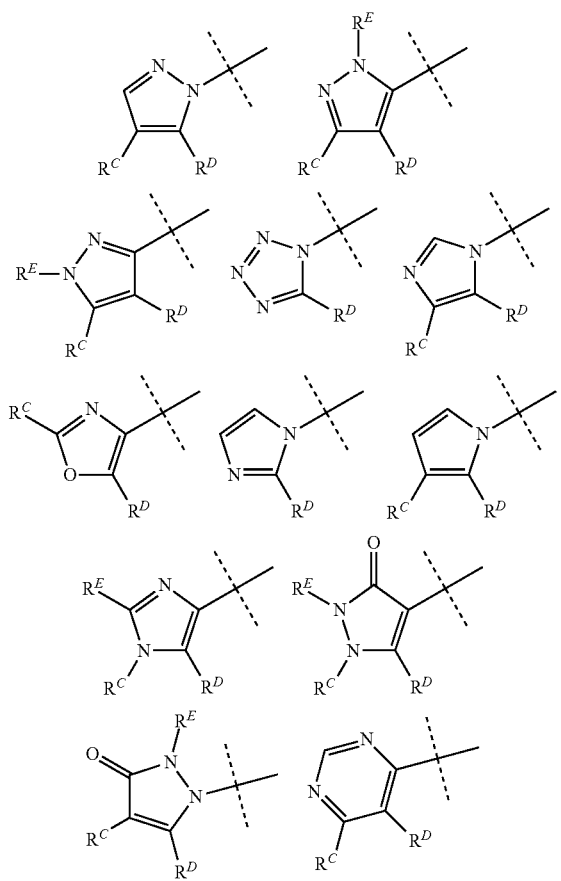

-continued

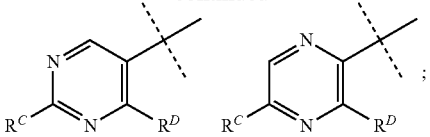

wherein $R^D$ is —N(R$^F$)—C(=c)XCH(R$^G$)—CY, and $R^C$ is —H, —CH$_3$ or —CF$_3$, Ring B is substituted or unsubstituted arylene or substituted or unsubstituted heteroarylene, Ring C is absent; L$^2$ is absent; L is —UV—Z—, wherein —UV— is —OW—, —WO—, —N(R$^J$)W—, —WN(R$^J$)—, —N(R$^J$)C(=)—, —SW—, —S(=)$_n$N(R$^F$)W—, or —C(=O)N(R$^J$)—, wherein W is substituted or unsubstituted C$_1$-C$_3$ alkylene; and n is 0, 1, or 2; or Ring B and Ring C independently are substituted or unsubstituted arylene or substituted or unsubstituted arylene L$^2$ is absent, L$^1$ is C$_1$-C$_6$ alkylene.

4A. The compound of embodiment 2A wherein Ring A has the structure of one of:

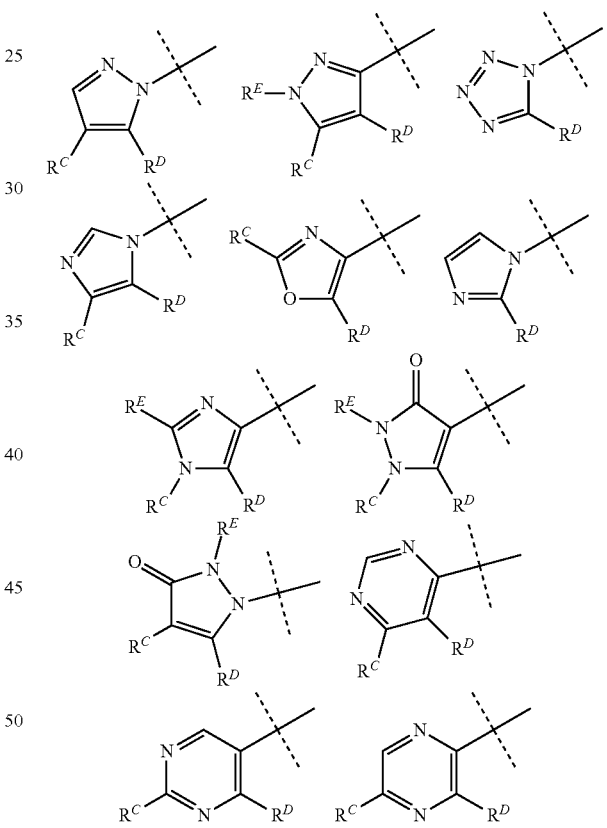

wherein Ring B is substituted or unsubstituted arylene and Ring C is substituted or unsubstituted arylene or is substituted or unsubstituted C$_3$-C$_{10}$ cycloalkylene, or Ring B is substituted or unsubstituted C$_3$-C$_{10}$ cycloalkylene and Ring C is substituted or unsubstituted arylene, L$^2$ is absent and L$^1$ is C$_1$-C$_6$ alkylene.

5A. The compound of embodiment 2A wherein L$^2$ is absent and L$^1$ is C$_1$-C$_6$ alkylene, or substituted or unsubstituted C$_3$-C$_6$ cycloalkylene, substituted or unsubstituted C$_1$-C$_6$ heteroalkylene or L$^2$ and Ring C are absent and L$^1$ is —UV—Z—, wherein —UV— is defined by —OW—, —WO—, —N(R$^J$)W—, —WN(R$^J$)—, —N(R$^J$)C(=O)—, —SW—, —S(=O)$_n$W—, or —C(=O)N(R$^J$)—, wherein W is substituted or unsubstituted C$_1$-C$_3$ alkylene; and n is 0, 1, or 2.

6A. The compound of embodiment 5A wherein L$^1$ is —UV—Z— wherein —UV— is defined by —OW—, —WO—, —N(R$^J$)W—, —WN(R$^J$)— or —C(=O)N(R$^J$)—, wherein W is substituted or unsubstituted C$_1$-C$_3$ alkylene.

7A. The compound of embodiment 5A wherein L$^1$ is —UV—Z—, wherein —UV— is defined by —WO—, —WN(R$^J$)— or —C(=O)N(R$^J$)—, wherein W is substituted or unsubstituted C$_1$-C$_3$ alkylene, and L$^2$ is absent.

8A. The compound of embodiment 7A wherein Z is substituted or unsubstituted C$_1$-C$_6$ alkylene.

9A. The compound of embodiment 7A wherein Z is substituted or unsubstituted C$_1$-C$_6$ alkylene and R$^A$ is —CO$_2$H or —CO$_2$R$^B$.

10A. The compound of embodiment 7A, wherein L$^1$ is —UV—Z—, wherein —UV— is defined by —C(=O)N(R$^J$)—, wherein R$^J$ is —H or —CH$_3$.

11A. The compound of embodiment 7A wherein L$^1$ is UV—Z—, wherein —UV—, is defined by —WO—.

12A. The compound of embodiment 7A wherein L$^1$ is UV—Z—, wherein —UV—, is defined by —WN(R$^J$)—, wherein R$^J$ is —H or —CH$_3$.

13A. The compound of embodiment 2A wherein L$^1$ is absent or a substituted or unsubstituted substituted C$_1$-C$_4$ alkylene or a substituted or unsubstituted C$_3$ cycloalkylene (i.e., cyclopropyl-di-yl).

14A. The compound of embodiment 2 wherein L$^1$ is —CH$_2$—,

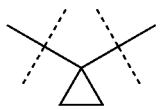

or —C(CH$_3$)$_2$—.

15A. The compound of embodiment 2 wherein Ring A has the structure of one of:

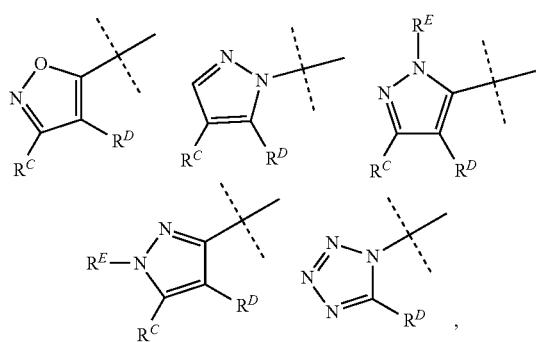

wherein R$^C$ is —H, —CN, —CH$_3$, or —CF$_3$, R$^D$ is —N(R$^F$)C(=O)XCH(R$^G$)—CY, —N(R$^F$)C(=O)XC(R$^G$)$_2$—CY, or —N(R$^F$)C(=O)X—CY and L$^1$ is —UV—Z— wherein —UV— is defined by —WO—, —WN(R)— or —C(=O)N(R$^J$)—.

16A. The compound of embodiment 15A wherein R$^C$ is —H, —CH$_3$ or —CF$_3$ and R$^D$ is —N(R$^F$)C(=O)XCH(R$^G$)—CY.

17A. The compound of embodiment 15A wherein R$^D$ is —N(R$^F$)C(=O)XCH(R$^G$)—CY, wherein —X— is —N(R$^F$)— or —O—; and wherein R$^G$ and each R$^F$, independently selected, are —H or —CH$_3$.

18A. The compound of embodiment 17A wherein R$^G$ is —CH$_3$, in the R or S configuration, and CY is substituted or unsubstituted phenyl or substituted or unsubstituted heteroaryl.

19A. The compound of embodiment 17A wherein R$^D$ is —N(R$^F$)C(=O)OCH(R$^G$)—CY, wherein CY is unsubstituted or substituted phenyl, wherein substituted phenyl is phenyl that is substituted with one or two of independently selected R$^J$.

20A. The compound of embodiment 17A, wherein R$^D$ is —N(R$^F$)C(=O)OCH(CH$_3$)—CY, wherein R$^F$ is —H, and wherein CY is unsubstituted phenyl.

21A. The compound of embodiment 17A, wherein R$^D$ is —N(R$^F$)—C(=O)OCH(CH$_3$)—CY, wherein R$^F$ is —H, and wherein CY is substituted phenyl, wherein substituted phenyl is phenyl that is substituted with one or two of independently selected R$^J$, wherein R$^J$ are halogens.

22A. The compound of embodiment 21A, wherein R$^D$ is —NH—C(=O)OCH(CH$_3$)—CY wherein CY is substituted phenyl, wherein substituted phenyl is phenyl that is substituted with one R$^H$, wherein R$^J$ is —F, —Cl or —Br.

23A. The compound of embodiment 21A, wherein R$^D$ is —NH—C(=O)OCH(CH$_3$)—CY, wherein CY is substituted phenyl, wherein substituted phenyl is phenyl that is substituted with one R$^H$, wherein R$^J$ is —Cl.

24A. The compound of embodiment 19A, wherein R$^D$ is —NH—C(=O)OCH(CH$_3$)—CY having the structure of

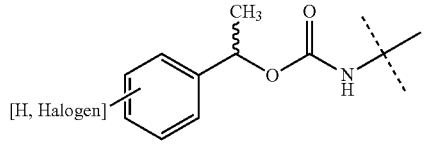

25A. The compound of claim 19A wherein R$^D$ is —NH—C(=O)OCH(CH$_3$)—CY wherein the methyl group in R$^D$ is in the R configuration.

26A. The compound of any one of embodiments 5-25 wherein Ring A has the structure of:

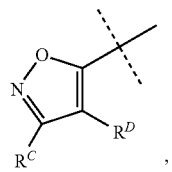

wherein L$^2$ is absent and Ring B is substituted or unsubstituted arylene, or substituted or unsubstituted heteroarylene, provided that when Ring C is not absent and L$^1$ is C$_1$-C$_6$ alkylene, or Ring C is absent and L$^1$ is —UV—Z, wherein —UV— is —N(R$^J$)C(=O)—, and R$^D$ has the structure of —N(R$^F$)—C(=O)XCH(R$^G$)—CY, —N(R$^F$)—C(=O)XC(R$^G$)$_2$—CY or —N(R$^F$)—C(=O)X—CY, and R$^A$ is —CO$_2$H, then R$^C$ is other than —H, —CH$_3$ and —CF$_3$.

27A. The compound of embodiment 26A wherein R$^C$ is —H, —CH$_3$ or —CF$_3$, and R$^D$ is —NH—C(=O)OCH(R$^G$)—CY, wherein R$^G$ is —H or —CH$_3$, in the R or S configuration, and —CY is substituted or unsubstituted phenyl.

28A. The compound of embodiment 26A wherein $L^2$ and Ring C are absent, Ring B is substituted or unsubstituted arylene, or substituted or unsubstituted heteroarylene, and $L^1$ is —UV—Z—, wherein —UV—, is defined by —WO—, —WN($R^J$)— or —C(=O)N($R^J$)—.

29A. The compound of embodiment 26A wherein $L^2$ and Ring C are absent, Ring B is substituted or unsubstituted arylene, or substituted or unsubstituted heteroarylene, and $L^1$ is —UV—Z—, wherein —UV—, is defined by —WN($R^J$)— or —C(=O)N($R^J$)—, wherein $R^J$ is —H or —$CH_3$.

30A. The compound of embodiment 29A wherein $L^1$ is —UV—Z—, wherein —UV— is defined by —C(=O)NH—, and wherein Z is substituted or unsubstituted $C_1$-$C_6$ alkylene.

31A. The compound of embodiment 29A wherein $L^1$ is —UV—Z—, wherein —UV— is defined by —WO—, wherein W is substituted or unsubstituted $C_1$-$C_3$ alkylene, and wherein Z is substituted or unsubstituted $C_1$-$C_6$ alkylene.

32A. The compound of embodiment 29A wherein $L^1$ is —UV—Z—, wherein —UV— is defined by —W—NH—, wherein W is substituted or unsubstituted $C_1$-$C_3$ alkylene, and wherein Z is substituted or unsubstituted $C_1$-$C_6$ alkylene.

33A. The compound of embodiment 26A wherein $L^1$ is —UV—Z—, wherein —UV— is defined by —WO—, —WN($R^J$)— or —C(=O)N($R^J$), wherein $R^J$ is —H or —$CH_3$, and wherein Z is substituted or unsubstituted $C_1$-$C_6$ alkylene, wherein the alkylene is —CH($CH_2$-cyclopropyl)-, —CH($CH_2$-aryl) or —CH($CH_2$-heteroaryl), wherein the aryl or heteroaryl is substituted or unsubstituted.

34A. The compound of embodiment 33A wherein $L^1$ is —UV—Z—, wherein —UV— is defined by —C(=O)NH—, —WO— or —W—NH—, wherein —W— is —$CH_2$—.

35A. The compound of embodiment 33A wherein $R^A$ is —$CO_2H$ or —$CO_2R^B$.

36A. The compound of embodiment 33A wherein $L^1$ is —UV—Z—, wherein —UV— is defined by —$CH_2O$—, —$CH_2$—NH— or —C(=O)NH—, wherein Z is substituted or unsubstituted $C_1$-$C_6$ alkylene, wherein the alkylene is —CH($CH_2$-cyclopropyl)-, —CH($CH_2$-aryl) or —CH($CH_2$-heteroaryl), wherein the aryl or heteroaryl is unsubstituted or substituted with 1, 2, or 3 independently selected substituted or unsubstituted $C_1$-$C_4$ alkyl or halogen.

37A. The compound of embodiment 36A wherein said substituted or unsubstituted $C_1$-$C_4$ alkyl or halogen substituent or substituents of the aryl or heteroaryl of —CH($CH_2$-aryl) or —CH($CH_2$-heteroaryl) are selected from the group consisting of —$CH_3$, —$CF_3$, —F, —Cl or —Br.

38A. The compound of embodiment 33A, wherein $L^1$ is —UV—Z— and wherein $R^A$ is —$CO_2H$ to which Z is attached to define -$L^1$-$R^A$ (i.e., —UV—Z—$R^A$), wherein —UV— is defined by —C(=O)NH—, —WO— or —W—NH—, wherein —W— is —$CH_2$—, and Z is —CH($CH_2$-aryl), wherein the aryl is substituted or unsubstituted, having the structure of one of

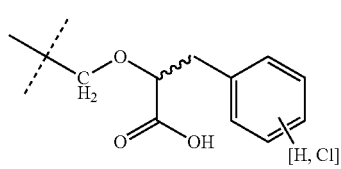
[H, Cl]

-continued

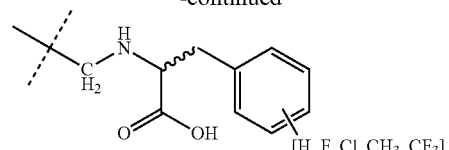
[H, F, Cl, $CH_3$, $CF_3$]

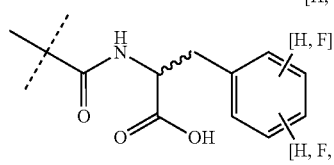
[H, F]

[H, F, Cl, Br, $CH_3$, $CF_3$].

39A. The compound of embodiment 36A wherein the —CH($CH_2$-aryl) substituent of Z in the -$L^1$-$R^A$ is in the R configuration.

40A. The compound of embodiment 33A wherein $L^1$ is —UV—Z— and wherein $R^A$ is —$CO_2H$ to which Z is attached to define -$L^1$-$R^A$ (i.e., —UV—Z—$R^A$), wherein —UV— is defined by —C(=O)NH—, —WO— or —W—NH—, wherein —W— is —$CH_2$—, and Z is —CH($CH_2$-cyclopropyl)-, having the structure of

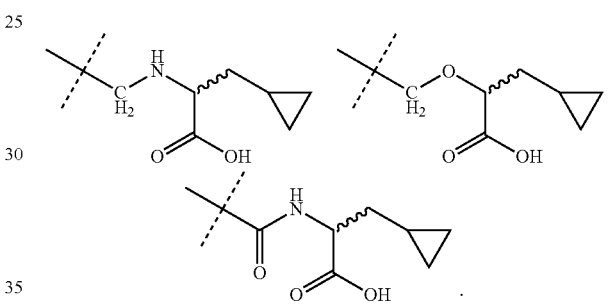

41A. The compound of embodiment 1A, 2A, 3A, or 4A, wherein the compound has the structure of Formula III

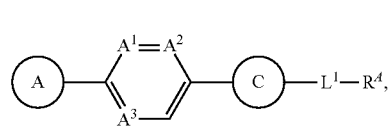

Formula III

A wherein $A^1$, $A^2$ and $A^3$ are independently —N=, =N—, =CH— or —CH=.

42A. The compound of embodiment 41A wherein Ring A wherein Ring A has the structure of one of:

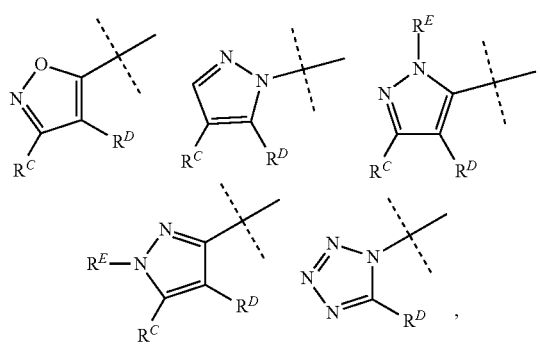

wherein when $L^1$ is $C_1$-$C_6$ alkylene, $R^D$ is —N($R^F$)—C(=O)XCH($R^G$)—CY, —N($R^F$)—C(=O)XC($R^G$)$_2$—CY, wherein $R^F$ is —H, $R^G$ is —H or —CH$_3$; $R^A$ is —CO$_2$H or CO$_2R^B$, and $R^C$ is —H or —CH$_3$, then Ring A has the structure of one of:

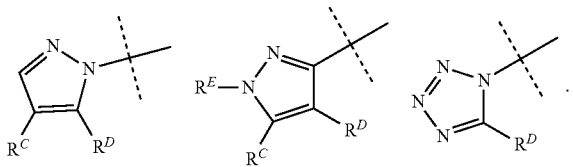

43A. The compound of embodiment 41A, wherein Ring A wherein Ring A has the structure of one of:

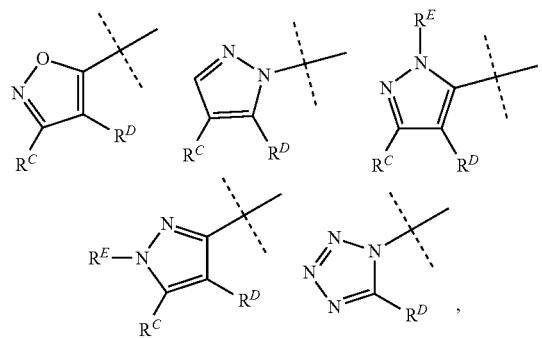

wherein Ring C is a substituted or unsubstituted arylene or heteroarylene, $L^1$ is $C_1$-$C_6$ alkylene, $R^A$ is —CO$_2$H or CO$_2R^B$, $R^D$ is —N($R^F$)—C(=O)XCH($R^G$)—CY, —N($R^F$)—C(=O)XC($R^G$)$_2$—CY, wherein $R^F$ is —H, $R^G$ is —CH$_3$ and CY is substituted phenyl and $R^C$ is —CN, —F, —Cl, —Br, —I, —O$C_1$-$C_4$ alkyl, —$C_2$-$C_4$ alkyl, —$C_3$-$C_6$ cycloalkyl, or —$C_2$-$C_4$ fluoroalkyl.

44A. The compound of embodiment 41A, wherein Ring A has the structure of one of:

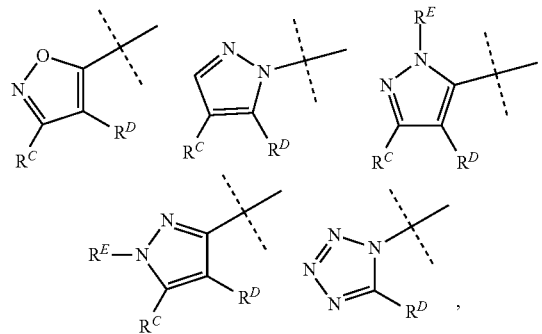

wherein Ring C is a substituted or unsubstituted arylene or heteroarylene, $L^1$ is $C_1$-$C_6$ alkylene, $R^A$ is —CO$_2$H or —CO$_2R^B$, $R^D$ is —N($R^F$)—C(=O)XCH($R^G$)—CY, —N($R^F$)—C(=O)XC($R^G$)$_2$—CY, wherein X is —O—, $R^F$ is —CH$_3$, $R^G$ is —H or —CH$_3$ and CY is substituted phenyl and $R^C$ is —H, —CN, —F, —Cl, —Br, —I, —O$C_1$-$C_4$ alkyl, —$C_1$-$C_4$ alkyl, —$C_3$-$C_6$ cycloalkyl, or —$C_1$-$C_4$ fluoroalkyl.

45A. The compound of embodiment 1A, 2A or 5A wherein the compound has the structure of Formula IV

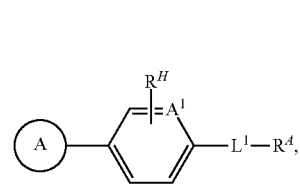

Formula IV wherein Ring A has the structure of one of:

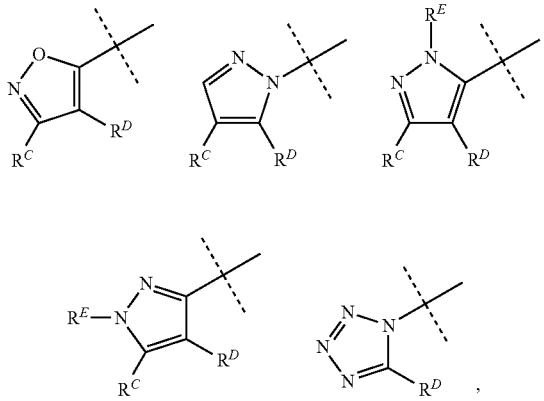

wherein $A^1$ is =N— or =C—; $R^D$ is —NR$^F$C(=O)OCH($R^G$)—CY; $L^1$ is —UV—Z—, wherein —UV— is defined by —C(=O)N($R^J$)—, wherein $R^J$ is —H or —CH$_3$; $R^F$ and $R^G$ independently are —H or —CH$_3$; and $R^A$ is —CO$_2$H or —CO$_2R^B$.

46A. The compound of embodiment 2A wherein the compound has the structure of Formula VII

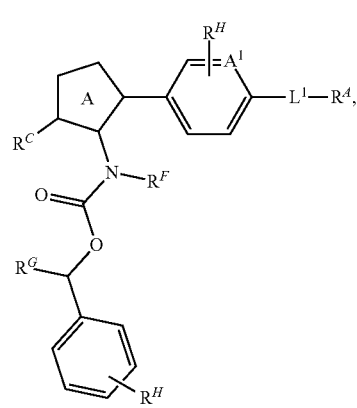

Formula VI wherein Ring A is a 5 membered heteroarene having one of the structures of:

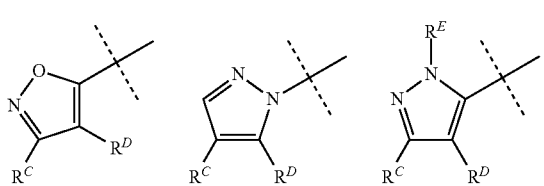

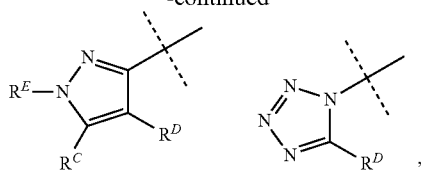

wherein $R^D$ is the —N($R^F$)C(=O)CH($R^G$)—CY substituent of Formula VI wherein CY is phenyl substituted with one $R^H$, and $R^C$ is —H, —CH$_3$, CF$_3$ or —F; $R^A$ is —CO$_2$H or —CO$_2$R$^B$; and $R^F$ and $R^G$ independently are —H or —CH$_3$; and $R^H$ independently are —H, halogen, —CH$_3$ or —CF$_3$.

47A. The compound of embodiment 2A wherein the compound has the structure of Formula VII

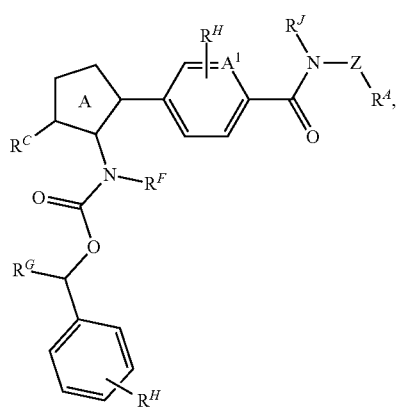

Formula VII wherein $A^1$ is =CH— or =N—; Ring A is a 5 membered heteroarene having the structure of one of:

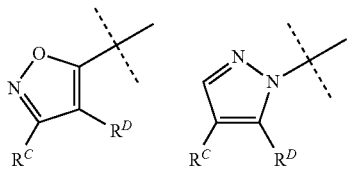

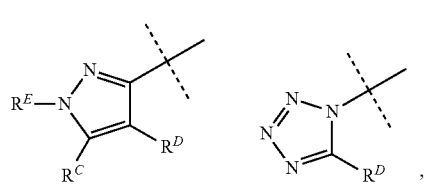

wherein $R^D$ is the —N($R^F$)C(=O)CH($R^G$)—CY substituent of Formula VII wherein CY is phenyl substituted with one $R^H$; and $R^C$ is —H, —CH$_3$, CF$_3$ or —F; $R^A$ is —CO$_2$H or —CO$_2$R$^B$; $R^E$ and $R^F$ independently are —H or C$_1$-C$_4$ alkyl; $R^G$ is —H or —CH$_3$; $R^H$ independently are —H, halogen, —CH$_3$ or —CF$_3$; and Z is —C($R^L$)$_2$, wherein one $R^L$ is —H and the other $R^L$ is —H or C$_1$-C$_4$ alkyl.

48A The compound of embodiment 2A wherein the compound has the structure of Formula VIII

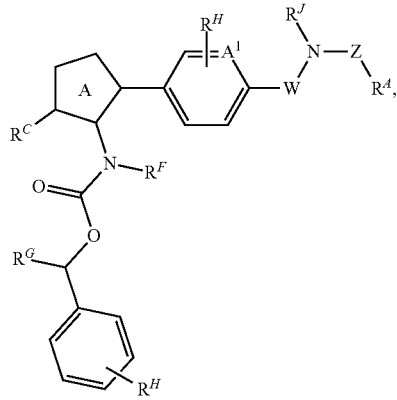

Formula VIII wherein $A^1$ is =CH— or =N—; wherein Ring A is a 5 membered heteroarene having the structure of one of

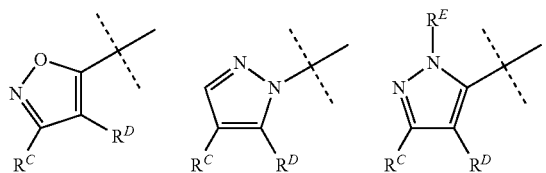

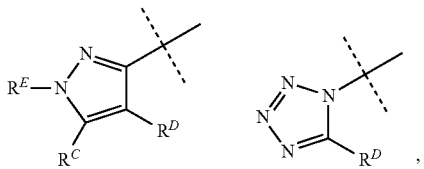

wherein $R^D$ is the —N($R^F$)C(=O)CH($R^G$)—CY substituent of Formula VII wherein CY is phenyl substituted with one $R^H$; $R^A$ is —CO$_2$H or —CO$_2$R$^B$; W is —C($R^L$)$_2$— or

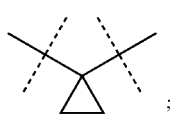

$R^E$ and $R^F$ independently are —H or C$_1$-C$_4$ alkyl; $R^G$ is —H or —CH$_3$; $R^H$ independently are —H, halogen, —CH$_3$ or —CF$_3$; and Z is —C($R^L$)$_2$, wherein one $R^L$ is —H and the other $R^L$ is —H or C$_1$-C$_4$ alkyl.

49A. The compound of embodiment 2A wherein the compound has the structure of Formula IX Formula IX

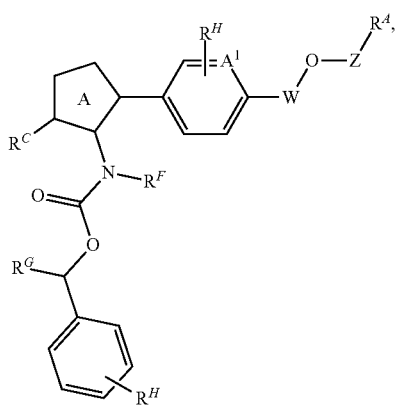

wherein A¹ is =CH— or =N—; wherein Ring A is a 5 membered heteroarene having the structure of one of

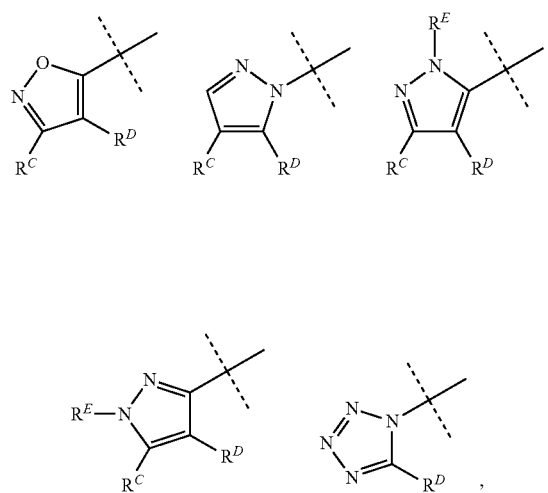

wherein $R^D$ is the —N($R^F$)C(=O)CH($R^G$)—CY substituent of Formula VII wherein CY is phenyl substituted with one $R^H$; $R^A$ is —CO$_2$H or —CO$_2$R$^B$;

wherein W is —C($R^L$)$_2$— or

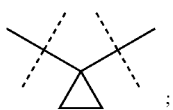

$R^E$ and $R^F$ independently are —H or C$_1$-C$_4$ alkyl; $R^G$ is —H or —CH$_3$; $R^H$ independently are —H, halogen, —CH$_3$ or —CF$_3$; and Z is —C($R^L$)$_2$, wherein one $R^L$ is —H and the other $R^L$ is —H or C$_1$-C$_4$ alkyl.

50A. The compound of embodiment 2A wherein the compound has the structure of Formula XII Formula XII

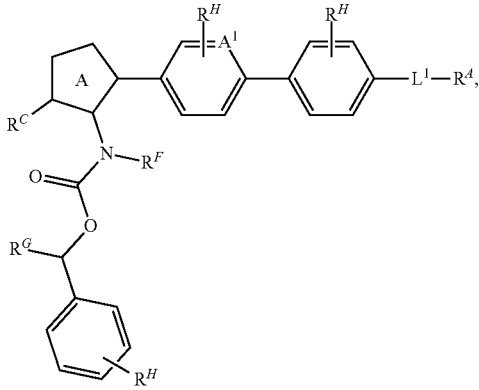

wherein A¹ is =CH— or =N—; wherein Ring A is a 5 membered heteroarene having the structure of one of

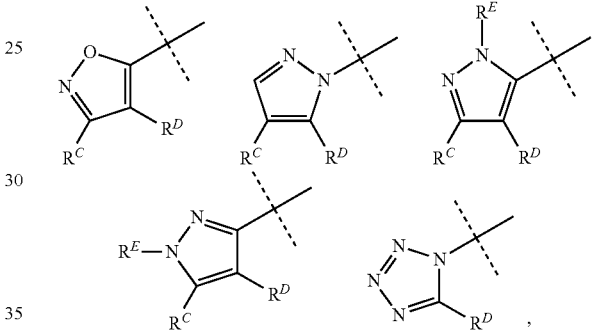

wherein $R^D$ is the —N($R^F$)C(=O)CH($R^G$)—CY substituent of Formula VII wherein CY is phenyl substituted with one $R^H$; $R^A$ is —CO$_2$H or —CO$_2$R$^B$; wherein W is —C($R^L$)$_2$— or

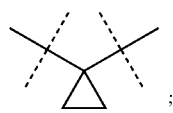

$R^E$ and $R^F$ independently are —H or C$_1$-C$_4$ alkyl; $R^G$ is —H or —CH$_3$; $R^H$ independently are —H, halogen, —CH$_3$ or —CF$_3$; and Z is —C($R^L$)$_2$, wherein one $R^L$ is —H and the other $R^L$ is —H or C$_1$-C$_4$ alkyl.

51A The compound of embodiment 2A wherein the compound is selected from Table 1.

52A. The compound of embodiment 51A wherein the compound is 1-(4-{4-[1-(2-Chloro-phenyl)-ethoxycarbonylamino]-3-methyl-isoxazol-5-yl}-benzoylamino)-cyclopropanecarboxylic acid, 2-(4-{4-[1-(2-Chloro-phenyl)-ethoxycarbonylamino]-3-methyl-isoxazol-5-yl}-benzoylamino)-indan-2-carboxylic acid, 2-(S)-(4-{4-[(R,S)-1-(2-Chloro-phenyl)-ethoxycarbonylamino]-3-methyl-isoxazol-5-yl}-benzoylamino) phenyl acetic acid, 2-(R)-(4-{4-[(R,S)-1-(2-Chloro-phenyl)-ethoxycarbonylamino]-3-methyl-isoxazol-5-yl}-benzoylamino) phenyl propanoic acid, 2(R)-[[4-[3-methyl-4-((R)-1-phenylethoxycarbonylamino)isoxazol-5-yl]benzoyl]amino]-3-phenyl-propanoic acid, 2(S)-[[4-[3-methyl-4-((R)-1-phenylethoxycarbonylamino)isoxazol-5-yl]benzoyl]amino]-3-phenyl-propanoic acid, (R)-2-[[4-[2,5-dimethyl-4-((R)-1-phenylethoxycarbonylamino)pyrazol-3-yl]benzoyl]amino]-3-phenyl-propanoic acid, (R)-2-[[4-[1,5-dimethyl-4-((R)-1-phenylethoxycarbonylamino)pyrazol-3-yl]benzoyl]amino]-3-phenyl-propanoic acid, (R)-2-[[4-[2,5-dimethyl-4-((R)-1-phenylethoxycarbonylamino)pyrazol-3-yl]benzoyl]amino]-3-(4-fluorophenyl)propanoic acid, (R)-2-[[4-[1,5-dimethyl-4-((R)-1-phenylethoxycarbonylamino)pyrazol-3-yl]benzoyl]amino]-3-(4-fluorophenyl)propanoic acid, (R)-3-(4-bromophenyl)-2-[[4-[2,5-dimethyl-4-((R)-1-phenylethoxycarbonyl-amino) pyrazol-3-yl]benzoyl]amino]propanoic acid, (R)-3-(4-bromophenyl)-2-[[4-[1,5-dimethyl-4-((R)-1-phenylethoxycarbonyl-amino)pyrazol-3-yl]benzoyl]amino]propanoic acid, (R)-3-(4-chlorophenyl)-2-[[4-[2,5-dimethyl-4-((R)-1-phenylethoxycarbonyl-amino)pyrazol-3-yl]benzoyl]amino]propanoic acid, (R)-3-(4-chlorophenyl)-2-[[4-[1,5-dimethyl-4-((R)-1-phenylethoxycarbonyl-amino)pyrazol-3-yl]benzoyl]amino]propanoic acid, (R)-3-(3,4-difluorophenyl)-2-[[4-[2,5-dimethyl-4-((R)-1-phenylethoxycarbonyl-amino) pyrazol-3-yl]benzoyl]amino]propanoic acid, (R)-3-(3,4-difluorophenyl)-2-[[4-[1,5-dimethyl-4-((R)-1-phenylethoxycarbonyl-amino)pyrazol-3-yl]benzoyl]amino]propanoic acid, (R)-2-(4-{4-[(R)-1-(2-chloro-phenyl)-ethoxycarbonylamino]-3-methyl-isoxazol-5-yl}-benzoylamino)-3-cyclopropyl-propionic acid, (R)-2-{4-[3-Methyl-4-((S)-1-phenyl-ethoxycarbonylamino)-isoxazol-5-yl]-benzoylamino}-3-phenyl-propionic acid, (S)-2-{4-[3-Methyl-4-((S)-1-phenyl-ethoxycarbonylamino)-isoxazol-5-yl]-benzoylamino}-3-phenyl-propionic acid, (R)-2-(4-{4-[(R)-1-(2-Chloro-phenyl)-ethoxycarbonylamino]-3-methyl-isoxazol-5-yl}-benzoylamino)-3-phenyl-propionic acid, (R)-2-(4-{4-[(R)-1-(2-Chloro-phenyl)-ethoxycarbonylamino]-3-methyl-isoxazol-5-yl}-benzoylamino)-3-(4-fluoro-phenyl)-propionic acid, (R)-3-(4-Chloro-phenyl)-2-(4-{4-[(R)-1-(2-chloro-phenyl)-ethoxycarbonylamino]-3-methyl-isoxazol-5-yl}-benzoylamino)-propionic acid, (R)-2-(4-{4-[(R)-1-(2-Chloro-phenyl)-ethoxycarbonylamino]-3-methyl-isoxazol-5-yl}-benzoylamino)-3-(3,4-difluoro-phenyl)-propionic acid, (R)-3-(2-Chloro-phenyl)-2-(4-{4-[(R)-1-(2-chloro-phenyl)-ethoxycarbonylamino]-3-methyl-isoxazol-5-yl}-benzoylamino)-propionic acid, (R)-3-(4-Bromo-phenyl)-2-(4-{4-[(R)-1-(2-chloro-phenyl)-ethoxycarbonylamino]-3-methyl-isoxazol-5-yl}-benzoylamino)-propionic acid, (R)-3-(4-Bromo-phenyl)-2-(4-{4-[(R)-1-(2-chloro-phenyl)-ethoxycarbonylamino]-3-methyl-isoxazol-5-yl}-benzoylamino)-propionic acid, (R)-2-(4-{4-[(R)-1-(2-Chloro-phenyl)-ethoxycarbonylamino]-3-methyl-isoxazol-5-yl}-benzoylamino)-3-(2-fluoro-phenyl)-propionic acid, (R)-2-(4-{4-[(R)-1-(2-Chloro-phenyl)-ethoxycarbonylamino]-3-methyl-isoxazol-5-yl}-benzoylamino)-3-p-tolyl-propionic acid, (R)-2-(4-{4-[(R)-1-(2-Chloro-phenyl)-ethoxycarbonylamino]-3-methyl-isoxazol-5-yl}-benzoylamino)-3-(4-trifluoromethyl-phenyl)-propionic acid, (R)-2-(4-{4-[(R)-1-(2-Chloro-phenyl)-ethoxycarbonylamino]-3-methyl-isoxazol-5-yl}-benzoylamino)-3-(4-cyano-phenyl)-propionic acid, (R)-2-(4-{5-[(R)-1-(2-Chloro-phenyl)-ethoxycarbonylamino]-4-methyl-pyrazol-1-yl}-benzoylamino)-3-phenyl-propionic acid, (R)-2-{4-[3-Methyl-4-((R)-1-phenyl-ethoxycarbonylamino)-isoxazol-5-yl]-benzylamino}-3-phenyl-propionic acid, (R)-3-(2-Fluoro-phenyl)-2-{4-[3-methyl-4-((R)-1-phenyl-ethoxycarbonylamino)-isoxazol-5-yl]-benzylamino}-propionic acid, (R)-2-{4-[3-Methyl-4-((R)-1-phenyl-ethoxycarbonylamino)-isoxazol-5-yl]-benzylamino}-3-(4-trifluoromethyl-phenyl)-propionic acid, (R)-3-Cyclopropyl-2-{4-[3-methyl-4-((R)-1-phenyl-ethoxycarbonylamino)-isoxazol-5-yl]-benzylamino}-propionic acid, (R)-3-(2-Chloro-phenyl)-2-{4-[3-methyl-4-((R)-1-phenyl-ethoxycarbonylamino)-isoxazol-5-yl]-benzylamino}-propionic acid, (R)-3-(4-Chloro-phenyl)-2-{4-[3-methyl-4-((R)-1-phenyl-ethoxycarbonylamino)-isoxazol-5-yl]-benzylamino}-propionic acid, (R)-2-(4-{4-[(R)-1-(2-Chloro-phenyl)-ethoxycarbonylamino]-3-methyl-isoxazol-5-yl}-benzylamino)-3-phenyl-propionic acid, (R)-2-(4-{4-[(R)_1-(2-Chloro-phenyl)-ethoxycarbonylamino]-3-methyl-isoxazol-5-yl}-benzylamino)-3-(2-fluoro-phenyl)-propionic acid, (R)-2-(4-{4-[(R)-1-(2-Chloro-phenyl)-ethoxycarbonylamino]-3-methyl-isoxazol-5-yl}-benzylamino)-3-(4-trifluoromethyl-phenyl)-propionic acid, (R)-3-(2-Chloro-phenyl)-2-(4-{4-[(R)-1-(2-chloro-phenyl)-ethoxycarbonylamino]-3-methyl-isoxazol-5-yl}-benzylamino)-propionic acid, (R)-2-(4-{4-[(R)-1-(2-Chloro-phenyl)-ethoxycarbonylamino]-3-methyl-isoxazol-5-yl}-benzylamino)-3-cyclopropyl-propionic acid, 2-{4-[3-Methyl-4-((R)-1-phenyl-ethoxycarbonylamino)-isoxazol-5-yl]-benzyloxy}-3-phenyl-propionic acid, (RS)-3-Cyclopropyl-2-{4-[3-methyl-4-((R)-1-phenyl-ethoxycarbonylamino)-isoxazol-5-yl]-benzyloxy}-propionic acid, (RS)-3-Cyclopropyl-2-{4-[3-methyl-4-((R)-1-phenyl-ethoxycarbonylamino)-isoxazol-5-yl]-benzyloxy}-propionic acid, 2-[4-[4-[5-[1-(2-chlorophenyl)ethoxycarbonylamino]-4-cyano-pyrazol-1-yl]phenyl]phenyl]acetic acid, (R)-1-[4-[4-[1,5-dimethyl-4-(1-phenylethoxycarbonylamino)pyrazol-3-yl]phenyl]phenyl]cyclopropane carboxylic acid, (R)-1-[4-[4-[2,5-dimethyl-4-(1-phenylethoxycarbonylamino)pyrazol-3-yl]phenyl]phenyl]cyclopropane carboxylic acid, (R)-1-(4'-{5-[1-(2-Chloro-phenyl)-ethoxycarbonylamino]-4-fluoro-pyrazol-1-yl}-3-fluoro-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-2-fluoro-biphenyl-4-yl)-cyclopropanecarboxylic acid, (R)-1-(2-Chloro-4'-{5-[1-(2-chloro-phenyl)-ethoxycarbonylamino]-4-fluoro-pyrazol-1-yl}-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-2-methyl-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-biphenyl-4-yl)-cyclopropanecarboxylic acid, (R)-1-{4'-[5-(1-Phenyl-ethoxycarbonylamino)-4-trifluoromethyl-pyrazol-1-yl]-biphenyl-4-yl}-cyclopropanecarboxylic acid, (R)-1-{2-Fluoro-4'-[5-(1-phenyl-ethoxycarbonylamino)-4-trifluoromethyl-pyrazol-1-yl]-biphenyl-4-yl}-cyclopropanecarboxylic acid, (R)-1-(4-{5-[5-(1-Phenyl-ethoxycarbonylamino)-pyrazol-1-yl]-pyridin-2-yl}-phenyl)-cyclopropanecarboxylic acid.

53A. A compound of any one of embodiments 1A-52A for preparation of mendicant for treating a LPA-dependent disease or condition.

The compounds of Table 1 are exemplary of the invention but not limiting, wherein compounds 57-458 are prepared according to the appropriately modified procedures of the examples for preparation of compounds 1-458.

TABLE 1

| Cpd | Name |
|---|---|
| 1 | 1-(4-{4-[1-(2-Chloro-phenyl)-ethoxycarbonylamino]-3-methyl-isoxazol-5-yl}-benzoylamino)-cyclopropanecarboxylic acid |
| 2 | 2-(4-{4-[1-(2-Chloro-phenyl)-ethoxycarbonylamino]-3-methyl-isoxazol-5-yl}-benzoylamino)-indan-2-carboxylic acid |
| 3 | 2-(S)-(4-{4-[(R,S)-1-(2-Chloro-phenyl)-ethoxycarbonylamino]-3-methyl-isoxazol-5-yl}-benzoylamino) phenyl acetic acid |
| 4 | 2-(R)-(4-{4-[(R,S)-1-(2-Chloro-phenyl)-ethoxycarbonylamino]-3-methyl-isoxazol-5-yl}-benzoylamino) phenyl propanoic acid |
| 5 | 2(R)-[[4-[3-methyl-4-((R)-1-phenylethoxycarbonylamino)isoxazol-5-yl]benzoyl]amino]-3-phenyl-propanoic acid |
| 6 | 2(S)-[[4-[3-methyl-4-((R)-1-phenylethoxycarbonylamino)isoxazol-5-yl]benzoyl]amino]-3-phenyl-propanoic acid |
| 7 | (R)-2-[[4-[2,5-dimethyl-4-((R)-1-phenylethoxycarbonylamino)pyrazol-3-yl]benzoyl]amino]-3-phenyl-propanoic acid |
| 8 | (R)-2-[[4-[1,5-dimethyl-4-((R)-1-phenylethoxycarbonylamino)pyrazol-3-yl]benzoyl]amino]-3-phenyl-propanoic acid |
| 9 | (R)-2-[[4-[2,5-dimethyl-4-((R)-1-phenylethoxycarbonylamino)pyrazol-3-yl]benzoyl]amino]-3-(4-fluorophenyl)propanoic acid |
| 10 | (R)-2-[[4-[1,5-dimethyl-4-((R)-1-phenylethoxycarbonylamino)pyrazol-3-yl]benzoyl]amino]-3-(4-fluorophenyl)propanoic acid |
| 11 | (R)-3-(4-bromophenyl)-2-[[4-[2,5-dimethyl-4-((R)-1-phenylethoxycarbonyl-amino)pyrazol-3-yl]benzoyl]amino]propanoic acid |
| 12 | (R)-3-(4-bromophenyl)-2-[[4-[1,5-dimethyl-4-((R)-1-phenylethoxycarbonyl-amino)pyrazol-3-yl]benzoyl]amino]propanoic acid |
| 13 | (R)-3-(4-chlorophenyl)-2-[[4-[2,5-dimethyl-4-((R)-1-phenylethoxycarbonyl-amino)pyrazol-3-yl]benzoyl]amino]propanoic acid |
| 14 | (R)-3-(4-chlorophenyl)-2-[[4-[1,5-dimethyl-4-((R)-1-phenylethoxycarbonyl-amino)pyrazol-3-yl]benzoyl]amino]propanoic acid |
| 15 | (R)-3-(3,4-difluorophenyl)-2-[[4-[2,5-dimethyl-4-((R)-1-phenylethoxycarbonyl-amino)pyrazol-3-yl]benzoyl]amino]propanoic acid |
| 16 | (R)-3-(3,4-difluorophenyl)-2-[[4-[1,5-dimethyl-4-((R)-1-phenylethoxycarbonyl-amino)pyrazol-3-yl]benzoyl]amino]propanoic acid |
| 17 | (R)-2-(4-{4-[(R)-1-(2-chloro-phenyl)-ethoxycarbonylamino]-3-methyl-isoxazol-5-yl}-benzoylamino)-3-cyclopropyl-propionic acid |
| 18 | (R)-2-{4-[3-Methyl-4-((S)-1-phenyl-ethoxycarbonylamino)-isoxazol-5-yl]-benzoylamino}-3-phenyl-propionic acid |
| 19 | (S)-2-{4-[3-Methyl-4-((S)-1-phenyl-ethoxycarbonylamino)-isoxazol-5-yl]-benzoylamino}-3-phenyl-propionic acid |
| 20 | (R)-2-(4-{4-[(R)-1-(2-Chloro-phenyl)-ethoxycarbonylamino]-3-methyl-isoxazol-5-yl}-benzoylamino)-3-phenyl-propionic acid |
| 21 | (R)-2-(4-{4-[(R)-1-(2-Chloro-phenyl)-ethoxycarbonylamino]-3-methyl-isoxazol-5-yl}-benzoylamino)-3-(4-fluoro-phenyl)-propionic acid |
| 22 | (R)-3-(4-Chloro-phenyl)-2-(4-{4-[(R)-1-(2-chloro-phenyl)-ethoxycarbonylamino]-3-methyl-isoxazol-5-yl}-benzoylamino)-propionic acid |
| 23 | (R)-2-(4-{4-[(R)-1-(2-Chloro-phenyl)-ethoxycarbonylamino]-3-methyl-isoxazol-5-yl}-benzoylamino)-3-(3,4-difluoro-phenyl)-propionic acid |
| 24 | (R)-3-(2-Chloro-phenyl)-2-(4-{4-[(R)-1-(2-chloro-phenyl)-ethoxycarbonylamino]-3-methyl-isoxazol-5-yl}-benzoylamino)-propionic acid |
| 25 | (R)-3-(4-Bromo-phenyl)-2-(4-{4-[(R)-1-(2-chloro-phenyl)-ethoxycarbonylamino]-3-methyl-isoxazol-5-yl}-benzoylamino)-propionic acid |
| 26 | (R)-2-(4-{4-[(R)-1-(2-Chloro-phenyl)-ethoxycarbonylamino]-3-methyl-isoxazol-5-yl}-benzoylamino)-3-(2-fluoro-phenyl)-propionic acid |
| 27 | (R)-2-(4-{4-[(R)-1-(2-Chloro-phenyl)-ethoxycarbonylamino]-3-methyl-isoxazol-5-yl}-benzoylamino)-3-p-tolyl-propionic acid |
| 28 | (R)-2-(4-{4-[(R)-1-(2-Chloro-phenyl)-ethoxycarbonylamino]-3-methyl-isoxazol-5-yl}-benzoylamino)-3-(4-trifluoromethyl-phenyl)-propionic acid |
| 29 | (R)-2-(4-{4-[(R)-1-(2-Chloro-phenyl)-ethoxycarbonylamino]-3-methyl-isoxazol-5-yl}-benzoylamino)-3-(4-cyano-phenyl)-propionic acid |
| 30 | (R)-2-(4-{5-[(R)-1-(2-Chloro-phenyl)-ethoxycarbonylamino]-4-methyl-pyrazol-1-yl}-benzoylamino)-3-phenyl-propionic acid |
| 31 | (R)-2-{4-[3-Methyl-4-((R)-1-phenyl-ethoxycarbonylamino)-isoxazol-5-yl]-benzylamino}-3-phenyl-propionic acid |
| 32 | (R)-3-(2-Fluoro-phenyl)-2-{4-[3-methyl-4-((R)-1-phenyl-ethoxycarbonylamino)-isoxazol-5-yl]-benzylamino}-propionic acid |
| 33 | (R)-2-{4-[3-Methyl-4-((R)-1-phenyl-ethoxycarbonylamino)-isoxazol-5-yl]-benzylamino}-3-(4-trifluoromethyl-phenyl)-propionic acid |
| 34 | (R)-3-Cyclopropyl-2-{4-[3-methyl-4-((R)-1-phenyl-ethoxycarbonylamino)-isoxazol-5-yl]-benzylamino}-propionic acid |
| 35 | (R)-3-(2-Chloro-phenyl)-2-{4-[3-methyl-4-((R)-1-phenyl-ethoxycarbonylamino)-isoxazol-5-yl]-benzylamino}-propionic acid |
| 36 | (R)-3-(4-Chloro-phenyl)-2-{4-[3-methyl-4-((R)-1-phenyl-ethoxycarbonylamino)-isoxazol-5-yl]-benzylamino}-propionic acid |
| 37 | (R)-2-(4-{4-[(R)-1-(2-Chloro-phenyl)-ethoxycarbonylamino]-3-methyl-isoxazol-5-yl}-benzylamino)-3-phenyl-propionic acid |
| 38 | (R)-2-(4-{4-[(R)__1-(2-Chloro-phenyl)-ethoxycarbonylamino]-3-methyl-isoxazol-5-yl}-benzylamino)-3-(2-fluoro-phenyl)-propionic acid |
| 39 | (R)-2-(4-{4-[(R)-1-(2-Chloro-phenyl)-ethoxycarbonylamino]-3-methyl-isoxazol-5-yl}-benzylamino)-3-(4-trifluoromethyl-phenyl)-propionic acid |

TABLE 1-continued

| Cpd | Name |
|---|---|
| 40 | (R)-3-(2-Chloro-phenyl)-2-(4-{4-[(R)-1-(2-chloro-phenyl)-ethoxycarbonylamino]-3-methyl-isoxazol-5-yl}-benzylamino)-propionic acid |
| 41 | (R)-2-(4-{4-[(R)-1-(2-Chloro-phenyl)-ethoxycarbonylamino]-3-methyl-isoxazol-5-yl}-benzylamino)-3-cyclopropyl-propionic acid |
| 42 | 2-{4-[3-Methyl-4-((R)-1-phenyl-ethoxycarbonylamino)-isoxazol-5-yl]-benzyloxy}-3-phenyl-propionic acid |
| 43 | 2-{4-[3-Methyl-4-((R)-1-phenyl-ethoxycarbonylamino)-isoxazol-5-yl]-benzyloxy}-3-phenyl-propionic acid |
| 44 | (RS)-3-Cyclopropyl-2-{4-[3-methyl-4-((R)-1-phenyl-ethoxycarbonylamino)-isoxazol-5-yl]-benzyloxy}-propionic acid |
| 45 | (RS)-3-(4-Chloro-phenyl)-2-{4-[3-methyl-4-((R)-1-phenyl-ethoxycarbonyloxy)-isoxazol-5-yl]-benzyloxy}-propionic acid |
| 46 | 2-[4-[4-[5-[1-(2-chlorophenyl)ethoxycarbonylamino]-4-cyano-pyrazol-1-yl]phenyl]phenyl]acetic acid |
| 47 | (R)-1-[4-[4-[1,5-dimethyl-4-(1-phenylethoxycarbonylamino)pyrazol-3-yl]phenyl]phenyl]cyclopropane carboxylic acid |
| 48 | (R)-1-[4-[4-[2,5-dimethyl-4-(1-phenylethoxycarbonylamino)pyrazol-3-yl]phenyl]phenyl]cyclopropane carboxylic acid |
| 49 | (R)-1-(4'-{5-[1-(2-Chloro-phenyl)-ethoxycarbonylamino]-4-fluoro-pyrazol-1-yl}-3-fluoro-biphenyl-4-yl)-cyclopropanecarboxylic acid |
| 50 | (R)-1-(4'-{5-[1-(2-Chloro-phenyl)-ethoxycarbonylamino]-4-fluoro-pyrazol-1-yl}-2-fluoro-biphenyl-4-yl)-cyclopropanecarboxylic acid |
| 51 | (R)-1-(2-Chloro-4'-{5-[1-(2-chloro-phenyl)-ethoxycarbonylamino]-4-fluoro-pyrazol-1-yl}-biphenyl-4-yl)-cyclopropanecarboxylic acid |
| 52 | (R)-1-(4'-{5-[1-(2-Chloro-phenyl)-ethoxycarbonylamino]-4-fluoro-pyrazol-1-yl}-2-methyl-biphenyl-4-yl)-cyclopropanecarboxylic acid |
| 53 | (R)-1-(4'-{5-[1-(2-Chloro-phenyl)-ethoxycarbonylamino]-4-fluoro-pyrazol-1-yl}-biphenyl-4-yl)-cyclopropanecarboxylic acid |
| 54 | (R)-1-{4'-[5-(1-Phenyl-ethoxycarbonylamino)-4-trifluoromethyl-pyrazol-1-yl]-biphenyl-4-yl}-cyclopropanecarboxylic acid |
| 55 | (R)-1-{2-Fluoro-4'-[5-(1-phenyl-ethoxycarbonylamino)-4-trifluoromethyl-pyrazol-1-yl]-biphenyl-4-yl}-cyclopropanecarboxylic acid |
| 56 | (R)-1-(4-{5-[5-(1-Phenyl-ethoxycarbonylamino)-pyrazol-1-yl]-pyridin-2-yl}-phenyl)-cyclopropanecarboxylic acid |
| 57 | 2-[[4-[3-methyl-4-(1-phenylethoxycarbonylamino)isoxazol-5-yl]benzoyl]amino]-3-phenyl-propanoic acid |
| 58 | 3-cyclopropyl-2-[[4-[3-methyl-4-(1-phenylethoxycarbonylamino)isoxazol-5-yl]benzoyl]amino]propanoic acid |
| 59 | 2-[[4-[3-methyl-4-(1-phenylethoxycarbonylamino)isoxazol-5-yl]benzoyl]amino]-3-phenoxy-propanoic acid |
| 60 | 2-[[4-[3-methyl-4-(1-phenylethoxycarbonylamino)isoxazol-5-yl]benzoyl]amino]-4-phenyl-butanoic acid |
| 61 | 2-[[4-[4-[1-(2-chlorophenyl)ethoxycarbonylamino]-3-methyl-isoxazol-5-yl]benzoyl]amino]-3-phenyl-propanoic acid |
| 62 | 2-[[4-[4-[1-(2-chlorophenyl)ethoxycarbonylamino]-3-methyl-isoxazol-5-yl]benzoyl]amino]-3-cyclopropyl-propanoic acid |
| 63 | 2-[[4-[4-[1-(2-chlorophenyl)ethoxycarbonylamino]-3-methyl-isoxazol-5-yl]benzoyl]amino]-4-phenyl-butanoic acid |
| 64 | 2-[[4-[4-[1-(2-chlorophenyl)ethoxycarbonylamino]-3-methyl-isoxazol-5-yl]benzoyl]amino]-3-phenoxy-propanoic acid |
| 65 | 2-[[4-[4-[1-(2-fluorophenyl)ethoxycarbonylamino]-3-methyl-isoxazol-5-yl]benzoyl]amino]-4-phenyl-butanoic acid |
| 66 | 2-[[4-[4-[1-(2-fluorophenyl)ethoxycarbonylamino]-3-methyl-isoxazol-5-yl]benzoyl]amino]-3-phenoxy-propanoic acid |
| 67 | 3-cyclopropyl-2-[[4-[4-[1-(2-fluorophenyl)ethoxycarbonylamino]-3-methyl-isoxazol-5-yl]benzoyl]amino]propanoic acid |
| 68 | 2-[[4-[4-[1-(2-fluorophenyl)ethoxycarbonylamino]-3-methyl-isoxazol-5-yl]benzoyl]amino]-3-phenyl-propanoic acid |
| 69 | 3-(4-methoxyphenyl)-2-[[4-[3-methyl-4-(1-phenylethoxycarbonylamino)isoxazol-5-yl]benzoyl]amino]propanoic acid |
| 70 | 3-(4-fluorophenyl)-2-[[4-[3-methyl-4-(1-phenylethoxycarbonylamino)isoxazol-5-yl]benzoyl]amino]propanoic acid |
| 71 | 3-(2,6-difluorophenyl)-2-[[4-[3-methyl-4-(1-phenylethoxycarbonylamino)isoxazol-5-yl]benzoyl]amino]propanoic acid |
| 72 | 3-(3-cyanophenyl)-2-[[4-[3-methyl-4-(1-phenylethoxycarbonylamino)isoxazol-5-yl]benzoyl]amino]propanoic acid |
| 73 | 3-(2-chlorophenyl)-2-[[4-[3-methyl-4-(1-phenylethoxycarbonylamino)isoxazol-5-yl]benzoyl]amino]propanoic acid |
| 74 | 3-(4-chlorophenyl)-2-[[4-[3-methyl-4-(1-phenylethoxycarbonylamino)isoxazol-5-yl]benzoyl]amino]propanoic acid |
| 75 | 2-[[4-[3-methyl-4-(1-phenylethoxycarbonylamino)isoxazol-5-yl]benzoyl]amino]-3-[4-(trifluoromethyl)phenyl]propanoic acid |
| 76 | 3-(4-hydroxyphenyl)-2-[[4-[3-methyl-4-(1-phenylethoxycarbonylamino)isoxazol-5-yl]benzoyl]amino]propanoic acid |
| 77 | 3-(3,4-difluorophenyl)-2-[[4-[3-methyl-4-(1-phenylethoxycarbonylamino)isoxazol-5-yl]benzoyl]amino]propanoic acid |
| 78 | 3-(4-bromophenyl)-2-[[4-[3-methyl-4-(1-phenylethoxycarbonylamino)isoxazol-5-yl]benzoyl]amino]propanoic acid |

TABLE 1-continued

| Cpd | Name |
|---|---|
| 79 | 2-[[4-[3-methyl-4-(1-phenylethoxycarbonylamino)isoxazol-5-yl]benzoyl]amino]-3-[4-(trifluoromethoxy)phenyl]propanoic acid |
| 80 | 2-[[4-[4-[1-(2-chlorophenyl)ethoxycarbonylamino]-3-methyl-isoxazol-5-yl]benzoyl]amino]-3-(4-methoxyphenyl)propanoic acid |
| 81 | 2-[[4-[4-[1-(2-chlorophenyl)ethoxycarbonylamino]-3-methyl-isoxazol-5-yl]benzoyl]amino]-3-(4-fluorophenyl)propanoic acid |
| 82 | 2-[[4-[4-[1-(2-chlorophenyl)ethoxycarbonylamino]-3-methyl-isoxazol-5-yl]benzoyl]amino]-3-(2,6-difluorophenyl)propanoic acid |
| 83 | 2-[[4-[4-[1-(2-chlorophenyl)ethoxycarbonylamino]-3-methyl-isoxazol-5-yl]benzoyl]amino]-3-(3-cyanophenyl)propanoic acid |
| 84 | 3-(2-chlorophenyl)-2-[[4-[4-[1-(2-chlorophenyl)ethoxycarbonylamino]-3-methyl-isoxazol-5-yl]benzoyl]amino]propanoic acid |
| 85 | 3-(4-chlorophenyl)-2-[[4-[4-[1-(2-chlorophenyl)ethoxycarbonylamino]-3-methyl-isoxazol-5-yl]benzoyl]amino]propanoic acid |
| 86 | 2-[[4-[4-[1-(2-chlorophenyl)ethoxycarbonylamino]-3-methyl-isoxazol-5-yl]benzoyl]amino]-3-[4-(trifluoromethyl)phenyl]propanoic acid |
| 87 | 2-[[4-[4-[1-(2-chlorophenyl)ethoxycarbonylamino]-3-methyl-isoxazol-5-yl]benzoyl]amino]-3-(4-hydroxyphenyl)propanoic acid |
| 88 | 3-(4-bromophenyl)-2-[[4-[4-[1-(2-chlorophenyl)ethoxycarbonylamino]-3-methyl-isoxazol-5-yl]benzoyl]amino]propanoic acid |
| 89 | 2-[[4-[4-[1-(2-chlorophenyl)ethoxycarbonylamino]-3-methyl-isoxazol-5-yl]benzoyl]amino]-3-(3,4-difluorophenyl)propanoic acid |
| 90 | 2-[[4-[4-[1-(2-chlorophenyl)ethoxycarbonylamino]-3-methyl-isoxazol-5-yl]benzoyl]amino]-3-[4-(trifluoromethoxy)phenyl]propanoic acid |
| 91 | 2-[[4-[4-[1-(2-fluorophenyl)ethoxycarbonylamino]-3-methyl-isoxazol-5-yl]benzoyl]amino]-3-(4-methoxyphenyl)propanoic acid |
| 92 | 3-(4-fluorophenyl)-2-[[4-[4-[1-(2-fluorophenyl)ethoxycarbonylamino]-3-methyl-isoxazol-5-yl]benzoyl]amino]propanoic acid |
| 93 | 3-(2,6-difluorophenyl)-2-[[4-[4-[1-(2-fluorophenyl)ethoxycarbonylamino]-3-methyl-isoxazol-5-yl]benzoyl]amino]propanoic acid |
| 94 | 3-(3-cyanophenyl)-2-[[4-[4-[1-(2-fluorophenyl)ethoxycarbonylamino]-3-methyl-isoxazol-5-yl]benzoyl]amino]propanoic acid |
| 95 | 3-(2-chlorophenyl)-2-[[4-[4-[1-(2-fluorophenyl)ethoxycarbonylamino]-3-methyl-isoxazol-5-yl]benzoyl]amino]propanoic acid |
| 96 | 3-(4-chlorophenyl)-2-[[4-[4-[1-(2-fluorophenyl)ethoxycarbonylamino]-3-methyl-isoxazol-5-yl]benzoyl]amino]propanoic acid |
| 97 | 2-[[4-[4-[1-(2-fluorophenyl)ethoxycarbonylamino]-3-methyl-isoxazol-5-yl]benzoyl]amino]-3-[4-(trifluoromethyl)phenyl]propanoic acid |
| 98 | 2-[[4-[4-[1-(2-fluorophenyl)ethoxycarbonylamino]-3-methyl-isoxazol-5-yl]benzoyl]amino]-3-(4-hydroxyphenyl)propanoic acid |
| 99 | 3-(3,4-difluorophenyl)-2-[[4-[4-[1-(2-fluorophenyl)ethoxycarbonylamino]-3-methyl-isoxazol-5-yl]benzoyl]amino]propanoic acid |
| 100 | 3-(4-bromophenyl)-2-[[4-[4-[1-(2-fluorophenyl)ethoxycarbonylamino]-3-methyl-isoxazol-5-yl]benzoyl]amino]propanoic acid |
| 101 | 2-[[4-[4-[1-(2-fluorophenyl)ethoxycarbonylamino]-3-methyl-isoxazol-5-yl]benzoyl]amino]-3-[4-(trifluoromethoxy)phenyl]propanoic acid |
| 102 | 2-[[4-[1,5-dimethyl-4-(1-phenylethoxycarbonylamino)pyrazol-3-yl]benzoyl]amino]-3-(4-methoxyphenyl)propanoic acid |
| 103 | 2-[[4-[1,5-dimethyl-4-(1-phenylethoxycarbonylamino)pyrazol-3-yl]benzoyl]amino]-3-(4-fluorophenyl)propanoic acid |
| 104 | 3-(2,6-difluorophenyl)-2-[[4-[1,5-dimethyl-4-(1-phenylethoxycarbonylamino)pyrazol-3-yl]benzoyl]amino]propanoic acid |
| 105 | 3-(3-cyanophenyl)-2-[[4-[1,5-dimethyl-4-(1-phenylethoxycarbonylamino)pyrazol-3-yl]benzoyl]amino]propanoic acid |
| 106 | 3-(2-chlorophenyl)-2-[[4-[1,5-dimethyl-4-(1-phenylethoxycarbonylamino)pyrazol-3-yl]benzoyl]amino]propanoic acid |
| 107 | 3-(4-chlorophenyl)-2-[[4-[1,5-dimethyl-4-(1-phenylethoxycarbonylamino)pyrazol-3-yl]benzoyl]amino]propanoic acid |
| 108 | 2-[[4-[1,5-dimethyl-4-(1-phenylethoxycarbonylamino)pyrazol-3-yl]benzoyl]amino]-3-[4-(trifluoromethyl)phenyl]propanoic acid |
| 109 | 2-[[4-[1,5-dimethyl-4-(1-phenylethoxycarbonylamino)pyrazol-3-yl]benzoyl]amino]-3-(4-hydroxyphenyl)propanoic acid |
| 110 | 3-(3,4-difluorophenyl)-2-[[4-[1,5-dimethyl-4-(1-phenylethoxycarbonylamino)pyrazol-3-yl]benzoyl]amino]propanoic acid |
| 111 | 3-(4-bromophenyl)-2-[[4-[1,5-dimethyl-4-(1-phenylethoxycarbonylamino)pyrazol-3-yl]benzoyl]amino]propanoic acid |
| 112 | 2-[[4-[1,5-dimethyl-4-(1-phenylethoxycarbonylamino)pyrazol-3-yl]benzoyl]amino]-3-[4-(trifluoromethoxy)phenyl]propanoic acid |
| 113 | 2-[[4-[4-[1-(2-chlorophenyl)ethoxycarbonylamino]-1,5-dimethyl-pyrazol-3-yl]benzoyl]amino]-3-(4-methoxyphenyl)propanoic acid |
| 114 | 2-[[4-[4-[1-(2-chlorophenyl)ethoxycarbonylamino]-1,5-dimethyl-pyrazol-3-yl]benzoyl]amino]-3-(4-fluorophenyl)propanoic acid |
| 115 | 2-[[4-[4-[1-(2-chlorophenyl)ethoxycarbonylamino]-1,5-dimethyl-pyrazol-3-yl]benzoyl]amino]-3-(2,6-difluorophenyl)propanoic acid |
| 116 | 2-[[4-[4-[1-(2-chlorophenyl)ethoxycarbonylamino]-1,5-dimethyl-pyrazol-3-yl]benzoyl]amino]-3-(3-cyanophenyl)propanoic acid |
| 117 | 3-(2-chlorophenyl)-2-[[4-[4-[1-(2-chlorophenyl)ethoxycarbonylamino]-1,5-dimethyl-pyrazol-3-yl]benzoyl]amino]propanoic acid |

TABLE 1-continued

| Cpd | Name |
|---|---|
| 118 | 3-(4-chlorophenyl)-2-[[4-[4-[1-(2-chlorophenyl)ethoxycarbonylamino]-1,5-dimethyl-pyrazol-3-yl]benzoyl]amino]propanoic acid |
| 119 | 2-[[4-[4-[1-(2-chlorophenyl)ethoxycarbonylamino]-1,5-dimethyl-pyrazol-3-yl]benzoyl]amino]-3-[4-(trifluoromethyl)phenyl]propanoic acid |
| 120 | 2-[[4-[4-[1-(2-chlorophenyl)ethoxycarbonylamino]-1,5-dimethyl-pyrazol-3-yl]benzoyl]amino]-3-(4-hydroxyphenyl)propanoic acid |
| 121 | 2-[[4-[4-[1-(2-chlorophenyl)ethoxycarbonylamino]-1,5-dimethyl-pyrazol-3-yl]benzoyl]amino]-3-(3,4-difluorophenyl)propanoic acid |
| 122 | 3-(4-bromophenyl)-2-[[4-[4-[1-(2-chlorophenyl)ethoxycarbonylamino]-1,5-dimethyl-pyrazol-3-yl]benzoyl]amino]propanoic acid |
| 123 | 2-[[4-[4-[1-(2-chlorophenyl)ethoxycarbonylamino]-1,5-dimethyl-pyrazol-3-yl]benzoyl]amino]-3-[4-(trifluoromethoxy)phenyl]propanoic acid |
| 124 | 2-[[4-[4-[1-(2-fluorophenyl)ethoxycarbonylamino]-1,5-dimethyl-pyrazol-3-yl]benzoyl]amino]-3-(4-methoxyphenyl)propanoic acid |
| 125 | 3-(4-fluorophenyl)-2-[[4-[4-[1-(2-fluorophenyl)ethoxycarbonylamino]-1,5-dimethyl-pyrazol-3-yl]benzoyl]amino]propanoic acid |
| 126 | 3-(2,6-difluorophenyl)-2-[[4-[4-[1-(2-fluorophenyl)ethoxycarbonylamino]-1,5-dimethyl-pyrazol-3-yl]benzoyl]amino]propanoic acid |
| 127 | 3-(3-cyanophenyl)-2-[[4-[4-[1-(2-fluorophenyl)ethoxycarbonylamino]-1,5-dimethyl-pyrazol-3-yl]benzoyl]amino]propanoic acid |
| 128 | 3-(2-chlorophenyl)-2-[[4-[4-[1-(2-fluorophenyl)ethoxycarbonylamino]-1,5-dimethyl-pyrazol-3-yl]benzoyl]amino]propanoic acid |
| 129 | 3-(4-chlorophenyl)-2-[[4-[4-[1-(2-fluorophenyl)ethoxycarbonylamino]-1,5-dimethyl-pyrazol-3-yl]benzoyl]amino]propanoic acid |
| 130 | 2-[[4-[4-[1-(2-fluorophenyl)ethoxycarbonylamino]-1,5-dimethyl-pyrazol-3-yl]benzoyl]amino]-3-[4-(trifluoromethyl)phenyl]propanoic acid |
| 131 | 2-[[4-[4-[1-(2-fluorophenyl)ethoxycarbonylamino]-1,5-dimethyl-pyrazol-3-yl]benzoyl]amino]-3-(4-hydroxyphenyl)propanoic acid |
| 132 | 3-(3,4-difluorophenyl)-2-[[4-[4-[1-(2-fluorophenyl)ethoxycarbonylamino]-1,5-dimethyl-pyrazol-3-yl]benzoyl]amino]propanoic acid |
| 133 | 3-(4-bromophenyl)-2-[[4-[4-[1-(2-fluorophenyl)ethoxycarbonylamino]-1,5-dimethyl-pyrazol-3-yl]benzoyl]amino]propanoic acid |
| 134 | 2-[[4-[4-[1-(2-fluorophenyl)ethoxycarbonylamino]-1,5-dimethyl-pyrazol-3-yl]benzoyl]amino]-3-[4-(trifluoromethoxy)phenyl]propanoic acid |
| 135 | 2-{p-[3-Fluoro-4-(1-phenylethoxycarbonylamino)-5-isoxazolyl]benzoylamino}-3-phenylpropionic acid |
| 136 | 2-(p-{4-[1-(o-Chlorophenyl)ethoxycarbonylamino]-3-fluoro-5-isoxazolyl}benzoylamino)-3-phenylpropionic acid |
| 137 | 3-Cyclopropyl-2-{p-[3-fluoro-4-(1-phenylethoxycarbonylamino)-5-isoxazolyl]benzoylamino}propionic acid |
| 138 | 2-(p-{4-[1-(o-Chlorophenyl)ethoxycarbonylamino]-3-fluoro-5-isoxazolyl}benzoylamino)-3-cyclopropylpropionic acid |
| 139 | 2-[({p-[3-Fluoro-4-(1-phenylethoxycarbonylamino)-5-isoxazolyl]phenyl}methyl)amino]-3-phenylpropionic acid |
| 140 | 2-{[(p-{4-[1-(o-Chlorophenyl)ethoxycarbonylamino]-3-fluoro-5-isoxazolyl}phenyl)methyl]amino}-3-phenylpropionic acid |
| 141 | 3-Cyclopropyl-2-[({p-[3-fluoro-4-(1-phenylethoxycarbonylamino)-5-isoxazolyl]phenyl}methyl)amino]propionic acid |
| 142 | 2-{[(p-{4-[1-(o-Chlorophenyl)ethoxycarbonylamino]-3-fluoro-5-isoxazolyl}phenyl)methyl]amino}-3-cyclopropylpropionic acid |
| 143 | 2-({p-[3-Fluoro-4-(1-phenylethoxycarbonylamino)-5-isoxazolyl]phenyl}methoxy)-3-phenylpropionic acid |
| 144 | 2-[(p-{4-[1-(o-Chlorophenyl)ethoxycarbonylamino]-3-fluoro-5-isoxazolyl}phenyl)methoxy]-3-phenylpropionic acid |
| 145 | 3-Cyclopropyl-2-({p-[3-fluoro-4-(1-phenylethoxycarbonylamino)-5-isoxazolyl]phenyl}methoxy)propionic acid |
| 146 | 2-[(p-{4-[1-(o-Chlorophenyl)ethoxycarbonylamino]-3-fluoro-5-isoxazolyl}phenyl)methoxy]-3-cyclopropylpropionic acid |
| 147 | 2-{p-[3-Cyano-4-(1-phenylethoxycarbonylamino)-5-isoxazolyl]benzoylamino}-3-phenylpropionic acid |
| 148 | 2-(p-{4-[1-(o-Chlorophenyl)ethoxycarbonylamino]-3-cyano-5-isoxazolyl}benzoylamino)-3-phenylpropionic acid |
| 149 | 2-{p-[3-Cyano-4-(1-phenylethoxycarbonylamino)-5-isoxazolyl]benzoylamino}-3-cyclopropylpropionic acid |
| 150 | 2-(p-{4-[1-(o-Chlorophenyl)ethoxycarbonylamino]-3-cyano-5-isoxazolyl}benzoylamino)-3-cyclopropylpropionic acid |
| 151 | 2-[({p-[3-Cyano-4-(1-phenylethoxycarbonylamino)-5-isoxazolyl]phenyl}methyl)amino]-3-phenylpropionic acid |
| 152 | 2-{[(p-{4-[1-(o-Chlorophenyl)ethoxycarbonylamino]-3-cyano-5-isoxazolyl}phenyl)methyl]amino}-3-phenylpropionic acid |
| 153 | 2-[({p-[3-Cyano-4-(1-phenylethoxycarbonylamino)-5-isoxazolyl]phenyl}methyl)amino]-3-cyclopropylpropionic acid |
| 154 | 2-{[(p-{4-[1-(o-Chlorophenyl)ethoxycarbonylamino]-3-cyano-5-isoxazolyl}phenyl)methyl]amino}-3-cyclopropylpropionic acid |
| 155 | 2-({p-[3-Cyano-4-(1-phenylethoxycarbonylamino)-5-isoxazolyl]phenyl}methoxy)-3-phenylpropionic acid |
| 156 | 2-[(p-{4-[1-(o-Chlorophenyl)ethoxycarbonylamino]-3-cyano-5-isoxazolyl}phenyl)methoxy]-3-phenylpropionic acid |

TABLE 1-continued

| Cpd | Name |
|---|---|
| 157 | 2-({p-[3-Cyano-4-(1-phenylethoxycarbonylamino)-5-isoxazolyl]phenyl}methoxy)-3-cyclopropylpropionic acid |
| 158 | 2-[(p-{4-[1-(o-Chlorophenyl)ethoxycarbonylamino]-3-cyano-5-isoxazolyl}phenyl)methoxy]-3-cyclopropylpropionic acid |
| 159 | 2-Benzyl-3-{5-[3-methyl-4-(1-phenylethoxycarbonylamino)-5-isoxazolyl]-2-pyridylamino}propionic acid |
| 160 | 2-Benzyl-3-(5-{4-[1-(o-chlorophenyl)ethoxycarbonylamino]-3-methyl-5-isoxazolyl}-2-pyridylamino)propionic acid |
| 161 | 2-(Cyclopropylmethyl)-3-{5-[3-methyl-4-(1-phenylethoxycarbonylamino)-5-isoxazolyl]-2-pyridylamino}propionic acid |
| 162 | 3-(5-{4-[1-(o-Chlorophenyl)ethoxycarbonylamino]-3-methyl-5-isoxazolyl}-2-pyridylamino)-2-(cyclopropylmethyl)propionic acid |
| 163 | 2-Benzyl-3-{5-[3-methyl-4-(1-phenylethoxycarbonylamino)-5-isoxazolyl]-2-pyridyloxy}propionic acid |
| 164 | 2-Benzyl-3-(5-{4-[1-(o-chlorophenyl)ethoxycarbonylamino]-3-methyl-5-isoxazolyl}-2-pyridyloxy)propionic acid |
| 165 | 2-(Cyclopropylmethyl)-3-{5-[3-methyl-4-(1-phenylethoxycarbonylamino)-5-isoxazolyl]-2-pyridyloxy}propionic acid |
| 166 | 3-(5-{4-[1-(o-Chlorophenyl)ethoxycarbonylamino]-3-methyl-5-isoxazolyl}-2-pyridyloxy)-2-(cyclopropylmethyl)propionic acid |
| 167 | 2-{5-[3-Methyl-4-(1-phenylethoxycarbonylamino)-5-isoxazolyl]-2-pyridylamino}-3-phenylpropionic acid |
| 168 | 2-(5-{4-[1-(o-Chlorophenyl)ethoxycarbonylamino]-3-methyl-5-isoxazolyl}-2-pyridylamino)-3-phenylpropionic acid |
| 169 | 2-(5-{4-[1-(o-Chlorophenyl)ethoxycarbonylamino]-3-methyl-5-isoxazolyl}-2-pyridylamino)-3-cyclopropylpropionic acid |
| 170 | 2-{5-[3-Methyl-4-(1-phenylethoxycarbonylamino)-5-isoxazolyl]-2-pyridyloxy}-3-phenylpropionic acid |
| 171 | 2-(5-{4-[1-(o-Chlorophenyl)ethoxycarbonylamino]-3-methyl-5-isoxazolyl}-2-pyridyloxy)-3-phenylpropionic acid |
| 172 | 3-Cyclopropyl-2-{5-[3-methyl-4-(1-phenylethoxycarbonylamino)-5-isoxazolyl]-2-pyridyloxy}propionic acid |
| 173 | 2-(5-{4-[1-(o-Chlorophenyl)ethoxycarbonylamino]-3-methyl-5-isoxazolyl}-2-pyridyloxy)-3-cyclopropylpropionic acid |
| 174 | 2-Benzyl-3-{5-[3-fluoro-4-(1-phenylethoxycarbonylamino)-5-isoxazolyl]-2-pyridylamino}propionic acid |
| 175 | 2-Benzyl-3-(5-{4-[1-(o-chlorophenyl)ethoxycarbonylamino]-3-fluoro-5-isoxazolyl}-2-pyridylamino)propionic acid |
| 176 | 2-(Cyclopropylmethyl)-3-{5-[3-fluoro-4-(1-phenylethoxycarbonylamino)-5-isoxazolyl]-2-pyridylamino}propionic acid |
| 177 | 3-(5-{4-[1-(o-Chlorophenyl)ethoxycarbonylamino]-3-fluoro-5-isoxazolyl}-2-pyridylamino)-2-(cyclopropylmethyl)propionic acid |
| 178 | 2-Benzyl-3-{5-[3-fluoro-4-(1-phenylethoxycarbonylamino)-5-isoxazolyl]-2-pyridyloxy}propionic acid |
| 179 | 2-Benzyl-3-(5-{4-[1-(o-chlorophenyl)ethoxycarbonylamino]-3-fluoro-5-isoxazolyl}-2-pyridyloxy)propionic acid |
| 180 | 2-(Cyclopropylmethyl)-3-{5-[3-fluoro-4-(1-phenylethoxycarbonylamino)-5-isoxazolyl]-2-pyridyloxy}propionic acid |
| 181 | 3-(5-{4-[1-(o-Chlorophenyl)ethoxycarbonylamino]-3-fluoro-5-isoxazolyl}-2-pyridyloxy)-2-(cyclopropylmethyl)propionic acid |
| 182 | 2-{5-[3-Fluoro-4-(1-phenylethoxycarbonylamino)-5-isoxazolyl]-2-pyridylamino}-3-phenylpropionic acid |
| 183 | 2-(5-{4-[1-(o-Chlorophenyl)ethoxycarbonylamino]-3-fluoro-5-isoxazolyl}-2-pyridylamino)-3-phenylpropionic acid |
| 184 | 3-Cyclopropyl-2-{5-[3-fluoro-4-(1-phenylethoxycarbonylamino)-5-isoxazolyl]-2-pyridylamino}propionic acid |
| 185 | 2-(5-{4-[1-(o-Chlorophenyl)ethoxycarbonylamino]-3-fluoro-5-isoxazolyl}-2-pyridylamino)-3-cyclopropylpropionic acid |
| 186 | 2-{5-[3-Fluoro-4-(1-phenylethoxycarbonylamino)-5-isoxazolyl]-2-pyridyloxy}-3-phenylpropionic acid |
| 187 | 2-(5-{4-[1-(o-Chlorophenyl)ethoxycarbonylamino]-3-fluoro-5-isoxazolyl}-2-pyridyloxy)-3-phenylpropionic acid |
| 188 | 3-Cyclopropyl-2-{5-[3-fluoro-4-(1-phenylethoxycarbonylamino)-5-isoxazolyl]-2-pyridyloxy}propionic acid |
| 189 | 2-(5-{4-[1-(o-Chlorophenyl)ethoxycarbonylamino]-3-fluoro-5-isoxazolyl}-2-pyridyloxy)-3-cyclopropylpropionic acid |
| 190 | 2-Benzyl-3-{5-[3-cyano-4-(1-phenylethoxycarbonylamino)-5-isoxazolyl]-2-pyridylamino}propionic acid |
| 191 | 2-Benzyl-3-(5-{4-[1-(o-chlorophenyl)ethoxycarbonylamino]-3-cyano-5-isoxazolyl}-2-pyridylamino)propionic acid |
| 192 | 3-{5-[3-Cyano-4-(1-phenylethoxycarbonylamino)-5-isoxazolyl]-2-pyridylamino}-2-(cyclopropylmethyl)propionic acid |
| 193 | 3-(5-{4-[1-(o-Chlorophenyl)ethoxycarbonylamino]-3-cyano-5-isoxazolyl}-2-pyridylamino)-2-(cyclopropylmethyl)propionic acid |
| 194 | 2-Benzyl-3-{5-[3-cyano-4-(1-phenylethoxycarbonylamino)-5-isoxazolyl]-2-pyridyloxy}propionic acid |
| 195 | 2-Benzyl-3-(5-{4-[1-(o-chlorophenyl)ethoxycarbonylamino]-3-cyano-5-isoxazolyl}-2-pyridyloxy)propionic acid |

TABLE 1-continued

| Cpd | Name |
|---|---|
| 196 | 3-{5-[3-Cyano-4-(1-phenylethoxycarbonylamino)-5-isoxazolyl]-2-pyridyloxy}-2-(cyclopropylmethyl)propionic acid |
| 197 | 3-(5-{4-[1-(o-Chlorophenyl)ethoxycarbonylamino]-3-cyano-5-isoxazolyl}-2-pyridyloxy)-2-(cyclopropylmethyl)propionic acid |
| 198 | 2-{5-[3-Cyano-4-(1-phenylethoxycarbonylamino)-5-isoxazolyl]-2-pyridylamino}-3-phenylpropionic acid |
| 199 | 2-(5-{4-[1-(o-Chlorophenyl)ethoxycarbonylamino]-3-cyano-5-isoxazolyl}-2-pyridylamino)-3-phenylpropionic acid |
| 200 | 2-{5-[3-Cyano-4-(1-phenylethoxycarbonylamino)-5-isoxazolyl]-2-pyridylamino}-3-cyclopropylpropionic acid |
| 201 | 2-(5-{4-[1-(o-Chlorophenyl)ethoxycarbonylamino]-3-cyano-5-isoxazolyl}-2-pyridylamino)-3-cyclopropylpropionic acid |
| 202 | 2-{5-[3-Cyano-4-(1-phenylethoxycarbonylamino)-5-isoxazolyl]-2-pyridyloxy}-3-phenylpropionic acid |
| 203 | 2-(5-{4-[1-(o-Chlorophenyl)ethoxycarbonylamino]-3-cyano-5-isoxazolyl}-2-pyridyloxy)-3-phenylpropionic acid |
| 204 | 2-{5-[3-Cyano-4-(1-phenylethoxycarbonylamino)-5-isoxazolyl]-2-pyridyloxy}-3-cyclopropylpropionic acid |
| 205 | 2-(5-{4-[1-(o-Chlorophenyl)ethoxycarbonylamino]-3-cyano-5-isoxazolyl}-2-pyridyloxy)-3-cyclopropylpropionic acid |
| 206 | 2-{p-[3-Fluoro-4-(1-phenylethoxycarbonylamino)-5-isoxazolyl]benzoylamino}-3-phenylpropionic acid |
| 207 | 2-(p-{4-[1-(o-Chlorophenyl)ethoxycarbonylamino]-3-fluoro-5-isoxazolyl}benzoylamino)-3-phenylpropionic acid |
| 208 | 3-Cyclopropyl-2-{p-[3-fluoro-4-(1-phenylethoxycarbonylamino)-5-isoxazolyl]benzoylamino}propionic acid |
| 209 | 2-(p-{4-[1-(o-Chlorophenyl)ethoxycarbonylamino]-3-fluoro-5-isoxazolyl}benzoylamino)-3-cyclopropylpropionic acid |
| 210 | 2-[({p-[3-Fluoro-4-(1-phenylethoxycarbonylamino)-5-isoxazolyl]phenyl}methyl)amino]-3-phenylpropionic acid |
| 211 | 2-{[(p-{4-[1-(o-Chlorophenyl)ethoxycarbonylamino]-3-fluoro-5-isoxazolyl}phenyl)methyl]amino}-3-phenylpropionic acid |
| 212 | 3-Cyclopropyl-2-[({p-[3-fluoro-4-(1-phenylethoxycarbonylamino)-5-isoxazolyl]phenyl}methyl)amino]propionic acid |
| 213 | 2-{[(p-{4-[1-(o-Chlorophenyl)ethoxycarbonylamino]-3-fluoro-5-isoxazolyl}phenyl)methyl]amino}-3-cyclopropylpropionic acid |
| 214 | 2-({p-[3-Fluoro-4-(1-phenylethoxycarbonylamino)-5-isoxazolyl]phenyl}methoxy)-3-phenylpropionic acid |
| 215 | 2-[(p-{4-[1-(o-Chlorophenyl)ethoxycarbonylamino]-3-fluoro-5-isoxazolyl}phenyl)methoxy]-3-phenylpropionic acid |
| 216 | 3-Cyclopropyl-2-({p-[3-fluoro-4-(1-phenylethoxycarbonylamino)-5-isoxazolyl]phenyl}methoxy)propionic acid |
| 217 | 2-[(p-{4-[1-(o-Chlorophenyl)ethoxycarbonylamino]-3-fluoro-5-isoxazolyl}phenyl)methoxy]-3-cyclopropylpropionic acid |
| 218 | 2-{p-[3-Cyano-4-(1-phenylethoxycarbonylamino)-5-isoxazolyl]benzoylamino}-3-phenylpropionic acid |
| 219 | 2-(p-{4-[1-(o-Chlorophenyl)ethoxycarbonylamino]-3-cyano-5-isoxazolyl}benzoylamino)-3-phenylpropionic acid |
| 220 | 2-{p-[3-Cyano-4-(1-phenylethoxycarbonylamino)-5-isoxazolyl]benzoylamino}-3-cyclopropylpropionic acid |
| 221 | 2-(p-{4-[1-(o-Chlorophenyl)ethoxycarbonylamino]-3-cyano-5-isoxazolyl}benzoylamino)-3-cyclopropylpropionic acid |
| 222 | 2-[({p-[3-Cyano-4-(1-phenylethoxycarbonylamino)-5-isoxazolyl]phenyl}methyl)amino]-3-phenylpropionic acid |
| 223 | 2-{[(p-{4-[1-(o-Chlorophenyl)ethoxycarbonylamino]-3-cyano-5-isoxazolyl}phenyl)methyl]amino}-3-phenylpropionic acid |
| 224 | 2-[({p-[3-Cyano-4-(1-phenylethoxycarbonylamino)-5-isoxazolyl]phenyl}methyl)amino]-3-cyclopropylpropionic acid |
| 225 | 2-{[(p-{4-[1-(o-Chlorophenyl)ethoxycarbonylamino]-3-cyano-5-isoxazolyl}phenyl)methyl]amino}-3-cyclopropylpropionic acid |
| 226 | 2-({p-[3-Cyano-4-(1-phenylethoxycarbonylamino)-5-isoxazolyl]phenyl}methoxy)-3-phenylpropionic acid |
| 227 | 2-[(p-{4-[1-(o-Chlorophenyl)ethoxycarbonylamino]-3-cyano-5-isoxazolyl}phenyl)methoxy]-3-phenylpropionic acid |
| 228 | 2-({p-[3-Cyano-4-(1-phenylethoxycarbonylamino)-5-isoxazolyl]phenyl}methoxy)-3-cyclopropylpropionic acid |
| 229 | 2-[(p-{4-[1-(o-Chlorophenyl)ethoxycarbonylamino]-3-cyano-5-isoxazolyl}phenyl)methoxy]-3-cyclopropylpropionic acid |
| 230 | 2-Benzyl-3-{5-[3-methyl-4-(1-phenylethoxycarbonylamino)-5-isoxazolyl]-2-pyridylamino}propionic acid |
| 231 | 2-Benzyl-3-(5-{4-[1-(o-chlorophenyl)ethoxycarbonylamino]-3-methyl-5-isoxazolyl}-2-pyridylamino)propionic acid |
| 232 | 2-(Cyclopropylmethyl)-3-{5-[3-methyl-4-(1-phenylethoxycarbonylamino)-5-isoxazolyl]-2-pyridylamino}propionic acid |
| 233 | 3-(5-{4-[1-(o-Chlorophenyl)ethoxycarbonylamino]-3-methyl-5-isoxazolyl}-2-pyridylamino)-2-(cyclopropylmethyl)propionic acid |
| 234 | 2-Benzyl-3-{5-[3-methyl-4-(1-phenylethoxycarbonylamino)-5-isoxazolyl]-2-pyridyloxy}propionic acid |

TABLE 1-continued

| Cpd | Name |
|---|---|
| 235 | 2-Benzyl-3-(5-{4-[1-(o-chlorophenyl)ethoxycarbonylamino]-3-methyl-5-isoxazolyl}-2-pyridyloxy)propionic acid |
| 236 | 2-(Cyclopropylmethyl)-3-{5-[3-methyl-4-(1-phenylethoxycarbonylamino)-5-isoxazolyl]-2-pyridyloxy}propionic acid |
| 237 | 3-(5-{4-[1-(o-Chlorophenyl)ethoxycarbonylamino]-3-methyl-5-isoxazolyl}-2-pyridyloxy)-2-(cyclopropylmethyl)propionic acid |
| 238 | 2-{5-[3-Methyl-4-(1-phenylethoxycarbonylamino)-5-isoxazolyl]-2-pyridylamino}-3-phenylpropionic acid |
| 239 | 2-(5-{4-[1-(o-Chlorophenyl)ethoxycarbonylamino]-3-methyl-5-isoxazolyl}-2-pyridylamino)-3-phenylpropionic acid |
| 240 | 3-Cyclopropyl-2-{5-[3-methyl-4-(1-phenylethoxycarbonylamino)-5-isoxazolyl]-2-pyridylamino}propionic acid |
| 241 | 2-(5-{4-[1-(o-Chlorophenyl)ethoxycarbonylamino]-3-methyl-5-isoxazolyl}-2-pyridylamino)-3-cyclopropylpropionic acid |
| 242 | 2-{5-[3-Methyl-4-(1-phenylethoxycarbonylamino)-5-isoxazolyl]-2-pyridyloxy}-3-phenylpropionic acid |
| 243 | 2-(5-{4-[1-(o-Chlorophenyl)ethoxycarbonylamino]-3-methyl-5-isoxazolyl}-2-pyridyloxy)-3-phenylpropionic acid |
| 244 | 3-Cyclopropyl-2-{5-[3-methyl-4-(1-phenylethoxycarbonylamino)-5-isoxazolyl]-2-pyridyloxy}propionic acid |
| 245 | 2-(5-{4-[1-(o-Chlorophenyl)ethoxycarbonylamino]-3-methyl-5-isoxazolyl}-2-pyridyloxy)-3-cyclopropylpropionic acid |
| 246 | 2-Benzyl-3-{5-[3-fluoro-4-(1-phenylethoxycarbonylamino)-5-isoxazolyl]-2-pyridylamino}propionic acid |
| 247 | 2-Benzyl-3-(5-{4-[1-(o-chlorophenyl)ethoxycarbonylamino]-3-fluoro-5-isoxazolyl}-2-pyridylamino)propionic acid |
| 248 | 2-(Cyclopropylmethyl)-3-{5-[3-fluoro-4-(1-phenylethoxycarbonylamino)-5-isoxazolyl]-2-pyridylamino}propionic acid |
| 249 | 3-(5-{4-[1-(o-Chlorophenyl)ethoxycarbonylamino]-3-fluoro-5-isoxazolyl}-2-pyridylamino)-2-(cyclopropylmethyl)propionic acid |
| 250 | 2-Benzyl-3-{5-[3-fluoro-4-(1-phenylethoxycarbonylamino)-5-isoxazolyl]-2-pyridyloxy}propionic acid |
| 251 | 2-Benzyl-3-(5-{4-[1-(o-chlorophenyl)ethoxycarbonylamino]-3-fluoro-5-isoxazolyl}-2-pyridyloxy)propionic acid |
| 252 | 2-(Cyclopropylmethyl)-3-{5-[3-fluoro-4-(1-phenylethoxycarbonylamino)-5-isoxazolyl]-2-pyridyloxy}propionic acid |
| 253 | 3-(5-{4-[1-(o-Chlorophenyl)ethoxycarbonylamino]-3-fluoro-5-isoxazolyl}-2-pyridyloxy)-2-(cyclopropylmethyl)propionic acid |
| 254 | 2-{5-[3-Fluoro-4-(1-phenylethoxycarbonylamino)-5-isoxazolyl]-2-pyridylamino}-3-phenylpropionic acid |
| 255 | 2-(5-{4-[1-(o-Chlorophenyl)ethoxycarbonylamino]-3-fluoro-5-isoxazolyl}-2-pyridylamino)-3-phenylpropionic acid |
| 256 | 3-Cyclopropyl-2-{5-[3-fluoro-4-(1-phenylethoxycarbonylamino)-5-isoxazolyl]-2-pyridylamino}propionic acid |
| 257 | 2-(5-{4-[1-(o-Chlorophenyl)ethoxycarbonylamino]-3-fluoro-5-isoxazolyl}-2-pyridylamino)-3-cyclopropylpropionic acid |
| 258 | 2-{5-[3-Fluoro-4-(1-phenylethoxycarbonylamino)-5-isoxazolyl]-2-pyridyloxy}-3-phenylpropionic acid |
| 259 | 2-(5-{4-[1-(o-Chlorophenyl)ethoxycarbonylamino]-3-fluoro-5-isoxazolyl}-2-pyridyloxy)-3-phenylpropionic acid |
| 260 | 3-Cyclopropyl-2-{5-[3-fluoro-4-(1-phenylethoxycarbonylamino)-5-isoxazolyl]-2-pyridyloxy}propionic acid |
| 261 | 2-(5-{4-[1-(o-Chlorophenyl)ethoxycarbonylamino]-3-fluoro-5-isoxazolyl}-2-pyridyloxy)-3-cyclopropylpropionic acid |
| 262 | 2-Benzyl-3-{5-[3-cyano-4-(1-phenylethoxycarbonylamino)-5-isoxazolyl]-2-pyridylamino}propionic acid |
| 263 | 2-Benzyl-3-(5-{4-[1-(o-chlorophenyl)ethoxycarbonylamino]-3-cyano-5-isoxazolyl}-2-pyridylamino)propionic acid |
| 264 | 3-{5-[3-Cyano-4-(1-phenylethoxycarbonylamino)-5-isoxazolyl]-2-pyridylamino}-2-(cyclopropylmethyl)propionic acid |
| 265 | 3-(5-{4-[1-(o-Chlorophenyl)ethoxycarbonylamino]-3-cyano-5-isoxazolyl}-2-pyridylamino)-2-(cyclopropylmethyl)propionic acid |
| 266 | 2-Benzyl-3-{5-[3-cyano-4-(1-phenylethoxycarbonylamino)-5-isoxazolyl]-2-pyridyloxy}propionic acid |
| 267 | 2-Benzyl-3-(5-{4-[1-(o-chlorophenyl)ethoxycarbonylamino]-3-cyano-5-isoxazolyl}-2-pyridyloxy)propionic acid |
| 268 | 3-{5-[3-Cyano-4-(1-phenylethoxycarbonylamino)-5-isoxazolyl]-2-pyridyloxy}-2-(cyclopropylmethyl)propionic acid |
| 269 | 3-(5-{4-[1-(o-Chlorophenyl)ethoxycarbonylamino]-3-cyano-5-isoxazolyl}-2-pyridyloxy)-2-(cyclopropylmethyl)propionic acid |
| 270 | 2-{5-[3-Cyano-4-(1-phenylethoxycarbonylamino)-5-isoxazolyl]-2-pyridylamino}-3-phenylpropionic acid |
| 271 | 2-(5-{4-[1-(o-Chlorophenyl)ethoxycarbonylamino]-3-cyano-5-isoxazolyl}-2-pyridylamino)-3-phenylpropionic acid |
| 272 | 2-{5-[3-Cyano-4-(1-phenylethoxycarbonylamino)-5-isoxazolyl]-2-pyridylamino}-3-cyclopropylpropionic acid |
| 273 | 2-(5-{4-[1-(o-Chlorophenyl)ethoxycarbonylamino]-3-cyano-5-isoxazolyl}-2-pyridylamino)-3-cyclopropylpropionic acid |

TABLE 1-continued

| Cpd | Name |
|---|---|
| 274 | 2-{5-[3-Cyano-4-(1-phenylethoxycarbonylamino)-5-isoxazolyl]-2-pyridyloxy}-3-phenylpropionic acid |
| 275 | 2-(5-{4-[1-(o-Chlorophenyl)ethoxycarbonylamino]-3-cyano-5-isoxazolyl}-2-pyridyloxy)-3-phenylpropionic acid |
| 276 | 2-{5-[3-Cyano-4-(1-phenylethoxycarbonylamino)-5-isoxazolyl]-2-pyridyloxy}-3-cyclopropylpropionic acid |
| 277 | 2-(5-{4-[1-(o-Chlorophenyl)ethoxycarbonylamino]-3-cyano-5-isoxazolyl}-2-pyridyloxy)-3-cyclopropylpropionic acid |
| 278 | 3-{p-[3-Methyl-4-(1-phenylethoxycarbonylamino)-5-isoxazolyl]benzoylamino}-4-phenylbutyric acid |
| 279 | 4-Cyclopropyl-3-{p-[3-methyl-4-(1-phenylethoxycarbonylamino)-5-isoxazolyl]benzoylamino}butyric acid |
| 280 | 3-[({p-[3-Methyl-4-(1-phenylethoxycarbonylamino)-5-isoxazolyl]phenyl}methyl)amino]-4-phenylbutyric acid |
| 281 | 4-Cyclopropyl-3-[({p-[3-methyl-4-(1-phenylethoxycarbonylamino)-5-isoxazolyl]phenyl}methyl)amino]butyric acid |
| 282 | 3-({p-[3-Methyl-4-(1-phenylethoxycarbonylamino)-5-isoxazolyl]phenyl}methoxy)-4-phenylbutyric acid |
| 283 | 4-Cyclopropyl-3-({p-[3-methyl-4-(1-phenylethoxycarbonylamino)-5-isoxazolyl]phenyl}methoxy)butyric acid |
| 284 | 3-{5-[3-Methyl-4-(1-phenylethoxycarbonylamino)-5-isoxazolyl]-2-pyridylamino}-4-phenylbutyric acid |
| 285 | 4-Cyclopropyl-3-{5-[3-methyl-4-(1-phenylethoxycarbonylamino)-5-isoxazolyl]-2-pyridylamino}butyric acid |
| 286 | 3-{5-[3-Methyl-4-(1-phenylethoxycarbonylamino)-5-isoxazolyl]-2-pyridyloxy}-4-phenylbutyric acid |
| 287 | 4-Cyclopropyl-3-{5-[3-methyl-4-(1-phenylethoxycarbonylamino)-5-isoxazolyl]-2-pyridyloxy}butyric acid |
| 288 | 2-[4-[4-[4-cyano-5-(1-phenylethoxycarbonylamino)pyrazol-1-yl]phenyl]phenyl]acetic acid |
| 289 | 1-[4-[4-[4-cyano-5-(1-phenylethoxycarbonylamino)pyrazol-1-yl]phenyl]phenyl]cyclopropanecarboxylic acid |
| 290 | 1-[4-[4-[5-[1-(2-chlorophenyl)ethoxycarbonylamino]-4-cyano-pyrazol-1-yl]phenyl]phenyl]cyclopropanecarboxylic acid |
| 291 | 2-[4-[4-[4-cyano-5-(1-phenylethoxycarbonylamino)pyrazol-1-yl]phenyl]phenyl]-2-methyl-propanoic acid |
| 292 | 2-[4-[4-[5-[1-(2-chlorophenyl)ethoxycarbonylamino]-4-cyano-pyrazol-1-yl]phenyl]phenyl]-2-methyl-propanoic acid |
| 293 | 1-{4'-[4-Fluoro-5-(1-phenylethoxycarbonylamino)-1H-pyrazol-1-yl]-4-biphenylyl}cyclopropanecarboxylic acid |
| 294 | 1-(4'-{5-[1-(o-Chlorophenyl)ethoxycarbonylamino]-4-fluoro-1H-pyrazol-1-yl}-4-biphenylyl)cyclopropanecarboxylic acid |
| 295 | 1-{3-Fluoro-4'-[4-fluoro-5-(1-phenylethoxycarbonylamino)-1H-pyrazol-1-yl]-4-biphenylyl}cyclopropanecarboxylic acid |
| 296 | 1-(4'-{5-[1-(o-Chlorophenyl)ethoxycarbonylamino]-4-fluoro-1H-pyrazol-1-yl}-3-fluoro-4-biphenylyl)cyclopropanecarboxylic acid |
| 297 | 1-{2-Fluoro-4'-[4-fluoro-5-(1-phenylethoxycarbonylamino)-1H-pyrazol-1-yl]-4-biphenylyl}cyclopropanecarboxylic acid |
| 298 | 1-(4'-{5-[1-(o-Chlorophenyl)ethoxycarbonylamino]-4-fluoro-1H-pyrazol-1-yl}-2-fluoro-4-biphenylyl)cyclopropanecarboxylic acid |
| 299 | 1-{2-Chloro-4'-[4-fluoro-5-(1-phenylethoxycarbonylamino)-1H-pyrazol-1-yl]-4-biphenylyl}cyclopropanecarboxylic acid |
| 300 | 1-(2-Chloro-4'-{5-[1-(o-chlorophenyl)ethoxycarbonylamino]-4-fluoro-1H-pyrazol-1-yl}-4-biphenylyl)cyclopropanecarboxylic acid |
| 301 | 1-(4-{p-[4-Fluoro-5-(1-phenylethoxycarbonylamino)-1H-pyrazol-1-yl]phenyl}tolyl)cyclopropanecarboxylic acid |
| 302 | 1-[4-(p-{5-[1-(o-Chlorophenyl)ethoxycarbonylamino]-4-fluoro-1H-pyrazol-1-yl}phenyl)tolyl]cyclopropanecarboxylic acid |
| 303 | 1-(p-{5-[5-(1-Phenylethoxycarbonylamino)-1H-pyrazol-1-yl]-2-pyridyl}phenyl)cyclopropanecarboxylic acid |
| 304 | 1-[p-(5-{5-[1-(o-Chlorophenyl)ethoxycarbonylamino]-1H-pyrazol-1-yl}-2-pyridyl)phenyl]cyclopropanecarboxylic acid |
| 305 | 1-(p-{5-[4-Methyl-5-(1-phenylethoxycarbonylamino)-1H-pyrazol-1-yl]-2-pyridyl}phenyl)cyclopropanecarboxylic acid |
| 306 | 1-[p-(5-{5-[1-(o-Chlorophenyl)ethoxycarbonylamino]-4-methyl-1H-pyrazol-1-yl}-2-pyridyl)phenyl]cyclopropanecarboxylic acid |
| 307 | 1-(2-Fluoro-4-{5-[5-(1-phenylethoxycarbonylamino)-1H-pyrazol-1-yl]-2-pyridyl}phenyl)cyclopropanecarboxylic acid |
| 308 | 1-[4-(5-{5-[1-(o-Chlorophenyl)ethoxycarbonylamino]-1H-pyrazol-1-yl}-2-pyridyl)-2-fluorophenyl]cyclopropanecarboxylic acid |
| 309 | 1-(3-Fluoro-4-{5-[5-(1-phenylethoxycarbonylamino)-1H-pyrazol-1-yl]-2-pyridyl}phenyl)cyclopropanecarboxylic acid |
| 310 | 1-[4-(5-{5-[1-(o-Chlorophenyl)ethoxycarbonylamino]-1H-pyrazol-1-yl}-2-pyridyl)-3-fluorophenyl]cyclopropanecarboxylic acid |
| 311 | 1-[p-(5-{5-[1-(o-Chlorophenyl)ethoxycarbonylamino]-4-methyl-1H-pyrazol-1-yl}-2-pyridyl)phenyl]cyclopropanecarboxylic acid |
| 312 | 1-(2-Fluoro-4-{5-[4-methyl-5-(1-phenylethoxycarbonylamino)-1H-pyrazol-1-yl]-2-pyridyl}phenyl)cyclopropanecarboxylic acid |

TABLE 1-continued

| Cpd | Name |
|---|---|
| 313 | 1-[4-(5-{5-[1-(o-Chlorophenyl)ethoxycarbonylamino]-4-methyl-1H-pyrazol-1-yl}-2-pyridyl)-2-fluorophenyl]cyclopropanecarboxylic acid |
| 314 | 1-(3-Fluoro-4-{5-[4-methyl-5-(1-phenylethoxycarbonylamino)-1H-pyrazol-1-yl]-2-pyridyl}phenyl)cyclopropanecarboxylic acid |
| 315 | 1-[4-(5-{5-[1-(o-Chlorophenyl)ethoxycarbonylamino]-4-methyl-1H-pyrazol-1-yl}-2-pyridyl)-3-fluorophenyl]cyclopropanecarboxylic acid |
| 316 | 1-(p-{5-[4-Fluoro-5-(1-phenylethoxycarbonylamino)-1H-pyrazol-1-yl]-2-pyridyl}phenyl)cyclopropanecarboxylic acid |
| 317 | 1-[p-(5-{5-[1-(o-Chlorophenyl)ethoxycarbonylamino]-4-fluoro-1H-pyrazol-1-yl}-2-pyridyl)phenyl]cyclopropanecarboxylic acid |
| 318 | 1-(2-Fluoro-4-{5-[4-fluoro-5-(1-phenylethoxycarbonylamino)-1H-pyrazol-1-yl]-2-pyridyl}phenyl)cyclopropanecarboxylic acid |
| 319 | 1-[4-(5-{5-[1-(o-Chlorophenyl)ethoxycarbonylamino]-4-fluoro-1H-pyrazol-1-yl}-2-pyridyl)-2-fluorophenyl]cyclopropanecarboxylic acid |
| 320 | 1-(3-Fluoro-4-{5-[4-fluoro-5-(1-phenylethoxycarbonylamino)-1H-pyrazol-1-yl]-2-pyridyl}phenyl)cyclopropanecarboxylic acid |
| 321 | 1-[4-(5-{5-[1-(o-Chlorophenyl)ethoxycarbonylamino]-4-fluoro-1H-pyrazol-1-yl}-2-pyridyl)-3-fluorophenyl]cyclopropanecarboxylic acid |
| 322 | 1-(p-{5-[4-Cyano-5-(1-phenylethoxycarbonylamino)-1H-pyrazol-1-yl]-2-pyridyl}phenyl)cyclopropanecarboxylic acid |
| 323 | 1-[p-(5-{5-[1-(o-Chlorophenyl)ethoxycarbonylamino]-4-cyano-1H-pyrazol-1-yl}-2-pyridyl)phenyl]cyclopropanecarboxylic acid |
| 324 | 1-(4-{5-[4-Cyano-5-(1-phenylethoxycarbonylamino)-1H-pyrazol-1-yl]-2-pyridyl}-2-fluorophenyl)cyclopropanecarboxylic acid |
| 325 | 1-[4-(5-{5-[1-(o-Chlorophenyl)ethoxycarbonylamino]-4-cyano-1H-pyrazol-1-yl}-2-pyridyl)-2-fluorophenyl]cyclopropanecarboxylic acid |
| 326 | 1-(4-{5-[4-Cyano-5-(1-phenylethoxycarbonylamino)-1H-pyrazol-1-yl]-2-pyridyl}-3-fluorophenyl)cyclopropanecarboxylic acid |
| 327 | 1-[4-(5-{5-[1-(o-Chlorophenyl)ethoxycarbonylamino]-4-cyano-1H-pyrazol-1-yl}-2-pyridyl)-3-fluorophenyl]cyclopropanecarboxylic acid |
| 328 | 2-{p-[1-Methyl-5-methyl-4-(1-phenylethoxycarbonylamino)-1H-pyrazol-3-yl]benzoylamino}-3-phenylpropionic acid |
| 329 | 3-Cyclopropyl-2-{p-[1-methyl-5-methyl-4-(1-phenylethoxycarbonylamino)-1H-pyrazol-3-yl]benzoylamino}propionic acid |
| 330 | 2-(p-{4-[1-(o-Chlorophenyl)ethoxycarbonylamino]-1-methyl-5-methyl-1H-pyrazol-3-yl}benzoylamino)-3-phenylpropionic acid |
| 331 | 2-(p-{4-[1-(o-Chlorophenyl)ethoxycarbonylamino]-1-methyl-5-methyl-1H-pyrazol-3-yl}benzoylamino)-3-cyclopropylpropionic acid |
| 332 | 2-[({p-[1-Methyl-5-methyl-4-(1-phenylethoxycarbonylamino)-1H-pyrazol-3-yl]phenyl}methyl)amino]-3-phenylpropionic acid |
| 333 | 3-Cyclopropyl-2-[({p-[1-methyl-5-methyl-4-(1-phenylethoxycarbonylamino)-1H-pyrazol-3-yl]phenyl}methyl)amino]propionic acid |
| 334 | 2-{[(p-{4-[1-(o-Chlorophenyl)ethoxycarbonylamino]-1-methyl-5-methyl-1H-pyrazol-3-yl}phenyl)methyl]amino}-3-phenylpropionic acid |
| 335 | 2-{[(p-{4-[1-(o-Chlorophenyl)ethoxycarbonylamino]-1-methyl-5-methyl-1H-pyrazol-3-yl}phenyl)methyl]amino}-3-cyclopropylpropionic acid |
| 336 | 2-({p-[1-Methyl-5-methyl-4-(1-phenylethoxycarbonylamino)-1H-pyrazol-3-yl]phenyl}methoxy)-3-phenylpropionic acid |
| 337 | 3-Cyclopropyl-2-({p-[1-methyl-5-methyl-4-(1-phenylethoxycarbonylamino)-1H-pyrazol-3-yl]phenyl}methoxy)propionic acid |
| 338 | 2-[(p-{4-[1-(o-Chlorophenyl)ethoxycarbonylamino]-1-methyl-5-methyl-1H-pyrazol-3-yl}phenyl)methoxy]-3-phenylpropionic acid |
| 339 | 2-[(p-{4-[1-(o-Chlorophenyl)ethoxycarbonylamino]-1-methyl-5-methyl-1H-pyrazol-3-yl}phenyl)methoxy]-3-cyclopropylpropionic acid |
| 340 | 3-{p-[1-Methyl-5-methyl-4-(1-phenylethoxycarbonylamino)-1H-pyrazol-3-yl]benzoylamino}-4-phenylbutyric acid |
| 341 | 4-Cyclopropyl-3-{p-[1-methyl-5-methyl-4-(1-phenylethoxycarbonylamino)-1H-pyrazol-3-yl]benzoylamino}butyric acid |
| 342 | 3-[({p-[1-Methyl-5-methyl-4-(1-phenylethoxycarbonylamino)-1H-pyrazol-3-yl]phenyl}methyl)amino]-4-phenylbutyric acid |
| 343 | 4-Cyclopropyl-3-[({p-[1-methyl-5-methyl-4-(1-phenylethoxycarbonylamino)-1H-pyrazol-3-yl]phenyl}methyl)amino]butyric acid |
| 344 | 3-({p-[1-Methyl-5-methyl-4-(1-phenylethoxycarbonylamino)-1H-pyrazol-3-yl]phenyl}methoxy)-4-phenylbutyric acid |
| 345 | 4-Cyclopropyl-3-({p-[1-methyl-5-methyl-4-(1-phenylethoxycarbonylamino)-1H-pyrazol-3-yl]phenyl}methoxy)butyric acid |
| 346 | 3-phenyl-2-[[4-[5-(1-phenylethoxycarbonylamino)oxazol-4-yl]benzoyl]amino]propanoic acid |
| 347 | 3-cyclopropyl-2-[[4-[5-(1-phenylethoxycarbonylamino)oxazol-4-yl]benzoyl]amino]propanoic acid |
| 348 | 4-phenyl-2-[[4-[5-(1-phenylethoxycarbonylamino)oxazol-4-yl]benzoyl]amino]butanoic acid |
| 349 | 3-phenoxy-2-[[4-[5-(1-phenylethoxycarbonylamino)oxazol-4-yl]benzoyl]amino]propanoic acid |
| 350 | 3-Phenyl-2-[({p-[5-(1-phenylethoxycarbonylamino)-1,3-oxazol-4-yl]phenyl}methyl)amino]propionic acid |

TABLE 1-continued

| Cpd | Name |
|---|---|
| 351 | 3-Cyclopropyl-2-[({p-[5-(1-phenylethoxycarbonylamino)-1,3-oxazol-4-yl]phenyl}methyl)amino]propionic acid |
| 352 | 3-Phenyl-2-({p-[5-(1-phenylethoxycarbonylamino)-1,3-oxazol-4-yl]phenyl}methoxy)propionic acid |
| 353 | 4-Phenyl-3-({p-[5-(1-phenylethoxycarbonylamino)-1,3-oxazol-4-yl]phenyl}methoxy)butyric acid |
| 354 | 4-Cyclopropyl-3-({p-[5-(1-phenylethoxycarbonylamino)-1,3-oxazol-4-yl]phenyl}methoxy)butyric acid |
| 355 | 2-[[4-[1-methyl-5-(1-phenylethoxycarbonylamino)imidazol-4-yl]benzoyl]amino]-3-phenyl-propanoic acid |
| 356 | 3-cyclopropyl-2-[[4-[1-methyl-5-(1-phenylethoxycarbonylamino)imidazol-4-yl]benzoyl]amino]propanoic acid |
| 357 | 2-[[4-[1-methyl-5-(1-phenylethoxycarbonylamino)imidazol-4-yl]benzoyl]amino]-4-phenyl-butanoic acid |
| 358 | 2-[[4-[1-methyl-5-(1-phenylethoxycarbonylamino)imidazol-4-yl]benzoyl]amino]-3-phenoxy-propanoic acid |
| 359 | 2-[({p-[1-Methyl-5-(1-phenylethoxycarbonylamino)-1H-imidazol-4-yl]phenyl}methyl)amino]-3-phenylpropionic acid |
| 360 | 3-Cyclopropyl-2-[({p-[1-methyl-5-(1-phenylethoxycarbonylamino)-1H-imidazol-4-yl]phenyl}methyl)amino]propionic acid |
| 361 | 2-({p-[1-Methyl-5-(1-phenylethoxycarbonylamino)-1H-imidazol-4-yl]phenyl}methoxy)-3-phenylpropionic acid |
| 362 | 3-Cyclopropyl-2-({p-[1-methyl-5-(1-phenylethoxycarbonylamino)-1H-imidazol-4-yl]phenyl}methoxy)propionic acid |
| 363 | 3-[({p-[1-Methyl-5-(1-phenylethoxycarbonylamino)-1H-imidazol-4-yl]phenyl}methyl)amino]-4-phenylbutyric acid |
| 364 | 4-Cyclopropyl-3-[({p-[1-methyl-5-(1-phenylethoxycarbonylamino)-1H-imidazol-4-yl]phenyl}methyl)amino]butyric acid |
| 365 | 3-({p-[1-Methyl-5-(1-phenylethoxycarbonylamino)-1H-imidazol-4-yl]phenyl}methoxy)-4-phenylbutyric acid |
| 366 | 4-Cyclopropyl-3-({p-[1-methyl-5-(1-phenylethoxycarbonylamino)-1H-imidazol-4-yl]phenyl}methoxy)butyric acid |
| 367 | 2-[[4-[1,2-dimethyl-3-oxo-5-(1-phenylethoxycarbonylamino)pyrazol-4-yl]benzoyl]amino]-3-phenyl-propanoic acid |
| 368 | 3-cyclopropyl-2-[[4-[1,2-dimethyl-3-oxo-5-(1-phenylethoxycarbonylamino)pyrazol-4-yl]benzoyl]amino]propanoic acid |
| 369 | 2-[[4-[1,2-dimethyl-3-oxo-5-(1-phenylethoxycarbonylamino)pyrazol-4-yl]benzoyl]amino]-4-phenyl-butanoic acid |
| 370 | 2-[[4-[1,2-dimethyl-3-oxo-5-(1-phenylethoxycarbonylamino)pyrazol-4-yl]benzoyl]amino]-3-phenoxy-propanoic acid |
| 371 | 2-[({p-[1,2-Dimethyl-3-oxo-5-(1-phenylethoxycarbonylamino)-1,2-dihydropyrazol-4-yl]phenyl}methyl)amino]-3-phenylpropionic acid |
| 372 | 3-Cyclopropyl-2-[({p-[1,2-dimethyl-3-oxo-5-(1-phenylethoxycarbonylamino)-1,2-dihydropyrazol-4-yl]phenyl}methyl)amino]propionic acid |
| 373 | 2-({p-[1,2-Dimethyl-3-oxo-5-(1-phenylethoxycarbonylamino)-1,2-dihydropyrazol-4-yl]phenyl}methoxy)-3-phenylpropionic acid |
| 374 | 3-Cyclopropyl-2-({p-[1,2-dimethyl-3-oxo-5-(1-phenylethoxycarbonylamino)-1,2-dihydropyrazol-4-yl]phenyl}methoxy)propionic acid |
| 375 | 3-[({p-[1,2-Dimethyl-3-oxo-5-(1-phenylethoxycarbonylamino)-1,2-dihydropyrazol-4-yl]phenyl}methyl)amino]-4-phenylbutyric acid |
| 376 | 4-Cyclopropyl-3-[({p-[1,2-dimethyl-3-oxo-5-(1-phenylethoxycarbonylamino)-1,2-dihydropyrazol-4-yl]phenyl}methyl)amino]butyric acid |
| 377 | 3-({p-[1,2-Dimethyl-3-oxo-5-(1-phenylethoxycarbonylamino)-1,2-dihydropyrazol-4-yl]phenyl}methoxy)-4-phenylbutyric acid |
| 378 | 4-Cyclopropyl-3-({p-[1,2-dimethyl-3-oxo-5-(1-phenylethoxycarbonylamino)-1,2-dihydropyrazol-4-yl]phenyl}methoxy)butyric acid |
| 379 | 3-phenyl-2-[[4-[5-(1-phenylethoxycarbonylamino)pyrimidin-4-yl]benzoyl]amino]propanoic acid |
| 380 | 3-cyclopropyl-2-[[4-[5-(1-phenylethoxycarbonylamino)pyrimidin-4-yl]benzoyl]amino]propanoic acid |
| 381 | 4-phenyl-2-[[4-[5-(1-phenylethoxycarbonylamino)pyrimidin-4-yl]benzoyl]amino]butanoic acid |
| 382 | 3-phenoxy-2-[[4-[5-(1-phenylethoxycarbonylamino)pyrimidin-4-yl]benzoyl]amino]propanoic acid |
| 383 | 3-Phenyl-2-[({p-[5-(1-phenylethoxycarbonylamino)-4-pyrimidinyl]phenyl}methyl)amino]propionic acid |
| 384 | 3-Cyclopropyl-2-[({p-[5-(1-phenylethoxycarbonylamino)-4-pyrimidinyl]phenyl}methyl)amino]propionic acid |
| 385 | 3-Phenyl-2-({p-[5-(1-phenylethoxycarbonylamino)-4-pyrimidinyl]phenyl}methoxy)propionic acid |
| 386 | 3-Cyclopropyl-2-({p-[5-(1-phenylethoxycarbonylamino)-4-pyrimidinyl]phenyl}methoxy)propionic acid |
| 387 | 4-Phenyl-3-[({p-[5-(1-phenylethoxycarbonylamino)-4-pyrimidinyl]phenyl}methyl)amino]butyric acid |
| 388 | 4-Cyclopropyl-3-[({p-[5-(1-phenylethoxycarbonylamino)-4-pyrimidinyl]phenyl}methyl)amino]butyric acid |
| 389 | 4-Phenyl-3-({p-[5-(1-phenylethoxycarbonylamino)-4-pyrimidinyl]phenyl}methoxy)butyric acid |

TABLE 1-continued

| Cpd | Name |
|---|---|
| 390 | 4-Cyclopropyl-3-({p-[5-(1-phenylethoxycarbonylamino)-4-pyrimidinyl]phenyl}methoxy)butyric acid |
| 391 | 2-[[4-[6-methyl-5-(1-phenylethoxycarbonylamino)pyrimidin-4-yl]benzoyl]amino]-3-phenyl-propanoic acid |
| 392 | 3-cyclopropyl-2-[[4-[6-methyl-5-(1-phenylethoxycarbonylamino)pyrimidin-4-yl]benzoyl]amino]propanoic acid |
| 393 | 2-[[4-[6-methyl-5-(1-phenylethoxycarbonylamino)pyrimidin-4-yl]benzoyl]amino]-4-phenyl-butanoic acid |
| 394 | 2-[[4-[6-methyl-5-(1-phenylethoxycarbonylamino)pyrimidin-4-yl]benzoyl]amino]-3-phenoxy-propanoic acid |
| 395 | 3-phenyl-2-[[4-[4-(1-phenylethoxycarbonylamino)pyrimidin-5-yl]benzoyl]amino]propanoic acid |
| 396 | 3-cyclopropyl-2-[[4-[4-(1-phenylethoxycarbonylamino)pyrimidin-5-yl]benzoyl]amino]propanoic acid |
| 397 | 4-phenyl-2-[[4-[4-(1-phenylethoxycarbonylamino)pyrimidin-5-yl]benzoyl]amino]butanoic acid |
| 398 | 3-phenoxy-2-[[4-[4-(1-phenylethoxycarbonylamino)pyrimidin-5-yl]benzoyl]amino]propanoic acid |
| 399 | 3-phenyl-2-[[4-[3-(1-phenylethoxycarbonylamino)pyrazin-2-yl]benzoyl]amino]propanoic acid |
| 400 | 3-cyclopropyl-2-[[4-[3-(1-phenylethoxycarbonylamino)pyrazin-2-yl]benzoyl]amino]propanoic acid |
| 401 | 4-phenyl-2-[[4-[3-(1-phenylethoxycarbonylamino)pyrazin-2-yl]benzoyl]amino]butanoic acid |
| 402 | 3-phenoxy-2-[[4-[3-(1-phenylethoxycarbonylamino)pyrazin-2-yl]benzoyl]amino]propanoic acid |
| 403 | 1-{p-[3-Methyl-4-(1-phenylethoxycarbonylamino)-5-isoxazolyl]phenyl}-4-piperidinecarboxylic acid |
| 404 | (1-{p-[3-Methyl-4-(1-phenylethoxycarbonylamino)-5-isoxazolyl]phenyl}-4-piperidyl)acetic acid |
| 405 | 1-(1-{p-[3-Methyl-4-(1-phenylethoxycarbonylamino)-5-isoxazolyl]phenyl}-4-piperidyl)cyclopropanecarboxylic acid |
| 406 | [1-(1-{p-[3-Methyl-4-(1-phenylethoxycarbonylamino)-5-isoxazolyl]phenyl}-4-piperidyl)cyclopropyl]acetic acid |
| 407 | 1-{5-[3-Methyl-4-(1-phenylethoxycarbonylamino)-5-isoxazolyl]-2-pyridyl}-4-piperidinecarboxylic acid |
| 408 | (1-{5-[3-Methyl-4-(1-phenylethoxycarbonylamino)-5-isoxazolyl]-2-pyridyl}-4-piperidyl)acetic acid |
| 409 | 1-(1-{5-[3-Methyl-4-(1-phenylethoxycarbonylamino)-5-isoxazolyl]-2-pyridyl}-4-piperidyl)cyclopropanecarboxylic acid |
| 410 | [1-(1-{5-[3-Methyl-4-(1-phenylethoxycarbonylamino)-5-isoxazolyl]-2-pyridyl}-4-piperidyl)cyclopropyl]acetic acid |
| 411 | 1-{p-[3-Fluoro-4-(1-phenylethoxycarbonylamino)-5-isoxazolyl]phenyl}-4-piperidinecarboxylic acid |
| 412 | (1-{p-[3-Fluoro-4-(1-phenylethoxycarbonylamino)-5-isoxazolyl]phenyl}-4-piperidyl)acetic acid |
| 413 | 1-(1-{p-[3-Fluoro-4-(1-phenylethoxycarbonylamino)-5-isoxazolyl]phenyl}-4-piperidyl)cyclopropanecarboxylic acid |
| 414 | [1-(1-{p-[3-Fluoro-4-(1-phenylethoxycarbonylamino)-5-isoxazolyl]phenyl}-4-piperidyl)cyclopropyl]acetic acid |
| 415 | 1-{5-[3-Fluoro-4-(1-phenylethoxycarbonylamino)-5-isoxazolyl]-2-pyridyl}-4-piperidinecarboxylic acid |
| 416 | (1-{5-[3-Fluoro-4-(1-phenylethoxycarbonylamino)-5-isoxazolyl]-2-pyridyl}-4-piperidyl)acetic acid |
| 417 | 1-(1-{5-[3-Fluoro-4-(1-phenylethoxycarbonylamino)-5-isoxazolyl]-2-pyridyl}-4-piperidyl)cyclopropanecarboxylic acid |
| 418 | [1-(1-{5-[3-Fluoro-4-(1-phenylethoxycarbonylamino)-5-isoxazolyl]-2-pyridyl}-4-piperidyl)cyclopropyl]acetic acid |
| 419 | 1-{p-[3-Cyano-4-(1-phenylethoxycarbonylamino)-5-isoxazolyl]phenyl}-4-piperidinecarboxylic acid |
| 420 | (1-{p-[3-Cyano-4-(1-phenylethoxycarbonylamino)-5-isoxazolyl]phenyl}-4-piperidyl)acetic acid |
| 421 | 1-(1-{p-[3-Cyano-4-(1-phenylethoxycarbonylamino)-5-isoxazolyl]phenyl}-4-piperidyl)cyclopropanecarboxylic acid |
| 422 | [1-(1-{p-[3-Cyano-4-(1-phenylethoxycarbonylamino)-5-isoxazolyl]phenyl}-4-piperidyl)cyclopropyl]acetic acid |
| 423 | 1-{5-[3-Cyano-4-(1-phenylethoxycarbonylamino)-5-isoxazolyl]-2-pyridyl}-4-piperidinecarboxylic acid |
| 424 | (1-{5-[3-Cyano-4-(1-phenylethoxycarbonylamino)-5-isoxazolyl]-2-pyridyl}-4-piperidyl)acetic acid |
| 425 | 1-(1-{5-[3-Cyano-4-(1-phenylethoxycarbonylamino)-5-isoxazolyl]-2-pyridyl}-4-piperidyl)cyclopropanecarboxylic acid |
| 426 | [1-(1-{5-[3-Cyano-4-(1-phenylethoxycarbonylamino)-5-isoxazolyl]-2-pyridyl}-4-piperidyl)cyclopropyl]acetic acid |
| 427 | 1-{p-[5-(1-Phenylethoxycarbonylamino)-1H-pyrazol-1-yl]phenyl}-4-piperidinecarboxylic acid |

TABLE 1-continued

| Cpd | Name |
|---|---|
| 428 | (1-{p-[5-(1-Phenylethoxycarbonylamino)-1H-pyrazol-1-yl]phenyl}-4-piperidyl)acetic acid |
| 429 | 1-(1-{p-[5-(1-Phenylethoxycarbonylamino)-1H-pyrazol-1-yl]phenyl}-4-piperidyl)cyclopropanecarboxylic acid |
| 430 | [1-(1-{p-[5-(1-Phenylethoxycarbonylamino)-1H-pyrazol-1-yl]phenyl}-4-piperidyl)cyclopropyl]acetic acid |
| 431 | 1-{5-[5-(1-Phenylethoxycarbonylamino)-1H-pyrazol-1-yl]-2-pyridyl}-4-piperidinecarboxylic acid |
| 432 | (1-{5-[5-(1-Phenylethoxycarbonylamino)-1H-pyrazol-1-yl]-2-pyridyl}-4-piperidyl)acetic acid |
| 433 | 1-(1-{5-[5-(1-Phenylethoxycarbonylamino)-1H-pyrazol-1-yl]-2-pyridyl}-4-piperidyl)cyclopropanecarboxylic acid |
| 434 | [1-(1-{5-[5-(1-Phenylethoxycarbonylamino)-1H-pyrazol-1-yl]-2-pyridyl}-4-piperidyl)cyclopropyl]acetic acid |
| 435 | 1-{p-[4-Methyl-5-(1-phenylethoxycarbonylamino)-1H-pyrazol-1-yl]phenyl}-4-piperidinecarboxylic acid |
| 436 | (1-{p-[4-Methyl-5-(1-phenylethoxycarbonylamino)-1H-pyrazol-1-yl]phenyl}-4-piperidyl)acetic acid |
| 437 | 1-(1-{p-[4-Methyl-5-(1-phenylethoxycarbonylamino)-1H-pyrazol-1-yl]phenyl}-4-piperidyl)cyclopropanecarboxylic acid |
| 438 | [1-(1-{p-[4-Methyl-5-(1-phenylethoxycarbonylamino)-1H-pyrazol-1-yl]phenyl}-4-piperidyl)cyclopropyl]acetic acid |
| 439 | 1-{5-[4-Methyl-5-(1-phenylethoxycarbonylamino)-1H-pyrazol-1-yl]-2-pyridyl}-4-piperidinecarboxylic acid |
| 440 | (1-{5-[4-Methyl-5-(1-phenylethoxycarbonylamino)-1H-pyrazol-1-yl]-2-pyridyl}-4-piperidyl)acetic acid |
| 441 | 1-(1-{5-[4-Methyl-5-(1-phenylethoxycarbonylamino)-1H-pyrazol-1-yl]-2-pyridyl}-4-piperidyl)cyclopropanecarboxylic acid |
| 442 | [1-(1-{5-[4-Methyl-5-(1-phenylethoxycarbonylamino)-1H-pyrazol-1-yl]-2-pyridyl}-4-piperidyl)cyclopropyl]acetic acid |
| 443 | 1-{p-[4-Fluoro-5-(1-phenylethoxycarbonylamino)-1H-pyrazol-1-yl]phenyl}-4-piperidinecarboxylic acid |
| 444 | (1-{p-[4-Fluoro-5-(1-phenylethoxycarbonylamino)-1H-pyrazol-1-yl]phenyl}-4-piperidyl)acetic acid |
| 445 | 1-(1-{p-[4-Fluoro-5-(1-phenylethoxycarbonylamino)-1H-pyrazol-1-yl]phenyl}-4-piperidyl)cyclopropanecarboxylic acid |
| 446 | [1-(1-{p-[4-Fluoro-5-(1-phenylethoxycarbonylamino)-1H-pyrazol-1-yl]phenyl}-4-piperidyl)cyclopropyl]acetic acid |
| 447 | 1-{5-[4-Fluoro-5-(1-phenylethoxycarbonylamino)-1H-pyrazol-1-yl]-2-pyridyl}-4-piperidinecarboxylic acid |
| 448 | (1-{5-[4-Fluoro-5-(1-phenylethoxycarbonylamino)-1H-pyrazol-1-yl]-2-pyridyl}-4-piperidyl)acetic acid |
| 449 | 1-(1-{5-[4-Fluoro-5-(1-phenylethoxycarbonylamino)-1H-pyrazol-1-yl]-2-pyridyl}-4-piperidyl)cyclopropanecarboxylic acid |
| 450 | [1-(1-{5-[4-Fluoro-5-(1-phenylethoxycarbonylamino)-1H-pyrazol-1-yl]-2-pyridyl}-4-piperidyl)cyclopropyl]acetic acid |
| 451 | 1-{p-[4-Cyano-5-(1-phenylethoxycarbonylamino)-1H-pyrazol-1-yl]phenyl}-4-piperidinecarboxylic acid |
| 452 | (1-{p-[4-Cyano-5-(1-phenylethoxycarbonylamino)-1H-pyrazol-1-yl]phenyl}-4-piperidyl)acetic acid |
| 453 | 1-(1-{p-[4-Cyano-5-(1-phenylethoxycarbonylamino)-1H-pyrazol-1-yl]phenyl}-4-piperidyl)cyclopropanecarboxylic acid |
| 454 | [1-(1-{p-[4-Cyano-5-(1-phenylethoxycarbonylamino)-1H-pyrazol-1-yl]phenyl}-4-piperidyl)cyclopropyl]acetic acid |
| 455 | 1-{5-[4-Cyano-5-(1-phenylethoxycarbonylamino)-1H-pyrazol-1-yl]-2-pyridyl}-4-piperidinecarboxylic acid |
| 456 | (1-{5-[4-Cyano-5-(1-phenylethoxycarbonylamino)-1H-pyrazol-1-yl]-2-pyridyl}-4-piperidyl)acetic acid |
| 457 | 1-(1-{5-[4-Cyano-5-(1-phenylethoxycarbonylamino)-1H-pyrazol-1-yl]-2-pyridyl}-4-piperidyl)cyclopropanecarboxylic acid |
| 458 | [1-(1-{5-[4-Cyano-5-(1-phenylethoxycarbonylamino)-1H-pyrazol-1-yl]-2-pyridyl}-4-piperidyl)cyclopropyl]acetic acid |

EXAMPLES

HPLC Methods

HPLC traces for examples synthesized were recorded using a HPLC consisting of Agilent HPLC pumps, degasser and UV detector, equipped with an Agilent 1100 series auto-sampler. A MS detector (APCI) PE Sciex API 150 EX was incorporated for purposes of recording mass spectral data. HPLC/mass traces were obtained using one of three chromatographic methods:

Method 1:
Column Zorbax C18, size 4.6 mm×7.5 cm; Solvent A: 0.05% TFA in water, Solvent B: 0.05% TFA in acetonitrile; Flow rate—0.7 mL/min; Gradient: 5% B to 100% B in 9 min, hold at 100% B for 4 min and 100% B to 5% B in 0.5 min; UV detector—channel 1=220 nm, channel 2=254 nm.

Method 2:
Column Zorbax C18, size 4.6 mm×7.5 cm;
Solvent A: 0.05% TFA in water, Solvent B: 0.05% TFA in acetonitrile;
Flow rate—0.7 mL/min; Gradient: 5% B to 100% B in 5 min, hold at 100% B for 2 min and 100% B to 5% B in 0.5 min; UV detector—channel 1=220 nm, channel 2=254 nm.

Method 3:
Column SunFire™ (Waters) C18, size 2.1 mm×50 mm; Solvent A: 0.05% TFA in water, Solvent B: 0.05% TFA in acetonitrile;
Flow rate—0.8 mL/min; Gradient: 10% B to 90% B in 2.4 min, hold at 90% B for 1.25 min and 90% B to 10% B in 0.25 min, hold at 10% B for 1.5 min.; UV detector—channel 1=220 nm, channel 2=254 nm.

Example 1: 1-(4-{4-[1-(2-Chloro-phenyl)-ethoxycarbonylamino]-3-methyl-isoxazol-5-yl}-benzoylamino)-cyclopropanecarboxylic acid

Step 1: 2-(4-carboxymethyl-benzoyl)-3-oxo-butyric acid t-butyl ester t-Butyl acetoacetate (15.1 mL, 89.0 mmol) was added to a suspension of magnesium chloride (8.48 g, 89.0 mmol) in dichloromethane (88 mL) that had been cooled to 000° C. To the mixture was added pyridine (13.8 mL, 171 mmol) and stirring continued for an additional 15 minutes. 4-(Chlorocarbonyl)benzoic acid methyl ester (17.0 g, 85.6 mmol) in dichloromethane (88 mL) was then added dropwise to the reaction. This mixture was stirred at 000° C. for 90 minutes and then at room temperature for 90 minutes. At this time the mixture was treated with 0.2M hydrochloric acid solution (10 mL). The organic layer was diluted with dichloromethane (70 mL), washed with 0.2M hydrochloric acid solution (30 mL), separated, dried over anhydrous $Na_2SO_4$, filtered and concentrated in vacuo. A yellow oil was obtained that was used directly in the next step (17.1 g, 68%).
Method 2, Rt 5.4 min. MS (ESI) m/z 321.2 [M+H$^+$].

Step 2: 5-(4-Methoxycarbonyl-phenyl)-3-methyl-isoxazole-4-carboxylic acid tert-butyl ester 5-(4-methylcarboxy-phenyl)-3-methyl-isoxazol-4-yl-carboxylic acid t-butyl ester A mixture of 2-(4-carboxymethyl-benzoyl)-3-oxo-butyric acid t-butyl ester [example 1, step 1](7.45 g, 23.2 mmol), hydroxylamine hydrochloride (5.17 g, 74.4 mmol), ethanol (46.5 mL) and water (32.2 mL) was heated at 60-62° C. for 2 hours. At this point the reaction was allowed to cool and the resulting mixture was partitioned between ethyl acetate and water. The organic layer was dried over anhydrous $MgSO_4$, filtered and concentrated in vacuo. A crude product was obtained that was purified by silica gel chromatography initially with hexane/ethyl acetate 9/1 as eluting solvent to afford 5-(4-Methoxycarbonyl-phenyl)-3-methyl-isoxazole-4-carboxylic acid tert-butyl ester (4.69 g, 64%)
Method 2, Rt 6.14 min. MS (ESI) m/z 318.2 [M+H$^+$].

Step 3: 5-(4-Methoxycarbonyl-phenyl)-3-methyl-isoxazole-4-carboxylic acid 5-(4-Methoxycarbonyl-phenyl)-3-methyl-isoxazole-4-carboxylic acid tert-butyl ester [Example 1, step 2] (6.35 g mg, 20 mmol) was dissolved in dichloromethane (100 mL) and to this was added trifluoroacetic acid (50 mL). The mixture was stirred for 2 hours at room temperature when the volatiles were removed. The product (5.2 g, 99%) was used as is in Step 4.
Method 2, Rt 4.08 min. MS (ESI) m/z 262 [M+H$^+$];

Step 4: 1-(4-{4-[1-(2-Chloro-phenyl)-ethoxycarbonylamino]-3-methyl-isoxazol-5-yl}-benzoic acid methyl ester 5-(4-methylcarboxy-phenyl)-3-methyl-isoxazol-4-yl-carboxylic acid

[Example 1, step 3] (3.91 g, 15.0 mmol) was suspended in toluene (120 mL) and to this was added diisopropylethylamine (3.13 mL, 18.0 mmol). To the resulting solution was added diphenylphosphoryl azide (3.56 mL, 16.5 mmol) and this mixture was heated to 90° C. After 15 minutes, 1-(2-chlorophenyl)-ethanol (2.98 mL, 22.5 mmol) was added slowly and heating maintained for 4 hours. The reaction was allowed to cool overnight. This mixture was diluted with toluene, transferred to a separatory funnel, extracted with water. The organic layer was dried over anhydrous $MgSO_4$, filtered and concentrated in vacuo to yield a crude product (8.34 g). The crude was purified by silica gel chromatography eluting with a gradient from 30% to 40% ethyl acetate in hexanes to afford purified product (3.59 g, 58%) as three fractions. Method 2, Rt 5.70 min. MS (ESI) m/z 415.4 [M+H$^+$].

Step 5: 1-(4-{4-[1-(2-Chloro-phenyl)-ethoxycarbonylamino]-3-methyl-isoxazol-5-yl}-benzoic acid 1-(4-{4-[1-(2-Chloro-phenyl)-ethoxycarbonylamino]-3-methyl-isoxazol-5-yl}-benzoic acid methyl ester [Example 1, step 4] (1.5 g, 3.62 mmol) was dissolved in THF/water (1/1: 20 mL) and treated with LiOH (5.1 mL of a 1M aqueous solution). The resulting mixture was stirred at room temperature for 3 hours. The reaction was acidified to pH2, transferred to a separatory funnel, diluted with water and extracted with dichloromethane. The organic layer was dried over anhydrous $MgSO_4$, filtered and concentrated in vacuo to afford the product (0.8 g, 55%). Method 2, Rt 4.77 min. MS (ESI) m/z 401.3 [M+H$^+$].

Step 6: 1-Aminocyclopropanecarboxylic acid methyl ester

1-Aminocyclopropanecarboxylic acid (202 mg, 2 mmol) in methanol (4 mL) was cooled to −10° C. and to this was added dropwise thionyl chloride (581 μL, 8 mmol). The mixture was allowed to warm and was then refluxed for 2 hours. Solvents were evaporated and the residue redissolved in boiling alcohol. To the cooled solution was added diethyl ether to the point of turbidity when the mixture was refrigerated for 2 days. The resulting precipitates afford the product (223 mg, 67%) that was used in Step 7.

Step 7: 1-(4-{4-[1-(2-Chloro-phenyl)-ethoxycarbonylamino]-3-methyl-isoxazol-5-yl}-benzoylamino)-cyclopropanecarboxylic acid methyl ester To 1-(4-{4-[1-(2-Chloro-phenyl)-ethoxycarbonylamino]-3-methyl-isoxazol-5-yl}-benzoic acid [Example 1, step 5] (49.8 mg, 0.12 mmol) was added 1-hydroxybenzotriazole (18 mg, 0.13 mmol), N-(3-dimethylaminopropyl)-ethylcarbodiimide (EDCl: 25 mg, 0.13 mmol), dichloromethane (2 mL), diisopropylethylamine (52 µL, 0.30 mmol), and 1-Aminocyclopropanecarboxylic acid methyl ester [example 1, step 6](20 mg, 0.13 mmol) and this mixture was stirred overnight. At this point the mixture was diluted with ethyl acetate (20 mL) and washed with saturated sodium bicarbonate solution (10 mL), citric acid solution (5 mL) and water. The organic layer was dried over anhydrous $MgSO_4$, filtered and concentrated in vacuo to yield a crude product (101 mg). The residue was purified by preparative TLC, eluting with a 40% mixture of ethyl acetate in hexane v/v. Following extraction of the purified band, the product was obtained (55 mg, 92%). Method 2, Rt 4.76 min. MS (ESI) m/z 498.4 [M+H$^+$].

Step 8: 1-(4-{4-[1-(2-Chloro-phenyl)-ethoxycarbonylamino]-3-methyl-isoxazol-5-yl}-benzoylamino)-cyclopropanecarboxylic acid 1-(4-{4-[1-(2-Chloro-phenyl)-ethoxycarbonylamino]-3-methyl-isoxazol-5-yl}-benzoylamino)-cyclopropanecarboxylic acid methyl ester [example 1, step 7](55 mg, 0.11 mmol) was dissolved in a 1:1 mixture of THF/water and treated with lithium hydroxide (8 mg, 0.33 mmol). The resulting mixture was stirred at room temperature for 2 days. At this point the pH was adjusted to 2 with hydrochloric acid and the mixture was extracted with ethyl acetate (3×20 mL). The organic layer was dried over anhydrous $MgSO_4$, filtered and concentrated in vacuo to yield a crude product (190 mg). The residue was purified by preparative TLC, eluting with a 45% mixture of acetone in dichloromethane v/v. Following extraction of the purified band, the product was obtained (22 mg, 41%).
Method 2, Rt 4.30 min. MS (ESI) m/z 484.6 [M+H$^+$].

Example 2: 2-(4-{4-[1-(2-Chloro-phenyl)-ethoxycarbonylamino]-3-methyl-isoxazol-5-yl}-benzoylamino)-indan-2-carboxylic acid

Step 1: 2-Amino-2-indancarboxylic acid methyl ester

2-Amino-2-indancarboxylic acid methyl ester was prepared according to a similar procedure as described for example 1, step 6 from 2-Amino-2-indancarboxylic acid hydrochloride (214 mg, 1 mmol) that was used directly. Yield 155 mg (68%)

Step 2: 2-(4-{4-[1-(2-Chloro-phenyl)-ethoxycarbonylamino]-3-methyl-isoxazol-5-yl}-benzoylamino)-indan-2-carboxylic acid methyl ester 2-(4-{4-[1-(2-Chloro-phenyl)-ethoxycarbonylamino]-3-methyl-isoxazol-5-yl}-benzoylamino)-indan-2-carboxylic acid methyl ester was prepared according to a similar procedure as described for example 1, step 7 from 1-(4-{4-[1-(2-Chloro-phenyl)-ethoxycarbonylamino]-3-methyl-isoxazol-5-yl}-benzoic acid [Example 1, step 5] (49.8 mg, 0.12 mmol) and 2-amino-2-indancarboxylic acid methyl ester [example 2, step 1]. Yield 55 mg, (81%). Method 2, Rt 5.49 min. MS (ESI) m/z 574.6 [M+H$^+$].

Step 3: 2-(4-{4-[1-(2-Chloro-phenyl)-ethoxycarbonylamino]-3-methyl-isoxazol-5-yl}-benzoylamino)-indan-2-carboxylic acid 2-(4-{4-[1-(2-Chloro-phenyl)-ethoxycarbonylamino]-3-methyl-isoxazol-5-yl}-benzoylamino)-indan-2-carboxylic acid was prepared according to a similar procedure as described for example 1, step 8 from 2-(4-{4-[1-(2-Chloro-phenyl)-ethoxycarbonylamino]-3-methyl-isoxazol-5-yl}-benzoylamino)-indan-2-carboxylic acid methyl ester [example 2, step 7](55 mg, 0.11 mmol). Yield 6 mg, (11%). Method 2, Rt 5.00 min. MS (ESI) m/z 560.3[M+H$^+$].

Example 3: 2-(S)-(4-{4-[(R,S)-1-(2-Chloro-phenyl)-ethoxycarbonylamino]-3-methyl-isoxazol-5-yl}-benzoylamino) phenyl acetic acid

Step 1

L-phenylglycine methyl ester was prepared according to a similar procedure as described for example 1, step 6 from L-phenylglycine (756 mg, 5 mmol) that was used directly. Yield 480 mg (58%).

Step 2: 2-(S)-(4-{4-[(R,S)-1-(2-Chloro-phenyl)-ethoxycarbonylamino]-3-methyl-isoxazol-5-yl}-benzoylamino) phenyl acetic acid methyl ester 2-(S)-(4-{4-[(R,S)-1-(2-Chloro-phenyl)-ethoxycarbonylamino]-3-methyl-isoxazol-5-yl}-benzoylamino) phenyl acetic acid methyl ester was prepared according to a similar procedure as described for example 1, step 7 from 1-(4-{4-[1-(2-Chloro-phenyl)-ethoxycarbonylamino]-3-methyl-isoxazol-5-yl}-benzoic acid [Example 1, step 5]((58.1 mg, 0.14 mmol) and L-phenylglycine methyl ester [Example 3, step 1] which was used without purification. Yield 60 mg (76%) Method 2, Rt 5.41 min. MS (ESI) m/z 548.6 [M+H$^+$].

Step 3: 2-(S)-(4-{4-[(R,S)-1-(2-Chloro-phenyl)-ethoxycarbonylamino]-3-methyl-isoxazol-5-yl}-benzoylamino) phenyl acetic acid 2-(S)-(4-{4-[(R,S)-1-(2-Chloro-phenyl)-ethoxycarbonylamino]-3-methyl-isoxazol-5-yl}-benzoylamino) phenyl acetic acid was prepared according to a similar procedure as described for example 1, step 8 from 2-(S)-(4-{4-[(R,S)-1-(2-Chloro-phenyl)-ethoxycarbonylamino]-3-methyl-isoxazol-5-yl}-benzoylamino) phenyl acetic acid methyl ester [example 3, step 2](60 mg, 0.11 mmol). Yield 4 mg (11%). Method 2, Rt 4.90 min. MS (ESI) m/z 534.4 [M+H$^+$].

Example 4: 2-(R)-(4-{4-[(R,S)-1-(2-Chloro-phenyl)-ethoxycarbonylamino]-3-methyl-isoxazol-5-yl}-benzoylamino) phenyl propanoic acid

Step 1: D-phenylalanine methyl ester

D-phenylalanine methyl ester was prepared according to a similar procedure as described for example 1, step 6 from D-phenylalanine (1.12 g, 7 mmol). Yield 650 mg (53%).

Step 2: 2-(R)-(4-{4-[(R,S)-1-(2-Chloro-phenyl)-
ethoxycarbonylamino]-3-methyl-isoxazol-5-yl}-
benzoylamino) phenyl propanoic acid methyl ester 2-(R)-(4-{4-[(R,S)-1-(2-Chloro-phenyl)-ethoxycarbonylamino]-3-methyl-isoxazol-5-yl}-benzoylamino) phenyl propanoic acid methyl ester was prepared according to a similar procedure as described for example 1, step 7 from 1-(4-{4-[1-(2-Chloro-phenyl)-ethoxycarbonylamino]-3-methyl-isoxazol-5-yl}-benzoic acid [Example 1, step 5] (58.1 mg, 0.14 mmol) and D-phenylalanine methyl ester [example 4, step 1] to yield the product (40 mg, 49%) which was used directly. Method 2, Rt 5.6 min. MS (ESI) m/z 562.2 [M+H$^+$].

Step 3: 2-(R)-(4-{4-[(R,S)-1-(2-Chloro-phenyl)-
ethoxycarbonylamino]-3-methyl-isoxazol-5-yl}-
benzoylamino) phenyl propanoic acid 2-(R)-(4-{4-[(R,S)-1-(2-Chloro-phenyl)-ethoxycarbonylamino]-3-methyl-isoxazol-5-yl}-benzoylamino) phenyl propanoic acid was prepared according to a similar procedure as described for example 1, step 8 from 2-(R)-(4-{4-[(R,S)-1-(2-Chloro-phenyl)-ethoxycarbonylamino]-3-methyl-isoxazol-5-yl}-benzoylamino) phenyl propanoic acid methyl ester [example 4, step 2](40 mg, 0.07 mmol). Yield 8 mg (21%). Method 2, Rt 4.94 min. MS (ESI) m/z 548.5 [M+H$^+$].

Example 5—2(R)-[[4-[3-methyl-4-((R)-1-phenylethoxycarbonylamino)isoxazol-5-yl]benzoyl]amino]-3-phenyl-propanoic acid Step 1: 2(R)-[[4-[3-methyl-4-((R)-1-phenylethoxycarbonylamino)isoxazol-5-yl]benzoic acid methyl ester 2(R)-[[4-[3-methyl-4-((R)-1-phenylethoxycarbonylamino)isoxazol-5-yl]benzoic acid methyl ester was prepared according to a similar procedure as described for example 1, step 4 from 5-(4-Methoxycarbonyl-phenyl)-3-methyl-isoxazole-4-carboxylic acid [Example 1, step 3](1.55 g, 5.9 mmol) and 1-(R)-(+)-phenyl-ethanol. Yield 1.18 g (52%).

Step 2: 2(R)-[[4-[3-methyl-4-((R)-1-phenylethoxycarbonylamino)isoxazol-5-yl]benzoic acid 2(R)-[[4-[3-methyl-4-((R)-1-phenylethoxycarbonylamino)isoxazol-5-yl]benzoic acid was prepared according to a similar procedure as described for example 1, step 5 from 2(R)-[[4-[3-methyl-4-((R)-1-phenylethoxycarbonylamino)isoxazol-5-yl]benzoic acid methyl ester [Example 5, step 1] (1.5 g, 3.62 mmol). Yield 1.04 g, (91%). Method 3, Rt 2.72 min. MS (ESI) m/z 367.3 [M+H$^+$].

Step 3: 2(R)-[[4-[3-methyl-4-((R)-1-phenylethoxycarbonylamino)isoxazol-5-yl]benzoyl]amino]-3-phenyl-propanoic acid methyl ester 2(R)-[[4-[3-methyl-4-((R)-1-phenylethoxycarbonylamino)isoxazol-5-yl]benzoyl]amino]-3-phenyl-propanoic acid methyl ester was prepared according to a similar procedure as described for example 1, step 7 from 2(R)-[[4-[3-methyl-4-((R)-1-phenylethoxycarbonylamino)isoxazol-5-yl]benzoic acid [Example 5, step 2] (64.7 mg, 0.18 mmol) and D-phenylalanine methyl ester [example 4, step 1]. Yield 100 mg, 92%).
Method 3, Rt 3.04 min. MS (ESI) m/z 528.3 [M+H$^+$].

Step 4: 2(R)-[[4-[3-methyl-4-((R)-1-phenylethoxycarbonylamino)isoxazol-5-yl]benzoyl]amino]-3-phenyl-propanoic acid (sodium salt)

2(R)-[[4-[3-methyl-4-((R)-1-phenylethoxycarbonylamino)isoxazol-5-yl]benzoyl]amino]-3-phenyl-propanoic acid was prepared according to a similar procedure as described for example 1, step 8 from 2(R)-[[4-[3-methyl-4-((R)-1-phenylethoxycarbonylamino)isoxazol-5-yl]benzoyl]amino]-3-phenyl-propanoic acid methyl ester [example 5, step 3](100 mg, 0.19 mmol). The crude material (21 mg) was dissolved in methanol and treated with 1N sodium hydroxide (40 μL) before drying to afford the product as its sodium salt (22 mg, 22%). Method 3, Rt 3.04 min. MS (ESI) m/z 514.3 [M+H$^+$].

Example 6: 2(S)-[[4-[3-methyl-4-((R)-1-phenylethoxycarbonylamino)isoxazol-5-yl]benzoyl]amino]-3-phenyl-propanoic acid The title compound was prepared according to an analagous procedure to that described for example 5 from 5-(4-Methoxycarbonyl-phenyl)-3-methyl-isoxazole-4-carboxylic acid [Example 1, step 3] (64.7 mg, 0.18 mmol) and L-phenylalanine methyl ester to afford the product as its sodium salt (18 mg, 18%). Method 3 Rt 3.05 min. MS (ESI) m/z 514.3 [M+H$^+$].

Example 7: (R)-2-[[4-[2,5-dimethyl-4-((R)-1-phenylethoxycarbonylamino)pyrazol-3-yl]benzoyl]amino]-3-phenyl-propanoic acid Step 1: 5-(4-Methoxycarbonyl-phenyl)-1,3-dimethyl-1H-pyrazole-4-carboxylic acid tert-butyl ester and 3-(4-Methoxycarbonyl-phenyl)-1,5-dimethyl-1H-pyrazole-4-carboxylic acid tert-butyl ester 4-(2-tert-Butoxycarbonyl-3-oxo-butyryl)-benzoic acid methyl ester [Example 1, Step 1](crude 76.0 g, 208.8 mmol on 100% purity basis) was dissolved in ethanol (2.2 L). Methyl hydrazine (9.72 g, 210.9 mmol) was added to the above solution dropwise under stirring at room temperature. The reaction mixture was stirred another 3 hrs at RT after finishing the addition. The completion of reaction was confirmed by LC/MS. The solvent was removed under vacuum. The residue was dissolved in EtOAc (700 mL) and washed with water (2×500 mL). The organics were dried over Na$_2$SO$_4$, filtered and evaporated. Mixture of products obtained as an oil, which was used in the next step without further purification. Crude yield 72.6 g. Method 3, Rt 3.12 min. MS (ESI) m/z 331.0 [M+H$^+$].

Step 2: 5-(4-Methoxycarbonyl-phenyl)-1,3-dimethyl-1H-pyrazole-4-carboxylic acid and 3-(4-Methoxycarbonyl-phenyl)-1,5-dimethyl-1H-pyrazole-4-carboxylic acid A mixture of 5-(4-Methoxycarbonyl-phenyl)-1,3-dimethyl-1H-pyrazole-4-carboxylic acid tert-butyl ester and 3-(4-Methoxycarbonyl-phenyl)-1,5-dimethyl-1H-pyrazole-4-carboxylic acid tert-butyl ester [Example 7, Step 1] (5.00 g., 15.13 mmol) was dissolved into CH$_2$Cl$_2$ (120.0 mL) and trifluoroacetic acid (40.0 mL) was added and the reaction mixture was stirred for 3 h at room temperature. The volatiles were removed under vacuum. The residue was dissolved into ethyl acetate (50.0 mL). It was then extracted with saturated aq. Na$_2$CO$_3$ solution (40 mL). Separated aqueous layer was washed with ethyl acetate (2×20 mL). Then it was treated with 1 M HCl to pH 2. Then it was extracted with ethyl acetate (2×35 mL), dried (Na$_2$SO$_4$), filtered and concentrated to yield white solid mixture of acids (3.0 g., 72%). TLC on silica plate (15% acetone in DCM): two fluorescent spots of two isomers Rf: 0.2 and Rf: 0.125. Method 3, Rt 2.94 min. MS (ESI) m/z 275.0 [M+H$^+$];

Step 3: 4-[2,5-Dimethyl-4-((R)-1-phenyl-ethoxycarbonylamino)-2H-pyrazol-3-yl]-benzoic acid methyl ester and 4-[1,5-Dimethyl-4-((R)-1-phenyl-ethoxycarbonylamino)-1H-pyrazol-3-yl]-benzoic acid methyl ester The mixture of acid isomers [Example 7, Step 2] (6.0 g., 21.88 mmol), was suspended in anhydrous toluene (180.0 mL), under nitrogen and stirring. Then diisopropylethyl amine (3.39 g., 26.24 mmol) was added. A clear solution was generated to which diphenyl phosphoryl azide 7.22 g, 26.24 mmol) was added. The reaction mixture was heated to 95° C. Then (R)-(+)-1-phenylethyl alcohol (4.008 g, 32.8 mmol) was added dropwise at 95° C. over a period of 40 minutes. Then the reaction mixture was heated for an additional 5 hr at 95° C., followed by stirring at room temperature overnight. Next day it was diluted with EtOAc (300 mL), washed with sat. aq. Na$_2$CO$_3$ solution (200.0 mL) and water (2×500 mL), dried (Na$_2$SO$_4$), filtered and concentrated to yield crude oily carbamate (12.5 g). The crude was purified by column chromatography (SiO$_2$), initial elution with DCM (250 mL) and then gradient elution Acetone:DCM (2% acetone in DCM to 10% acetone in DCM). Two pure isomers were obtained. Fast moving isomer (1.667 g, 19.4%) and slow moving isomer (2.132 g, 24.77%) were obtained [>95% by HPLC purity]. A fraction containing a mixture of isomers (0.812 g, 9.4%) was obtained. A) Slow moving spot: Method 3, Rt 2.78 min. MS (ESI) m/z 394.2 [M+H$^+$]; tentatively assigned as (R)-4-[1,5-Dimethyl-4-(1-phenyl-ethoxycarbonylamino)-1H-pyrazol-3-yl]-benzoic acid methyl ester. B) Fast moving spot: Method 3, Rt 2.80 min. MS (ESI) m/z 394.4 [M+H$^+$]; tentatively assigned as (R)-4-[2,5-Dimethyl-4-((R)-1-phenyl-ethoxycarbonylamino)-2H-pyrazol-3-yl]-benzoic acid methyl ester.

Step 4: 4-[2,5-Dimethyl-4-((R)-1-phenyl-ethoxycarbonylamino)-2H-pyrazol-3-yl]-benzoic acid 4-[2,5-Dimethyl-4-((R)-1-phenyl-ethoxycarbonylamino)-2H-pyrazol-3-yl]-benzoic acid methyl ester [Example 7, Step 3B] (240 mg, 0.61 mmol) was dissolved in THF/water (2/1 v/v, 2.25 mL) and treated with LiOH (1.2 mL of a 1M aqueous solution, 2 eq.). The resulting mixture was stirred at room temperature overnight. The reaction was acidified to pH2, diluted with water and extracted with EtOAc (2×40 mL). The organic layer was dried over anhydrous MgSO$_4$, filtered and concentrated in vacuo to afford the product (180 mg, 78%). Method 3, Rt 2.81 min. MS (ESI) m/z 380.2 [M+H$^+$].

Step 5: (R)-2-{4-[2,5-Dimethyl-4-((R)-1-phenyl-ethoxycarbonylamino)-2H-pyrazol-3-yl]-benzoylamino}-3-phenyl-propionic acid methyl ester To 4-[2,5-Dimethyl-4-((R)-1-phenyl-ethoxycarbonylamino)-2H-pyrazol-3-yl]-benzoic acid [Example 7, step 4] (100 mg, 0.26 mmol) was added 1-hydroxybenzotriazole (43 mg, 0.32 mmol), EDCl (67 mg, 0.34 mmol), dimethylformamide (2 mL), diisopropylethylamine (184 µL, 1.06 mmol), and D-phenylalanine methyl ester [Example 4, Step 1] (86 mg, 0.39 mmol) and this mixture was stirred overnight. At this point the mixture was diluted with ethyl acetate (20 mL) and washed with 1N sodium hydroxide solution (10 mL), and water. The organic layer was dried over anhydrous MgSO$_4$, filtered and concentrated in vacuo to yield the crude product (193 mg), which was purified by silica gel chromatography, eluting with an ethyl acetate/dichloromethane gradient to provide the title compound (95 mg, 68%). >95% by HPLC purity. Method 3, Rt 2.91 min. MS (ESI) m/z 541.3 [M+H$^+$].

Step 6: (R)-2-[[4-[2,5-dimethyl-4-((R)-1-phenylethoxycarbonylamino)pyrazol-3-yl]benzoyl]amino]-3-phenyl-propanoic acid (R)-2-{4-[2,5-Dimethyl-4-((R)-1-phenyl-ethoxycarbonylamino)-2H-pyrazol-3-yl]-benzoylamino}-3-phenyl-propionic acid methyl ester [Example 7, step 5] (95 mg, 0.176 mmol) was dissolved in a 2:1 mixture of THF/water (2.25 mL) and treated with 1M lithium hydroxide solution (2 mL). The resulting mixture was stirred at room temperature overnight. The pH of the aqueous layer was adjusted to 2 with hydrochloric acid and the mixture was extracted with ethyl acetate (3×20 mL). The organic layer was dried over anhydrous MgSO$_4$, filtered and concentrated in vacuo to yield the crude product (112 mg). The crude material was purified by silica-gel chromatography, eluting with a dichloromethane/acetone gradient. (90 mg, 97%). Method 3, Rt 2.90 min. MS (ESI) m/z 527.5 [M+H$^+$].

Example 8: (R)-2-[[4-[1,5-dimethyl-4-((R)-1-phenylethoxycarbonylamino)pyrazol-3-yl]benzoyl]amino]-3-phenyl-propanoic acid Step 1: 4-[1,5-Dimethyl-4-((R)-1-phenyl-ethoxycarbonylamino)-1H-pyrazol-3-yl]-benzoic acid 4-[1,5-Dimethyl-4-((R)-1-phenyl-ethoxycarbonylamino)-1H-pyrazol-3-yl]-benzoic acid methyl ester [Example 7, Step 3A] (240 mg, 0.61 mmol) was dissolved in THF/water (2/1 v/v, 2.25 mL) and treated with LiOH (1.2 mL of a 1M aqueous solution, 2 eq.). The resulting mixture was stirred at room temperature overnight. The reaction was acidified to pH2, transferred to a separatory funnel, diluted with water and extracted with EtOAc (2×40 mL). The organic layer was dried over anhydrous MgSO$_4$, filtered and concentrated in vacuo to afford the product (205 mg, 89%). Purity is 97% by HPLC. Method 3, Rt 2.43 min. MS (ESI) m/z 380.2 [M+H$^+$].

Step 2: (R)-2-{4-[1,5-Dimethyl-4-((R)-1-phenyl-ethoxycarbonylamino)-1H-pyrazol-3-yl]-benzoylamino}-3-phenyl-propionic acid methyl ester 4-[1,5-Dimethyl-4-((R)-1-phenyl-ethoxycarbonylamino)-1H-pyrazol-3-yl]-benzoic acid [Example 8, Step 1] (100 mg, 0.26 mmol) was added 1-hydroxybenzotriazole (43 mg, 0.32 mmol), EDCl (67 mg, 0.34 mmol), dimethylformamide (2 mL), diisopropylethylamine (184 µL, 1.06 mmol), and D-phenylalanine methyl ester [Example 4, Step 1] (86 mg, 0.39 mmol) and this mixture was stirred overnight. At this point the mixture was diluted with ethyl acetate (20 mL) and washed with 1N sodium hydroxide solution (10 mL), and water. The organic layer was dried over anhydrous MgSO$_4$, filtered and concentrated in vacuo to yield the crude product (150 mg) which was purified by silica gel chromatography, eluting with a ethyl acetate/dichloromethane gradient to provide the product (75 mg, 53%). Purity>97% by HPLC. Method 3, Rt 3.05 min. MS (ESI) m/z 541.2 [M+H$^+$].

Step 3: (R)-2-[[4-[1,5-dimethyl-4-((R)-1-phenylethoxycarbonylamino)pyrazol-3-yl]benzoyl]amino]-3-phenyl-propanoic acid (R)-2-{4-[1,5-Dimethyl-4-((R)-1-phenyl-ethoxycarbonylamino)-1H-pyrazol-3-yl]-benzoylamino}-3-phenyl-propionic acid methyl ester [Example 8, step 2] (75 mg, 0.139 mmol) was dissolved in a 2:1 mixture of THF/water (1.5 mL) and treated with 1M lithium hydroxide solution (0.28 mL). The resulting mixture was stirred at room temperature overnight. The pH of the aqueous layer was adjusted to 2 with hydrochloric acid and the mixture was extracted with ethyl acetate (3×20 mL). The organic layer was dried over anhydrous MgSO$_4$, filtered and concentrated in vacuo to yield the product [>95% HPLC purity] (60 mg, 82%). Method 3, Rt 2.69 min. MS (ESI) m/z 527.5 [M+H$^+$].

Example 9: (R)-2-[[4-[2,5-dimethyl-4-((R)-1-phenylethoxycarbonylamino)pyrazol-3-yl]benzoyl]amino]-3-(4-fluorophenyl)propanoic acid Step 1: (R)-2-Amino-3-(4-fluoro-phenyl)-propionic acid methyl ester hydrochloride (R)-2-Amino-3-(4-fluoro-phenyl)-propionic acid methyl ester hydrochloride was prepared according to a similar procedure as described for example 1, step 6 from D-4-Fluorophenyl alanine (1 g, 5.46 mmol). Yield 900 mg, (71%). Method 3, Rt 0.54 min. MS (ESI) m/z 198.3 [M+H$^+$].

Step 2: (R)-2-{4-[2,5-Dimethyl-4-((R)-1-phenyl-ethoxycarbonylamino)-2H-pyrazol-3-yl]-benzoylamino}-3-(4-fluoro-phenyl)-propionic acid methyl ester (R)-2-{4-[2,5-Dimethyl-4-((R)-1-phenyl-ethoxycarbonylamino)-2H-pyrazol-3-yl]-benzoylamino}-3-(4-fluorophenyl)-propionic acid methyl ester was prepared according to a similar procedure as described for example 7, step 5 from (R)-4-[2,5-Dimethyl-4-(1-phenyl-ethoxycarbonylamino)-2H-pyrazol-3-yl]-benzoic acid [Example 7, Step 4] (50 mg, 0.132 mmol) and (R)-2-Amino-3-(4-fluorophenyl)-propionic acid methyl ester hydrochloride [Example 9, Step 1]. Yield 59 mg (80%).

Step 3: (R)-2-[[4-[2,5-dimethyl-4-((R)-1-phenylethoxycarbonylamino)pyrazol-3-yl]benzoyl]amino]-3-(4-fluorophenyl)propanoic acid (R)-2-[[4-[2,5-dimethyl-4-((R)-1-phenylethoxycarbonylamino)pyrazol-3-yl]benzoyl]amino]-3-(4-fluorophenyl) propanoic acid was prepared according to a similar procedure as described for example 7, step 6 from (R)-2-{4-[2,5-Dimethyl-4-((R)-1-phenyl-ethoxycarbonylamino)-2H-pyrazol-3-yl]-benzoylamino}-3-(4-fluoro-phenyl)-propionic acid methyl ester [Example 9, Step 2] (59 mg, 0.11 mmol) to afford the product 55 mg (87%). Method 3, Rt 2.73 min. MS (ESI) m/z 545.4 [M+H$^+$].

Example 10: (R)-2-[[4-[1,5-dimethyl-4-((R)-1-phenylethoxycarbonylamino)pyrazol-3-yl]benzoyl]amino]-3-(4-fluorophenyl)propanoic acid The title compound was prepared according to an analogous procedure to that described for example 8 from 4-[1,5-Dimethyl-4-((R)-1-phenyl-ethoxycarbonylamino)-1H-pyrazol-3-yl]-benzoic acid [Example 8, Step 1] (50 mg, 0.132 mmol) and (R)-2-Amino-3-(4-fluoro-phenyl)-propionic acid methyl ester hydrochloride [Example 9, Step 1]. Yield 55 mg, (87%). Method 3, Rt 2.69 min. MS (ESI) m/z 545.4 [M+H$^+$].

Example 11: (R)-3-(4-bromophenyl)-2-[[4-[2,5-dimethyl-4-((R)-1-phenylethoxycarbonyl-amino)pyrazol-3-yl]benzoyl]amino]propanoic acid Step 1: (R)-2-Amino-3-(4-bromo-phenyl)-propionic acid methyl ester hydrochloride The title compound was prepared using a similar procedure as described for example 1, step 6 from D-4-bromophenyl alanine (1 g, 4.1 mmol). Yield 550 mg (46%). Method 3, Rt 1.70 min. MS (ESI) m/z 258.1 [M+H$^+$].

Step 2: (R)-3-(4-bromophenyl)-2-[[4-[2,5-dimethyl-4-((R)-1-phenylethoxycarbonylamino)-pyrazol-3-yl]benzoyl]amino]propanoic acid The title compound was prepared according to an analogous procedure to that described for example 9 (steps 2 & 3) from 4-[2,5-Dimethyl-4-((R)-1-phenyl-ethoxycarbonylamino)-2H-pyrazol-3-yl]-benzoic acid [Example 7, Step 4] and (R)-2-Amino-3-(4-bromo-phenyl)-propionic acid methyl ester hydrochloride [Example 11, Step 1]. Yield 30 mg (65%). Method 3, Rt 3.03 min. MS (ESI) m/z 607.4 [M+H$^+$].

Example 12: (R)-3-(4-bromophenyl)-2-[[4-[1,5-dimethyl-4-((R)-1-phenylethoxycarbonyl-amino)pyrazol-3-yl]benzoyl]amino]propanoic acid The title compound was prepared according to an analogous procedure to that described for example 8 from 4-[1,5-Dimethyl-4-((R)-1-phenyl-ethoxycarbonylamino)-1H-pyrazol-3-yl]-benzoic acid [Example 8, Step 1] (50 mg, 0.132 mmol) and 3-(4-bromo-phenyl)-propionic acid methyl ester hydrochloride [Example 11, Step 1]. Yield 60 mg, (80%). Method 3, Rt 3.02 min. MS (ESI) m/z 619.2 [M+H$^+$].

Example 13: (R)-3-(4-chlorophenyl)-2-[[4-[2,5-dimethyl-4-((R)-1-phenylethoxycarbonyl-amino)pyrazol-3-yl]benzoyl]amino]propanoic acid Step 1: (R)-2-Amino-3-(4-chloro-phenyl)-propionic acid methyl ester hydrochloride (R)-2-Amino-3-(4-chloro-phenyl)-propionic acid methyl ester hydrochloride was prepared using a similar procedure as described for example 1, step 6 from D-4-chlorophenyl alanine (1 g, 5 mmol). Yield 940 mg (75%). Method 3, Rt 0.03 min. MS (ESI) m/z 214.0 [M+H$^+$].

Step 2: (R,R)-3-(4-chlorophenyl)-2-[[4-[2,5-dimethyl-4-(1-phenylethoxycarbonylamino)-pyrazol-3-yl]benzoyl]amino]propanoic acid The title compound was prepared according to an analogous procedure to that described for example 9 (steps 2 & 3)

from (R)-4-[2,5-Dimethyl-4-(1-phenyl-ethoxycarbonylamino)-2H-pyrazol-3-yl]-benzoic acid [Example 7, Step 4] and (R)-2-Amino-3-(4-chloro-phenyl)-propionic acid methyl ester hydrochloride [Example 13, Step 1]. Yield 40 mg (55%). Method 3, Rt 2.80 min. MS (ESI) m/z 561.3 [M+H$^+$].

Example 14: (R)-3-(4-chlorophenyl)-2-[[4-[1,5-dimethyl-4-((R)-1-phenylethoxycarbonyl-amino) pyrazol-3-yl]benzoyl]amino]propanoic acid The title compound was prepared according to an analogous procedure to that described for example 8 from 4-[1,5-Dimethyl-4-((R)-1-phenyl-ethoxycarbonylamino)-1H-pyrazol-3-yl]-benzoic acid [Example 8, Step 1] and (R)-2-Amino-3-(4-chloro-phenyl)-propionic acid methyl ester hydrochloride [Example 8, Step 1]. Yield 40 mg (54%) Method 3, Rt 3.00 min. MS (ESI) m/z 561.3 [M+H$^+$].

Example 15: (R)-3-(3,4-difluorophenyl)-2-[[4-[2,5-dimethyl-4-((R)-1-phenylethoxycarbonyl-amino) pyrazol-3-yl]benzoyl]amino]propanoic acid Step 1: (R)-2-Amino-3-(3,4-difluoro-phenyl)-propionic acid methyl ester hydrochloride (R)-2-Amino-3-(3,4-difluoro-phenyl)-propionic acid methyl ester hydrochloride was prepared using a similar procedure as described for example 1, step 6 from D-3,4-difluorophenyl alanine (1 g, 4.97 mmol). Yield 1.04 g, 83%). Method 3, Rt 0.16 min. MS (ESI) m/z 216.0 [M+H$^+$];

Step 2: (R)-3-(3,4-difluorophenyl)-2-[[4-[2,5-dimethyl-4-((R)-1-phenylethoxycarbonylamino)-pyrazol-3-yl]benzoyl]amino]propanoic acid The title compound was prepared according to an analogous procedure to that described for example 9 (steps 2 & 3) from (R)-4-[2,5-Dimethyl-4-(1-phenyl-ethoxycarbonylamino)-2H-pyrazol-3-yl]-benzoic acid [Example 7, Step 4] (50 mg, 0.132 mmol) and (R)-2-Amino-3-(3,4-difluoro-phenyl)-propionic acid methyl ester hydrochloride [Example 15, Step 1]. Yield 30 mg (61%). Method 3, Rt 2.96 min. MS (ESI) m/z 563.4 [M+H$^+$].

Example 16: (R)-3-(3,4-difluorophenyl)-2-[[4-[1,5-dimethyl-4-((R)-1-phenylethoxycarbonyl-amino) pyrazol-3-yl]benzoyl]amino]propanoic acid The title compound was prepared according to an analogous procedure to that described for example 8 from 4-[1,5-Dimethyl-4-((R)-1-phenyl-ethoxycarbonylamino)-1H-pyrazol-3-yl]-benzoic acid [Example 8, Step 1] (50 mg, 0.132 mmol) and (R)-2-Amino-3-(3,4-difluoro-phenyl)-propionic acid methyl ester hydrochloride [Example 15, Step 1]. Yield 20 mg (56%). Method 3, Rt 2.71 min. MS (ESI) m/z 563.3 [M+H$^+$].

Example 17: (R)-2-(4-{4-[(R)-1-(2-chloro-phenyl)-ethoxycarbonylamino]-3-methyl-isoxazol-5-yl}-benzoylamino)-3-cyclopropyl-propionic acid Step 1: (R)-2-Amino-3-cyclopropylpropionic acid methyl ester hydrochloride (R)-2-Amino-3-cyclopropylpropionic acid methyl ester hydrochloride was prepared using a similar procedure as described for example 1, step 6 from (R)-2-Amino-3-cyclopropylpropionic acid and used directly. Yield 350 mg (100%).

Step 2: 4-{4-[1-((R)-2-Chloro-phenyl)-ethoxycarbonylamino]-3-methyl-isoxazol-5-yl}-benzoic acid methyl ester Prepared in analogous fashion as in Example 5 Step 1 using 5-(4-methoxycarbonyl-phenyl)-3-methyl-isoxazole-4-carboxylic acid [Example 1, step 3] (3.47 g, 13.28 mmol) and (R)-1-(2-chlorophenyl)-ethanol. Yield=1.81 g (4.36 mmol, 25%). HPLC (254 nm): Method 3 Rt 3.31 min. MS (ESI) m/z 415.5 [M+H$^+$].

Step 3: 4-{4-[1-((R-2-Chloro-phenyl)-ethoxycarbonylamino]-3-methyl-isoxazol-5-yl}-benzoic acid Prepared in analogous fashion as in Example 5, Step 2 using 4-{4-[1-((R)-2-chloro-phenyl)-ethoxycarbonylamino]-3-methyl-isoxazol-5-yl}-benzoic acid methyl ester [Example 17, step 2](1.81 g, 4.46 mmol). Yield=1.70 g (4.25 mmol, 95%). HPLC (254 nm): Method 3 Rt 3.01 min. MS (ESI) m/z 401.2 [M+H$^+$].

Step 4: (R)-2-(4-{4-[1-((R)-2-Chloro-phenyl)-ethoxycarbonylamino]-3-methyl-isoxazol-5-yl}-benzoylamino)-3-cyclopropyl-propionic acid The title compound was prepared according to an analogous procedure to that described for example 5 from 4-{4-[1-((R)-2-chloro-phenyl)-ethoxycarbonylamino]-3-methyl-isoxazol-5-yl}-benzoic acid [Example 17, step 3] (50 mg, 0.13 mmol) and (R)-2-Amino-3-cyclopropylpropionic acid methyl ester hydrochloride [Example 17, step 1]. Yield 22 mg (34%). Method 3, Rt 3.27 min. MS (ESI) m/z 512.5 [M+H$^+$].

Example 18: (R)-2-{4-[3-Methyl-4-((S)-1-phenyl-ethoxycarbonylamino)-isoxazol-5-yl]-benzoylamino}-3-phenyl-propionic acid Step 1: 4-[3-Methyl-4-((S)-1-phenyl-ethoxycarbonylamino)-isoxazol-5-yl]-benzoic acid 4-[3-Methyl-4-((S)-1-phenyl-ethoxycarbonylamino)-isoxazol-5-yl]-benzoic acid was prepared in analogous fashion to example 17 [steps & 3] from 5-(4-methoxycarbonyl-phenyl)-3-methyl-isoxazole-4-carboxylic acid [Example 1, step 3] (1 g, 3.3 mmol) and (S)-1-(2-chlorophenyl)-ethanol. Yield=800 mg (2.19 mmol, 60%). HPLC (254 nm): Method 3 Rt 2.67 min. MS (ESI) m/z 367.4 [M+H$^+$].

Step 2: (S,R)-2-{4-[3-Methyl-4-(1-phenyl-ethoxycarbonylamino)-isoxazol-5-yl]-benzoylamino}-3-phenyl-propionic acid The title compound was prepared according to an analogous procedure to that described for example 5 from (S)-4-[3-Methyl-4-(1-phenyl-ethoxycarbonylamino)-isoxazol-5-yl]-benzoic acid [Example 18, step 2] (61 mg, 0.12 mmol) and D-phenylalanine methyl ester hydrochloride. Yield=30 mg (0.06 mmol, 49%). HPLC (254 nm): Method 3 Rt 3.05 min. MS (ESI) m/z 514.5 [M+H+].

Example 19: (S)-2-{4-[3-Methyl-4-((S)-1-phenyl-ethoxycarbonylamino)-isoxazol-5-yl]-benzoylamino}-3-phenyl-propionic acid The title compound was prepared according to an analogous procedure to that described for example 18 from 4-[3-Methyl-4-((S)-1-phenyl-ethoxycarbonylamino)-isoxazol-5-yl]-benzoic acid [Example 18, step 2] (61 mg, 0.12 mmol) and L-phenylalanine methyl ester hydrochloride. Yield=22 mg (0.04 mmol, 36%). HPLC (254 nm): Method 3 Rt 2.87 min. MS (ESI) m/z 514.5 [M+H$^+$].

Example 20: (R)-2-(4-{4-[(R)-1-(2-Chloro-phenyl)-ethoxycarbonylamino]-3-methyl-isoxazol-5-yl}-benzoylamino)-3-phenyl-propionic acid The title compound was prepared according to an analogous procedure to that described for example 17 from 4-{4-[1-((R)-2-Chloro-phenyl)-ethoxycarbonylamino]-3-methyl-isoxazol-5-yl}-benzoic acid [Example 17, step 3] (60 mg, 0.15 mmol) and D-phenylalanine methyl ester. Yield=65 mg (0.12 mmol, 77%). HPLC (254 nm): Method 3 Rt 2.93 min. MS (ESI) m/z 566.3 [M+H$^+$].

Example 21: (R)-2-(4-{4-[(R)-1-(2-Chloro-phenyl)-ethoxycarbonylamino]-3-methyl-isoxazol-5-yl}-benzoylamino)-3-(4-fluoro-phenyl)-propionic acid The title compound was prepared according to an analogous procedure to that described for example 17 from 4-{4-[1-((R)-2-Chloro-phenyl)-ethoxycarbonylamino]-3-methyl-isoxazol-5-yl}-benzoic acid [Example 17, step 3] (60 mg, 0.15 mmol) and D-4-fluorophenylalanine methyl ester. Yield=65 mg (0.12 mmol, 77%). HPLC (254 nm): Method 3 Rt 2.93 min. MS (ESI) m/z 566.3 [M+H$^+$].

Example 22 (R)-3-(4-Chloro-phenyl)-2-(4-{4-[(R)-1-(2-chloro-phenyl)-ethoxycarbonylamino]-3-methyl-isoxazol-5-yl}-benzoylamino)-propionic acid The title compound was prepared according to an analogous procedure to that described for example 17 from 4-{4-[1-((R)-2-Chloro-phenyl)-ethoxycarbonylamino]-3-methyl-isoxazol-5-yl}-benzoic acid [Example 17, step 3] (60 mg, 0.15 mmol) and D-4-chlorophenylalanine methyl ester. Yield=64 mg (0.11 mmol, 74%). HPLC (254 nm): Method 3 Rt 3.11 min. MS (ESI) m/z 583.4 [M+H$^+$].

Example 23: (R)-2-(4-{4-[(R)-1-(2-Chloro-phenyl)-ethoxycarbonylamino]-3-methyl-isoxazol-5-yl}-benzoylamino)-3-(3,4-difluoro-phenyl)-propionic acid The title compound was prepared according to an analogous procedure to that described for example 17 from 4-{4-[1-((R)-2-Chloro-phenyl)-ethoxycarbonylamino]-3-methyl-isoxazol-5-yl}-benzoic acid [Example 17, step 3] (60 mg, 0.15 mmol) and D-3,4-difluorophenylalanine methyl ester hydrochloride. Yield=41 mg (0.07 mmol, 47%). HPLC (254 nm): Method 3 Rt 2.96 min. MS (ESI) m/z 584.1 [M+H$^+$].

Example 24: (R)-3-(2-Chloro-phenyl)-2-(4-{4-[(R)-1-(2-chloro-phenyl)-ethoxycarbonylamino]-3-methyl-isoxazol-5-yl}-benzoylamino)-propionic acid The title compound was prepared according to an analogous procedure to that described for example 17 from 4-{4-[1-((R)-2-Chloro-phenyl)-ethoxycarbonylamino]-3-methyl-isoxazol-5-yl}-benzoic acid [Example 17, step 3] (60 mg, 0.15 mmol) and D-2-chlorophenylalanine methyl ester hydrochloride. Yield=41 mg (0.07 mmol, 47%). HPLC (254 nm): Method 3 Rt 3.06 min. MS (ESI) m/z 584.2 [M+H$^+$].

Example 25: (R)-3-(4-Bromo-phenyl)-2-(4-{4-[(R)-1-(2-chloro-phenyl)-ethoxycarbonylamino]-3-methyl-isoxazol-5-yl}-benzoylamino)-propionic acid The title compound was prepared according to an analogous procedure to that described for example 17 from 4-{4-[(R)-1-(2-chloro-phenyl)-ethoxycarbonylamino]-3-methyl-isoxazol-5-yl}-benzoic acid [Example 17, step 3] (60 mg, 0.15 mmol) and D-4-bromophenylalanine methyl ester hydrochloride. Yield=65 mg (0.10 mmol, 35%). HPLC (254 nm): Method 3 Rt 3.28 min. MS (ESI) m/z 626.3, 628.4 [M+H$^+$].

Example 26: (R)-2-(4-{4-[(R)-1-(2-Chloro-phenyl)-ethoxycarbonylamino]-3-methyl-isoxazol-5-yl}-benzoylamino)-3-(2-fluoro-phenyl)-propionic acid The title compound was prepared according to an analogous procedure to that described for example 17 from 4-{4-[(R)-1-(2-chloro-phenyl)-ethoxycarbonylamino]-3-methyl-isoxazol-5-yl}-benzoic acid [Example 17, step 3] (60 mg, 0.15 mmol) and D-2-fluorophenylalanine methyl ester hydrochloride. Yield=70 mg (0.12 mmol, 52%). HPLC (254 nm): Method 3 Rt 3.12 min. MS (ESI) m/z 566.5, 567.8 [M+H$^+$].

Example 27: (R)-2-(4-{4-[(R)-1-(2-Chloro-phenyl)-ethoxycarbonylamino]-3-methyl-isoxazol-5-yl}-benzoylamino)-3-p-tolyl-propionic acid The title compound was prepared according to an analogous procedure to that described for example 17 from 4-{4-[(R)-1-(4-chloro-phenyl)-ethoxycarbonylamino]-3-methyl-isoxazol-5-yl}-benzoic acid [Example 17, step 3] (60 mg, 0.15 mmol) and D-4-methylphenylalanine methyl ester hydrochloride. Yield=37 mg (0.07 mmol, 43%). HPLC (254 nm): Method 3 Rt 3.13 min. MS (ESI) m/z 562.3 [M+H$^+$].

Example 28: (R)-2-(4-{4-[(R)-1-(2-Chloro-phenyl)-ethoxycarbonylamino]-3-methyl-isoxazol-5-yl}-benzoylamino)-3-(4-trifluoromethyl-phenyl)-propionic acid The title compound was prepared according to an analogous procedure to that described for example 17 from 4-{4-[(R)-1-(4-bromo-phenyl)-ethoxycarbonylamino]-3-methyl-isoxazol-5-yl}-benzoic acid [Example 17, step 3] (60 mg, 0.15 mmol) and D-4-trifluoromethylphenylalanine methyl ester hydrochloride. Yield=40 mg (0.06 mmol, 44%). HPLC (254 nm): Method 3 Rt 3.00 min. MS (ESI) m/z 616.2 [M+H$^+$].

Example 29: (R)-2-(4-{4-[(R)-1-(2-Chloro-phenyl)-ethoxycarbonylamino]-3-methyl-isoxazol-5-yl}-benzoylamino)-3-(4-cyano-phenyl)-propionic acid The title compound was prepared according to an analogous procedure to that described for example 17 from 4-{4-[(R)-1-(4-bromo-phenyl)-ethoxycarbonylamino]-3-methyl-isoxazol-5-yl}-benzoic acid [Example 17, step 3] (60 mg, 0.15 mmol) and D-4-cyanophenylalanine methyl ester hydrochloride. Yield=17 mg (0.03 mmol, 20%). HPLC (254 nm): Method 3 Rt 2.93 min. MS (ESI) m/z 573.2 [M+H$^+$].

Example 30: (R)-2-(4-{5-[(R)-1-(2-Chloro-phenyl)-ethoxycarbonylamino]-4-methyl-pyrazol-1-yl}-benzoylamino)-3-phenyl-propionic acid Step 1: 2-(4-Cyano-phenyl)-4-methyl-2H-pyrazole-3-carboxylic acid ethyl ester A solution of trichloroacetyl chloride (12.92 mL, 115.8 mmol) in dichloromethane (30 mL) was cooled to −10° C. under a nitrogen atmosphere. A solution of ethyl propenyl ether (12.82 mL, 115.8 mmol) and pyridine (9.36 mL, 115.8 mmol) was added dropwise at a rate to maintain the internal temperature at −10° C. After addition was complete, the reaction was warmed to room temperature and stirred for 24 hours. The mixture was filtered and the solids were washed with dichloromethane (50 mL). The filtrates were evaporated to dryness under vacuum to yield an oil (31.71 g). This material was dissolved in ethanol (400 mL) and treated with 4-cyanophenylhydrazine hydrochloride (24.81 g, 139 mmol). The resulting mixture was refluxed for 3 hours and then cooled to room temperature. The volatiles were evaporated in vacuo, the residue was dissolved in EtOAc (1 L) and washed with 1 N aqueous HCl solution (2×300 mL). The organic layer was separated, washed with water, dried over anhydrous Na$_2$SO$_4$, filtered and concentrated in vacuo to obtain a yellow solid (27.8 g). This was triturated with EtOAc (130 mL) and the remaining solids removed by filtration (do not contain product). The filtrates were concentrated to 50 mL volume and the precipitated solids were filtered (do not contain product). The filtrates were concentrated and purified by silica gel chromatography, eluting with a 100/0 to 88/12 hexanes/acetone gradient. Collected fractions containing a mixture of the two isomeric products, which were concentrated to dryness and triturated with methanol to yield the desired isomer [2-(4-cyano-phenyl)-4-methyl-2H-pyrazole-3-carboxylic acid ethyl ester] as a yellow solid (3.77 g, 14.8 mmol, 13%). HPLC (254 nm): Method 3 Rt 2.93 min. MS (ESI) m/z 256.3 [M+H$^+$]. $^1$H NMR (500 MHz, CDCl$_3$) δ 7.73 (d, J=8.5 Hz, 2H); 7.58 (s, 1H); 7.52 (d, J=8.5 Hz, 2H); 4.27 (q, J=7.1 Hz, 2H); 2.35 (s, 3H); 1.26 (t, J=7.1 Hz, 3H).

Step 2: 2-(4-Cyano-phenyl)-4-methyl-2H-pyrazole-3-carboxylic acid

A stirred solution of 2-(4-Cyano-phenyl)-4-methyl-2H-pyrazole-3-carboxylic acid ethyl ester [Example 30, step 1](500 mg, 1.96 mmol) in THF (10 mL) was treated with LiOH 1 N aqueous solution (10 mL) and the resulting mixture was stirred at room temperature for 6 hours, after which time analysis by HPLC/MS indicates approximately 60% conversion to product. The reaction mixture was diluted with ethyl acetate (100 mL) and washed with 1 N aqueous NaOH solution (100 mL). The organic layer contained unreacted starting material. The aqueous layer was acidified to pH 1 with 1 N HCl aqueous solution and the resulting suspension was extracted with ethyl acetate (100 mL). The organic layer was separated, dried over anhydrous MgSO$_4$, filtered and concentrated in vacuo to afford the pure product as a white solid (289 mg, 1.27 mmol, 65%). HPLC (254 nm): Method 3 Rt 2.56 min. MS (ESI) m/z 228.3 [M+H$^+$].

Step 3: [2-(4-Cyano-phenyl)-4-methyl-2H-pyrazol-3-yl]-carbamic acid (R)-1-(2-chloro-phenyl)-ethyl ester 2-(4-Cyano-phenyl)-4-methyl-2H-pyrazole-3-carboxylic acid [Example 30, step 2] (218 mg, 0.96 mmol) was suspended in toluene (10 mL) and treated with diisopropylethylamine (200 μL, 1.16 mmol). The resulting solution was treated with diphenylphosphoryl azide (230 μL, 1.06 mmol) and heated to 65° C. (R)-1-(2-chloro-phenyl)-ethanol (227 mg, 1.44 mmol) was added to the reaction mixture and the temperature was increased to 105° C. for 30 minutes, during which time vigorous gas evolution was observed. The reaction was brought to 65° C. and stirred at that temperature for 4 hours. The reaction was deemed complete by HPLC/MS. After cooling, the volatiles were removed in vacuo and the crude residue was purified by silica gel chromatography, eluting with a hexanes/ethyl acetate gradient. Product was isolated as a white solid (120 mg, 0.31 mmol, 33%). HPLC (254 nm): Method 3 Rt 3.84 min. MS (ESI) m/z 381.2 [M+H$^+$].

Step 4: 4-{5-[(R)-1-(2-Chloro-phenyl)-ethoxycarbonylamino]-4-methyl-pyrazol-1-yl}-benzoic acid A solution containing (R)-[2-(4-Cyano-phenyl)-4-methyl-2H-pyrazol-3-yl]-carbamic acid 1-(2-chloro-phenyl)-ethyl ester (120 mg, 0.32 mmol) and THF (1.5 mL) was treated with a 1 N aqueous LiOH solution (1.5 mL) and the resulting mixture was stirred at room temperature for 36 hours, followed by heating to 45° C. for 24 hours. The reaction mixture was diluted with ethyl acetate (50 mL) and washed with 1 N aqueous NaOH solution (50 mL). The aqueous layer was acidified to pH 1 with 1 N HCl aqueous solution and the resulting suspension was extracted with ethyl acetate (50 mL). The organic layer was separated, dried over anhydrous MgSO$_4$, filtered and concentrated in vacuo to afford the pure product as a white solid. Yield=62 mg (0.16 mmol, 49%). HPLC (254 nm): Method 3 Rt 3.14 min. MS (ESI) m/z 399.2 [M+H$^+$].

Step 3: (R)-2-(4-{5-[(R)-1-(2-Chloro-phenyl)-ethoxycarbonylamino]-4-methyl-pyrazol-1-yl}-benzoylamino)-3-phenyl-propionic acid methyl ester 4-{5-[(R)-1-(2-Chloro-phenyl)-ethoxycarbonylamino]-4-methyl-pyrazol-1-yl}-benzoic acid (62 mg, 0.16 mmol), was dissolved in DMF (1.4 mL) and treated with diisopropylethylamine (112 μL, 0.62 mmol) under nitrogen. EDCl (40 mg, 0.20 mmol) and HOBt (26 mg, 0.19 mmol) was added and the resulting mixture was stirred for 30 minutes. D-Phenylalanine methyl ester hydrochloride (50 mg, 0.23 mmol) was added and the resulting mixture stirred at room temperature overnight. The reaction was diluted with EtOAc (50 mL) and transferred to a separatory funnel. The organics were washed with 1 N HCl aqueous solution and brine, dried over anhydrous MgSO$_4$, filtered and concentrated in vacuo. The crude residue was purified by preparative TLC plate (1000 μm), eluting with a 7:3 v/v hexanes/ethyl acetate mixture. The product was obtained as a white solid. Yield=35 mg (0.06 mmol, 39%). HPLC (254 nm): Method 3 Rt 3.28 min. MS (ESI) m/z 561.3, 563.3 [M+H$^+$].

Step 4: (R)-2-(4-{5-[(R)-1-(2-Chloro-phenyl)-ethoxycarbonylamino]-4-methyl-pyrazol-1-yl}-benzoylamino)-3-phenyl-propionic acid A solution containing (R)-2-(4-{5-[(R)-1-(2-Chloro-phenyl)-ethoxycarbonylamino]-4-methyl-pyrazol-1-yl}-benzoylamino)-3-phenyl-propionic acid methyl ester (35 mg, 0.06 mmol), and THF (1 mL) was treated with a 1 N aqueous LiOH solution (125 µL) and the resulting mixture was stirred at room temperature for 18 hours. The reaction mixture was diluted with ethyl acetate (50 mL) and acidified to pH 1 with 1 N HCl aqueous solution. The organic layer was separated, dried over anhydrous MgSO$_4$, filtered and concentrated in vacuo to afford the pure product as a white solid. Yield=20 mg (0.04 mmol, 61%). HPLC (254 nm): Method 3 Rt 3.19 min. MS (ESI) m/z 547.6, 550.6 [M+H$^+$].

Example 31: (R)-2-{4-[3-Methyl-4-((R)-1-phenyl-ethoxycarbonylamino)-isoxazol-5-yl]-benzylamino}-3-phenyl-propionic acid Step 1: 5-(4-Chloromethyl-phenyl)-3-methyl-isoxazole-4-carboxylic acid tert-butyl ester A stirred suspension of MgCl$_2$ (2.97 g, 31.2 mmol) in dichloromethane (30 mL) under nitrogen was treated dropwise with tert-butyl acetoacetate (5.17 mL, 31.2 mmol) and the resulting mixture was cooled to 0° C. The mixture was stirred at that temperature for 15 minutes and then treated with dropwise addition of pyridine (4.85 mL, 60.0 mmol). After 15 minutes, a solution of 4-(chloromethyl)benzoyl chloride (5.67 g, 30.0 mmol) in dichloromethane (30 mL) was added dropwise. The resulting mixture was maintained at 0° C. for 1 hour and then at room temperature for an additional hour. The reaction was quenched with careful addition of water (100 mL) and the mixture was transferred to a separatory funnel. The organic layer was washed with a 1 N HCl aqueous solution (2×100 mL) then dried over anhydrous MgSO$_4$, filtered and concentrated in vacuo. The crude residue was dissolved in ethanol (60 mL) and treated with a solution of NH$_2$OH.HCl (6.67 g, 96.0 mmol) in water (13 mL). This mixture was heated to 60° C. for 2 hours and at room temperature overnight. A thick white precipitate formed which was filtered, rinsed with ethanol and air-dried. The mother liquor was concentrated and cooled to 0° C. to yield a second crop of solid which was filtered and air-dried. Combined yield=5.82 g (19.0 mmol, 63%). HPLC (254 nm): Method 3 Rt 3.49 min. MS (ESI) m/z 308.4 [M+H$^+$].

Step 2: 5-(4-Chloromethyl-phenyl)-3-methyl-isoxazole-4-carboxylic acid 5-(4-Chloromethyl-phenyl)-3-methyl-isoxazole-4-carboxylic acid tert-butyl ester (4.61 g, 15.0 mmol) was dissolved in dichloromethane (7.5 mL) and treated with trifluoroacetic acid (7.5 mL). The resulting mixture was stirred at room temperature for 18 hours, after which time the reaction was deemed complete by HPLC/MS. The volatiles were removed in vacuo to yield the crude product as a white solid (3.8 g, 15.0 mmol, quant.), which was used as is in the next step.

Step 3: [5-(4-Chloromethyl-phenyl)-3-methyl-isoxazol-4-yl]-carbamic acid (R)-1-phenyl-ethyl ester 5-(4-Chloromethyl-phenyl)-3-methyl-isoxazole-4-carboxylic acid (3.0 g, 12.0 mmol) was suspended in toluene (120 mL) and treated with triethylamine (2.02 mL, 14.4 mmol). The resulting solution was treated with diphenyl-phosphoryl azide (2.85 mL, 13.2 mmol) and heated to 65° C. (R)-1-(phenyl)-ethanol (1.9 g, 15.6 mmol) was added to the reaction mixture and the temperature was increased to 105° C. for 30 minutes, during which time vigorous gas evolution was observed. The reaction was brought to 65° C. and stirred at that temperature for 4 hours. The reaction was deemed complete by HPLC/MS. After cooling, the volatiles were removed in vacuo and the crude residue was purified by silica gel chromatography, eluting with a hexanes/ethyl acetate gradient. Product isolated as a white solid (3.16 g, 8.52 mmol, 71%). HPLC (254 nm): Method 3 Rt 3.02 min. MS (ESI) m/z 371.2 [M+H$^+$].

Step 4: (R)-2-{4-[3-Methyl-4-((R-1-phenyl-ethoxycarbonylamino)-isoxazol-5-yl]-benzylamino}-3-phenyl-propionic acid methyl ester A solution containing [5-(4-Chloromethyl-phenyl)-3-methyl-isoxazol-4-yl]-carbamic acid (R)-1-phenyl-ethyl ester (74 mg, 0.2 mmol), DMF (2 mL) and triethylamine (224 µL, 1.6 mmol) was treated with D-phenylalanine methyl ester hydrochloride (173 mg, 0.80 mmol) and heated to 80° C. for 3 hours. The reaction was deemed complete by HPLC/MS. The reaction was cooled, partitioned between EtOAc and water and transferred to a separatory funnel. The organic layer was washed with water and brine, dried over anhydrous MgSO$_4$, filtered and concentrated in vacuo. The crude yellow oily residue was purified by silica gel chromatography eluting with a hexanes/EtOAc gradient. The product was obtained as a colorless film (77 mg, 0.15 mmol, 75%). HPLC (254 nm): Method 3 Rt 2.67 min. MS (ESI) m/z 514.4 [M+H$^+$].

Step 5: (R)-2-{4-[3-Methyl-4-((R)-1-phenyl-ethoxycarbonylamino)-isoxazol-5-yl]-benzylamino}-3-phenyl-propionic acid A solution containing (R)-2-{4-[3-Methyl-4-((R)-1-phenyl-ethoxycarbonylamino)-isoxazol-5-yl]-benzylamino}-3-phenyl-propionic acid methyl ester (77 mg, 0.15 mmol) and THF (1.5 mL) was treated with a 1 N aqueous LiOH solution (1.5 mL) and the resulting mixture was stirred at room temperature for 18 hours. The reaction mixture was diluted with ethyl acetate (50 mL) and acidified to pH~5 with 1 N HCl aqueous solution. The organic layer was separated, dried over anhydrous MgSO$_4$, filtered and concentrated in vacuo. The residue was triturated with diethyl ether to afford the pure product as a white solid (9 mg, 0.018 mmol, 12%). HPLC (254 nm): Method 3 Rt 2.74 min. MS (ESI) m/z 500.5 [M+H$^+$].

Example 32: (R)-3-(2-Fluoro-phenyl)-2-{4-[3-methyl-4-((R)-1-phenyl-ethoxycarbonylamino)-isoxazol-5-yl]-benzylamino}-propionic acid The title compound was prepared in analogous fashion as in Example 31 using [5-(4-chloromethyl-phenyl)-3-methyl-isoxazol-4-yl]-carbamic acid (R)-1-phenyl-ethyl ester [Example 31, step 3](100 mg, 0.27 mmol), and D-2-fluorophenyl-alanine methyl ester hydrochloride. Yield=10 mg (0.02 mmol, 7%). HPLC (254 nm): Method 3 Rt 2.64 min. MS (ESI) m/z 518.4 [M+H$^+$].

Example 33: (R)-2-{4-[3-Methyl-4-((R)-1-phenyl-ethoxycarbonylamino)-isoxazol-5-yl]-benzylamino}-3-(4-trifluoromethyl-phenyl)-propionic acid The title compound was prepared in analogous fashion as in Example 31 using [5-(4-chloromethyl-phenyl)-3-methyl-isoxazol-4-yl]-carbamic acid (R)-1-phenyl-ethyl ester [Example 31, step 3](100 mg, 0.27 mmol), and D-4-trifluoromethylphenyl-alanine methyl ester hydrochloride. Yield=18 mg (0.03 mmol, 11%). HPLC (254 nm): Method 3 Rt 3.10 min. MS (ESI) m/z 568.5 [M+H$^+$].

Example 34: (R)-3-Cyclopropyl-2-{4-[3-methyl-4-((R)-1-phenyl-ethoxycarbonylamino)-isoxazol-5-yl]-benzylamino}-propionic acid The title compound was prepared in analogous fashion as in Example 31 using [5-(4-chloromethyl-phenyl)-3-methyl-isoxazol-4-yl]-carbamic acid (R)-1-phenyl-ethyl ester [Example 31, step 3](100 mg, 0.27 mmol), and (R)-2-Amino-3-cyclopropylpropionic acid methyl ester hydrochloride [Example 17, step 1]. Yield=13 mg (0.03 mmol, 35%). HPLC (254 nm): Method 3 Rt 2.82 min. MS (ESI) m/z 464.5 [M+H$^+$].

Example 35: (R)-3-(2-Chloro-phenyl)-2-{4-[3-methyl-4-((R)-1-phenyl-ethoxycarbonylamino)-isoxazol-5-yl]-benzylamino}-propionic acid The title compound was prepared in analogous fashion as in Example 31 using [5-(4-chloromethyl-phenyl)-3-methyl-isoxazol-4-yl]-carbamic acid (R)-1-phenyl-ethyl ester [Example 31, step 3](100 mg, 0.27 mmol), and D-2-chlorophenyl-alanine methyl ester hydrochloride. Yield=38 mg (0.07 mmol, 27%). HPLC (254 nm): Method 3 Rt 3.05 min. MS (ESI) m/z 534.2 [M+H$^+$].

Example 36: (R)-3-(4-Chloro-phenyl)-2-{4-[3-methyl-4-((R)-1-phenyl-ethoxycarbonylamino)-isoxazol-5-yl]-benzylamino}-propionic acid The title compound was prepared in analogous fashion as in Example 31 using [5-(4-chloromethyl-phenyl)-3-methyl-isoxazol-4-yl]-carbamic acid (R)-1-phenyl-ethyl ester [Example 31, step 3](100 mg, 0.27 mmol), and D-4-chlorophenyl-alanine methyl ester hydrochloride. Yield=8 mg (0.01 mmol, 5%). HPLC (254 nm): Method 3 Rt 3.13 min. MS (ESI) m/z 534.4 [M+H$^+$].

Example 37: (R)-2-(4-{4-[(R)-1-(2-Chloro-phenyl)-ethoxycarbonylamino]-3-methyl-isoxazol-5-yl}-benzylamino)-3-phenyl-propionic acid Step 1: [5-(4-Chloromethyl-phenyl)-3-methyl-isoxazol-4-yl]-carbamic acid (R)-1-(2-chloro-phenyl)-ethyl ester

[5-(4-Chloromethyl-phenyl)-3-methyl-isoxazol-4-yl]-carbamic acid (R)-1-(2-chloro-phenyl)-ethyl ester was prepared in analogous fashion as in Example 31, steps 1-3 from 5-(4-chloromethyl-phenyl)-3-methyl-isoxazole-4-carboxylic acid [Example 31, step 2](1.95 g, 7.75 mmol) and (R)-1-(2-chlorophenyl)-ethanol (1.82 g, 11.62 mmol). Yield=1.33 g (3.28 mmol, 42%). HPLC (254 nm): Method 3 Rt 3.31 min. MS (ESI) m/z 405.3 [M+H$^+$].

Step 2: (R)-2-(4-{4-[(R)-1-(2-Chloro-phenyl)-ethoxycarbonylamino]-3-methyl-isoxazol-5-yl}-benzylamino)-3-phenyl-propionic acid methyl ester (R)-2-(4-{4-[(R)-1-(2-Chloro-phenyl)-ethoxycarbonylamino]-3-methyl-isoxazol-5-yl}-benzylamino)-3-phenyl-propionic acid methyl ester was prepared in analogous fashion as in Example 31, steps 4 from [5-(4-Chloromethyl-phenyl)-3-methyl-isoxazol-4-yl]-carbamic acid (R)-1-(2-chloro-phenyl)-ethyl ester [Example 37, step 1] (101 mg, 0.25 mmol) and D-phenylalanine methyl ester hydrochloride. Yield=45 mg (0.08 mmol, 33%). HPLC (254 nm): Method 3 Rt 2.90 min. MS (ESI) m/z 548.5 [M+H$^+$].

Step 3: (R)-2-(4-{4-[(R)-1-(2-Chloro-phenyl)-ethoxycarbonylamino]-3-methyl-isoxazol-5-yl}-benzylamino)-3-phenyl-propionic acid Prepared in analogous fashion as in Example J, Step 5 using the following reagents and amounts: (R)-2-(4-{4-[(R)-1-(2-Chloro-phenyl)-ethoxycarbonylamino]-3-methyl-isoxazol-5-yl}-benzylamino)-3-phenyl-propionic acid methyl ester [Example 37, step 2] (45 mg, 0.08 mmol). Yield=6 mg (0.01 mmol, 14%). HPLC (254 nm): Method 3 Rt 2.69 min. MS (ESI) m/z 534.3 [M+H$^+$].

Example 38: (R)-2-(4-{4-[(R)_1-(2-Chloro-phenyl)-ethoxycarbonylamino]-3-methyl-isoxazol-5-yl}-benzylamino)-3-(2-fluoro-phenyl)-propionic acid The title compound was prepared in analogous fashion as in Example 31 using [5-(4-Chloromethyl-phenyl)-3-methyl-isoxazol-4-yl]-carbamic acid (R)-1-(2-chloro-phenyl)-ethyl ester [Example 37, step 1](101 mg, 0.25 mmol), and D-2-fluorophenyl-alanine methyl ester hydrochloride. Yield=30 mg (0.05 mmol, 22%). HPLC (254 nm): Method 3 Rt 2.57 min. MS (ESI) m/z 552.3 [M+H$^+$].

Example 39: (R)-2-(4-{4-[(R)-1-(2-Chloro-phenyl)-ethoxycarbonylamino]-3-methyl-isoxazol-5-yl}-benzylamino)-3-(4-trifluoromethyl-phenyl)-propionic acid The title compound was prepared in analogous fashion as in Example 31 using [5-(4-Chloromethyl-phenyl)-3-methyl-isoxazol-4-yl]-carbamic acid (R)-1-(2-chloro-phenyl)-ethyl ester [Example 37, step 1](101 mg, 0.25 mmol), and D-4-trifluoromethylphenyl-alanine methyl ester hydrochloride. Yield=38 mg (0.06 mmol, 25%). HPLC (254 nm): Method 3 Rt 3.06 min. MS (ESI) m/z 602.6 [M+H$^+$].

Example 40: (R)-3-(2-Chloro-phenyl)-2-(4-{4-[(R)-1-(2-chloro-phenyl)-ethoxycarbonylamino]-3-methyl-isoxazol-5-yl}-benzylamino)-propionic acid The title compound was prepared in analogous fashion as in Example 31 using [5-(4-Chloromethyl-phenyl)-3-methyl-isoxazol-4-yl]-carbamic acid (R)-1-(2-chloro-phenyl)-ethyl ester [Example 37, step 1](101 mg, 0.25 mmol), and D-2-chlorophenyl-alanine methyl ester hydrochloride. Yield=8 mg (0.01 mmol, 5%). HPLC (254 nm): Method 3 Rt 2.78 min. MS (ESI) m/z 569.3 [M+H$^+$].

Example 41: (R)-2-(4-{4-[(R)-1-(2-Chloro-phenyl)-ethoxycarbonylamino]-3-methyl-isoxazol-5-yl}-benzylamino)-3-cyclopropyl-propionic acid The title compound was prepared in analogous fashion as in Example 31 using [5-(4-Chloromethyl-phenyl)-3-methyl-isoxazol-4-yl]-carbamic acid (R)-1-(2-chloro-phenyl)-ethyl ester [Example 37, step 1](101 mg, 0.25 mmol), and (R)-2-Amino-3-cyclopropylpropionic acid methyl ester hydrochloride [Example 17, step 1]. Yield=8 mg (0.01 mmol, 3%). HPLC (254 nm): Method 3 Rt 2.80 min. MS (ESI) m/z 498.4 [M+H$^+$].

Example 42: 2-{4-[3-Methyl-4-((R)-1-phenyl-ethoxycarbonylamino)-isoxazol-5-yl]-benzyloxy}-3-phenyl-propionic acid Step 1: {p-[3-Methyl-4-((R)-1-phenylethoxycarbonylamino)-5-isoxazolyl]phenyl}methyl acetate

[5-(4-Chloromethyl-phenyl)-3-methyl-isoxazol-4-yl]-carbamic acid (R)-1-phenyl-ethyl ester [Example 31, step 3] (1 g, 2.8 mmole) was mixed with potassium acetate (2 g, 14 mmol) and sodium iodide (0.5 g, 2.8 mmole) and to this was added N,N-dimethylacetamide (20 mL). The mixture was sonicated and then heated to 80° C. for 1.5 hrs. The mixture was cooled to room temperature and partitioned between saturated sodium chloride solution and ethyl acetate. The organic layer was further washed with water 4 times and then saturated sodium chloride solution before drying over magnesium sulfate. The filtered solution was evaporated to give a solid that was used directly. Yield=0.94 g (2.4 mmol, 87%). HPLC (254 nm): Method 3 Rt 2.89 min. MS (ESI) m/z 395.3 [M+H$^+$].

Step 2: [5-(4-Hydroxymethyl-phenyl)-3-methyl-isoxazol-4-yl]-carbamic acid (R)-1-phenyl-ethyl ester {p-[3-Methyl-4-((R)-1-phenylethoxycarbonylamino)-5-isoxazolyl]phenyl}methyl acetate [Example 42, step 1] (0.94 g, 2.4 mmole) was dissolved in THF (20 mL) and methanol (20 mL) and to this was added potassium carbonate (981 mg, 7.1 mmole). The resulting mixture was allowed to stir for 1.5 hours at room temperature when LC/MS indicated formation of a single product [HPLC (254 nm): Method 3 Rt 2.93 min. MS (ESI) m/z 353.2 [M+H$^+$]. Solvents were evaporated and the residue was partitioned between saturated sodium chloride solution and ethyl acetate. The organic phase was dried over magnesium sulfate, filtered and evaporated to give a residue that was chromatographed in a gradient of 0-50% ethyl acetate in hexanes to afford the product. Yield 0.63 g (1.79 mmole, 74%).

Step 3: Methyl-2-diazo-phenylpropanoate

D-phenylalanine methyl ester hydrochloride (2 g, 9.3 mmole) was partitioned between saturated sodium bicarbonate solution and ethyl acetate. The organic phase was dried over magnesium sulfate, filtered and evaporated to give a residue that was used directly. D-phenylalanine methyl ester (836 mg, 4.7 mmole) was dissolved in chloroform (20 mL) and acetic acid (0.055 mL, 0.94 mmole) was added. The solution was warmed to reflux with the slow drop wise addition of isoamyl nitrite (0.76 mL, 5.6 mmole) which was complete prior to solvent boiling. The mixture was refluxed for a further 30 minutes to afford a yellow solution that was cooled to 000° C. The organic solution was washed with 1N sulfuric acid (25 mL), water (20 mL), saturated sodium bicarbonate solution (25 mL), water (25 mL) and 1N sulfuric acid (25 mL). The organic phase was dried over magnesium sulfate, filtered and evaporated to give a residue that was chromatographed in a gradient of 0-5% ethyl acetate in hexanes to afford the product. Yield 0.65 g (3.4 mmole, 72%).

Step 4: 2-{4-[3-Methyl-4-((R)-1-phenyl-ethoxycarbonylamino)-isoxazol-5-yl]-benzyloxy}-3-phenyl-propionic acid methyl ester

[5-(4-Hydroxymethyl-phenyl)-3-methyl-isoxazol-4-yl]-carbamic acid (R)-1-phenyl-ethyl ester [Example 42, step 2] (100 mg, 0.28 mmole) and Methyl-2-diazo-phenylpropanoate [Example 42, step 3] (61 mg, 0.39 mmole) were suspended in benzene (3 mL) in a screw cap vial. To this was added diRhodium tetraacetate (1 mg, 0.002 mmole). After 10 minutes at room temperature the vial was heated to 90° C. for 1 hour. The mixture was cooled to room temperature and the mixture chromatographed in a gradient of 0-20% ethyl acetate in hexanes to afford the product. Yield=52 mg (0.1 mmol, 36%). HPLC (254 nm): Method 3 Rt 3.56 min. MS (ESI) m/z 515.5 [M+H$^+$].

Step 5: 2-{4-[3-Methyl-4-((R)-1-phenyl-ethoxycarbonylamino)-isoxazol-5-yl]-benzyloxy}-3-phenyl-propionic acid 2-{4-[3-Methyl-4-((R)-1-phenyl-ethoxycarbonylamino)-isoxazol-5-yl]-benzyloxy}-3-phenyl-propionic acid methyl ester (52 mg, 0.10 mmole) was dissolved in 2/1 v/v THF/water (4.5 mL) and the mixture stirred for 24 hours. The reaction mixture was diluted with ethyl acetate (50 mL) and washed with saturated sodium bicarbonate solution. The aqueous layer was acidified to pH 3 with 6 N HCl and extracted with ethyl acetate. The organic layer was separated, dried over anhydrous MgSO$_4$, filtered and concentrated in vacuo. The residue was co-evaporated with diethyl ether to afford the pure product as a white solid (22 mg, 0.043 mmol, 44%). HPLC (254 nm): Method 3 Rt 3.03 min. MS (ESI) m/z 501.5 [M+H$^+$].

Example 43: 2-{4-[3-Methyl-4-((R)-1-phenyl-ethoxycarbonylamino)-isoxazol-5-yl]-benzyloxy}-3-phenyl-propionic acid Example 43 was prepared in analogous fashion to example 42 from [5-(4-Hydroxymethyl-phenyl)-3-methyl-isoxazol-4-yl]-carbamic acid (R)-1-phenyl-ethyl ester [Example 42, step 2] (100 mg, 0.28 mmole) dissolved in 15% THF in benzene (1.15 mL) using Methyl-2-diazo-phenylpropanoate that was synthesized from L-phenylalanine methyl ester hydrochloride (2 g, 9.3 mmole). Yield 20 mg (0.04 mmole, 14%). HPLC (254 nm): Method 3 Rt 2.96 min. MS (ESI) m/z 501.6 [M+H$^+$].

Example 44: (RS)-3-Cyclopropyl-2-{4-[3-methyl-4-((R)-1-phenyl-ethoxycarbonylamino)-isoxazol-5-yl]-benzyloxy}-propionic acid Step 1: D,L-2-amino-cyclopropylpropanoic acid methyl ester Prepared in analogous fashion to Example 1, step 6 from D,L-2-amino-cyclopropylpropanoic acid (500 mg, 3.87 mmole). The crude residue was partitioned between saturated sodium bicarbonate solution and ethyl acetate. The organic phase was dried over magnesium sulfate, filtered and evaporated to give a residue that was used directly. Yield 295 mg (2.06 mmole, 53%)

Step 2: R,S Methyl-2-diazo-cyclopropylpropanoate

Prepared in analogous fashion to Example 42, step 3 from D,L-2-amino-cyclopropylpropanoic acid methyl ester (295 mg, 2.06 mmole) and used directly. Yield 200 mg (1.29 mmole, 62%)

Step 3: (RS)-3-Cyclopropyl-2-{4-[3-methyl-4-((R)-1-phenyl-ethoxycarbonylamino)-isoxazol-5-yl]-benzyloxy}-propionic acid methyl ester Prepared in analogous fashion to Example 42, step 4 from [5-(4-Hydroxymethyl-phenyl)-3-methyl-isoxazol-4-yl]-carbamic acid (R)-1-phenyl-ethyl ester [Example 42, step 2](90 mg, 0.25 mmole) dissolved in 15% THF in benzene (1 mL) and R,S Methyl-2-diazo-cyclopropylpropanoate [Example 44, step 2] (118 mg, 0.75 mmole]. Yield 50 mg (0.1 mmole, 40%). HPLC (254 nm): Method 3 Rt 2.99 min. MS (ESI) m/z 479.1 [M+H$^+$].

Step 4: (RS)-3-Cyclopropyl-2-{4-[3-methyl-4-((R)-1-phenyl-ethoxycarbonylamino)-isoxazol-5-yl]-benzyloxy}-propionic acid Prepared in analogous fashion to Example 42, step 5 from (RS)-3-Cyclopropyl-2-{4-[3-methyl-4-((R)-1-phenyl-ethoxycarbonylamino)-isoxazol-5-yl]-benzyloxy}-propionic acid methyl ester [Example 44, step 3] (50 mg, 0.1 mmole). Yield 21 mg (0.1 mmole, 40%). HPLC (254 nm): Method 3 Rt 3.06 min. MS (ESI) m/z 465 [M+H$^+$].

Example 45: (RS)-3-(4-Chloro-phenyl)-2-{4-[3-methyl-4-((R)-1-phenyl-ethoxycarbonyloxy)-isoxazol-5-yl]-benzyloxy}-propionic acid

Step 1: D,L-2-Amino-3(4-chlorophenyl)propanoic acid methyl ester

Prepared in analogous fashion to Example 1, step 6 from D,L-2-Amino-3(4-chlorophenyl)propanoic acid (600 mg, 3 mmole). The crude residue was partitioned between saturated sodium bicarbonate solution and ethyl acetate. The organic phase was dried over magnesium sulfate, filtered and evaporated to give a residue that was used directly. Yield 698 mg (3.3 mmole, 100%)

Step 2: R,S Methyl-2-diazo-3(4-chlorophenyl)propanoate

Prepared in analogous fashion to Example 42, step 3 from D,L-2-Amino-3(4-chlorophenyl)propanoic acid methyl ester [Example 45, step 1](698 mg, 3.3 mmole) and used directly. Yield 275 mg (1.33 mmole, 40%)

Step 3: (RS)-3-(4-Chloro-phenyl)-2-{4-[3-methyl-4-((R)-1-phenyl-ethoxycarbonyloxy)-isoxazol-5-yl]-benzyloxy}-propionic acid methyl ester Prepared in analogous fashion to Example 42, step 4 from [5-(4-Hydroxymethyl-phenyl)-3-methyl-isoxazol-4-yl]-carbamic acid (R)-1-phenyl-ethyl ester [Example 42, step 2](90 mg, 0.25 mmole) dissolved in 15% THF in benzene (1 mL) and R,S Methyl-2-diazo-3(4-chlorophenyl)propanoate [Example 45, step 2] (200 mg, 0.89 mmole). Yield 55 mg (0.1 mmole, 40%). HPLC (254 nm): Method 3 Rt 3.49 min. MS (ESI) m/z 549.6 [M+H$^+$].

Step 4: (RS)-3-(4-Chloro-phenyl)-2-{4-[3-methyl-4-((R)-1-phenyl-ethoxycarbonyloxy)-isoxazol-5-yl]-benzyloxy}-propionic acid Prepared in analogous fashion to Example 42, step 5 from (RS)-3-Cyclopropyl-2-{4-[3-methyl-4-((R)-1-phenyl-ethoxycarbonylamino)-isoxazol-5-yl]-benzyloxy}-propionic acid methyl ester [Example 44, step 3] (55 mg, 0.1 mmole). Yield 20 mg (0.04 mmole, 37%). HPLC (254 nm): Method 3 Rt 3.26 min. MS (ESI) m/z 535 [M+H$^+$].

Example 46: 2-[4-[4-[5-[1-(2-chlorophenyl)ethoxycarbonylamino]-4-cyano-pyrazol-1-yl]phenyl]phenyl]acetic acid

Step 1—5-amino-1-(4-bromophenyl)pyrazole-4-carbonitrile (4-bromophenyl)hydrazine hydrochloride (2.24 g, 10 mmol) was suspended in ethanol (20 mL) and treated with triethylamine (1.53 mL, 11 mmol). The resulting solution was then treated with malononitrile (1.22 g, 10 mmol) added portionwise. After a small exotherm was observed, the reaction was heated to reflux for 1 hour. The reaction was cooled to room temperature; the solids were collected by vacuum filtration and rinsed with cold ethanol. The solids were air-dried. Yield=0.93 g, 3.5 mmol (35%). HPLC (254 nm): Method 2, Rt 5.82 min. MS (ESI) m/z 265 [M+H$^+$]; 263 [M+H$^+$]; 184 [(M–Br)+H$^+$].

Step 2—1-(2-chlorophenyl)ethyl N-[2-(4-bromophenyl)-4-cyano-pyrazol-3-yl]carbamate A solution of 5-amino-1-(4-bromophenyl)pyrazole-4-carbonitrile [Example 46, step 1](26 mg, 0.1 mmol) in CH$_2$Cl$_2$ (1 mL) was treated with triethylamine (28 µL, 0.2 mmol), followed by phosgene (100 µL of a 20% v/v solution in toluene, 0.2 mmol est.). The resulting solution was stirred at room temperature for 30 minutes. (±)-1-(2-chlorophenyl)ethanol (23 mg, 0.15 mmol) was added and the resulting mixture stirred at room temperature overnight. The reaction was concentrated in vacuo to remove volatiles, and the residue was purified by chromatography on silica-gel, eluting with a 4:1 mixture of hexanes/ethyl acetate v/v. The product was obtained as a colorless film. Yield=27 mg (0.06 mmol, 61%). HPLC (254 nm): Method 1, Rt 6.31 min. MS (ESI) m/z 447 [M+H$^+$]; 445 [M+H$^+$]. $^1$H NMR (500 MHz, CDCl$_3$) (7.90 (s, 1H); 7.57 (d, J=8.8 Hz, 2H); 7.37-7.35 (m, 1H); 7.32 (d, J=8.8 Hz, 2H); 7.27 (m, 3H); 6.70 (br, 1H); 6.14 (q, J=6.5 Hz, 1H); 1.54 (d, J=6.5 Hz, 3H).

Step 3—ethyl 2-[4-[4-[5-[1-(2-chlorophenyl)ethoxycarbonylamino]-4-cyano-pyrazol-1-yl]phenyl]phenyl]acetate In a pressure vessel, 1-(2-chlorophenyl)ethyl N-[2-(4-bromophenyl)-4-cyano-pyrazol-3-yl]carbamate [Example 46, step 2] (80 mg, 0.18 mmol) was dissolved in a 2:1 v/v mixture of toluene and ethanol (2 mL) and treated with Na$_2$CO$_3$ (0.6 mL of a 2N aqueous solution) and [4-(2-ethoxy-2-oxo-ethyl)phenyl]boronic acid (75 mg, 0.36 mmol). The resulting mixture was degassed under Ar for 15 minutes, then treated with Pd[Ph$_3$P]$_4$ (8 mg, 0.007 mmol). The vessel was capped and immersed in an oil bath at 80° C., with vigorous magnetic stirring. Reaction was deemed complete after 14 hours. Reaction cooled to room temperature and partitioned between ethyl acetate and water. The organic layer was washed with water and brine. The combined aqueous layers were back-extracted with ethyl acetate. The combined organic layers were dried over anhydrous MgSO$_4$, filtered and concentrated in vacuo. The residue was purified by chromatography on silica-gel, eluting with a 4:1 mixture of hexanes/ethyl acetate v/v. The product was obtained as a white solid. Yield=82 mg (0.16 mmol, 89%).

HPLC (254 nm): Method 1, Rt 6.94 min. MS (ESI) m/z 529.3 [M+H$^+$]; 485.1 [(M−EtO)+H$^+$].

Step 4: 2-[4-[4-[5-[1-(2-chlorophenyl)ethoxycarbonylamino]-4-cyano-pyrazol-1-yl]phenyl]phenyl] acetic acid Ethyl 2-[4-[4-[5-[1-(2-chlorophenyl)ethoxycarbonylamino]-4-cyano-pyrazol-1-yl]phenyl]phenyl]acetate [Example 46, step 3] (45 mg, 0.085 mmol) was dissolved in THF (1 mL) and treated with LiOH (1 mL of a 1M aqueous solution). The resulting mixture was stirred at room temperature for 2 hours. The reaction was transferred to a separatory funnel, diluted with water and extracted with ethyl acetate. The organic layer was discarded and the aqueous layer was brought to pH 2 with a 0.1 N HCl solution. The product was extracted with ethyl acetate. The organic layer was dried over anhydrous MgSO$_4$, filtered and concentrated in vacuo to yield a white solid as the pure product. Yield=42 mg (0.085 mmol, quantitative). HPLC (254 nm): Method 1, Rt 6.99 min. MS (ESI) m/z 501.3 [M+H$^+$]; 457.2 [(M−CO$_2$H)+H$^+$]. $^1$H NMR (500 MHz, DMSO-d$_6$) δ 12.39 (br, 1H); 10.42 (br, 1H); 8.31 (s, 1H); 7.82 (d, J=8.6 Hz, 2H); 7.67 (d, J=8.3 Hz, 2H); 7.56 (d, J=8.6 Hz, 2H); 7.43 (d, J=7.7 Hz, 1H); 7.39 (d, J=8.3 Hz, 2H); 7.33-7.29 (m, 3H); 5.94 (q, J=6.5 Hz, 1H); 3.64 (s, 2H); 1.44 (br, 3H).

Example 47: (R)-1-[4-[4-[1,5-dimethyl-4-(1-phenylethoxycarbonylamino)pyrazol-3-yl]phenyl]phenyl] cyclopropane carboxylic acid Step 1: 2-(4-Bromo-benzoyl)-3-oxo-butyric acid ethyl ester Ethyl acetoacetate (1.97 mL, 15.6 mmole) was added to a suspension of magnesium chloride (1.49 g, 15.6 mmole) in dichloromethane (15 mL) that had been cooled to 0° C. To the mixture was added pyridine (2.43 mL, 30 mmole) and stirring continued for an additional 15 minutes. 4-Bromobenzoyl chloride (3.29 g, 15 mmole) in dichloromethane (15 mL) was then added to the reaction. This mixture was stirred at 000° C. for 15 minutes and then at room temperature for 1 hour. At this time the mixture was treated with 6N hydrochloric acid solution (20 mL). The organic layer was separated, dried over anhydrous MgSO$_4$, filtered and concentrated in vacuo to give a colorless oil that was used directly in the next step.

Step 2: 3-(4-Bromo-phenyl)-1,5-dimethyl-1H-pyrazole-4-carboxylic acid ethyl ester and 5-(4-Bromophenyl)-1,3-dimethyl-1H-pyrazole-4-carboxylic acid ethyl ester 2-(4-Bromo-benzoyl)-3-oxo-butyric acid ethyl ester [example 47, step 1] (4.7 g, 15 mmole), methylhydrazine (0.79 mL, 15.1 mmole), p-toluenesulfonic acid (0.15 g) were mixed with ethanol (150 mL) and this mixture was heated to 78° C. for 2 hours. At this point the reaction was allowed to cool and the resulting mixture was partitioned between ethyl acetate and water. The organic layer was dried over anhydrous MgSO$_4$, filtered and concentrated in vacuo. A crude product was obtained that was purified by silica gel chromatography initially with hexane/ethyl acetate 95/5 as eluting solvent and then with hexane/ethyl acetate 88/12 to afford 3-(4-Bromo-phenyl)-1,5-dimethyl-1H-pyrazole-4-carboxylic acid ethyl ester (600 mg, 12%) and 5-(4-Bromophenyl)-1,3-dimethyl-1H-pyrazole-4-carboxylic acid ethyl ester (190 mg, 4%).

Step 3: 3-(4-Bromophenyl)-1,5-dimethyl-1H-pyrazole-4-carboxylic acid

A mixture of 3-(4-Bromophenyl)-1,5-dimethyl-1H-pyrazole-4-carboxylic acid ethyl ester [example 47, step 2] (600 mg, 1.85 mmole), 1N sodium hydroxide solution (18.5 mL) and dioxane (18.5 mL) was stirred at 100° C. for 3 hours. Upon cooling the mixture was acidified to pH 3-4 with 3N hydrochloric acid solution and this was extracted with ethyl acetate. The organic layer was dried over anhydrous MgSO$_4$, filtered and concentrated in vacuo to yield the product as a solid (422 mg, 77%).

Step 4: (R)-1-(phenyl)ethyl N-[2-(4-bromophenyl)-1,5-dimethyl-1H-pyrazol-3-yl]carbamate A suspension of 3-(4-Bromophenyl)-1,5-dimethyl-1H-pyrazole-4-carboxylic acid [example 47, step 3] (50 mg, 0.17 mmol) in toluene (1 mL) and triethylamine (17 mg, 0.17 mmole) was treated with diphenylphosphoryl azide (44 μL, 0.20 mmole) and the mixture stirred at 45° C. for 3 hours and then 95° C. with the evolution of a gas. After 30 minutes (R)-(+)-1-phenylethanol (25 mg, 0.20 mmole) was added. Heating was continued for a further 1 hour before the mixture was allowed to cool. The reaction was concentrated in vacuo and the residue dissolved in ethyl acetate and the solution washed with 0.1M potassium carbonate solution and then brine. The organic layer was dried over anhydrous MgSO$_4$, filtered and concentrated in vacuo to afford the product (64 mg, 91%) that was used directly in the next step. HPLC (254 nm): Method 3 Rt 3.10 min. MS (ESI) m/z 416.2, 414.4 [M+H$^+$].

Step 5: 2-[4-(4,4,5,5-tetramethyl-1,3,2-dioxaborolan-2-yl)phenyl]cyclopropane carboxylic acid methyl ester Methyl 1-(4-bromophenyl)cyclopropanecarboxylate (1 g, 3.92 mmole), potassium acetate (461 mg, 4.7 mmole), and bis(pinacolato)diboron (1.19 g, 4.70 mmole) were mixed in dioxane (10 mL) and degassed for 10 minutes under a stream of argon. [1,1'-bis(diphenylphosphino)ferrocene]palladium (II) dichloride (32 mg) was added and the mixture was heated at 95° C. for 2 hours. At this point the mixture was allowed to cool and the mixture was partitioned between ethyl acetate and water. The organic layer was dried over anhydrous MgSO$_4$, filtered and concentrated in vacuo. A crude product was obtained that was purified by silica gel chromatography with hexane/ethyl acetate 95/5 as eluting solvent to afford the product as a white solid (1.02 g, 86%).

Step 6: (R)-1-[4-[4-[1,5-dimethyl-4-(1-phenylethoxycarbonylamino)pyrazol-3-yl]phenyl]phenyl] cyclopropanecarboxylic acid methyl ester In a pressure vessel, (R)-1-(phenyl)ethyl N-[2-(4-bromophenyl)-1,5-dimethyl-1H-pyrazol-3-yl]carbamate [example 47, step 4] (64 mg, 0.16 mmol) was dissolved in a 2:1 v/v mixture of toluene and ethanol (2 mL) and treated with Na$_2$CO$_3$ (0.5 mL of a 2N aqueous solution) and 2-[4-(4,4,5,5-tetramethyl-1,3,2-dioxaborolan-2-yl)phenyl]cyclopropane carboxylic acid methyl ester [Example 47, step 5] (52 mg, 0.17 mmol). The resulting mixture was degassed under argon for 15 minutes, and then treated with tetrakis (triphenyl-phosphine)palladium(0) (1 mg, 0.006 mmol). The vessel was capped and immersed in an oil bath at 80° C., with vigorous magnetic stirring overnight. This reaction was cooled to room temperature and partitioned between ethyl acetate and water. The organic layer was washed with water and brine. The combined aqueous layers were back-extracted with ethyl acetate. The combined organic layers were dried over anhydrous $MgSO_4$, filtered and concentrated in vacuo. This material was purified by preparative TLC eluting with hexane/ethyl acetate 1/1 v/v to give the product as a yellow film (10 mg, 13%).

Step 7: (R)-1-[4-[4-[2,5-dimethyl-4-(1-phenylethoxycarbonylamino)pyrazol-3-yl]phenyl]phenyl] cyclopropanecarboxylic acid (R)-1-[4-[4-[1,5-dimethyl-4-(1-phenylethoxycarbonylamino)pyrazol-3-yl]phenyl]phenyl]cyclopropanecarboxylic acid methyl ester [example 47, step 6] (10 mg, 0.02 mmole) was dissolved in THF (1 mL) and treated with LiOH (1 mL of a 2M aqueous solution). The resulting mixture was stirred overnight and then refluxed for 5 hours. The reaction was cooled and transferred to a separatory funnel, diluted with water and extracted with ethyl acetate. The organic layer was discarded and the aqueous layer was brought to pH 1 with a 0.1 N HCl solution when the product was extracted with ethyl acetate. This organic layer was dried over anhydrous $MgSO_4$, filtered and concentrated in vacuo. A residue was obtained which was triturated with dimethoxyethane. The solids were filtered and the filtrate evaporated to dryness to yield a residue that was purified by preparative TLC, eluting with ethyl acetate/hexane 2/1 v/v. The product was obtained as a white solid (3 mg, 28%). HPLC (254 nm): Method 3 Rt 3.12 min. MS (ESI) m/z 496.6 [M+H$^+$].

Example 48: (R)-1-[4-[4-[2,5-dimethyl-4-(1-phenylethoxycarbonylamino)pyrazol-3-yl]phenyl]phenyl] cyclopropane carboxylic acid

Step 1: 5-(4-Bromo-phenyl)-1,3-dimethyl-1H-pyrazole-4-carboxylic acid

A mixture of 5-(4-Bromo-phenyl)-1,3-dimethyl-1H-pyrazole-4-carboxylic acid ethyl ester [example 47, step 2] (190 mg, 0.59 mmole), 1N sodium hydroxide solution (5.9 mL) and dioxane (5.9 mL) was stirred at 100° C. for 1 hour. Upon cooling the mixture was acidified to pH 3-4 with 3N hydrochloric acid solution and this was extracted with ethyl acetate. The organic layer was dried over anhydrous $MgSO_4$, filtered and concentrated in vacuo to yield the product as a solid (170 mg, 98%).

Step 2: (R)-1-(phenyl)ethyl N-[5-(4-Bromo-phenyl)-1,3-dimethyl-1H-pyrazole-4-yl]-carbamate 5-(4-Bromo-phenyl)-1,3-dimethyl-1H-pyrazole-4-carboxylic acid [example 48, step 1](50 mg, 0.17 mmol) was used to prepare (R)-1-(phenyl)ethyl N-[5-(4-Bromo-phenyl)-1,3-dimethyl-1H-pyrazole-4-yl]carbamate according to the procedure described for example 47, step 4 to afford the product (64 mg, 91%) that was used in the next step. HPLC (254 nm): Method 3 Rt 3.03 min. MS (ESI) m/z 416.5 [M+H$^+$].

Step 3: (R)-1-[4-[4-[2,5-dimethyl-4-(1-phenylethoxycarbonylamino)pyrazol-3-yl]phenyl]-phenyl] cyclopropane carboxylic acid methyl ester In a pressure vessel, (R)-1-(phenyl)ethyl N-[5-(4-Bromo-phenyl)-1,3-dimethyl-1H-pyrazole-4-yl]carbamate [example 48, step 2) (64 mg, 0.16 mmol) was used to prepare the product as an oil (32 mg, 41%) using a similar procedure to that described for example 47, step 6

Step 4: (R)-1-[4-[4-[2,5-dimethyl-4-(1-phenylethoxycarbonylamino)pyrazol-3-yl]phenyl]phenyl] cyclopropane carboxylic acid (R)-1-[4-[4-[2,5-dimethyl-4-(1-phenylethoxycarbonylamino) pyrazol-3-yl]phenyl]phenyl]cyclopropane carboxylic acid methyl ester [example 48, step 3] (32 mg, 0.06 mmole) was dissolved in THF (3 mL) and treated with LiOH (3 mL of a 2M aqueous solution). The resulting mixture was stirred overnight and then refluxed for 5 hours. The reaction was cooled and transferred to a separatory funnel, diluted with water and extracted with ethyl acetate. The organic layer was discarded and the aqueous layer was brought to pH 1 with a 0.1 N HCl solution when the product was extracted with ethyl acetate. This organic layer was dried over anhydrous $MgSO_4$, filtered and concentrated in vacuo. A residue was obtained which was triturated with dimethoxyethane. The solids were filtered and the filtrate evaporated to dryness to yield a residue that was purified by preparative TLC, eluting with ethyl acetate/hexane 2/1 v/v. The product was obtained as a white solid (10 mg, 32%). HPLC (254 nm): Method 3 Rt 2.92 min. MS (ESI) m/z 496.6 [M+H$^+$].

Example 49: (R)-1-(4'-{5-[1-(2-Chloro-phenyl)-ethoxycarbonylamino]-4-fluoro-pyrazol-1-yl}-3-fluoro-biphenyl-4-yl)-cyclopropanecarboxylic acid

Step 1: Ethyl (E)-4-(dimethylamino)-2-oxo-but-3-enoate

Ethyl pyruvate (5 g, 43.1 mmol) was dissolved in $CH_2Cl_2$ (86 mL) and treated with dimethylformamide dimethylacetal (5.73 mL, 43.1 mmol). The reaction was stirred at room temperature for 2 hours and concentrated in vacuo. The crude was used as is in the next step. Yield=7.4 g.

Step 2: ethyl 2-(4-bromophenyl)pyrazole-3-carboxylate

4-Bromophenyl hydrazine hydrochloride (2.0 g, 8.95 mmol) was dissolved in MeOH (18 mL) and treated with crude ethyl (E)-4-(dimethylamino)-2-oxo-but-3-enoate [example 3, step 1] (1.54 g, 9.0 mmol). The resulting mixture was stirred at room temperature for 6 hours. The volatiles were removed in vacuo and the residue was purified by chromatography on silica-gel, eluting with a 95:5 mixture of hexanes/ethyl acetate v/v, increasing the polarity to 9:1 over time. Two isomeric products were isolated: ethyl 2-(4-bromophenyl)pyrazole-3-carboxylate as an orange solid (0.82 g, 2.78 mmol, 31%) and ethyl 1-(4-bromophenyl) pyrazole-3-carboxylate as a red solid (0.44 g, 1.49 mmol, 17%).

Ethyl 2-(4-bromophenyl)pyrazole-3-carboxylate: HPLC (254 nm): Method 2 Rt 5.22 min. MS (ESI) m/z 297 [M+H$^+$]; 294.8 [M+H$^+$]; 252 [(M−EtO)+H$^+$]; 250 [(M−EtO)+H$^+$]. $^1$H NMR (500 MHz, CDCl$_3$) δ 7.69 (d, J=1.9 Hz, 1H); 7.58 (d, J=8.7 Hz, 2H); 7.32 (d, J=8.7 Hz, 2H); 7.03 (d, J=1.9 Hz, 1H); 4.26 (q, J=7.1 Hz, 2H); 1.28 (t, J=7.1 Hz, 3H).

Ethyl 1-(4-bromophenyl)pyrazole-3-carboxylate: $^1$H NMR (500 MHz, CDCl$_3$) δ 7.91 (d, J=2.4 Hz, 1H); 7.65 (d, J=7.2 Hz, 2H); 7.60 (d, J=7.2 Hz, 2H); 7.00 (d, J=2.4 Hz, 1H); 4.44 (q, J=7.0 Hz, 2H); 1.43 (t, J=7.0 Hz, 3H).

Step 3: 2-(4-Bromo-phenyl)-4-fluoro-2H-pyrazole-3-carboxylic acid ethyl ester Ethyl 2-(4-bromophenyl)pyrazole-3-carboxylate (1.08 g, 3.68 mmol) was dissolved in acetonitrile (12 mL) and the resulting mixture was treated with glacial acetic acid (4.6 mL). To this solution, 1-chloromethyl-4-fluoro-1,4-diazoniabicyclo[2.2.2]octane bis(tetrafluoroborate) (Selectfluor®, 3.91 g, 11.04 mmol) was added in one portion and the resulting mixture was heated to 105° C. for 18 hours. The mixture was cooled to room temperature and the volatiles were removed in vacuo. The crude residue was loaded directly onto a silica-gel column and purified by elution with 95:5 mixture of hexanes/ethyl acetate v/v, increasing the polarity to 9:1 over time. The product was isolated as a white solid (410 mg, 1.31 mmol, 36%) and starting material was recovered (272 mg, 0.93 mmol, 25%). For 2-(4-Bromo-phenyl)-4-fluoro-2H-pyrazole-3-carboxylic acid ethyl ester: HPLC (254 nm): Method 3 Rt 2.97 min. MS (ESI) m/z 313.1 [M+H$^+$]. $^1$H NMR (500 MHz, CDCl$_3$) δ 7.60 (s, 1H); 7.58 (d, J=9 Hz, 2H); 7.29 (d, J=9 Hz, 2H); 4.30 (q, J=7.1 Hz, 2H); 1.28 (t, J=7.1 Hz, 3H).

Step 4: 2-(4-Bromo-phenyl)-4-fluoro-2H-pyrazole-3-carboxylic acid

A stirred solution of 2-(4-bromo-phenyl)-4-fluoro-2H-pyrazole-3-carboxylic acid ethyl ester (410 mg, 1.31 mmol) in THF (13 mL) was treated with LiOH 1 N aqueous solution (13 mL) and the resulting mixture was stirred at room temperature overnight. The reaction was deemed complete by thin layer chromatography and HPLC/MS. The reaction mixture was partitioned between ethyl acetate and 1 N aqueous HCl solution (100 mL v/v) and transferred to a separatory funnel. The organic layer was separated and the aqueous layer was back-extracted with ethyl acetate (30 mL). The combined organic layers were dried over anhydrous MgSO$_4$, filtered and concentrated in vacuo to afford the pure product as a white solid (347 mg, 1.22 mmol, 93%). HPLC (254 nm): Method 3 Rt 2.82 min. MS (ESI) m/z 285.1 [M+H$^+$].

Step 5: (R)-[2-(4-Bromo-phenyl)-4-fluoro-2H-pyrazol-3-yl]-carbamic acid 1-(2-chloro-phenyl)-ethyl ester 2-(4-Bromo-phenyl)-4-fluoro-2H-pyrazole-3-carboxylic acid (347 mg, 1.22 mmol) was suspended in toluene (12 mL) and treated with triethylamine (205 µL, 1.46 mmol). The resulting solution was treated with diphenylphosphoryl azide (316 µL, 1.46 mmol) and heated to 65° C. (R)-1-(2-Chloro-phenyl)-ethanol (230 mg, 1.46 mmol) was added to the reaction mixture and the temperature was increased to 105° C. for 30 minutes, during which time vigorous gas evolution was observed. The reaction was brought to 65° C. and stirred at that temperature for 4 hours. The reaction was deemed complete by HPLC/MS. After cooling, the volatiles were removed in vacuo and the crude residue was purified by silica gel chromatography, eluting with a hexanes/ethyl acetate gradient. Product isolated as a white solid (452 mg, 1.03 mmol, 85%). HPLC (254 nm): Method 3 Rt 3.16 min. MS (ESI) m/z 440.1 [M+H$^+$].

Step 6: (R)-1-(4'-{5-[1-(2-Chloro-phenyl)-ethoxycarbonylamino]-4-fluoro-pyrazol-1-yl}-3-fluoro-biphenyl-4-yl)-cyclopropanecarboxylic acid A stirred suspension of (R)-[2-(4-Bromo-phenyl)-4-fluoro-2H-pyrazol-3-yl]-carbamic acid 1-(2-chloro-phenyl)-ethyl ester (88 mg, 0.2 mmol), 2:1 v/v toluene/ethanol (2 mL), 2 M aqueous solution of Na$_2$CO$_3$ (670 µL) and 1-(4-borono-2-fluorophenyl)cyclopropane-1-carboxylic acid (45 mg, 0.2 mmol) was degassed under nitrogen for 10 minutes and treated with Pd[Ph$_3$P]$_4$ (12 mg, 0.01 mmol). The resulting mixture was immersed in an oil bath with stirring at 90° C. for 12 hours. The reaction was cooled, transferred to a separatory funnel and diluted with ethyl acetate (50 mL). The mixture was carefully treated with 1 N aqueous HCl solution (20 mL). The organic layer was separated, washed with brine, dried over anhydrous MgSO$_4$, filtered and concentrated in vacuo. The crude residue was purified by preparative TLC plate (1000 µm), eluting with a 1:1 v/v hexanes/ethyl acetate mixture. The product was obtained as a tan solid. Yield=35 mg (35%). HPLC (254 nm): Method 3, Rt 3.11 min. MS (ESI) m/z 538.3 [M+H$^+$].

Example 50: (R)-1-(4'-{5-[1-(2-Chloro-phenyl)-ethoxycarbonylamino]-4-fluoro-pyrazol-1-yl}-2-fluoro-biphenyl-4-yl)-cyclopropanecarboxylic acid The title compound was prepared in analogous fashion as in Example 49 using (R)-[2-(4-Bromo-phenyl)-4-fluoro-2H-pyrazol-3-yl]-carbamic acid 1-(2-chloro-phenyl)-ethyl ester (Example 49, Step 5 (88 mg, 0.2 mmol), and 1-[4-(dihydroxyboranyl)-3-fluorophenyl]-cyclopropane-1-carboxylic acid. Yield 40 mg (37%) as a light yellow solid. HPLC (254 nm): Method 3, Rt 3.14 min. MS (ESI) m/z 538.3 [M+H$^+$].

Example 51: (R)-1-(2-Chloro-4'-{5-[1-(2-chloro-phenyl)-ethoxycarbonylamino]-4-fluoro-pyrazol-1-yl}-biphenyl-4-yl)-cyclopropanecarboxylic acid The title compound was prepared in analogous fashion as in Example 49 using (R)-[2-(4-Bromo-phenyl)-4-fluoro-2H-pyrazol-3-yl]-carbamic acid 1-(2-chloro-phenyl)-ethyl ester (Example 49, Step 5 (88 mg, 0.2 mmol), and 1-[3-chloro-4-(dihydroxyboranyl)phenyl]-cyclopropane-1-carboxylic acid. Yield 24 mg (22%) as a light yellow solid. HPLC (254 nm): Method 3, Rt 3.40 min. MS (ESI) m/z 554.4 [M+H$^+$].

Example 52: (R)-1-(4'-{5-[1-(2-Chloro-phenyl)-ethoxycarbonylamino]-4-fluoro-pyrazol-1-yl}-2-methyl-biphenyl-4-yl)-cyclopropanecarboxylic acid The title compound was prepared in analogous fashion as in Example 49 using (R)-[2-(4-Bromo-phenyl)-4-fluoro-2H-pyrazol-3-yl]-carbamic acid 1-(2-chloro-phenyl)-ethyl ester (Example 49, Step 5 (88 mg, 0.2 mmol), and 1-[4-(dihydroxyboranyl)-3-methylphenyl]cyclo-propane-1-carboxylic acid. Yield 36 mg (34%) as a light yellow solid. HPLC (254 nm): Method 3, Rt 3.19 min. MS (ESI) m/z 534.3 [M+H$^+$].

Example 53: (R)-1-(4'-{5-[1-(2-Chloro-phenyl)-ethoxycarbonylamino]-4-fluoro-pyrazol-1-yl}-biphenyl-4-yl)-cyclopropanecarboxylic acid The title compound was prepared in analogous fashion as in Example 49 using (R)-[2-(4-Bromo-phenyl)-4-fluoro-2H- pyrazol-3-yl]-carbamic acid 1-(2-chloro-phenyl)-ethyl ester (Example 49, Step 5 (88 mg, 0.2 mmol), and 4-(1-carboxycyclopropyl)phenylboronic acid, pinacol ester. Yield 9 mg (9%) as a white solid. HPLC (254 nm): Method 3, Rt 3.20 min. MS (ESI) m/z 520.0 [M+H$^+$].

Example 54: (R)-1-{4'-[5-(1-Phenyl-ethoxycarbonylamino)-4-trifluoromethyl-pyrazol-1-yl]-biphenyl-4-yl}-cyclopropanecarboxylic acid

Step 1: 2-(4-Bromo-phenyl)-4-iodo-2H-pyrazole-3-carboxylic acid ethyl ester Ethyl 2-(4-bromophenyl)pyrazole-3-carboxylate (Example 49, Step 2, 294 mg, 1.0 mmol) was dissolved in methanol (3 mL) and treated dropwise with iodine monochloride (115 µL, 2.3 mmol). The resulting mixture was heated to 50° C. for 3 hours. Another aliquot of iodine monochloride (120 µL) was added and heating continued for additional 3 hours. The reaction was deemed complete by HPLC/MS. After cooling to room temperature, the reaction mixture was diluted with ethyl acetate (30 mL) and transferred to a separatory funnel. The organic layer was washed successively with 1 N Na$_2$S$_2$O$_3$ aqueous (30 mL) and brine (30 mL). The organic layer was separated, washed with brine, dried over anhydrous MgSO$_4$, filtered and concentrated in vacuo. The product [2-(4-bromo-phenyl)-4-iodo-2H-pyrazole-3-carboxylic acid ethyl ester] was obtained as a pale yellow solid (420 mg, quant.) and used as is in the next step. HPLC (254 nm): Method 3, Rt 3.33 min. MS (ESI) m/z 421.0, 423.0 [M+H$^+$].

Step 2: 2-(4-Bromo-phenyl)-4-trifluoromethyl-2H-pyrazole-3-carboxylic acid ethyl ester 2-(4-Bromo-phenyl)-4-iodo-2H-pyrazole-3-carboxylic acid ethyl ester (420 mg, 1.0 mmol) was dissolved in DMF (4 mL) and the resulting solution was degassed with nitrogen for 10 minutes. (1,10-Phenanthroline)(trifluoromethyl)copper (I) (Trifluoromethylator™, 520 mg, 1.5 mmol) was added in one portion under an inert atmosphere and the resulting mixture was stirred at 50° C. for 18 hours. The reaction was cooled to room temperature and filtered through a pad of Celite and rinsed thoroughly with ethyl acetate. The filtrates were washed with 1 N HCl aqueous, brine, dried over anhydrous MgSO$_4$, filtered and concentrated in vacuo. The crude product 2-(4-bromo-phenyl)-4-trifluoromethyl-2H-pyrazole-3-carboxylic acid ethyl ester was used as is in the next step (291 mg, 0.80 mmol, 80%). HPLC (254 nm): Method 3, Rt 3.23 min. MS (ESI) m/z 365.2 [M+H$^+$].

Step 3: 2-(4-Bromo-phenyl)-4-trifluoromethyl-2H-pyrazole-3-carboxylic acid 2-(4-Bromo-phenyl)-4-trifluoromethyl-2H-pyrazole-3-carboxylic acid ethyl ester (291 mg, 0.80 mmol) in THF (8 mL) was treated with LiOH 1 N aqueous solution (8 mL) and the resulting mixture was stirred at room temperature for 3 hours. The reaction was deemed complete by thin layer chromatography and HPLC/MS. The reaction mixture was partitioned between ethyl acetate and 1 N aqueous HCl solution (100 mL v/v) and transferred to a separatory funnel. The organic layer was separated and the aqueous layer was back-extracted with ethyl acetate (30 mL). The combined organic layers were dried over anhydrous MgSO$_4$, filtered and concentrated in vacuo to afford the pure product as a white solid (268 mg, 0.80 mmol, quant.). HPLC (254 nm): Method 3 Rt 2.97 min. MS (ESI) m/z 335.2 [M+H$^+$].

Step 4: (R)-[2-(4-Bromo-phenyl)-4-trifluoromethyl-2H-pyrazol-3-yl]-carbamic acid 1-phenyl-ethyl ester 2-(4-Bromo-phenyl)-4-trifluoromethyl-2H-pyrazole-3-carboxylic acid (268 mg, 0.80 mmol) was suspended in toluene (8 mL) and treated with triethylamine (135 µL, 0.97 mmol). The resulting solution was treated with diphenylphosphoryl azide (209 µL, 0.97 mmol) and heated to 65° C. (R)-1-(phenyl)-ethanol (118 mg, 0.97 mmol) was added to the reaction mixture and the temperature was increased to 105° C. for 30 minutes, during which time vigorous gas evolution was observed. The reaction was brought to 65° C. and stirred at that temperature for 4 hours. The reaction was deemed complete by HPLC/MS. After cooling, the volatiles were removed in vacuo and the crude residue was purified by silica gel chromatography, eluting with a hexanes/ethyl acetate gradient. Product isolated as a white solid (195 mg, 0.43 mmol, 54%). HPLC (254 nm): Method 3 Rt 3.23 min. MS (ESI) m/z 454.0, 456.1 [M+H$^+$].

Step 5: (R)-1-{4'-[5-(1-Phenyl-ethoxycarbonylamino)-4-trifluoromethyl-pyrazol-1-yl]-biphenyl-4-yl}-cyclopropanecarboxylic acid A stirred suspension of (R)-[2-(4-Bromo-phenyl)-4-trifluoromethyl-2H-pyrazol-3-yl]-carbamic acid 1-phenyl-ethyl ester (98 mg, 0.22 mmol), 2:1 v/v toluene/ethanol (2.2 mL), 2 M aqueous solution of Na$_2$CO$_3$ (720 µL) and 4-(1-carboxycyclopropyl)phenylboronic acid, pinacol ester (124 mg, 0.43 mmol) was degassed under nitrogen for 10 minutes and treated with Pd[Ph$_3$P]$_4$ (12 mg, 0.01 mmol). The resulting mixture was immersed in an oil bath with stirring at 95° C. for 3 hours. The reaction was cooled, transferred to a separatory funnel and diluted with ethyl acetate (50 mL). The mixture was carefully treated with 1 N aqueous HCl solution (20 mL). The organic layer was separated, washed with brine, dried over anhydrous MgSO$_4$, filtered and concentrated in vacuo. The crude residue was purified by preparative TLC plate (1000 µm), eluting with a 1:1 v/v hexanes/ethyl acetate mixture. The product was obtained as a tan solid. Yield=6.8 mg (6%). HPLC (254 nm): Method 3, Rt 3.21 min. MS (ESI) m/z 536.3 [M+H$^+$].

Example 55: (R)-1-{2-Fluoro-4'-[5-(1-phenyl-ethoxycarbonylamino)-4-trifluoromethyl-pyrazol-1-yl]-biphenyl-4-yl}-cyclopropanecarboxylic acid The title compound was prepared in analogous fashion as in Example 54 using (R)-[2-(4-Bromo-phenyl)-4-trifluoromethyl-2H-pyrazol-3-yl]-carbamic acid 1-phenyl-ethyl ester (Example 54, Step 4 (98 mg, 0.22 mmol) and 1-[4-(dihydroxyboranyl)-3-fluorophenyl]cyclopropane-1-carboxylic acid. Yield 7 mg (6%) as a white solid. HPLC (254 nm): Method 3, Rt 3.11 min. MS (ESI) m/z 554.4 [M+H$^+$]

Example 56: (R)-1-(4-{5-[5-(1-Phenyl-ethoxycarbonylamino)-pyrazol-1-yl]-pyridin-2-yl}-phenyl)-cyclopropanecarboxylic acid

Step 1: 2-(6-Chloro-pyridin-3-yl)-2H-pyrazole-3-carboxylic acid ethyl ester 2-(6-Chloro-pyridin-3-yl)-2H-pyrazole-3-carboxylic acid ethyl ester was prepared in analogous fashion as in Example 49, Step 2 using (6-chloro-pyridin-3-yl)-hydrazine hydrochloride (9.89 g, 48.68 mmol; prepared according to WO2005/92856A1) and ethyl (E)-4-(dimethylamino)-2-oxo-but-3-enoate (7.82 g, 45.68 mmol, Example 49, Step 1). Yield=1.35 g (5.38 mmol, 12%). HPLC (254 nm): Method 3 Rt 2.87 min. MS (ESI) m/z 252.2 [M+H$^+$]. $^1$H NMR (500 MHz, CDCl$_3$) δ 8.50 (d, J=3.0 Hz, 1H); 7.77 (dd, J$_1$=3.0 Hz, J$_2$=8.5 Hz, 1H); 7.74 (d, J=2.0 Hz, 1H); 7.43 (d, J=8.5 Hz, 1H); 7.08 (d, J=2.0 Hz, 1H); 4.28 (q, J=7.5 Hz, 2H); 1.30 (t, J=7.5 Hz, 3H).

Step 2: 2-(6-Chloro-pyridin-3-yl)-2H-pyrazole-3-carboxylic acid hydrochloride salt A stirred solution of 2-(6-Chloro-pyridin-3-yl)-2H-pyrazole-3-carboxylic acid ethyl ester [Example 56, step 1] (1.35 g, 5.4 mmol) in THF/water 8:2 v/v (35 mL) was treated with LiOH 1 N aqueous solution (6.5 mL) and the resulting mixture was stirred at room temperature for 3 hours. The reaction was deemed complete by thin layer chromatography and HPLC/MS. The reaction mixture was diluted with water (100 mL) and washed with dichloromethane (60 mL). The aqueous layer was acidified with 1 N aqueous HCl solution to pH 2 resulting in a white suspension. The solids were filtered, rinsed with water and air-dried to afford the title compound as a white solid. Yield=0.90 g (3.46 mmol, 64%). HPLC (254 nm): Method 3 Rt 2.65 min. MS (ESI) m/z 224.3 [M+H$^+$].

Step 3: (R)-[2-(6-Chloro-pyridin-3-yl)-2H-pyrazol-3-yl]-carbamic acid 1-phenyl-ethyl ester 2-(6-Chloro-pyridin-3-yl)-2H-pyrazole-3-carboxylic acid hydrochloride salt [Example 56, step 2] (0.90 g, 4.03 mmol) was suspended in toluene (27 mL) and treated with di-isoproprylethylamine (1.28 mL, 8.86 mmol). The resulting solution was treated with diphenylphosphoryl azide (855 μL, 4.83 mmol) and heated to 65° C. (R)-1-(phenyl)-ethanol (600 μL, 6.03 mmol) was added to the reaction mixture and the temperature was increased to 105° C. for 30 minutes, during which time vigorous gas evolution was observed. The reaction was brought to 65° C. and stirred at that temperature for 4 hours. The reaction was deemed complete by HPLC/MS. After cooling, volatiles were removed in vacuo and the crude residue purified by silica gel chromatography, eluting with a hexanes/ethyl acetate gradient. Product isolated as a white solid. Yield=0.60 g (1.75 mmol, 44%). HPLC (254 nm): Method 3 Rt 3.05 min. MS (ESI) m/z 343.2 [M+H$^+$].

Step 4: (R)-1-(4-{5-[4-Methyl-5-(1-phenyl-ethoxycarbonylamino)-pyrazol-1-yl]-pyridin-2-yl}-phenyl)-cyclopropanecarboxylic acid methyl ester A stirred suspension of (R)-[2-(6-Chloro-pyridin-3-yl)-2H-pyrazol-3-yl]-carbamic acid 1-phenyl-ethyl ester [Example 56, step 3] (240 mg, 0.70 mmol) in 2:1 v/v toluene/ethanol (7 mL), 2 M aqueous solution of Na$_2$CO$_3$ (1.5 mL) and 1-[4-(4,4,5,5-tetramethyl-[1,3,2]dioxaborolan-2-yl)-phenyl]-cyclopropanecarboxylic acid methyl ester (260 mg, 0.84 mmol) was degassed under nitrogen for 10 minutes and treated with Pd[Ph$_3$P]$_4$ (42 mg, 0.036 mmol). The resulting mixture was immersed in an oil bath with stirring at 90° C. for 15 hours. The reaction was cooled, transferred to a separatory funnel and diluted with ethyl acetate (50 mL). The mixture was carefully treated with 1 N aqueous HCl solution (20 mL). The organic layer was separated, washed with brine, dried over anhydrous MgSO$_4$, filtered and concentrated in vacuo. The crude residue was purified by silica gel chromatography, eluting with a 0-30% hexanes/ethyl acetate gradient of increasing polarity. The product was obtained as a tan solid. Yield=136 mg (0.28 mmol, 40%). HPLC (254 nm): Method 3 Rt 2.93 min. MS (ESI) m/z 483.4 [M+H$^+$].

Step 6: (R)-1-(4-{5-[5-(1-Phenyl-ethoxycarbonylamino)-pyrazol-1-yl]-pyridin-2-yl}-phenyl)-cyclopropanecarboxylic acid A solution of (R)-1-(4-{5-[4-Methyl-5-(1-phenyl-ethoxycarbonylamino)-pyrazol-1-yl]-pyridin-2-yl}-phenyl)-cyclopropanecarboxylic acid methyl ester (136 mg, 0.28 mmol) in a 2:1 v/v mixture of THF/water (3 mL) was treated with a 1 N LiOH aqueous solution (420 μL) and stirred at ambient temperature for 16 hours. The reaction was brought to pH 1 by addition of a 1 N HCl aqueous solution. The mixture was extracted with EtOAc and washed with water. The organic layer was dried over anhydrous Na$_2$SO$_4$, filtered and concentrated in vacuo. The product was obtained as an off white solid Prepared in analogous fashion as in Example M1, Step 6 using the following reagents and amounts: (R)-1-(4-{5-[5-(1-phenyl-ethoxycarbonylamino)-pyrazol-1-yl]-pyridin-2-yl}-phenyl)-cyclopropanecarboxylic acid methyl ester (136 mg, 0.28 mmol), THF/water 2:1 v/v (3 mL), 1 N aqueous LiOH solution (420 μL). Yield=15 mg (0.032 mmol, 11%). HPLC (254 nm): Method 3 Rt 2.93 min. MS (ESI) m/z 483.3 [M+H$^+$].

Compounds 57-458 of Table 1 and derivatives thereof are prepared from the according to procedures outlined for compounds 1-56. The heterocyclic amines or esters required to assemble the corresponding carbamates were prepared based on methods described in citations 1-24.

Certain isoxazole substitutions are prepared following construction of the appropriate aryl isoxazole (3, Scheme 1). Direct fluorination or bromination and cyanation provides arylbromide (4) or acid (5) after palladium catalyzed carbonylation.

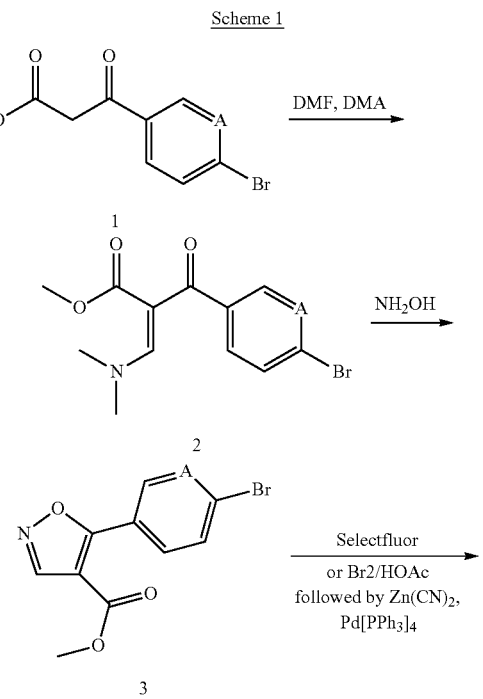

Scheme 1

-continued

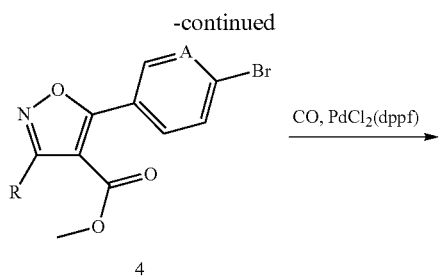

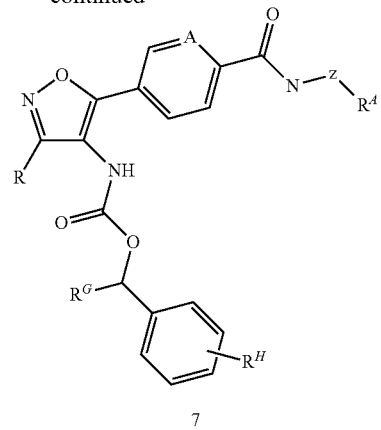

F = F, Br, CN
A = CH, N

The acid (5) may be reduced to alcohol (8) and/or converted to its chloride (9) as in scheme 3. Alcohols may be converted to their ether analogs (10) by rhodium catalyzed insertion into diazo intermediates $_2N^+$-z-$R^B$, or the amines (11) may be generated from chlorides (IX)

F = F, Br, CN
A = Ch, N

Acid (5, scheme 2) may be directly coupled with amines to afford amide intermediates (6) which may be converted to the carbamate products (7) following acid hydrolysis, Curtius rearrangement and deprotection with acid.

Scheme 3

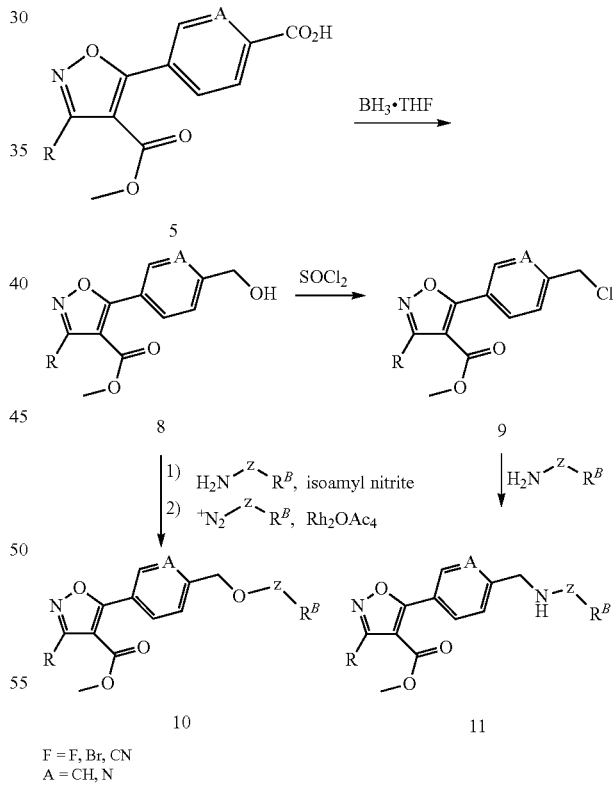

Scheme 2

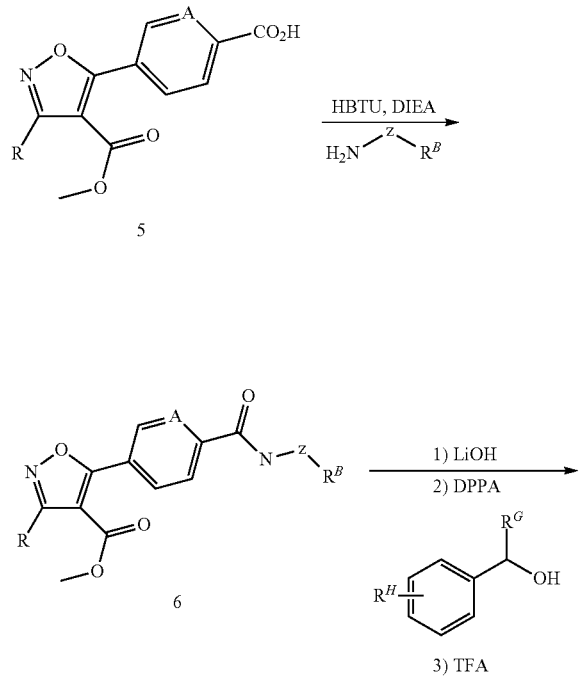

Alternatively the bromides (4) may be directly coupled to alcohols or amines (UV—Z—$R^B$) whereby U is —OH or —NH2 by thermal or metal catalyzed halide displacement as in scheme 4. All key intermediates (10-12) may be further modified to produce final products as described in scheme 1 using acid hydrolysis, Curtius rearrangement followed by acid deprotection

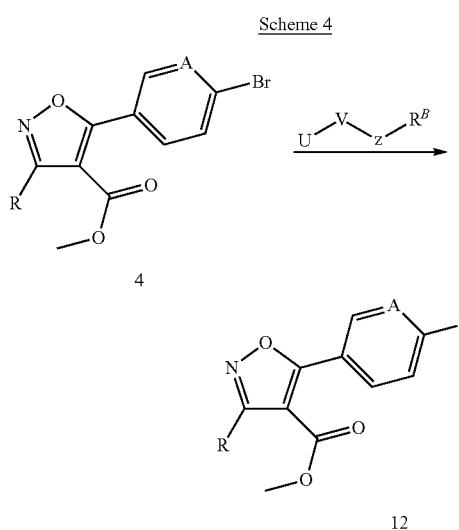

Scheme 4

4

12

Example 57. Receptor Binding Assays

Binding affinity of compounds of Formula I-XII were determined based on their ability to displace tritiated lyso-phosphatidic acid ([$^3$H]-LPA) from CHO cells expressing LPA1R in a protocol similar to that described in reference 17. In a 96 well format, CHO cells expressing human LPA1R [Cerep] were treated with [$^3$H]-LPA (2 nM). Test compounds were added in increasing concentration to each well and incubated at room temperature for 90 minutes. At this time the plates were washed and the wells counted for radioactivity. Results were compared to a control in which cells were treated with [$^3$H]-LPA in the presence of 10 μM unlabeled LPA. The specific ligand binding to the receptors was defined as the difference between the total binding and the nonspecific binding determined in the presence of an excess of unlabelled ligand. The results were expressed as a percent of control specific binding ((measured specific binding/control specific binding)×100) and as a percent inhibition of control specific binding (100−((measured specific binding/control specific binding)×100)) obtained in the presence of the test compounds. The $IC_{50}$ value (concentration causing a half-maximal inhibition of control specific binding) and Hill coefficient (nH) were determined by non-linear regression analysis of the competition curve generated with mean replicate values using Hill equation curve fitting (Y=D+[(A−D)/(1+(C/C50)nH)], where Y=specific binding, D=minimum specific binding, A=maximum specific binding, C=compound concentration, C50=IC50, and nH=slope factor). This analysis was performed using a software developed at Cerep (Hill software) and validated by comparison with data generated by the commercial software Sigma-Plot® 4.0 for Windows® (© 1997 by SPSS Inc.). The inhibition constant (Ki) was calculated using the Cheng Prusoff equation (Ki=IC50/(1+(L/KD)), where L=concentration of radioligand in the assay, and KD=affinity of the radioligand for the receptor). A scatchard plot was used to determine the Kd.

Example 58. Calcium Flux Assay

Inhibition of LPA-stimulated $Ca^{2+}$ flux was used to assess compound potency using FLIPR technology in a 96 well plate format. The assay buffer used was a modified Hanks Balanced Salt Solution (HBSS) where HBSS was supplemented to contain 20 mM HEPES and 2.5 mM Probenecid at pH7.4 (Millipore, GPCR Profiler®). LPA1R expressing cells (Millipore) were plated and prepared 24 hours prior to assay of test articles. $Ca^{2+}$ ion flux was assessed from fluorescence of a Fluo-based No Wash $Ca^{2+}$ dye. Antagonist data are generated from plates with LPA concentrations sufficient to generate 80% efficacy [$EC_{80}$]. Percentage inhibition was calculated from a reduction of efficacy according to concentration of compounds of Formula I-VI. For dose responses the inhibition data was used to calculate compound $IC_{50}$.

The agonist assay was conducted on a FLIPR$^{TETRA}$ instrument where the test compound(s), vehicle controls, and reference agonist were added to the assay plate after a fluorescence baseline was established. The agonist assay was a total of 180 seconds and was used to assess each compound's ability to activate each GPCR assayed. Upon completion of the agonist assay, the assay plate was removed from the FLIPR$^{TETRA}$ and incubated at 25° C. for seven (7) minutes. After the incubation period, the assay plate was placed back in the FLIPR$^{TETRA}$ and the antagonist assay was initiated.

Antagonist Assay:

Using $EC_{80}$ potency values determined during the agonist assay, all pre-incubated sample compound wells were challenged with $EC_{80}$ concentration of reference agonist after establishment of a fluorescence baseline. The antagonist assay was conducted using the same assay plate that was used for the agonist assay. The antagonist assay was conducted on a FLIPR$^{TETRA}$ instrument where 9 vehicle controls and $EC_{80}$ concentration of reference agonist were added to appropriate wells. The antagonist assay was a total of 180 seconds and was used to assess each compound's ability to inhibit each GPCR assayed.

Data Processing:

All assay plate data were subjected to appropriate baseline corrections. After baseline corrections were applied, maximum fluorescence values were exported and data processed to calculate percentage activation (relative to Emax reference agonist and vehicle control values), percentage inhibition (relative to EC80 and vehicle control values), and additional statistical values (i.e. Z', percentage variation between replicate data values) to assess the quality of each plate. Where assay plate data were rejected, additional experiments were conducted. All dose response curves were generated using GraphPad Prism. The curves were fit by utilizing "Sigmoidal Dose Response (Variable Slope)" equation where the bottom parameter was fixed to "0." Where appropriate, the top parameter was fixed to "100" to better predict potency values when a full curve was not generated by the concentrations assayed.

Antagonist activity data for representative compounds prepared according to the synthetic methods disclosed herein are presented in Table 2.

TABLE 2

In vitro biological data for representative compounds of Formula
I-XII Unless otherwise noted, compounds that were tested had
an $IC_{50}$ of less than 50 μM in the LPA1R $Ca^{2+}$ flux functional assay.

| Example Number | LPA1R Antagonist Activity |
| --- | --- |
| 1 | C |
| 2 | C |
| 3 | D |
| 4 | B |

TABLE 2-continued

In vitro biological data for representative compounds of Formula I-XII Unless otherwise noted, compounds that were tested had an $IC_{50}$ of less than 50 μM in the LPA1R $Ca^{2+}$ flux functional assay.

| Example Number | LPA1R Antagonist Activity |
|---|---|
| 5 | A |
| 6 | D |
| 7 | D |
| 8 | D |
| 9 | D |
| 10 | D |
| 11 | D |
| 12 | D |
| 13 | D |
| 14 | D |
| 15 | D |
| 16 | D |
| 17 | A |
| 18 | D |
| 19 | D |
| 20 | A |
| 21 | A |
| 22 | A |
| 23 | A |
| 24 | A |
| 25 | A |
| 26 | A |
| 27 | A |
| 28 | A |
| 29 | C |
| 30 | D |
| 30 | C |
| 31 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | B |
| 44 | A |
| 45 | A |
| 46 | C |
| 47 | B |
| 48 | C |
| 49 | A |
| 50 | A |
| 51 | A |
| 52 | A |
| 53 | A |
| 54 | B |
| 55 | B |
| 56 | A |

Unless otherwise noted, compounds that were tested had an $IC_{50}$ of less than 50 μM in the LPA1R $Ca^{2+}$ flux functional assay. A=less than 0.3 μM; B=greater than 0.3 μM and less than 1 μM; C=greater than 1 μM and less than 50 μM; D=greater than 50 μM

CITATIONS

[1] 1) Gyorkos A. C., Corrette C. P., ChoS. Y., Turner T. M., Aso K., Kori M., Gyoten M., Condroski K. R., Siedem C. S., Boyd S. A. WO2005099688, 2005

[2] 2) Maiti, Swarupananda; Sridharan, Vellaisamy; Menendez, J. Carlos; Journal of Combinatorial Chemistry, 2010, vol. 12, #5 p. 713-722

[3] 3) Takagi M., Nakamura T., Matsuda I., Kiguchi T., Ogawa N., Ozeki H. US2009/36450 A1, 2009

[4] 4) Lee, Len F.; Schleppnik, Francis M.; Howe, Robert K.; Journal of Heterocyclic Chemistry, 1985, vol. 22, p. 1621-1630

[5] 5) Dehmel, Florian; Abarbri, Mohamed; Knochel, Paul; Synlett, 2000, #3 p. 345-346

[6] 6) Abarbri, Mohamed; Thibonnet, Jerome; Berillon, Kaurent; Dahmel, Florian; Rottlaender, Mario; Knochel, Paul; Journal of Organic Chemistry, 2000, vol. 65, #15 p. 4618-4634

[7] 7) Gagnon et al.; Canadian Journal of Chemistry, 1953, vol. 31, p. 673, 682

[8] 8) Malki, Fatiha; Touati, Abdelkader; Rahal, Said; Moulay, Saad; Asian Journal of Chemistry, 2011, vol. 23, #3 p. 961-967

[9] 9) Ohata S., Kato K., Toriyabe K., Ito Y., Hamaguchi R., Nakano Y., EP2202226 A1, 2010

[10] 10) Maekawa T., Hara R., Odaka H., Kimura H., Mizufune H., Fukatsu K., WO03099793, 2003

[11] 11) Sam, Sik Kim; Bo, Seung Choi; Jae, Hoon Lee; Ki, Kon Lee; Tae, Hee Lee; Shin, Hyunik; Young, Ho Kim; Synlett, 2009, #4 p. 599-602

[12] 12) Zhu, Yulin; Pan, Yuanjiang; Huang, Shenlin; Synthetic Communications, 2004, vol. 34, #17 p. 3167-3174

[13] 13) Pathak, Vijai Nath; Gupta, Ragini; Varshney, Bindu; Indian Journal of Chemistry, Section B: Organic Chemistry Including Medicinal Chemistry, 2008, vol. 47, #3 p. 434-438

[14] 14) Pierre, Fabrice; O'Brien, Sean E.; Haddach, Mustapha; Bourbon, Pauline; Schwaebe, Michael K.; Stefan, Eric; Darjania, Levan; Stansfield, Ryan; Ho, Caroline; Siddiqui-Jain, Adam; Streiner, Nicole; Rice, William G.; Anderes, Kenna; Ryckman, David M.; Bioorganic and Medicinal Chemistry Letters, 2011, vol. 21, #6 p. 1687-1691

[15] 15) Boes M., Galley G., Godel T., Hoffmann T., Hunkeler W., Schnider P., Stadler H. U.S. Pat. No. 6,756, 380, 2004

[16] 16) Aissaoui H., Boss C., Hazemann J., Koberstein R., Siegrist R., Sifferlen T. US2011105491, 2011

[17] 17) An S., Dickens M. A., Bleu T., Hallmark O. G., Goetzl E. J. Biochemical and Biophysical Research Communications (1997) 231, 619-622

[18] 18) P Schenone, P Fossa, G Menozzi, (1991) Journal of Heterocyclic Chemistry, 1991, vol. 28, #2 p. 453-457

[19] 19) T Kimura, N Ohkawa, A Nakao, T Nagasaki, T Shimozato, (2006). EP1632488 A1,

[20] 20) N D Smith, S P Govek, M Kahraman, J D Julien, J Y Nagasawa, K L Douglas, C L Bonnefous, A G Lai. (2013) WO2013/142266 A1

[21] 21) B Cottyn, F Terrier, D Vichard, P Nioche, Pierre; Raman. (2007) Synlett, #8 p. 1203-1206

[22] 22) S L Buchwald, T D Senecal, W Shu, Wei. (2013) Angewandte Chemie—International Edition, 2013, vol. 52, #38 p. 10035-10039.

[23] 23) X Guo, W Hu, H Huang, (2007) Angewandte Chemie—International Edition, 2007, vol. 46, #8 p. 1337-1339

[24] 24) S K Shah, Q T Truong, H Qi, W K Hagmann (2005). WO2005044785A1

What is claimed is:

1. A method for treatment of a lysophosphatidic acid-dependent disease or condition in a subject in need thereof, the method comprising:

administering to the subject a therapeutically effective amount of a compound having the structure of Formula I

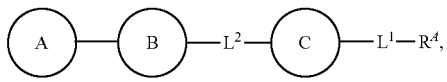

Formula I or a pharmaceutically acceptable salt or prodrug thereof, wherein $R^A$ is —$CO_2H$, —$CO_2R^B$, —CN, tetrazolyl, —C(=O)$NH_2$, —C(=O)$NHR^B$, —C(=O)$NHSO_2R^B$, or —C(=O)$NHCH_2CH_2SO_3H$ or a carboxylic acid isostere selected from the group consisting of

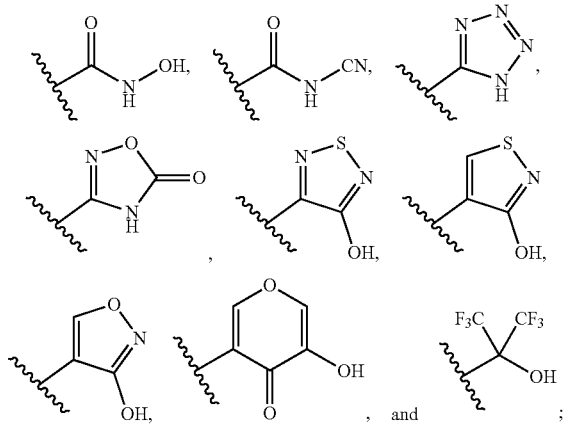

wherein $R^B$ is —H or —$C_1$-$C_4$ alkyl or has the structure of one of:

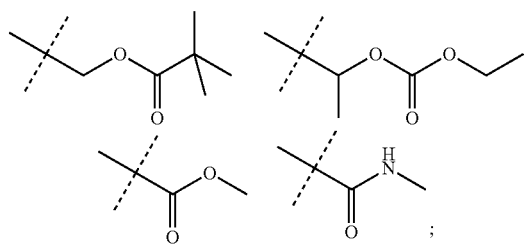

$L^1$ is absent or substituted or unsubstituted $C_1$-$C_6$ alkylene, substituted or unsubstituted $C_3$-$C_6$ cycloalkylene, substituted or unsubstituted $C_1$-$C_6$ fluoroalkylene, or substituted or unsubstituted $C_1$-$C_6$ heteroalkylene;

$L^2$ is absent;

Ring B has the structure of:

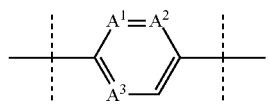

and is substituted or unsubstituted arylene, or substituted or unsubstituted heteroarylene, where when Ring B is substituted then Ring B is substituted with 1, 2, or 3 independently selected $R^H$, wherein $A^1$, $A^2$, and $A^3$ are independently N or C;

Ring A is a 5 membered heteroarene selected from one of:

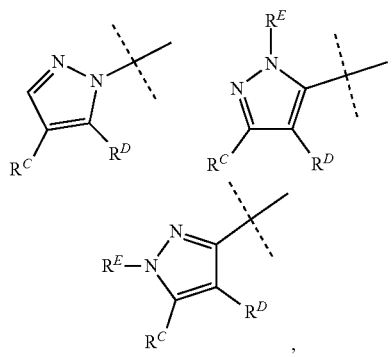

wherein the dashed line indicates the point of attachment of Ring A to Ring B, wherein $R^C$ is —CN, —F, —Cl, —Br, —I, —O$C_1$-$C_4$ alkyl, or $C_1$-$C_4$ fluoroalkyl;

and $R^D$ is —N($R^F$)—C(=O)XCH($R^G$)—CY, —N($R^F$)C(=O)XC($R^G$)$_2$—CY, —N($R^F$)C(=O)X—CY, —C(=O)N($R^F$)CH($R^G$)X—CY, or —C(=O)—N($R^F$)C($R^G$)$_2$X—CY, wherein X is absent, —O—, —NH— or —$CH_2$—;

$R^E$ is —H, —$C_1$-$C_4$ alkyl or —$C_1$-$C_4$ fluoroalkyl;

$R^F$ is —H or $C_1$-$C_4$ alkyl;

$R^G$ is independently selected from $R^E$, or one $R^G$ is $C_1$-$C_4$ alkyl and is taken together with CY and the carbon atom to which $R^G$ and CY are attached to define a substituted or unsubstituted carbocycle or a substituted or unsubstituted heterocycle, and the other $R^G$, when present, is as defined for $R^E$;

CY is substituted or unsubstituted $C_1$-$C_6$ alkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl, wherein when CY is substituted then CY is substituted with 1, 2, or 3 independently selected $R^H$;

wherein each $R^H$ is independently selected from —H, halogen, —CN, —$NO_2$, —OH, —$OR^J$, —$SR^J$, —S(=O)$R^J$, —S(=O)$_2R^J$, —N($R^J$)S(=O)$_2R^J$, —S(=O)$_2$N($R^L$)$_2$, —C(=O)$R^J$, OC(=O)$R^J$, —C(=O)$OR^J$, —OC(=O)$OR^J$, —N($R^L$)$_2$, —C(=O)N($R^L$)$_2$, —OC(=O)N($R^L$)$_2$, —N($R^J$)C(=O)N($R^L$)$_2$, —N($R^J$)C(=O)$R^J$, —N($R^J$)C(=O)$OR^J$, $C_1$-$C_4$ alkyl, $C_1$-$C_4$ fluoroalkyl, $C_1$-$C_4$ fluoroalkoxy, $C_1$-$C_4$ alkoxy, and $C_1$-$C_4$ heteroalkyl, wherein each $R^J$ is independently substituted or unsubstituted $C_1$-$C_6$ alkyl, substituted or unsubstituted $C_1$-$C_6$ heteroalkyl, substituted or unsubstituted $C_1$-$C_6$ fluoroalkyl, substituted or unsubstituted $C_3$-$C_6$ cycloalkyl, substituted or unsubstituted heterocycloalkyl, substituted or unsubstituted aryl, substituted or unsubstituted heteroaryl, —$C_1$-$C_4$ alkylene-(substituted or unsubstituted $C_3$-$C_6$ cycloalkyl), —$C_1$-$C_4$ alkylene-(substituted or unsubstituted heterocycloalkyl), —$C_1$-$C_4$ alkylene-(substituted or unsubstituted aryl), or —$C_1$-$C_4$ alkylene-(substituted or unsubstituted heteroaryl);

wherein each $R^L$ is independently —H, substituted or unsubstituted $C_1$-$C_6$ alkyl, substituted or unsubstituted $C_1$-$C_6$ heteroalkyl, substituted or unsubstituted $C_1$-$C_6$ fluoroalkyl, substituted or unsubstituted $C_3$-$C_6$ cycloalkyl, substituted or unsubstituted heterocycloalkyl, substituted or unsubstituted aryl, substituted or unsubstituted heteroaryl, —$C_1$-$C_4$ alkylene-(substituted or unsubstituted cycloalkyl), —$C_1$-$C_4$ alkylene-(substituted or unsubstituted heterocycloalkyl), —$C_1$-$C_4$ alkylene(substituted or unsubstituted aryl), or —$C_1$-$C_4$ alkylene-(substituted or unsubstituted heteroaryl), or when $R^H$ is —S(=O)$_2$N($R^L$)$_2$, —N($R^L$)$_2$, —C(=O)N($R^L$)$_2$, —OC(=O)N($R^L$)$_2$ or N($R^J$)C(=O)N($R^L$)$_2$, each $R^L$ is independently —H or $C_1$-$C_6$ alkyl, or the $R^L$ groups independently are $C_1$-$C_6$ alkyl, which are taken together with the N atom to which they are attached to define a substituted or unsubstituted heterocycle; and Ring C is substituted or unsubstituted $C_3$-$C_{10}$ cycloalkylene, substituted or unsubstituted $C_2$-$C_{10}$ heterocycloalkylene, substituted or unsubstituted arylene, or substituted or unsubstituted heteroarylene, where when Ring C is substituted then Ring C is substituted with 1, 2, or 3 independently selected $R^H$, wherein $R^H$ is as previously defined.

2. The method according to claim 1, wherein the compound is selected from: 2-[4-[4-[5-[1-(2-chlorophenyl)ethoxycarbonylamino]-4-cyano-pyrazol-1-yl]phenyl]phenyl]acetic acid, (R)-1-(4'-{5-[1-(2-Chloro-phenyl)-ethoxycarbonylamino]-4-fluoro-pyrazol-1-yl}-3-fluoro-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-2-fluoro-biphenyl-4-yl)-cyclopropanecarboxylic acid, (R)-1-(2-Chloro-4'-{5-[1-(2-chloro-phenyl)-ethoxycarbonylamino]-4-fluoro-pyrazol-1-yl}-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-2-methyl-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-biphenyl-4-yl)-cyclopropanecarboxylic acid, (R)-1-{4'-[5-(1-Phenyl-ethoxycarbonylamino)-4-trifluoromethyl-pyrazol-1-yl]-biphenyl-4-yl}-cyclopropanecarboxylic acid, (R)-1-{2-Fluoro-4'-[5-(1-phenyl-ethoxycarbonylamino)-4-trifluoromethyl-pyrazol-1-yl]-biphenyl-4-yl}-cyclopropanecarboxylic acid, 2-[4-[4-[4-cyano-5-(1-phenylethoxycarbonylamino)pyrazol-1-yl]phenyl]phenyl]acetic acid, 1-[4-[4-[4-cyano-5-(1-phenylethoxycarbonylamino)pyrazol-1-yl]phenyl]phenyl]cyclopropanecarboxylic acid, 1-[4-[4-[5-[1-(2-chlorophenyl)ethoxycarbonylamino]-4-cyano-pyrazol-1-yl]phenyl]phenyl]cyclopropanecarboxylic acid, 2-[4-[4-[4-cyano-5-(1-phenylethoxycarbonylamino)pyrazol-1-yl]phenyl]phenyl]-2-methyl-propanoic acid, 2-[4-[4-[5-[1-(2-chlorophenyl)ethoxycarbonylamino]-4-cyano-pyrazol-1-yl]phenyl]phenyl]-2-methyl-propanoic acid, 1-{4'-[4-Fluoro-5-(1-phenylethoxycarbonylamino)-1H-pyrazol-1-yl]-4-biphenylyl}cyclopropanecarboxylic acid, 1-(4'-{5-[1-(o-Chlorophenyl)ethoxycarbonylamino]-4-fluoro-1H-pyrazol-1-yl}-4-biphenylyl)cyclopropanecarboxylic acid, 1-{3-Fluoro-4'-[4-fluoro-5-(1-phenylethoxycarbonylamino)-1H-pyrazol-1-yl]-4-biphenylyl}cyclopropanecarboxylic acid, 1-(4'-5-[1-(o-Chlorophenyl)ethoxycarbonylamino]-4-fluoro-1H-pyrazol-1-yl}-3-fluoro-4-biphenylyl)cyclopropanecarboxylic acid, 1-{2-Fluoro-4'-[4-fluoro-5-(1-phenylethoxycarbonylamino)-1H-pyrazol-1-yl]-4-biphenylyl}cyclopropanecarboxylic acid, 1-(4'-5-[1-(o-Chlorophenyl)ethoxycarbonylamino]-4-fluoro-1H-pyrazol-1-yl-2-fluoro-4-biphenylyl)cyclopropanecarboxylic acid, 1-(2-Chloro-4'-{5-[1-(o-chlorophenyl)ethoxycarbonylamino]-4-fluoro-1H-pyrazol-1-yl}-4-biphenylyl)cyclopropanecarboxylic acid, 1-(4-{p-[4-Fluoro-5-(1-phenylethoxycarbonylamino)-1H-pyrazol-1-yl]phenyl}tolyl)cyclopropanecarboxylic acid, 1-[4-(p-{5-[1-(o-Chlorophenyl)ethoxycarbonylamino]-4-fluoro-1H-pyrazol-1-yl}phenyl)tolyl]cyclopropanecarboxylic acid, 1-(p-{5-[4-Fluoro-5-(1-phenylethoxycarbonylamino)-1H-pyrazol-1-yl]-2-pyridyl}phenyl)cyclopropanecarboxylic acid, 1-[p-(5-{5-[1-(o-Chlorophenyl)ethoxycarbonylamino]-4-fluoro-1H-pyrazol-1-yl}-2-pyridyl)phenyl]cyclopropanecarboxylic acid, 1-(2-Fluoro-4-{5-[4-fluoro-5-(1-phenylethoxycarbonylamino)-1H-pyrazol-1-yl]-2-pyridyl}phenyl)cyclopropanecarboxylic acid, 1-[4-(5-{5-[1-(o-Chlorophenyl)ethoxycarbonylamino]-4-fluoro-1H-pyrazol-1-yl}-2-pyridyl)-2-fluorophenyl]cyclopropanecarboxylic acid, 1-(3-Fluoro-4-{5-[4-fluoro-5-(1-phenylethoxycarbonylamino)-1H-pyrazol-1-yl]-2-pyridyl}phenyl)cyclopropanecarboxylic acid, 1-[4-(5-{5-[1-(o-Chlorophenyl)ethoxycarbonylamino]-4-fluoro-1H-pyrazol-1-yl}-2-pyridyl)-3-fluorophenyl]cyclopropanecarboxylic acid, 1-(p-{5-[4-Cyano-5-(1-phenylethoxycarbonylamino)-1H-pyrazol-1-yl]-2-pyridyl}phenyl)cyclopropanecarboxylic acid, 1-[p-(5-{5-[1-(o-Chlorophenyl)ethoxycarbonylamino]-4-cyano-1H-pyrazol-1-yl}-2-pyridyl)phenyl]cyclopropanecarboxylic acid, 1-(4-{5-[4-Cyano-5-(1-phenylethoxycarbonylamino)-1H-pyrazol-1-yl]-2-pyridyl}-2-fluorophenyl)cyclopropanecarboxylic acid, 1-[4-(5-{5-[1-(o-Chlorophenyl)ethoxycarbonylamino]-4-cyano-1H-pyrazol-1-yl}-2-pyridyl)-2-fluorophenyl]cyclopropanecarboxylic acid, 1-(4-{5-[4-Cyano-5-(1-phenylethoxycarbonylamino)-1H-pyrazol-1-yl]-2-pyridyl}-3-fluorophenyl)cyclopropanecarboxylic acid, and 1-[4-(5-{5-[1-(o-Chlorophenyl)ethoxycarbonylamino]-4-cyano-1H-pyrazol-1-yl}-2-pyridyl)-3-fluorophenyl]cyclopropanecarboxylic acid.

3. The method according to claim 1, wherein the compound is (R)-1-(4'-{5-[1-(2-Chloro-phenyl)-ethoxycarbonylamino]-4-fluoro-pyrazol-1-yl}-2-fluoro-biphenyl-4-yl)-cyclopropanecarboxylic acid.

4. The method according to claim 1, wherein the compound is 1-{4'-[4-Fluoro-5-(1-phenylethoxycarbonylamino)-1H-pyrazol-1-yl]-4-biphenylyl}cyclopropanecarboxylic acid.

5. The method according to claim 1, wherein the lysophosphatidic acid-dependent disease or condition is liver fibrosis.

6. The method according to claim 1, wherein the lysophosphatidic acid-dependent disease or condition is nonalcoholic steatohepatitis (NASH).

7. The method according to claim 6, further comprising: coadministering to the subject a therapeutically active agent selected from the group consisting of pioglitazone, lovastatin, simvastatin, pravastatin, fluvastatin, atorvastatin, nisvastatin, rosuvastatin, and chemokine receptor antagonists.

8. The method according to claim 1, wherein the lysophosphatidic acid-dependent disease or condition is nephropathy.

9. The method according to claim 1, wherein the lysophosphatidic acid-dependent disease or condition is diabetic nephropathy.

10. The method according to claim 9, further comprising: coadministering to the subject a therapeutically active agent selected from the group consisting of losartan, valsartan, candesartan, irbesartan, telmisartan, olmesartan, enalapril, mast cell stabilizers, antihistamines, ketotifen, olopatadine, and rupatadine.

11. A method for treatment of a lysophosphatidic acid-dependent disease or condition in a subject in need thereof, the method comprising:

administering to the subject a therapeutically effective amount of a pharmaceutical composition comprising an active compound and a pharmaceutically acceptable excipient, the active compound having the structure of Formula I

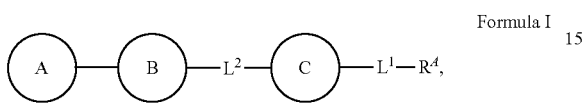

Formula I or a pharmaceutically acceptable salt or prodrug thereof, wherein $R^A$ is —$CO_2H$, —$CO_2R^B$, —CN, tetrazolyl, —C(=O)$NH_2$, —C(=O)$NHR^B$, —C(=O)$NHSO_2R^B$, or —C(=O)$NHCH_2CH_2SO_3H$ or a carboxylic acid isostere selected from the group consisting of

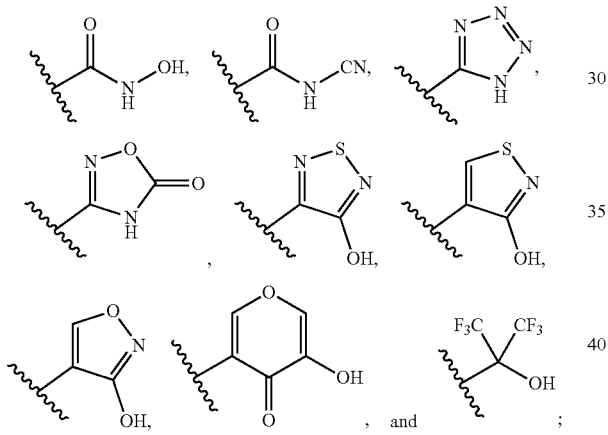

wherein $R^B$ is —H or —$C_1$-$C_4$ alkyl or has the structure of one of:

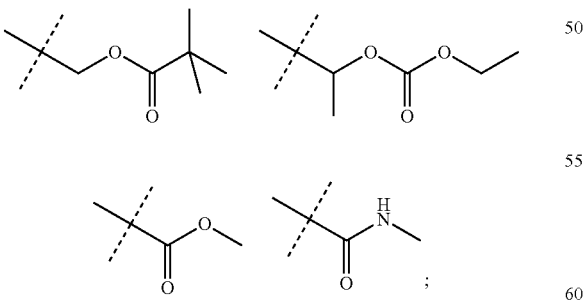

$L^1$ is absent or substituted or unsubstituted $C_1$-$C_6$ alkylene, substituted or unsubstituted $C_3$-$C_6$ cycloalkylene, substituted or unsubstituted $C_1$-$C_6$ fluoroalkylene, or substituted or unsubstituted $C_1$-$C_6$ heteroalkylene;

$L^2$ is absent;

Ring B has the structure of:

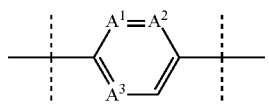

and is substituted or unsubstituted arylene, or substituted or unsubstituted heteroarylene, where when Ring B is substituted then Ring B is substituted with 1, 2, or 3 independently selected $R^H$, wherein $A^1$, $A^2$, and $A^3$ are independently N or C;

Ring A is a 5 membered heteroarene selected from one of:

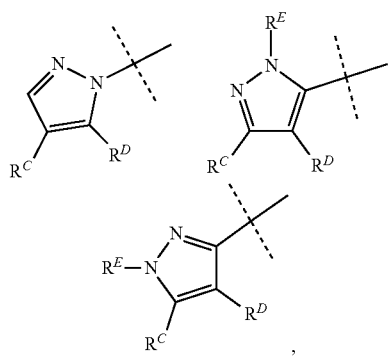

wherein the dashed line indicates the point of attachment of Ring A to Ring B, wherein $R^C$ is —CN, —F, —Cl, —Br, —I, —$OC_1$-$C_4$ alkyl, or $C_1$-$C_4$ fluoroalkyl;

and $R^D$ is —N($R^F$)—C(=O)XCH($R^G$)—CY, —N($R^F$)C(=O)XC($R^G$)$_2$—CY, —N($R^F$)C(=O)X—CY, —C(=O)N($R^F$)CH($R^G$)X—CY, or —C(=O)—N($R^F$)C($R^G$)$_2$X—CY, wherein X is absent, —O—, —NH— or —$CH_2$—;

$R^E$ is —H, —$C_1$-$C_4$ alkyl or —$C_1$-$C_4$ fluoroalkyl;

$R^F$ is —H or $C_1$-$C_4$ alkyl;

$R^G$ is independently selected from $R^E$, or one $R^G$ is $C_1$-$C_4$ alkyl and is taken together with CY and the carbon atom to which $R^G$ and CY are attached to define a substituted or unsubstituted carbocycle or a substituted or unsubstituted heterocycle, and the other $R^G$, when present, is as defined for $R^E$;

CY is substituted or unsubstituted $C_1$-$C_6$ alkyl, substituted or unsubstituted $C_3$-$C_{10}$ cycloalkyl, substituted or unsubstituted $C_2$-$C_{10}$ heterocycloalkyl, substituted or unsubstituted aryl, or substituted or unsubstituted heteroaryl, wherein when CY is substituted then CY is substituted with 1, 2, or 3 independently selected $R^H$;

wherein each $R^H$ is independently selected from —H, halogen, —CN, —$NO_2$, —OH, —$OR^J$, —$SR^J$, —S(=O)$R^J$, —S(=O)$_2R^J$, —N($R^J$)S(=O)$_2R^J$, —S(=O)$_2N(R^L)_2$, —C(=O)$R^J$, OC(=O)$R^J$, —C(=O)$OR^J$, —OC(=O)$OR^J$, —N($R^L$)$_2$, —C(=O)N($R^L$)$_2$, —OC(=O)N($R^L$)$_2$, —N($R^J$)C(=O)N($R^L$)$_2$, —N($R^J$)C(=O)$R^J$, —N($R^J$)C(=O)$OR^J$, $C_1$-$C_4$ alkyl, $C_1$-$C_4$ fluoroalkyl, $C_1$-$C_4$ fluoroalkoxy, $C_1$-$C_4$ alkoxy, and $C_1$-$C_4$ heteroalkyl, wherein each $R^J$ is independently substituted or unsubstituted $C_1$-$C_6$ alkyl, substituted or unsubstituted $C_1$-$C_6$ heteroalkyl, substituted or unsubstituted $C_1$-$C_6$ fluoroalkyl, substituted or unsubstituted $C_3$-$C_6$ cycloalkyl, substituted or unsubstituted heterocycloalkyl, substituted or unsubstituted aryl, substituted or unsubstituted heteroaryl, —$C_1$-$C_4$ alkylene-(substituted or unsubstituted $C_3$-$C_6$ cycloalkyl), —$C_1$-$C_4$ alkylene-(substituted or unsubstituted heterocycloalkyl), —$C_1$-$C_4$ alkylene-(substituted or unsubstituted aryl), or —$C_1$-$C_4$ alkylene-(substituted or unsubstituted heteroaryl);
wherein each $R^L$ is independently —H, substituted or unsubstituted $C_1$-$C_6$ alkyl, substituted or unsubstituted $C_1$-$C_6$ heteroalkyl, substituted or unsubstituted $C_1$-$C_6$ fluoroalkyl, substituted or unsubstituted $C_3$-$C_6$ cycloalkyl, substituted or unsubstituted heterocycloalkyl, substituted or unsubstituted aryl, substituted or unsubstituted heteroaryl, —$C_1$-$C_4$ alkylene-(substituted or unsubstituted cycloalkyl), —$C_1$-$C_4$ alkylene-(substituted or unsubstituted heterocycloalkyl), —$C_1$-$C_4$ alkylene(substituted or unsubstituted aryl), or —$C_1$-$C_4$ alkylene-(substituted or unsubstituted heteroaryl),
or when $R^H$ is —S(=O)$_2$N($R^L$)$_2$, —N($R^L$)$_2$, —C(=O)N($R^L$)$_2$, —OC(=O)N($R^L$)$_2$ or N($R^J$)C(=O)N($R^L$)$_2$, each $R^L$ is independently —H or $C_1$-$C_6$ alkyl, or the $R^L$ groups independently are $C_1$-$C_6$ alkyl, which are taken together with the N atom to which they are attached to define a substituted or unsubstituted heterocycle; and
Ring C is substituted or unsubstituted $C_3$-$C_{10}$ cycloalkylene, substituted or unsubstituted $C_2$-$C_{10}$ heterocycloalkylene, substituted or unsubstituted arylene, or substituted or unsubstituted heteroarylene, where when Ring C is substituted then Ring C is substituted with 1, 2, or 3 independently selected $R^H$, wherein $R^H$ is as previously defined.

12. The method according to claim 11, wherein the pharmaceutical composition comprises one or two active compounds having the structure of Formula I.

13. The method according to claim 11, wherein the pharmaceutical composition is a solid formulation selected from the group consisting of a tablet, a capsule, a caplet, and a gelcap, and the administering is performed orally.

14. The method according to claim 11, wherein the pharmaceutical composition is a liquid formulation selected from the group consisting of a syrup, a gel, and an ointment, and the administering is performed parenterally or enterally.

15. The method according to claim 11, further comprising:
coadministering to the subject a therapeutically active agent selected from the group consisting of corticosteroids, immunosuppressants, analgesics, anti-cancer agents, anti-inflammatories, chemokine receptor antagonists, bronchodilators, leukotriene receptor antagonists, leukotriene formation inhibitors, platelet activating factor receptor antagonists, monoacylglycerol kinase inhibitors, phospholipase A1 inhibitors, phospholipase A2 inhibitors, and lysophospholipase D (lysoPLD) inhibitors, autotaxin inhibitors, decongestants, mast cell stabilizers, antihistamines, mucolytics, anticholinergics, antitussives, expectorants, β-2 agonists, and combinations thereof.

16. The method according to claim 11, further comprising:
coadministering to the subject a therapeutic agent selected from the group consisting of gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, trastuzumab, BAY 11-7082, PKC412, PD 184352, paclitaxel, and analogs of Taxol, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; amino glutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; deazaguanine; deazaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin II, interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spiro germanium hydrochloride; spiromustine; spiroplatin; streptonigrin; streptozotocin; sulofenur; talisomycin; tecogalan sodium; tegafur; teloxantrone hydrochloride; temoporfm; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, mechloroethamine, cyclophosphamide, chlorambucil, meiphalan, ethylenimine, hexamethylmelamine, thiotepa, busulfan, carmustine, lomusitne, semustine, streptozocin, ortriazenes, dacarbazine, methotrexate, fluorouracil, floxouridine, Cytarabine, mercaptopurine, thioguanine, pentostatin, hydroxyprogesterone caproate, megestrol acetate, medroxyprogesterone acetate, estrogens, diethylstilbestrol, ethinyl estradiol, tamoxifen, testosterone propionate, fluoxymesterone, flutamide, leuprolide, cisplatin, carboblatin, mitoxantrone, procarbazine, mitotane, amino glutethimide, Erbulozole, Dolastatin 10, Mivobulin isethionate, Vincristine, NSC-639829, Discodermolide, ABT-751, Altorhyrtin A and Altorhyrtin C, Spongistatins 1-9, Cemadotin hydrochloride, Epothilone A, Epothilone B, Epothilone C, Epothilone D, Epothilone E, Epothilone F, Epothilone B N-oxide, Epothilone AN-oxide, 16-aza-epothilone B, 21 aminoepothilone B, 21-hydroxyepothilone D, 26-fluoroepothilone, Auristatin PE, Soblidotin, Cryptophycin 52, Vitilevuamide, Tubulysin A, Canadensol, Centaureidin, Oncocidin A1 Fijianolide B, Laulimalide, Narcosine, Nascapine, Hemiasterlin, Vanadocene acetylacetonate, Indanocine Eleutherobins, Caribaeoside, Caribaeolin, Halichondrin B, Diazonamide A, Taccalonolide A, Diozostatin, (−)-Phenylahistin, Myoseverin B, Resverastatin phosphate sodium, Aprepitant, *cannabis*, marinol, dronabinol, erythropoetin-α, Filgrastim, rituximab, natalizumab, cyclophosphamide, penicillamine, cyclosporine, nitrosoureas, cisplatin, carboplatin, oxaliplatin, methotrexate, azathioprine, mercaptopurine, pyrimidine analogues, protein synthesis inhibitors, dactinomycin, anthracyclines, mitomycin C, bleomycin, mithramycin, Atgam® Thymoglobuline®, OKT3®, basiliximab, daclizumab, cyclosporin, tacrolimus, sirolimus, Interferons, opioids, infliximab, etanercept, adalimumab, golimumab, leflunomide, sulfasalazine, hydroxychloroquinine, minocycline, rapamicin, mycophenolic acid, mycophenolate mofetil, FTY720, Cyclosporin A (CsA) or tacrolimus (FK506), aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, valdecoxib, parecoxib, etoricoxib, lumiracoxib, betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, ulobetasol, pioglitazone, clofibrate, fenofibrate gemfibrozil, folic acid, isbogrel, ozagrel, ridogrel, dazoxiben, lovastatin, simvastatin, pravastatin, fluvastatin, atorvastatin, nisvastatin, and rosuvastatin, edaravone, vitamin C, citicoline and minicycline, (2R)-2-propyloctanoic acid, propranolol, nadolol, timolol, pindolol, labetalol, metoprolol, atenolol, esmolol and acebutolol, memantine, traxoprodil, tirofiban lamifiban, argatroban, enalapril, cyclandelate, losartan, valsartan, candesartan, irbesartan, telmisartan, olmesartan mepyramine pyrilamine, antazoline, diphenhydramine, carbinoxamine, doxylamine, clemastine, dimenhydrinate, pheniramine, chlorphenamine chlorpheniramine, dexchlorpheniramine, brompheniramine, triprolidine, cetirizine, cyclizine, chlorcyclizine, hydroxyzine, meclizine, loratadine, desloratidine, promethazine, alimemazine, trimeprazine, cyproheptadine, azatadine, ketotifen, acrivastine, astemizole, cetirizine, mizolastine, terfenadine, azelastine, epinastine, levocabastine, olopatadine, levocetirizine, fexofenadine, rupatadine, bepotastine, mucolytics, anticholinergics, antitussives, analgesics, expectorants, albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, pranlukast, tomelukast, zafirlukast, ambrisentan, bosentan, enrasentan, sitaxsentan, tezosentan, iloprost, treprostinil, pirfenidone, epinephrine, isoproterenol, orciprenaline, xanthines, zileuton, and combinations thereof.

17. The method according to claim 11, wherein the lysophosphatidic acid-dependent disease or condition is fibrosis, liver disease, acute hepatitis, chronic hepatitis, liver fibrosis, liver cirrhosis, portal hypertension, regenerative failure, nonalcoholic steatohepatitis (NASH), liver hypofunction, hepatic blood flow disorder, cell proliferative disease, cancer, inflammatory disease, psoriasis, nephropathy, diabetic nephropathy, pneumonia, gastrointestinal tract disease, irritable bowel syndrome (IBS), inflammatory bowel disease (IBD), abnormal pancreatic secretion, renal disease, urinary tract-associated disease, benign prostatic hyperplasia, symptoms associated with neuropathic bladder disease, spinal cord tumor, hernia of intervertebral disk, spinal canal stenosis, symptoms derived from diabetes, lower urinary tract disease, inflammatory disease of lower urinary tract, dysuria, frequent urination, pancreas disease, abnormal angiogenesis-associated disease, arterial obstruction, scleroderma, brain-associated disease, cerebral infarction, cerebral hemorrhage, nervous system diseases, neuropathic pain, peripheral neuropathy, pruritus, ocular disease, age-related macular degeneration (AMD), diabetic retinopathy, uveitis, proliferative vitreo-retinopathy (PVR), cicatricial pemphigoid, or glaucoma filtration surgery scarring.

18. The method according to claim 11, wherein the lysophosphatidic acid-dependent disease or condition is liver fibrosis, nonalcoholic steatohepatitis, nephropathy, or diabetic nephropathy.

19. The method according to claim 11, wherein the active compound comprises at least one of (R)-1-(4'-{5-[1-(2-Chloro-phenyl)-ethoxycarbonylamino]-4-fluoro-pyrazol-1-yl}-2-fluoro-biphenyl-4-yl)-cyclopropanecarboxylic acid, and 1-{4'-[4-Fluoro-5-(1-phenylethoxycarbonylamino)-1H-pyrazol-1-yl]-4-biphenylyl}cyclopropanecarboxylic acid.

20. A method for reducing signal transduction through a lysophosphatidic acid receptor (LPAR), the method comprising:
contacting the LPAR with a compound having the structure of Formula I

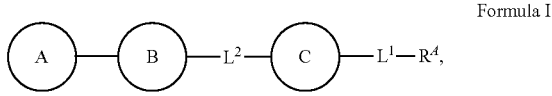
Formula I or a pharmaceutically acceptable salt or prodrug thereof,
wherein $R^A$ is —CO$_2$H, —CO$_2$R$^B$, —CN, tetrazolyl, —C(=O)NH$_2$, —C(=O)NHR$^B$, —C(=O)NHSO$_2$R$^B$, or —C(=O)NHCH$_2$CH$_2$SO$_3$H or a carboxylic acid isostere selected from the group consisting of

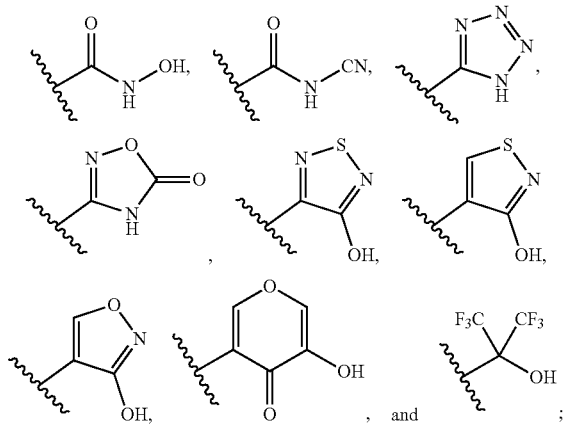

wherein $R^B$ is —H or —C$_1$-C$_4$ alkyl, or has the structure of one of:

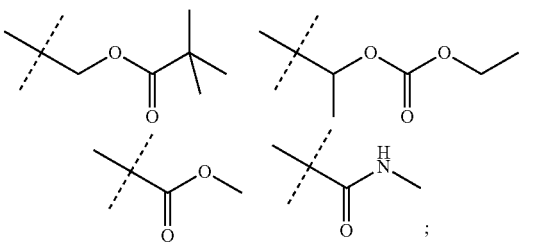

L$^1$ is absent or substituted or unsubstituted C$_1$-C$_6$ alkylene, substituted or unsubstituted C$_3$-C$_6$ cycloalkylene, substituted or unsubstituted C$_1$-C$_6$ fluoroalkylene, or substituted or unsubstituted C$_1$-C$_6$ heteroalkylene;
L$^2$ is absent;
Ring B has the structure of:

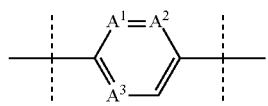

and is substituted or unsubstituted arylene, or substituted or unsubstituted heteroarylene, where when Ring B is substituted then Ring B is substituted with 1, 2, or 3 independently selected R$^H$,
wherein A$^1$, A$^2$, and A$^3$ are independently N or C;

Ring A is a 5 membered heteroarene selected from one of:

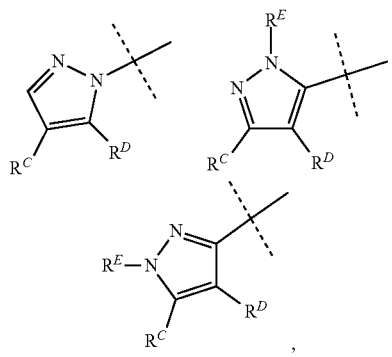

wherein the dashed line indicates the point of attachment of Ring A to Ring B,
wherein $R^C$ is —CN, —F, —Cl, —Br, —I, —OC$_1$-C$_4$ alkyl, or C$_1$-C$_4$ fluoroalkyl;
and $R^D$ is —N(R$^F$)—C(=O)XCH(R$^G$)—CY, —N(R$^F$)C(=O)XC(R$^G$)$_2$—CY, —N(R$^F$)C(=O)X—CY, —C(=O)N(R$^F$)CH(R$^G$)X—CY, or —C(=O)—N(R$^F$)C(R$^G$)$_2$X—CY, wherein X is absent, —O—, —NH— or —CH$_2$—;
$R^E$ is —H, —C$_1$-C$_4$ alkyl or —C$_1$-C$_4$ fluoroalkyl;
$R^F$ is —H or C$_1$-C$_4$ alkyl;
$R^G$ is independently selected from R$^E$, or one R$^G$ is C$_1$-C$_4$ alkyl and is taken together with CY and the carbon atom to which R$^G$ and CY are attached to define a substituted or unsubstituted carbocycle or a substituted or unsubstituted heterocycle, and the other R$^G$, when present, is as defined for R$^E$;
CY is substituted or unsubstituted C$_1$-C$_6$ alkyl, substituted or unsubstituted C$_3$-C$_{10}$ cycloalkyl, substituted or unsubstituted C$_2$-C$_{10}$ heterocycloalkyl, substituted or unsubstituted aryl, or substituted or unsubstituted heteroaryl, wherein when CY is substituted then CY is substituted with 1, 2, or 3 independently selected R$^H$;
wherein each R$^H$ is independently selected from —H, halogen, —CN, —NO$_2$, —OH, —OR$^J$, —SR$^J$, —S(=O)R$^J$, —S(=O)$_2$R$^J$, —N(R$^J$)S(=O)$_2$R$^J$, —S(=O)$_2$N(R$^L$)$_2$, —C(=O)R$^J$, OC(=O)R$^J$, —C(=O)OR$^J$, —OC(=O)OR$^J$, —N(R$^L$)$_2$, —C(=O)N(R$^L$)$_2$, —OC(=O)N(R$^L$)$_2$, —N(R$^J$)C(=O)N(R$^L$)$_2$, —N(R$^J$)C(=O)R$^J$, —N(R$^J$)C(=O)OR$^J$, C$_1$-C$_4$ alkyl, C$_1$-C$_4$ fluoroalkyl, C$_1$-C$_4$ fluoroalkoxy, C$_1$-C$_4$ alkoxy, and C$_1$-C$_4$ heteroalkyl,
wherein each R$^J$ is independently substituted or unsubstituted C$_1$-C$_6$ alkyl, substituted or unsubstituted C$_1$-C$_6$ heteroalkyl, substituted or unsubstituted C$_1$-C$_6$ fluoroalkyl, substituted or unsubstituted C$_3$-C$_6$ cycloalkyl, substituted or unsubstituted heterocycloalkyl, substituted or unsubstituted aryl, substituted or unsubstituted heteroaryl, —C$_1$-C$_4$ alkylene-(substituted or unsubstituted C$_3$-C$_6$ cycloalkyl), —C$_1$-C$_4$ alkylene-(substituted or unsubstituted heterocycloalkyl), —C$_1$-C$_4$ alkylene-(substituted or unsubstituted aryl), or —C$_1$-C$_4$ alkylene-(substituted or unsubstituted heteroaryl);
wherein each R$^L$ is independently —H, substituted or unsubstituted C$_1$-C$_6$ alkyl, substituted or unsubstituted C$_1$-C$_6$ heteroalkyl, substituted or unsubstituted C$_1$-C$_6$ fluoroalkyl, substituted or unsubstituted C$_3$-C$_6$ cycloalkyl, substituted or unsubstituted heterocycloalkyl, substituted or unsubstituted aryl, substituted or unsubstituted heteroaryl, —C$_1$-C$_4$ alkylene-(substituted or unsubstituted cycloalkyl), —C$_1$-C$_4$ alkylene- (substituted or unsubstituted heterocycloalkyl), —$C_1$-$C_4$ alkylene(substituted or unsubstituted aryl), or —$C_1$-$C_4$ alkylene-(substituted or unsubstituted heteroaryl), or when $R^H$ is —$S(=O)_2N(R^L)_2$, —$N(R^L)_2$, —$C(=O)N(R^L)_2$, —$OC(=O)N(R^L)_2$ or $N(R^J)C(=O)N(R^L)_2$, each $R^L$ is independently —H or $C_1$-$C_6$ alkyl, or the $R^L$ groups independently are $C_1$-$C_6$ alkyl, which are taken together with the N atom to which they are attached to define a substituted or unsubstituted heterocycle; and Ring C is substituted or unsubstituted $C_3$-$C_{10}$ cycloalkylene, substituted or unsubstituted $C_2$-$C_{10}$ heterocycloalkylene, substituted or unsubstituted arylene, or substituted or unsubstituted heteroarylene, where when Ring C is substituted then Ring C is substituted with 1, 2, or 3 independently selected $R^H$, wherein $R^H$ is as previously defined.

21. The method according to claim 20, wherein the compound is selected from: 2-[4-[4-[5-[1-(2-chlorophenyl)ethoxycarbonylamino]-4-cyano-pyrazol-1-yl]phenyl]phenyl]acetic acid, (R)-1-(4'-{5-[1-(2-Chloro-phenyl)-ethoxycarbonylamino]-4-fluoro-pyrazol-1-yl}-3-fluoro-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-2-fluoro-biphenyl-4-yl)-cyclopropanecarboxylic acid, (R)-1-(2-Chloro-4'-{5-[1-(2-chloro-phenyl)-ethoxycarbonylamino]-4-fluoro-pyrazol-1-yl}-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-2-methyl-biphenyl-4-yl)-cyclopropanecarboxylic acid, (R)-1-(4'-{5-[1-(2-Chloro-phenyl)-ethoxycarbonylamino]-4-fluoro-pyrazol-1-yl}-biphenyl-4-yl)-cyclopropanecarboxylic acid, (R)-1-{4'-[5-(1-Phenyl-ethoxycarbonylamino)-4-trifluoromethyl-pyrazol-1-yl]-biphenyl-4-yl}-cyclopropanecarboxylic acid, (R)-1-{2-Fluoro-4'-[5-(1-phenyl-ethoxycarbonylamino)-4-trifluoromethyl-pyrazol-1-yl]-biphenyl-4-yl}-cyclopropanecarboxylic acid, 2-[4-[4-[4-cyano-5-(1-phenylethoxycarbonylamino)pyrazol-1-yl]phenyl]phenyl]acetic acid, 1-[4-[4-[4-cyano-5-(1-phenylethoxycarbonylamino)pyrazol-1-yl]phenyl]phenyl]cyclopropanecarboxylic acid, 1-[4-[4-[5-[1-(2-chlorophenyl)ethoxycarbonylamino]-4-cyano-pyrazol-1-yl]phenyl]phenyl]cyclopropanecarboxylic acid, 2-[4-[4-[4-cyano-5-(1-phenylethoxycarbonylamino)pyrazol-1-yl]phenyl]phenyl]-2-methyl-propanoic acid, 2-[4-[4-[5-[1-(2-chlorophenyl)ethoxycarbonylamino]-4-cyano-pyrazol-1-yl]phenyl]phenyl]-2-methyl-propanoic acid, 1-{4'-[4-Fluoro-5-(1-phenylethoxycarbonylamino)-1H-pyrazol-1-yl]-4-biphenylyl}cyclopropanecarboxylic acid, 1-(4'-{5-[1-(o-Chlorophenyl)ethoxycarbonylamino]-4-fluoro-1H-pyrazol-1-yl}-4-biphenylyl)cyclopropanecarboxylic acid, 1-{3-Fluoro-4'-[4-fluoro-5-(1-phenylethoxycarbonylamino)-1H-pyrazol-1-yl]-4-biphenylyl}cyclopropanecarboxylic acid, 1-(4'-{5-[1-(o-Chlorophenyl)ethoxycarbonylamino]-4-fluoro-1H-pyrazol-1-yl}-3-fluoro-4-biphenylyl)cyclopropanecarboxylic acid, 1-{2-Fluoro-4'-[4-fluoro-5-(1-phenylethoxycarbonylamino)-1H-pyrazol-1-yl]-4-biphenylyl}cyclopropanecarboxylic acid, 1-(4'-{5-[1-(o-Chlorophenyl)ethoxycarbonylamino]-4-fluoro-1H-pyrazol-1-yl}-2-fluoro-4-biphenylyl)cyclopropanecarboxylic acid, 1-(2-Chloro-4'-{5-[1-(o-chlorophenyl)ethoxycarbonylamino]-4-fluoro-1H-pyrazol-1-yl}-4-biphenylyl)cyclopropanecarboxylic acid, 1-(4-{p-[4-Fluoro-5-(1-phenylethoxycarbonylamino)-1H-pyrazol-1-yl]phenyl}tolyl)cyclopropanecarboxylic acid, 1-[4-(p-{5-[1-(o-Chlorophenyl)ethoxycarbonylamino]-4-fluoro-1H-pyrazol-1-yl}phenyl)tolyl]cyclopropanecarboxylic acid, 1-(p-{5-[4-Fluoro-5-(1-phenylethoxycarbonylamino)-1H-pyrazol-1-yl]-2-pyridyl}phenyl)cyclopropanecarboxylic acid, 1-[p-(5-{5-[1-(o-Chlorophenyl)ethoxycarbonylamino]-4-fluoro-1H-pyrazol-1-yl}-2-pyridyl)phenyl]cyclopropanecarboxylic acid, 1-(2-Fluoro-4-{5-[4-fluoro-5-(1-phenylethoxycarbonylamino)-1H-pyrazol-1-yl]-2-pyridyl}phenyl)cyclopropanecarboxylic acid, 1-[4-(5-{5-[1-(o-Chlorophenyl)ethoxycarbonylamino]-4-fluoro-1H-pyrazol-1-yl}-2-pyridyl)-2-fluorophenyl]cyclopropanecarboxylic acid, 1-(3-Fluoro-4-{5-[4-fluoro-5-(1-phenylethoxycarbonylamino)-1H-pyrazol-1-yl]-2-pyridyl}phenyl)cyclopropanecarboxylic acid, 1-[4-(5-{5-[1-(o-Chlorophenyl)ethoxycarbonylamino]-4-fluoro-1H-pyrazol-1-yl}-2-pyridyl)-3-fluorophenyl]cyclopropanecarboxylic acid, 1-(p-{5-[4-Cyano-5-(1-phenylethoxycarbonylamino)-1H-pyrazol-1-yl]-2-pyridyl}phenyl)cyclopropanecarboxylic acid, 1-[p-(5-{5-[1-(o-Chlorophenyl)ethoxycarbonylamino]-4-cyano-1H-pyrazol-1-yl}-2-pyridyl)phenyl]cyclopropanecarboxylic acid, 1-(4-{5-[4-Cyano-5-(1-phenylethoxycarbonylamino)-1H-pyrazol-1-yl]-2-pyridyl}-2-fluorophenyl)cyclopropanecarboxylic acid, 1-[4-(5-{5-[1-(o-Chlorophenyl)ethoxycarbonylamino]-4-cyano-1H-pyrazol-1-yl}-2-pyridyl)-2-fluorophenyl]cyclopropanecarboxylic acid, 1-(4-{5-[4-Cyano-5-(1-phenylethoxycarbonylamino)-1H-pyrazol-1-yl]-2-pyridyl}-3-fluorophenyl)cyclopropanecarboxylic acid, and 1-[4-(5-{5-[1-(o-Chlorophenyl)ethoxycarbonylamino]-4-cyano-1H-pyrazol-1-yl}-2-pyridyl)-3-fluorophenyl]cyclopropanecarboxylic acid.

22. The method according to claim 20, wherein the LPAR is in a subject having a lysophosphatidic acid-dependent disease.

23. The method according to claim 16, wherein the analogs of Taxol are selected from the group consisting of Taxotere, U0126, PD98059, PD184352, PD0325901, ARRY-142886, SB239063, SP600 125, BAY 43-9006, wortmannin, LY294002, and combinations thereof.

24. The method according to claim 16, wherein the Eleutherobins are selected from the group consisting of Desmethyleleutherobin, Desacetyleleutherobin, Isoeleutherobin A, Z-Eleutherobin, and combinations thereof.

* * * * *

UNITED STATES PATENT AND TRADEMARK OFFICE
CERTIFICATE OF CORRECTION

| | | |
|---|---|---|
| PATENT NO. | : 10,570,103 B2 | Page 1 of 1 |
| APPLICATION NO. | : 16/000283 | |
| DATED | : February 25, 2020 | |
| INVENTOR(S) | : Graham Beaton et al. | |

It is certified that error appears in the above-identified patent and that said Letters Patent is hereby corrected as shown below:

In the Specification

<u>Column 1:</u>
Line 20 Delete "DK092005" and insert --DK090025-- therefor

Signed and Sealed this
Twenty-second Day of July, 2025

Coke Morgan Stewart
*Acting Director of the United States Patent and Trademark Office*